United States Patent
Banville et al.

(10) Patent No.: US 6,350,892 B1
(45) Date of Patent: Feb. 26, 2002

(54) TRIFLUOROMETHYL KETONE ANALOGS AS SELECTIVE CPLA2 INHIBITORS

(75) Inventors: Jacques Banville, St-Hubert (CA); Yonghua Gai, Killingworth, CT (US); Graham Johnson, Madison, CT (US); Fred Christopher Zusi, Hamden, CT (US); James R. Burke, Upper Holland, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/507,782

(22) Filed: Feb. 18, 2000

Related U.S. Application Data

(63) Continuation-in-part of application No. 09/300,111, filed on Apr. 27, 1999, now Pat. No. 6,255,496, which is a continuation of application No. 09/151,002, filed on Sep. 10, 1998, now abandoned.

(60) Provisional application No. 60/063,518, filed on Oct. 27, 1997, and provisional application No. 60/059,597, filed on Sep. 23, 1997.

(51) Int. Cl.[7] ............... C07F 7/04; C07F 7/08; C07C 211/00; C07C 315/00; C07C 317/00

(52) U.S. Cl. ............ 556/436; 514/63; 514/648; 514/676; 514/709; 556/440; 564/316; 568/31; 568/43

(58) Field of Search ............ 548/541; 514/143, 514/63, 648, 676, 709; 556/436, 440; 564/316; 568/31, 43

(56) References Cited

U.S. PATENT DOCUMENTS

| | | | | |
|---|---|---|---|---|
| 4,229,479 A | * | 10/1980 | Brickl et al. | 454/331 |
| 5,453,443 A | * | 9/1995 | Perrier et al. | 514/570 |
| 5,478,857 A | * | 12/1995 | Clemens et al. | 514/381 |
| 6,255,496 B1 | * | 7/2001 | Banville et al. | 548/541 |

FOREIGN PATENT DOCUMENTS

| | | | |
|---|---|---|---|
| JP | 92-68153 | * | 10/1997 |
| WO | 98-25893 | * | 6/1998 |

* cited by examiner

Primary Examiner—Floyd D. Higel
(74) Attorney, Agent, or Firm—David M. Morse

(57) ABSTRACT

Selective inhibitors of the $cPLA_2$ enzymes are provided which are of use in controlling a wide variety of inflammatory diseases. The inhibitors of the present invention have the general formula

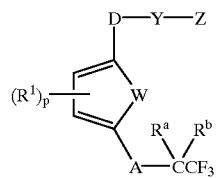

where (R'), p, D, Y, Z, $R^a$, $R^b$ and A are as defined in the specification.

8 Claims, No Drawings

TRIFLUOROMETHYL KETONE ANALOGS AS SELECTIVE CPLA2 INHIBITORS

CROSS-REFERENCE TO RELATED APPLICATIONS

This application is a continuation-in-part of U.S. Ser. No. 09/300,111 filed Apr. 27, 1999, now U.S. Pat. No. 6,255,496, which is a continuation of U.S. Ser. No. 09/151,002 filed Sep. 10, 1998, now abandoned, which claims the priority of U.S. Provisional Application Ser. No. 60/063,518 filed Oct. 27, 1997 and U.S. Provisional Application Ser. No. 60/059,597 filed Sep. 23, 1997.

BACKGROUND OF THE INVENTION

Inflammatory diseases of the skin, such as psoriasis and atopic dermatitis, afflict greater than 5% of the population. Currently, the treatment of these disorders typically involves the use of topical steroids. However, these agents also have undesirable side effects such as skin atrophy which limit the duration of therapy. In addition, topical application of a drug is difficult for many patients where the affected area may be very large.

Phospholipase $A_2$ ($PLA_2$) is the common name for phosphatide 2-acylhydrolase which catalyzes the hydrolysis of the sn-2-acyl ester bond of phosphoglycerides and results in production of lysophospholipids and free fatty acids. When the fatty acid is arachidonic acid, further action by cyclooxygenase and 5-lipoxygenase enzymes results in eicosanoid production, which is implicated in inflammation, and leukotrienes which are linked to asthma. Lysophophospholipid metabolism results in production of platelet activating factor and both lysophospholipids and platelet activating factor also play a role in inflammation.

$PLA_2$ enzymes existas secreted forms (MW~12,000–15,000) and cytosolic forms (MW~85,000). The cytosolic or $cPLA_2$ enzymes appear to play a key role in the pathway leading to the formation of platelet activating factor and the eicosanoids.

Inappropriate activation of the cytosolic $PLA_2$ enzymes, therefore, can result in a variety of chronic and acute conditions including asthma, cerebral ischemia (Clemens et al, *Stroke* 1996, 27, 527–535), Alzheimer's Disease (Stephenson et al, *Neurobiology of Stroke*, 1996, 3, 51–63 and see also U.S. Pat. No. 5,478,857), rheumatoid arthritis, neutrophil and platelet activation (Huang et al, *Mediators of Inflammation* 1994, 3, 307–308), chronic skin inflammation and damage to the skin resulting from exposure to ultraviolet light (Gresham et al., *American Journal of Physiology*, 1996, 270; *Cell Physiology* 39:C1037–C1050) and macrophage activation (Balsinde et al, *Journal of Biological Chemistry*, 1996, 271, 6758–6765).

Selective inhibitors of the $cPLA_2$ enzymes may, therefore, be of use in controlling a wide variety of inflammatory diseases. The literature describes a significant number of compounds said to be phospholipase $A_2$ inhibitors, but few selective inhibitors for the $cPLA_2$ enzymes are available. The present inventors had as their goal the synthesis of novel compounds which would be selective and potent inhibitors of the $cPLA_2$ enzymes. As used herein, the term "selective inhibitors of the $cPLA_2$ enzymes" means that the inhibitors inhibit the $cPLA_2$ enzymes with a potency 20-fold or greater than they inhibit the lower molecular weight synovial $PLA_2$ enzymes.

*Biochemistry* 32: 5935–5940, 1993, discloses a trifluoromethyl ketone analog of arachidonic acid having the formula

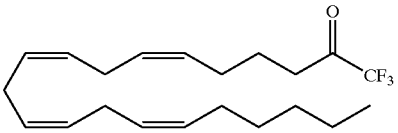

as a selective inhibitor of $cPLA_2$.

*Bioorganic Med. Chem. Lett.* 5: 519–522, 1995, discloses selective $cPLA_2$ inhibitors of the formula

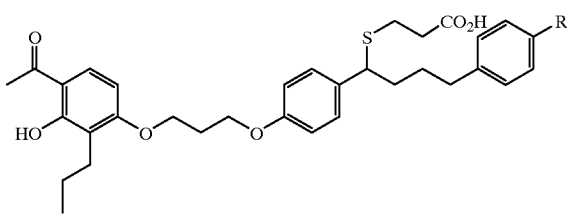

where R is either H or OH.

Japanese published patent application JP09268153A (Derwent No. 97-554679/51) discloses $cPLA_2$ inhibitors of the formula $RCOCF_3$ where RCO is an acyl residue of an n-3 series highly unsaturated fatty acid. The compounds are said to be useful as antiinflammatory or antiallergic drugs.

Published PCT Application WO 98/25893 discloses arylsulfonamide compounds of the general formula

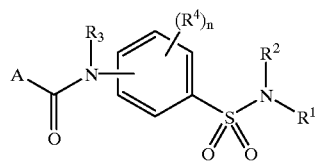

wherein

A represents a $C_4$–$C_{10}$ alkyl group, an aryl group, an arylalkyl group, radicals selected from the group consisting of —CH=CH—B,—O—B,—S—B, and —NH—B, or radicals of formula —$CH_2$—X, wherein B represents a non-aromatic $C_3$–$C_8$ carbocycle, a $C_3$–$C_8$ alkyl group, a heterocycle or an arylalkyl group, each of which is optionally substituted with one or more members independently selected from the group consisting of a halogen atom, a $C_1$–$C_4$ alkyl group, a $C_1$–$C_4$ alkoxy group, cyano, nitro, a heterocycle, an aryl group and an aryloxy group, and X is a member selected from the group consisting of a halogen atom, —S—aryl,—S—heterocycle, and —$PO_3R_2$ wherein each R is independently selected from the group consisting of a hydrogen atom and $C_1$–$C_3$ alkyl;

$R^1$ and $R^2$ each independently represent a hydrogen atom, a lower alkyl group, or a group represented by the formula: —$(CH_2)_q$—A' wherein q is an integer of 2 to 4, and A' is a member selected from the group consisting of a hydroxyl group, a group represented by the formula:

—N⟨R⁵/R⁶ wherein R⁵ and R⁶ each independently represent a hydrogen atom, a lower alkyl group, or a group represented by the formula:

[pyridyl group with R⁷ substituent]

wherein R⁷ represents a hydrogen atom, a lower alkyl group, or a group represented by the formula:

[phenyl-CH₂-N(cyclic)(CH₂)ₛ]

wherein s is an integer of 2 to 5; or

R¹ and R² each independently represent an unsubstituted cycloalkyl group, or a cycloalkyl substituted with a lower alkyl or halogen or condensed with an aromatic ring, a bicycloalkyl, or tricycloalkyl, said bicycloalkyl or tricycloalkyl being an aliphatic saturated hydrocarbon group made of two or three rings, respectively, with at least two carbon atoms being common to each ring, or an azabicycloalkyl group which is a bicycloalkyl group as described above in which one carbon atom is replaced by a nitrogen atom or a group represented by the formula:

[bicyclic structure with (CH₂)g and (CH₂)h and N—B']

wherein g and h are each an integer of 1 to 4, and B' stands for a lower alkyl group, an arylalkyl group, an arylalkyl group substituted by lower alkyl; halogen or a lower alkoxy group, or a pyridylalkyl group, or a pyridylalkyl group substituted with a lower alkyl group, a halogen or a lower alkoxy group; or R¹ and R² may be combined together to form a 6- or 7-membered ring which may contain a nitrogen or oxygen atom in addition to the nitrogen atom to which R¹ and R² are bonded, and said 6- or 7-membered ring may be substituted with a lower alkyl, arylalkyl, cycloalkylalkyl or heteroarylalkyl group;

R³ represents a hydrogen atom, a lower alkyl group, or a C₃–C₈ cycloalkyl group;

R⁴ represents a hydrogen atom, a lower alkyl group, a lower alkoxy group or a halogen atom;

n is an integer of 1 to 4, provided that when n is 2, the two R⁴ groups may form a cyclohexenyl or phenyl ring together with two adjacent carbon atoms constituting the benzene ring; and any pharmacologically acceptable salts thereof as inhibitors of phospholipase A₂ activity, particularly cPLA₂.

*Drugs* 1998, Vol. 1, No. 1, pp. 49–50 discloses cPLA₂ inhibitors of the type

[structure of formula (1) with R₂-X-phenyl-O-CH₂-C(O)-CH₂-O-R₁ and p-methylbenzoic acid]

| R₁ | R₂ | X |
|---|---|---|
| CH₃ | CH₃(CH₂)₉— | O |
| (1) | CH₃(CH₂)₉— | O |
| (1) | Ph(CH₂)₅ | S |
| (1) | CH₃(CH₂)₉— | SO₂ |

(1)

U.S. Pat. No. 5,453,443 discloses a series of biaryl ketones which are reported to inhibit PLA₂ enzymes, but it is not indicated whether these compounds are selective for the cytosolic enzymes or even whether they inhibit the cytosolic enzymes. These compounds have the generic formula

[structure: Q(CR¹R⁵)ₘ-phenyl(R⁸,R¹⁰)-A(C(R⁶)₂)ₙB-phenyl(R⁹)-CH(X¹(C(R²)₂)ᵣCO₂R¹⁵)((C(R³)₂)ₛZ)]

wherein:
R¹ is selected from
  (a) hydrogen,
  (b) —C₁₋₆alkyl, and
  (c) —C₁₋₆alkyl-phenyl;
or wherein R¹ and R⁵ are joined such that together with the carbon atoms to which they are attached there is formed a saturated or unsaturated carbon ring of 3, 4, 5, 6, 7 or 8 atoms; R² and R³ are each independently selected from
  (a) hydrogen,
  (b) —C₁₋₆alkyl, and
  (c) —C₁alkyl-phenyl,
or wherein two R² or two R³ are joined such that together with the carbon atoms to which they are attached there is formed a saturated or unsaturated carbon ring of 3, 4, 5, 6, 7 or 8 atoms;
R⁵ is as defined above or is selected from
  (a) hydrogen
  (b) —C₁₋₆alkyl
  (c) —C₁₋₆alkyl-phenyl C₁₋₆alkyl,
  (d) —OH
  (e) —O—C₁₋₆alkyl, or
  (f) —C₁₋₆alkyl-phenyl C₁₋₆alkyl;
R⁶ is selected from
  (a) hydrogen
  (b) —C₁₋₆alkyl
  (c) —C₁₋₆alkyl-phenyl, wherein the phenyl is optionally substituted with C₁₋₂alkyl;
  (d) —OH,
  (e) —O—C₁₋₆alkyl, or
  (f) —O—C₁₋₆alkyl-phenyl, wherein the phenyl is optionally substituted with C₁₋₂alkyl;
or wherein two R⁶ are joined to form O= or are joined together such that together with the carbon atom to which they are attached there is formed a saturated or unsaturated carbon ring of 3, 4, 5, 6, 7 or 8 atoms;

$R^8$, $R^9$ and $R^{14}$ are each independently selected from
(a) H,
(b) —$C_{1-6}$alkyl
(c) halo
(d) —CN
(e) —OH
(f) —$OC_{1-6}$alkyl,
(g) —$OC_{1-6}$alkyl-phenyl
(h) —$SR^{11}$
(i) $S(O)R^{11}$, or
(j) $S(O)_2R^{11}$;

$R^{10}$, $R^{15}$, $R^{16}$ and $R^{17}$ are each independently selected from
(a) hydrogen,
(b) —$C_{1-6}$ alkyl, and
(c) —$C_{1-6}$ alkyl-phenyl;

$R^{11}$ is selected from
(a) —$C_{1-6}$ alkyl,
(b) —$C_{2-6}$ alkenyl,
(c) —$CF_3$,
(d) -phenyl$(R^{12})_2$, or
(e) —$C_{2-6}$ alkenyl-phenyl$(R^{12})_2$, $R^{12}$ is
(a) hydrogen,
(b) —$C_{1-6}$alkyl,
(c) Cl, F, I or Br;

$R^{13}$ is perfluoro$C_{1-6}$alkyl;

A and B are each independently
(a) covalent bond,
(b) O,
(c) S,
(d) S(O), or
(e) $S(O)_2$;

Q is selected from
(a) —$CH(OH)R^{13}$,
(b) —$COR^{13}$,
(C) —$COR^{16}$, or
(d) —$C_{1-4}$alkyl$COCOOR^{17}$;

$X^1$ is selected from
(a) —O—
(b) —S—
(c) —S(O)—,
(d) —$S-(O)_2$—;

Z is
(a) H, or
(b) -phenyl-$(R^{14})_3$, m is 0, 1, 2, 3 or 4;
n is 2, 3, 4, 5, 6 or 7; and
r and s are each independently 0, 1, 2, 3, 4, 5, 6, 7 or 8.

J. Prakt. Chem., Vol. 337, pp. 34–37 (1995) discloses the compound of the formula

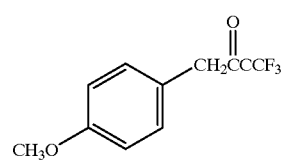

Anal. Chem., Vol. 63, No. 6, pp. 596–603 (1991) discloses the compound of the formula

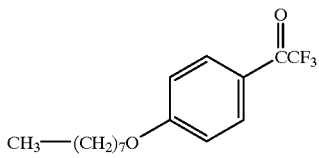

SUMMARY OF THE INVENTION

The present invention is directed to selective cytosolic $PLA_2$ inhibitor compounds of the formula

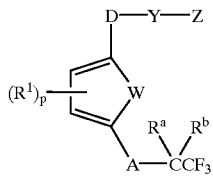

wherein

W is CH=CH, CH=N, O or S;

$R^1$ is $(C_1-C_6)$alkyl, $(C_2-C_6)$alkenyl, $(C_2-C_6)$alkynyl, $(C_1-C_6)$alkoxy, $(C_1-C_6)$alkylthio, halo, hydroxy, cyano,

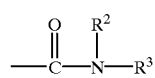

in which $R^2$ and $R^3$ are each independently hydrogen or $(C_1-C_6)$alkyl, —COO—$(C_1-C_6)$alkyl, $CF_3$, $(C_1-C_6)$alkylphenyl, phenyl or phenyl substituted by one or more, preferably 1–3, of $(C_1-C_6)$alkyl, —COO—$(C_1-C_6)$alkyl,

in which
$R^2$ and $R^3$ are as defined above, halo, hydroxy, —O—$(C_1-C_6)$alkyl, —S—$(C_1-C_6)$alkyl, or $(C_2-C_6)$alkenyl;

p is 0, 1 or 2;

A is V—$(R^c)_n$—;

$R^c$ is a straight or branched chain alkyl group;

n is 0 or an integer of from 1 to 6;

$R^a$ and $R^b$ when taken together form an oxo (=O) group, or $R^a$ and $R^b$ are each independently hydrogen or OH;

V is O, —S—, —SO—, —$SO_2$, —CONH or NHCO when n is an integer of from 1 to 6 or V is $(C_2-C_6)$ alkenyl or a bond when n is 0 or an integer of from 1 to 6;

D is —$(CH_2)_m$ or a bond linking the

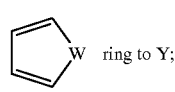

m is an integer of from 1 to 6;

Y is —O—, —S—, —SO—, —SO$_2$;

or a bond;

R$^4$ is as defined below for R$^7$;

Z is:

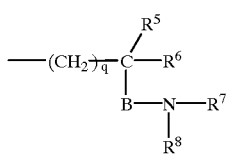
(a)

in which B is:

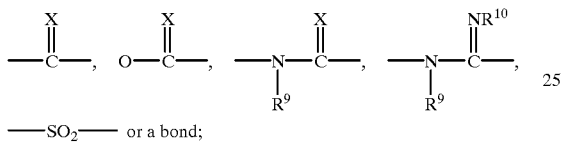

—SO$_2$— or a bond;

X is S or O;

q is an integer from 1 to 6;

R$^9$ is hydrogen or (C$_1$–C$_6$)alkyl;

R$^{10}$ is hydrogen, CN, NO$_2$, OH, —O—(C$_1$–C$_6$)alkyl, (C$_1$–C$_6$) alkyl, phenyl or (C$_1$–C$_6$)alkylphenyl;

R$^5$ and R$^6$ are each independently hydrogen or (C$_1$–C$_{18}$) alkyl;

R$^7$ and R$^8$ are each independently;
(a) hydrogen;
(b) (C$_1$–C$_{18}$)alkyl;
(c) (C$_1$–C$_{18}$)alkyl substituted by one or more of
 (1) phenyl;
 (2) phenyl substituted by 1–5 fluoro, 1–3 (for each of the following phenyl substituents) halo (other than fluoro), 1–3(C$_1$–C$_6$)alkoxy, 1–3(C$_1$–C$_6$)alkyl, nitro, cyano, hydroxy, trifluoromethyl, (C$_1$–C$_6$) alkylthio, amino, 1–3 (C$_1$–C$_6$) alkylamino, di(C$_1$–C$_6$)alkylamino, —CO$_2$H, —COO—(C$_1$–C$_6$)alkyl, —SO$_3$H, —SO$_2$NHR$^{15}$ in which R$^{15}$ is hydrogen or (C$_1$–C$_6$)alkyl, or

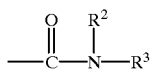

in which R$^2$ and R$^3$ are as defined above;
(3) heterocyclic selected from oxadiazolyl, isoxazolyl, oxazolyl, furyl and thiazolyl;
(4) heterocyclic substituted by one or more of, preferably 1–3, phenyl, phenyl substituted by 1–3 (for each of the following) halo, (C$_1$–C$_6$)alkoxy, (C$_1$–C$_6$)alkyl, nitro, cyano, hydroxy, trifluoromethyl, (C$_1$–C$_6$) alkylthio, amino, (C$_1$–C$_6$) alkylamino, di(C$_1$–C$_6$) alkylamino, CO$_2$H, —COO—(C$_1$–C$_6$) alkyl, —SO$_3$H, SO$_2$NHR$^{15}$ in which R$^{15}$ is hydrogen or (C$_1$–C$_6$) alkyl, or

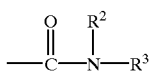

in which R$^2$ and R$^3$ are as defined above, (C$_1$–C$_6$) alkyl or (C$_1$–C$_6$) alkyl substituted by one or more, preferably 1–3, phenyl or heterocyclic groups, said phenyl or heterocyclic group being unsubstituted or substituted by 1–3 (for each of the following) halo, 1–3 (C$_1$–C$_6$) alkoxy, 1–3 (C$_1$–C$_6$) alkyl, nitro, cyano, hydroxy, trifluoromethyl, (C$_1$–C$_6$) alkylthio, amino, 1—3 (C$_1$–C$_6$) alkylamino, di(C$_1$–C$_6$) alkylamino, COOH, —COO—(C$_1$–C$_6$) alkyl, —SO$_3$H, —SO$_2$NHR$^{15}$ in which R$^{15}$ is hydrogen or (C$_1$–C$_6$) alkyl, or

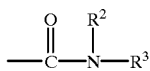

in which R$^2$ and R$^3$ are each independently hydrogen or (C$_1$–C$_6$) alkyl, the heterocyclic radical being selected from imidazolyl, oxadiazolyl, isoxazolyl, pyrrolyl, pyrazolyl, oxazolyl, furyl, thianyl or thiazolyl;

(5) carboxy or —COO—(C$_1$–C$_6$) alkyl;

(6) hydroxy, halo, —O—(C$_1$–C$_6$) alkyl or —S—(C$_1$–C$_6$) alkyl, with the proviso that the OH, ethers or thioethers cannot be on the carbon bearing the heteroatoms;

(7) cyano;

(8) halo, trifluoromethyl or trifluoroacetyl;

(9) CH$_2$ L—R$^{16}$ in which L is

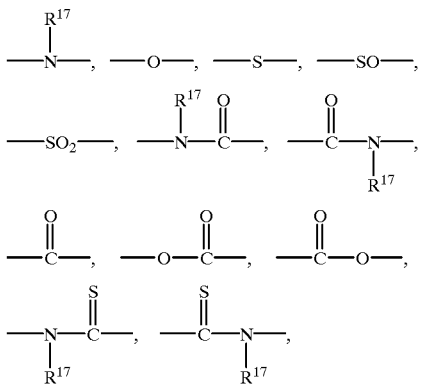

or —O—SiR$^{16}$R$^{18}$R$^{19}$ or a bond in which R$^{16}$ and R$^{17}$ are each independently (C$_1$–C$_{18}$)alkyl or (C$_2$–C$_{18}$)alkenyl or (C$_1$–C$_{18}$)alkyl or (C$_2$–C$_{18}$) alkenyl substituted by one or more, preferably 1–3, phenyl or heterocyclic radicals, said phenyl or heterocyclic radicals being unsubstituted or substituted by 1–5 fluoro, 1–3 halo (other than fluoro), 1–3 (C$_1$–C$_6$)alkoxy, 1–3(C$_1$–C$_6$)alkyl, nitro, cyano, hydroxy, 1–3 trifluoromethyl, 1–3 (C$_1$–C$_6$)alkylthio, amino, 1–3(C$_1$–C$_6$)alkylamino, 1–3 di($C_1$–$C_6$)alkylamino, $CO_2H$, 1–3 —COO($C_1$–$C_6$)alkyl,

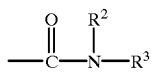

or —$SO_2NHR^9$ in which $R^9$ is hydrogen or ($C_1$–$C_6$)alkyl and $R^2$ and $R^3$ are as defined above;

(b)

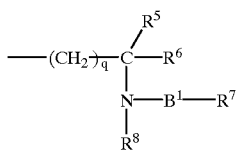

in which $B^1$ is

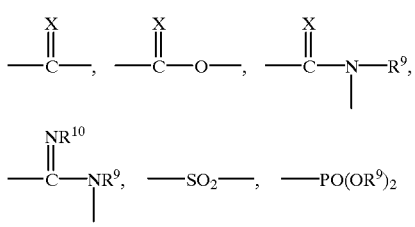

or a bond;

providing that when $B^1$ is —$PO(OR^9)_2$, then $R^7$ becomes $R^9$, and when $B^1$ is

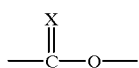

or —$SO_2$—, then $R^7$ cannot be hydrogen;

X, q, $R^5$, $R^6$, $R^7$, $R^8$, $R^9$ and $R^{10}$ are as defined in (a);

(c)

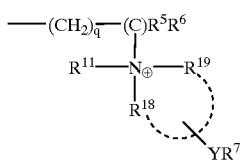

in which q, $R^5$ and $R^6$ are as defined above;

$R^{18}$, $R^{19}$ and $R^{11}$ are as defined above for $R^7$ and $R^8$ except that they may not be hydrogen, or $R^{18}$ and $R^{19}$ taken together with the nitrogen to which they are attached represent a 4, 5- or 6-membered heterocyclic ring and Y, $R^7$ and $R^{11}$ are as defined above, or $R^{18}$, $R^{19}$ and $R^{11}$ taken together with the nitrogen to which they are attached represent pyridinium, said pyridinium group being unsubstituted or substituted by ($C_1$–$C_{12}$)alkyl, ($C_1$–$C_{12}$)alkoxy, amino, ($C_1$–$C_{12}$)alkylamino, di($C_1$–$C_{12}$)alkylamino,

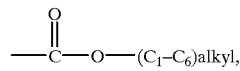

—S—($C_1$–$C_{12}$)alkyl,

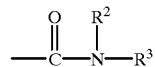

in which $R^2$ and $R^3$ are as defined above, phenyl or phenyl ($C_1$–$C_{10}$)alkyl;

d)

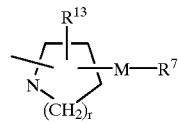

in which $R^{13}$ is ($C_1$–$C_{18}$)alkyl or ($C_1$–$C_{18}$)alkyl substituted by carboxy,

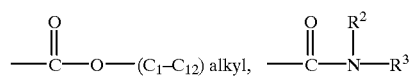

in which $R^2$ and $R^3$ are as defined above, hydroxy, —O—($C_1$–$C_6$) alkyl, —O—($C_1$–$C_6$) alkyl or —S—($C_1$–$C_6$) alkyl substituted by 1 or 2 phenyl or substituted phenyl groups, the substituents for the substituted phenyl groups being 1–5 fluoro or 1–3 (for each of the following phenyl substituents) halo (other than fluoro), ($C_1$–$C_6$) alkoxy, ($C_1$–$C_6$) alkyl, nitro, cyano, hydroxy, trifluoromethyl, ($C_1$–$C_6$) alkylthio, amino, ($C_1$–$C_6$) alkylamino, di($C_1$–$C_6$) alkylamino, $CO_2H$, COO—($C_1$–$C_6$) alkyl, $SO_3H$, $SO_2NHR^{15}$ in which $R^{15}$ is hydrogen or ($C_1$–$C_6$) alkyl or

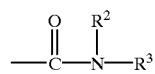

in which $R^2$ and $R^3$ are as defined above;

r is 0 or an integer of from 1 to 3;

$R^7$ is as defined above;

M is —($CH_2$—)$_m$T where

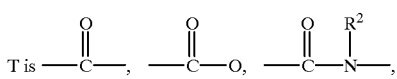

in which $R^2$ is as defined above, —$SO_2$— or a bond when $MR^7$ is on nitrogen and providing that when

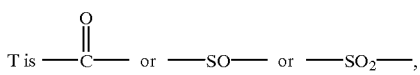

then R⁷ cannot be hydrogen, and

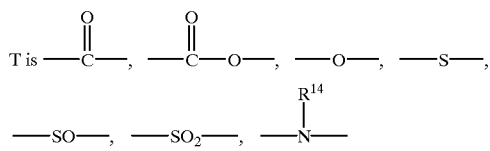

or a bond when MR⁷ is on a carbon atom of the heterocyclic ring;

R¹⁴ is hydrogen or (C₁–C₆)alkyl;

m is 0 or an integer of 1–6;

e) 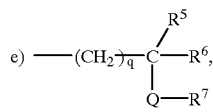

wherein Q is —O—, —S—, —SO— or —SO₂—, and q, R⁵, R⁶ and R⁷ are as defined above, providing that when Q is —SO— or —SO₂—, R⁷ cannot be hydrogen;

f) R⁷ wherein R⁷ is defined above, providing that when Y is —SO— or —SO₂—, R⁷ cannot be hydrogen, and providing that when Y is O and D is a bond, R⁷ cannot be (C₁–C₁₈) alkyl; and R¹⁸ and R¹⁹ are phenyl or phenyl substituted by 1–3 halo, (C₁–C₆) alkoxy, (C₁–C₆) alkyl, nitro, cyano, hydroxy, trifluoromethyl, (C₁–C₆) alkylthio, amino, (C₁–C₆) alkylamino, di(C₁–C₆) alkylamino, CO₂H, —COO— (C₁–C₆) alkyl, —SO₃H, SO₂NHR¹⁵ in which R¹⁵ is hydrogen or (C₁–C₆) alkyl, or

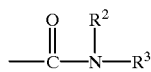

in which R² and R³ are as defined above; or pharmaceutically acceptable salts, solvates or prodrugs thereof.

Also provided by this invention are methods for inhibiting cytosolic PLA₂ in a mammal in need thereof which comprises administering to said mammal a therapeutically effective amount of a compound of formula I and methods for using the compounds of formula I to treat various diseases characterized by inappropriate activation of the cytosolic PLA₂ enzymes such as asthma, allergic rhinitis, cerebral ischemia, Alzheimer's Disease, rheumatoid arthritis, acute pancreatitis, inflammatory bowel disease, psoriasis, gout, neutrophil and platelet activation, chronic skin inflammation, shock, trauma-induced inflammation such as spinal cord injury, damage to the skin resulting from UV light or burns and macrophage activation. In further aspects, the present invention provides pharmaceutical compositions comprising a therapeutically effective amount of a compound of formula I and a pharmaceutically acceptable carrier and processes for preparing the compounds of formula I.

DETAILED DESCRIPTION

The object of this invention was to discover a selective cPLA₂ inhibitor which is active, both topically and orally, in treating inflammary disease of the skin and other tissues as well as other chronic and acute conditions which have been linked to inappropriate activation of the cPLA₂ enzymes. Preferably such compound would also be devoid of undesirable lipid-perturbing activities associated with skin irritation.

The above-mentioned objectives have been met by the compounds of formula I described above.

In the present application the numbers in the subscript after the symbol "C" define the number of carbon atoms a particular group can contain. For example, C₁₋₁₈alkyl refers to straight and branched chain alkyl groups with 1 to 18 carbon atoms. Similarly, C₂–C₁₈ alkenyl refers to a straight or branched unsaturated hydrocarbon group containing from 2 to 18 carbon atoms and at least one carbon-carbon double bond. Likewise, C₂–C₁₈ alkynyl refers to a straight or branched unsaturated hydrocarbon group containing from 2 to 18 carbon atoms and at least one carbon-carbon triple bond.

The term "halogen" or "halo" as used herein refers to fluorine, chlorine, bromine or iodine.

Aryl as used herein refers to a C₆ monocyclic aromatic ring system or a C₉ or C₁₀ bicyclic carbocyclic ring system having one or two aromatic rings such as phenyl or naphthyl. Unless otherwise indicated, "substituted aryl" refers to aryl groups substituted with one or more (preferably from 1 to 3) substituents independently selected from (C₁–C₆)alkyl, haloalkyl, (C₁–C₆)alkoxy, (C₁–C₆)alkoxy-carbonyl, (C₁–C₆)alkanoyl, hydroxy, halo, mercapto, nitro, amino, cyano, (C₁–C₆)alkylamino, di(C₁–C₆)alkylamino, carboxy, aryl, aryl (C₁–C₆)alkyl, aryl (C₁–C₆)alkoxy, heterocyclic, heterocyclic (C₁–C₆)alkyl and the like.

The term "heterocyclic" as used herein refers to a 4-, 5- or 6-membered ring containing one, two or three heteroatoms selected from N, O and S. The 5-membered ring has 0–2 double bonds and the 6-membered ring has 0–3 double bonds. The nitrogen heteroatoms can be optionally quaternized or N-oxidized. The sulfur heteroatoms can be optionally S-oxidized. The term "heterocyclic" also includes bicyclic groups in which any of the above heterocyclic rings is fused to a benzene ring or a cyclohexane ring or another heterocyclic ring. Heterocyclics include: pyrrolyl, pyrrolinyl, pyrrolidinyl, pyrazolyl, pyrazolinyl, pyrazolidinyl, imidazolyl, imidazolidinyl, pyridyl, piperidyl, pyrazinyl, piperazinyl, pyrimidinyl, pyridazinyl, oxazolyl, oxazolinyl, oxazolidinyl, isoxazolyl, isoxazolinyl, isoxazolidinyl, morpholinyl, thiazolyl, thiazolidinyl, isothiazolyl, isothiazolidinyl, indolyl, quinolinyl, benzimidazolyl, benzothiazolyl, benzoxazolyl, benzofuranyl, furyl, dihydrofuranyl, tetrahydrofuranyl, pyranyl, dihydropyranyl, dioxolanyl, thienyl, benzothienyl and diaxanyl.

Some of the compounds described herein contain one or more asymmetric centers and may thus give rise to diastereomers and optical isomers. The present invention is meant to include such possible diastereomers as well as their racemic and resolved, enantiomerically pure forms, and pharmaceutically acceptable salts thereof.

As mentioned above the invention also includes pharmaceutically acceptable salts of the compounds of formula I. A compound of the invention can possess a sufficiently acidic, a sufficiently basic, or both functional groups. Accordingly, a compound may react with any of a number of inorganic bases, and organic and inorganic acids, to form a pharmaceutically acceptable salt.

The term "pharmaceutically acceptable salt" as used herein refers to salts of the compounds of formula I which are substantially non-toxic to living organisms. Typical pharmaceutically acceptable salts include those salts prepared by reaction of the compounds of the present invention with a pharmaceutically acceptable mineral or organic acid or an inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogen phosphate, dihydrogen phosphate, metaphosphate, pyrophosphate, chloride, bromide, iodide, acetate, propionate, decanoate, caprylate, acrylate, formate, isobutyrate, caproate, heptanoate, propionate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, $\mu$-hydroxybutyrate, glycolate, tartrate, methanesulfonate, propanesulfonate, naphthalene-1-sulfonate, napthalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. Suitable organic bases include trialkylamines such as triethylamine, procaine, dibenzylamine, N-benzyl-β-phenethylamine, 1-ephenamine, N,N'-dibenzylethylene-diamine, dehydroabietylamine, N-ethylpiperidine, benzylamine, dicyclohexylamine, or the like pharmaceutically acceptable amines. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole.

The present invention also includes solvated forms of the compounds of formula I, particularly hydrates, in which the trifluoromethyl ketone group exists as a mixture of ketonic I and hydrated forms II and are each independently interconvertible and pharmacologically active.

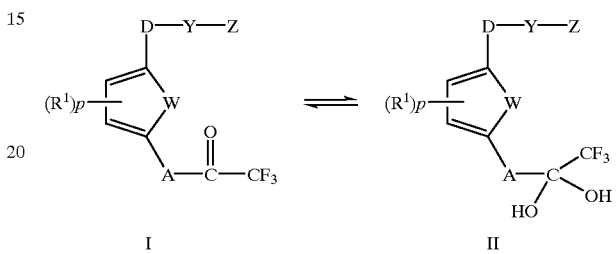

The present invention also includes prodrug forms of the compounds of formula I or II above such as trifluoromethylketone enol ester derivatives, enol phosphate derivatives, cyclic or acylic unsubstituted or substituted O,O-ketals, O,S-ketals, O,N-ketals or S,N-ketals such as cyclic cysteamyl derivatives, cyclic glycolates, thioglycolates, glyoxylates or oxalates, and the like. It also includes trifluoromethylalcohols obtained by chemical reduction of trifluoromethylketones. Such forms are physiologically hydrolyzable groups which are converted in vivo to a pharmacologically active compound of formula I or II, or a crystalline form of such compounds, see scheme below.

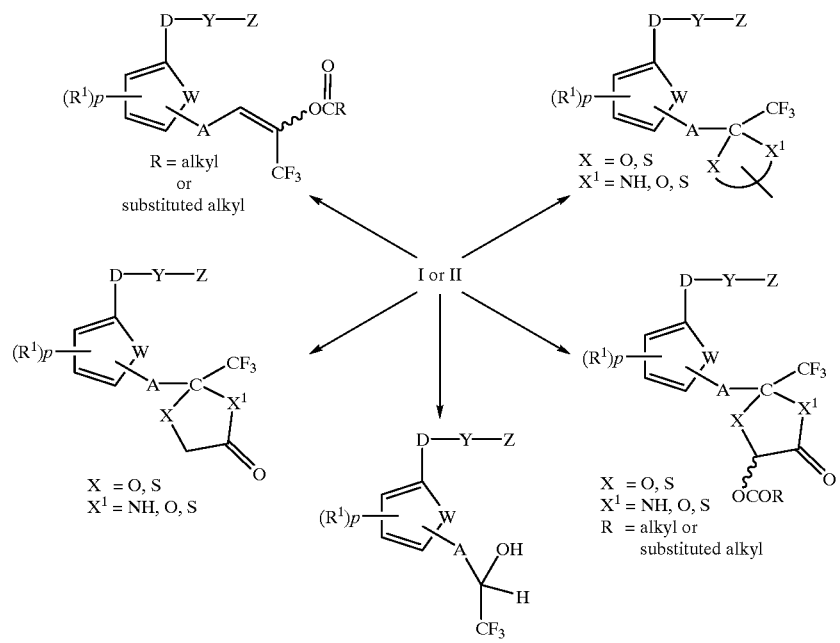

Preferred compounds of formula I are those where the

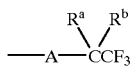

substituent is linked to the phenyl ring at the para or meta position, most preferably at the para position.

Preferred embodiments of the compounds of general formula I include (a) compounds of formula I wherein W is CH=CH, D is a bond linking Y to the ring and Y is —O—;

(b) compounds of (a) immediately above wherein $R^1$ is benzyl, A is V—$(CH_2)_n$—, V is ($C_2$-$C_6$) alkenyl or a bond, p is 0, 1 or 2, and n is 0 or an integer of from 1 to 6; and (c) compounds of (b) immediately above wherein A is —$(CH_2)_n$, is 0 or an integer of from 1 to 6, and the group —$(CH_2)_n COCF_3$ is in the meta or para position of the phenyl ring.

Another preferred embodiment comprises a compound of the formula

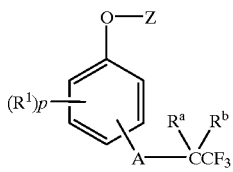

wherein $R^1$ is benzyl; p is 0, 1 or 2; A is V—$(CH_2)_n$—; V is ($C_2$-$C_6$) alkenyl or a bond; n is 0 or an integer of from 1 to 6; $R^a$ and $R^b$ are as defined above and Z is

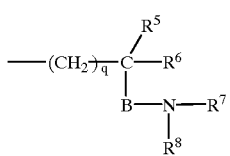 (a)

in which B is

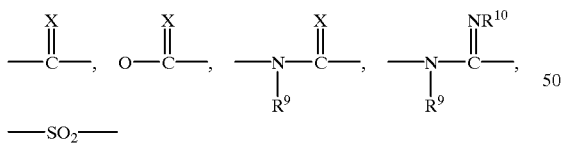

or a bond;

X is S or O;

q is an integer of from 1 to 6;

$R^9$ is hydrogen or ($C_1$-$C_6$) alkyl;

$R^{10}$ is hydrogen, CN, $NO_2$, OH, —O—($C_1$-$C_6$) alkyl, ($C_1$-$C_6$) alkyl, phenyl or ($C_1$-$C_6$) alkylphenyl;

$R^5$ and $R^6$ are each independently hydrogen or ($C_1$-$C_6$) alkyl; and $R^7$ and $R^8$ are each independently
  a) hydrogen;
  b) ($C_1$-$C_{18}$) alkyl;
  c) ($C_1$-$C_{18}$) alkyl substituted by one or more of, preferably 1–3, (1) phenyl;

(2) phenyl substituted by 1–5 fluoro, 1–3 halo (other than fluoro), 1–3 ($C_1$-$C_6$) alkoxy, 1–3 ($C_1$-$C_6$) alkyl, nitro, cyano, hydroxy, trifluoromethyl, ($C_1$-$C_6$) alkylthio, amino, 1–3 ($C_1$-$C_6$) alkylamino, di($C_1$-$C_6$) alkylamino, —$CO_2H$, —COO—($C_1$-$C_6$) alkyl; —$SO_3H$, —$SO_2NHR^{15}$ in which $R^{15}$ is hydrogen or ($C_1$-$C_6$) alkyl, or

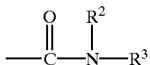

in which $R^2$ and $R^3$ are each independently hydrogen or ($C_1$-$C_6$) alkyl;

(3) heterocyclic selected from oxadiazolyl, isoxazolyl, oxazolyl, furyl and thiazolyl;

(4) heterocyclic substituted by one or more of, preferably 1–3, phenyl, phenyl substituted by 1–3 halo, ($C_1$-$C_6$)alkoxy, ($C_1$-$C_6$)alkyl, nitro, cyano, hydroxy, trifluoromethyl, ($C_1$-$C_6$) alkylthio, amino, ($C_1$-$C_6$) alkylamino, di($C_1$-$C_6$) alkylamino, $CO_2H$, —COO—($C_1$-$C_6$) alkyl, —$SO_3H$, $SO_2NHR^{15}$ in which $R^{15}$ is hydrogen or ($C_1$-$C_6$) alkyl, or

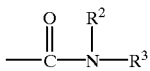

in which $R^2$ and $R^3$ are as defined above, ($C_1$-$C_6$) alkyl or ($C_1$-$C_6$) alkyl substituted by one or more, preferably 1–3, phenyl or heterocyclic groups, said phenyl or heterocyclic group being unsubstituted or substituted by 1–3 halo, 1–3 ($C_1$-$C_6$) alkoxy, 1–3 ($C_1$-$C_6$) alkyl, nitro, cyano, hydroxy, trifluoromethyl, ($C_1$-$C_6$) alkylthio, amino, 1–3 ($C_1$-$C_6$) alkylamino, di($C_1$-$C_6$) alkylamino, COOH, —COO—($C_1$-$C_6$) alkyl, —$SO_3H$, —$SO_2NHR^{15}$ in which $R^{15}$ is hydrogen or ($C_1$-$C_6$) alkyl, or

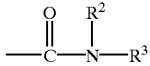

in which $R^2$ and $R^3$ are each independently hydrogen or ($C_1$-$C_6$) alkyl, the heterocyclic radical being selected from imidazolyl, oxadiazolyl, isoxazolyl, pyrrolyl, pyrazolyl, oxazolyl, furyl, thianyl or thiazolyl;

(5) carboxy or —COO—($C_1$-$C_6$) alkyl;

(6) hydroxy, halo, —O—($C_1$-$C_6$) alkyl or —S($C_1$-$C_6$) alkyl, with the proviso that the OH, ethers or thioethers cannot be on the carbon bearing the heteroatoms;

(7) cyano;

(8) halogen, trifluoromethyl or trifluoroacetyl; or (9) $CH_2$ L—$R^{16}$ in which L is

-continued

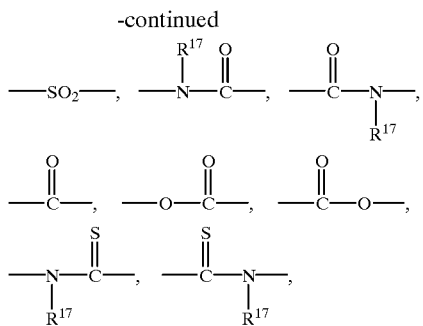

or —O—SiR$^{16}$R$^{18}$R$^{19}$ or a bond in which R$^{16}$ and R$^{17}$ are each independently (C$_1$–C$_{18}$)alkyl or (C$_2$–C$_{18}$)alkenyl or (C$_1$–C$_{18}$)alkyl or (C$_2$–C$_{18}$) alkenyl substituted by one or more, preferably 1–3, phenyl or heterocyclic radicals, said phenyl or heterocyclic radicals being unsubstituted or substituted by 1–5 fluoro, 1–3 halo (other than fluoro), 1–3 (C$_1$–C$_6$)alkoxy, 1–3(C$_1$–C$_6$)alkyl, nitro, cyano, hydroxy, 1–3 trifluoromethyl, 1–3 (C$_1$–C$_6$)alkylthio, amino, 1–3(C$_1$–C$_6$)alkylamino 1–3 di(C$_1$–C$_6$)alkylamino, CO$_2$H, 1–3 —COO (C$_1$–C$_6$)alkyl,

or —SO$_2$NHR$^9$ in which R$^9$ is hydrogen or (C$_1$–C$_6$)alkyl and R$^2$ and R$^3$ are as defined above; and R$^{18}$ and R$^{19}$ are phenyl or phenyl substituted by 1–3 halo, (C$_1$–C$_6$) alkoxy, (C$_1$–C$_6$) alkyl, nitro, cyano, hydroxy, trifluoromethyl, (C$_1$–C$_6$) alkylthio, amino, (C$_1$–C$_6$) alkylamino, di(C$_1$–C$_6$) alkylamino, CO$_2$H, —COO—(C$_1$–C$_6$) alkyl, —SO$_3$H, SO$_2$NHR$^{15}$ in which R$^{15}$ is hydrogen or (C$_1$–C$_6$) alkyl, or

in which R$^2$ and R$^3$ are as defined above; or pharmaceutically acceptable salts, solvates or prodrugs thereof.

(b)

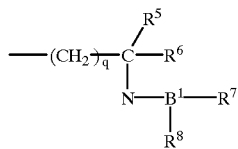

in which B$^1$ is

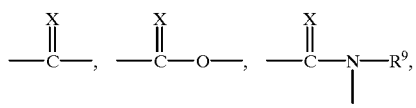

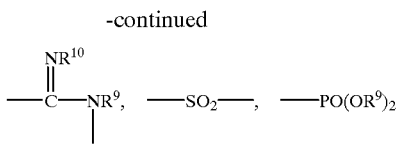

or a bond; providing that when B$^1$ is —PO(OR$^9$)$_2$, then R$^7$ becomes R$^9$, and when

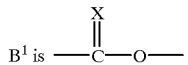

or —SO$_2$—, then R$^7$ cannot be hydrogen; and

X, q, R$^5$, R$^6$, R$^7$, R$^8$, R$^9$ and R$^{10}$ are as defined above in (a);

(c)

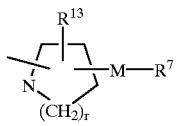

in which R$^{13}$ is (C$_1$–C$_{18}$)alkyl or (C$_1$–C$_{18}$)alkyl substituted by carboxy,

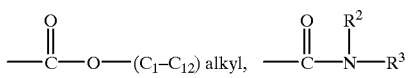

in which R$^2$ and R$^3$ are as defined above, hydroxy, —O—(C$_1$–C$_6$) alkyl, —O—(C$_1$–C$_6$) alkyl or —S—(C$_1$–C$_6$) alkyl substituted by 1 or 2 phenyl or substituted phenyl groups, the substituents for the substituted phenyl groups being 1–5 fluoro or 1–3 halo (other than fluoro), (C$_1$–C$_6$) alkoxy, (C$_1$–C$_6$) alkyl, nitro, cyano, hydroxy, trifluoromethyl, (C$_1$–C$_6$) alkylthio, amino, (C$_1$–C$_6$) alkylamino, di(C$_1$–C$_6$) alkylamino, CO$_2$H, COO—(C$_1$–C$_6$) alkyl, SO$_3$H, SO$_2$NHR$^{15}$ in which R$^{15}$ is hydrogen or (C$_1$–C$_6$) alkyl

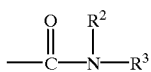

in which R$^2$ and R$^3$ are as defined above;

r is 0 or an integer of from 1 to 3;

R$^7$ is as defined above;

M is —(CH$_2$—)$_m$T where

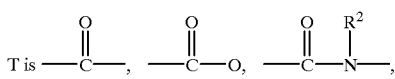

in which R$^2$ is as defined above, —SO$_2$— or a bond when MR$^7$ is on nitrogen and providing that when T is 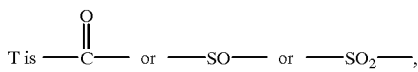

then $R^7$ cannot be hydrogen, and

T is 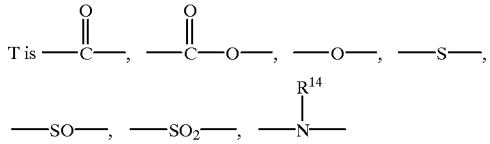

or a bond when $MR^7$ is on a carbon atom of the heterocyclic ring;
$R^{14}$ is hydrogen or $(C_1-C_6)$alkyl;
m is 0 or an integer of 1–6;

(d)

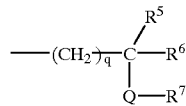

wherein Q is —O—, —S—, —SO—, or —SO$_2$— and q, $R^5$, $R^6$ and $R^7$ are as defined above, providing that when Q is —SO— or —SO$_2$—, $R^7$ cannot be hydrogen; or (e) $R^7$ where $R^7$ is as defined above, providing that when Y is —SO— or —SO$_2$—, $R^7$ cannot be hydrogen and providing that when Y is O, $R^7$ cannot be $(C_1-C_{18})$ alkyl; or a pharmaceutically acceptable salt, solvate or prodrug thereof.

Another preferred embodiment comprises a compound of the formula

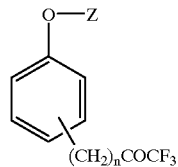

wherein n is 0 or an integer of from 1 to 6, the substituent —$(CH_2)_n COCF_3$ is in the meta or para position of the phenyl ring and Z is

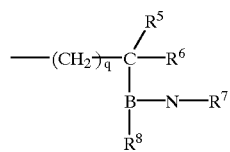

in which B is

or a bond; X is S or O; q is an integer of from 1 to 6; and $R^5$, $R^6$, $R^7$ and $R^8$ are as defined above; or a pharmaceutically acceptable salt, hydrate or prodrug thereof.

Another preferred embodiment comprises a compound of the formula

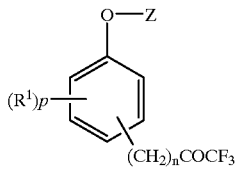

in which $R^1$ is benzyl; p is 0, 1 or 2; n is 0 or an integer of from 1 to 6; the substituent —$(CH_2)_n COCF_3$ is in the meta or para position of the phenyl ring; and Z is

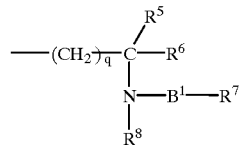

in which $B^1$ is

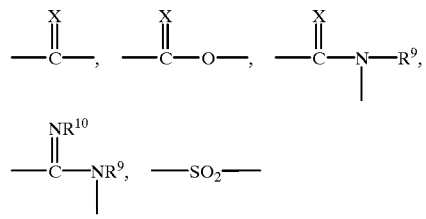

or a bond;
q is an integer of from 1 to 6;
X is S or O;
and $R^5$, $R^6$, $R^7$, $R^8$, $R^9$ and $R^{10}$ are as defined above; or a pharmaceutically acceptable salt, solvate or prodrug thereof. Within this embodiment, it is preferred that the substituent —$(CH_2)_n COCF_3$ is in the para position of the phenyl ring, $R^5$ and $R^6$ are both hydrogen, q is 1,2 or 3, n is 2 or 3, $B^1$ is

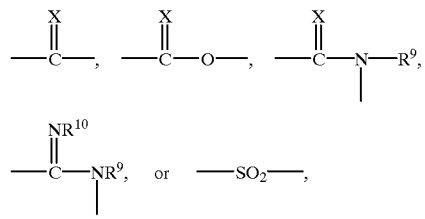

and $R^7$ and $R^8$ are each independently hydrogen or $(C_1-C_{18})$ alkyl. Especially preferred are compounds where q is 1, n is 2 and

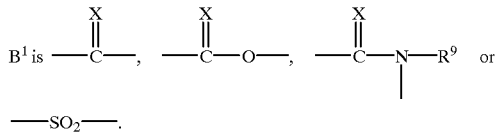

Another preferred embodiment comprises a compound of the formula

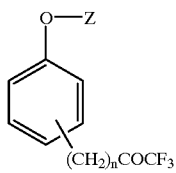

wherein n is 0 or an integer of from 1 to 6; the substituent —(CH$_2$)$_n$COCF$_3$ is in the meta or para position of the phenyl ring; and Z is

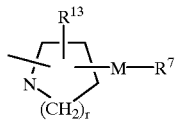

in which R$^{13}$, r, M and R$^7$ are as defined above, or a pharmaceutically acceptable salt, solvate or prodrug thereof.

Another preferred embodiment comprises a compound of the formula

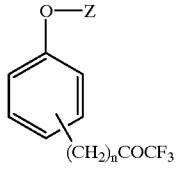

which n is 0 or an integer of from 1 to 6, the substituent —(CH$_2$)$_n$COCF$_3$ is in the meta or para position of the phenyl ring; and Z is

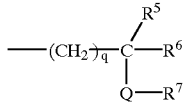

wherein q is an integer of from 1 to 6; R$^5$ and R$^6$ are each independently hydrogen or (C$_1$–C$_{18}$)alkyl; and Q and R$^7$ are as defined above, or a pharmaceutically acceptable salt, solvate or prodrug thereof.

Another preferred embodiment comprises a compound of the formula

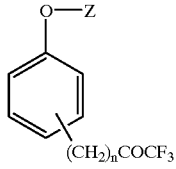

in which n is 0 or an integer of from 1 to 6; the substituent —(CH$_2$)$_n$COCF$_3$ is in the meta or para position of the phenyl ring; and Z is
(a) hydrogen;
(b) (C$_1$–C$_{18}$)alkyl substituted by one or more, preferably 1–3, of
  (1) phenyl;
  (2) phenyl substituted by 1–5 fluoro, 1–3 halo (other than fluoro), 1–3(C$_1$–C$_6$)alkoxy, 1–3(C$_1$–C$_6$)alkyl, nitro, cyano, hydroxy, trifluoromethyl, (C$_1$–C$_6$) alkylthio, amino, 1–3 (C$_1$–C$_6$) alkylamino, di(C$_1$–C$_6$)alkylamino, —CO$_2$H, —COO—(C$_1$–C$_6$) alkyl, —SO$_3$H, —SO$_2$NHR$^{15}$ in which R$^{15}$ is hydrogen or (C$_1$–C$_6$)alkyl, or

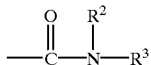

in which R$^2$ and R$^3$ are each independently hydrogen or (C$_1$–C$_6$) alkyl;
(3) heterocyclic selected from oxadiazolyl, isoxazolyl, oxazolyl, furyl and thiazolyl;
(4) heterocyclic substituted by one or more, preferably 1–3, of phenyl, phenyl substituted by 1–3 halo, (C$_1$–C$_6$)alkoxy, (C$_1$–C$_6$)alkyl, nitro, cyano, hydroxy, trifluoromethyl, (C$_1$–C$_6$) alkylthio, amino, (C$_1$–C$_6$) alkylamino, di(C$_1$–C$_6$) alkylamino, CO$_2$H, —COO—(C$_1$–C$_6$) alkyl, —SO$_3$H, SO$_2$NHR$^{15}$ in which R$^{15}$ is hydrogen or (C$_1$–C$_6$) alkyl, or

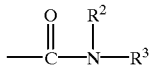

in which R$^2$ and R$^3$ are as defined above, (C$_1$–C$_6$) alkyl or (C$_1$–C$_6$) alkyl substituted by one or more, preferably 1–3, phenyl or heterocyclic groups, said phenyl or heterocyclic group being unsubstituted or substituted by 1–3 halo, 1–3 (C$_1$–C$_6$) alkoxy, 1–3 (C$_1$–C$_6$) alkyl, nitro, cyano, hydroxy, trifluoromethyl, (C$_1$–C$_6$) alkylthio, amino, 1–3 (C$_1$–C$_6$) alkylamino, di(C$_1$–C$_6$) alkylamino, COOH, —COO—(C$_1$–C$_6$) alkyl, —SO$_3$H, —SO$_2$NHR$^{15}$ in which R$^{15}$ is hydrogen or (C$_1$–C$_6$) alkyl, or

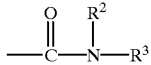

in which R$^2$ and R$^3$ are each independently hydrogen or (C$_1$–C$_6$) alkyl, the heterocyclic radical being selected from imidazolyl, oxadiazolyl, isoxazolyl, pyrrolyl, pyrazolyl, oxazolyl, furyl, thianyl or thiazolyl;
(5) carboxy or —COO—(C$_1$–C$_6$) alkyl;
(6) hydroxy, halo, —O—(C$_1$–C$_6$) alkyl or —S—(C$_1$–C$_6$) alkyl, with the proviso that the OH, ethers or thioethers cannot be on the carbon bearing the heteroatoms;
(7) cyano;
(8) halogen, trifluoromethyl or trifluoroacetyl;
(9) CH$_2$ L—R$^{16}$ in which L is

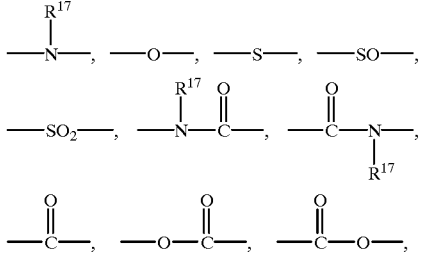

-continued

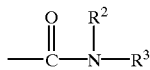

or —O—SiR$^{16}$R$^{18}$R$^{19}$ or a bond in which R$^{16}$ and R$^{17}$ are each independently (C$_1$–C$_{18}$)alkyl or (C$_2$–C$_{18}$)alkenyl or (C$_1$–C$_{18}$)alkyl or (C$_2$–C$_{18}$) alkenyl substituted by one or more, preferably 1–3, phenyl or heterocyclic radicals, said phenyl or heterocyclic radicals being unsubstituted or substituted by 1–5 fluoro, 1–3 halo (other than fluoro), 1–3 (C$_1$–C$_6$)alkoxy, 1–3(C$_1$–C$_6$)alkyl, nitro, cyano, hydroxy, 1–3 trifluoromethyl, 1–3 (C$_1$–C$_6$)alkylthio, amino, 1–3(C$_1$–C$_6$)alkylamino, 1–3 di(C$_1$–C$_6$) alkylamino, CO$_2$H, 1–3 —COO(C$_1$–C$_6$)alkyl,

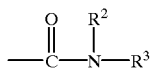

or —SO$_2$NHR$^9$ in which R$^9$ is hydrogen or (C$_1$–C$_6$) alkyl and R$^2$ and R$^3$ are as defined above; and R$^{18}$ and R$^{19}$ are phenyl or phenyl substituted by 1–3 halo, (C$_1$–C$_6$) alkoxy, (C$_1$–C$_6$) alkyl, nitro, cyano, hydroxy, trifluoromethyl, (C$_1$–C$_6$) alkylthio, amino, (C$_1$–C$_6$) alkylamino, di(C$_1$–C$_6$) alkylamino, CO$_2$H, —COO—(C$_1$–C$_6$) alkyl, —SO$_3$H, SO$_2$NHR$^{15}$ in which R$^{15}$ is hydrogen or (C$_1$–C$_6$) alkyl, or

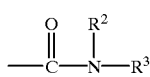

in which R$^2$ and R$^3$ are as defined above; or pharmaceutically acceptable salts, solvates or prodrugs thereof.

A most preferred embodiment of the present invention comprises a compound of the formula

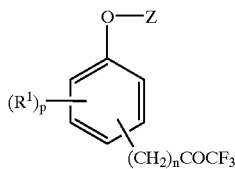

wherein R$^1$ is (C$_1$–C$_6$)alkyl, (C$_2$–C$_6$)alkenyl, (C$_2$–C$_6$) alkynyl, (C$_1$–C$_6$)alkoxy, (C$_1$–C$_6$)alkylthio, halo, hydroxy, cyano,

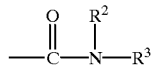

in which R$^2$ and R$^3$ are each independently hydrogen or (C$_1$–C$_6$)alkyl, —COO—(C$_1$–C$_6$)alkyl, CF$_3$, (C$_1$–C$_6$) alkylphenyl, phenyl or phenyl substituted by one or more, preferably 1—3, of (C$_1$–C$_6$)alkyl, —COO—(C$_1$–C$_6$)alkyl,

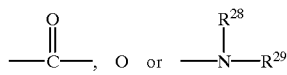

in which R$^2$ and R$^3$ are as defined above, halo, hydroxy, —O—(C$_1$–C$_6$)alkyl, —S— (C$_1$–C$_6$)alkyl or (C$_2$–C$_6$) alkenyl;

p is 0, 1 or 2;

n is 0 or an integer of from 1–6; and

Z is (C$_1$–C$_{18}$)alkyl, (C$_2$–C$_{18}$)alkenyl or (C$_2$–C$_{18}$)alkynyl in which one or more carbon atoms in such alkyl, alkenyl or alkynyl group is optionally replaced by S, SO, SO$_2$,

in which R$^{28}$ and R$^{29}$ are each independently hydrogen, —COCF$_3$, —CO-phenyl, —COO—(C$_1$–C$_6$)alkyl,

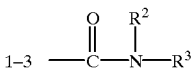

in which R$^2$ and R$^3$ are each independently hydrogen or (C$_1$–C$_6$)alkyl, (C$_1$–C$_{18}$)alkyl or (C$_1$–C$_{18}$)alkyl substituted by one or more of phenyl or phenyl substituted by 1–5 fluoro, 1–3 halo (other than fluoro), 1–3 (C$_1$–C$_6$)alkoxy, 1–3 (C$_1$–C$_6$)alkyl, 1–3 nitro, 1–3 cyano, 1–3 hydroxy, 1–3 trifluoromethyl, 1–3 (C$_1$–C$_6$)alkylthio, 1–3 amino, 1–3 (C$_1$–C$_6$) alkylamino, 1–3 di (C$_1$–C$_6$)alkylamino, 1–3 carboxyl, 1–3 —COO—(C$_1$–C$_6$)alkyl, 1–3 —SO$_3$H, 1–3 —SO$_2$NHR$^{15}$ in which R$^{15}$ is hydrogen or (C$_1$–C$_6$)alkyl, or 1–3 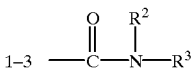

in which R$^2$ and R$^3$ are each independently hydrogen or (C$_1$–C$_6$)alkyl; providing that when Y' is O, Z cannot be (C$_1$–C$_{18}$)alkyl; or a pharmaceutically acceptable salt or prodrug thereof.

Within the above-mentioned most preferred embodiment, the most preferred compounds of the present invention are those in which Z is (a)

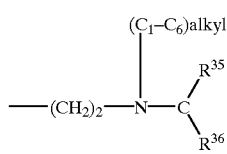

in which R$^{35}$ and R$^{36}$ are phenyl or phenyl substituted by 1–5 fluoro, 1–3 halo (other than fluoro), 1–3 (C$_1$–C$_6$)alkoxy, 1–3 (C$_1$–C$_6$)alkyl, 1–3 nitro, 1–3 cyano, 1–3 hydroxy, 1–3 trifluoromethyl, 1–3 (C$_1$–C$_6$)alkylthio, 1–3 amino, 1–3 (C$_1$–C$_6$)alkylamino, 1–3 di (C$_1$–C$_6$)alkylamino, 1–3 carboxyl, 1–3 —COO—($C_1$–$C_6$)alkyl, 1–3 —$SO_3H$, 1–3 —$SO_2NHR^{15}$ in which $R^{15}$ is hydrogen or ($C_1$–$C_6$)alkyl, or

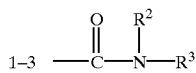

in which $R^2$ and $R^3$ are each independently hydrogen or ($C_1$–$C_6$)alkyl;

(b)

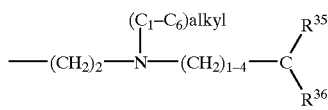

which $R^{35}$ and $R^{36}$ are as defined above;

(c)

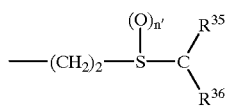

in which n' is 0, 1 or 2 and $R^{35}$ and $R^{36}$ are as defined above;

(d)

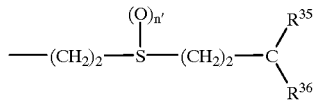

in which n', $R^{35}$ and $R^{36}$ are as defined above; or pharmaceutically acceptable salts and/or prodrugs thereof.

Another preferred embodiment comprises a compound of the formula

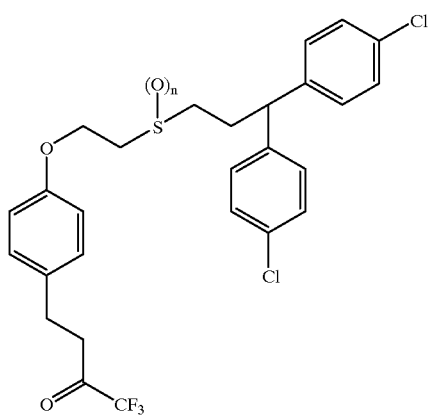

in which n is 0, 1 or 2; or a pharmaceutically acceptable salt or prodrug thereof.

Preferred embodiments comprise a compound selected from those of the following

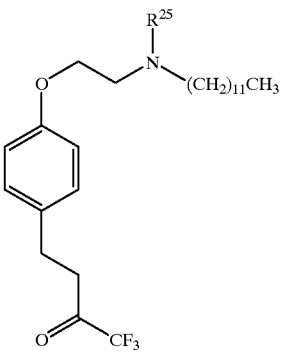

wherein
(a) $R^{25}$ is —$(CH_2)_3CH_3$;
(b) $R^{25}$ is —$(CH_2)_3CO_2C_2H_5$;
(c) $R^{25}$ is —$(CH_2)_3CONHC_2H_5$;
(d) $R^{25}$ is —$COCF_3$;
(e) $R^{25}$ is —$COC_6H_5$; and
(f) $R^{25}$ is —$PO(OC_2H_5)_2$; or a pharmaceutically acceptable salt thereof.

Still other preferred embodiments comprise a compound of the formula

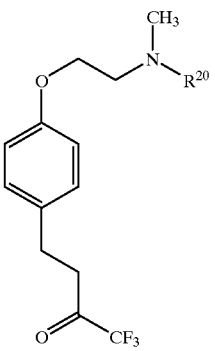

wherein
(a) $R^{20}$ is —$CO(CH_2)_{10}CH_3$;
(b) $R^{20}$ is —COCH(p-chlorophenyl)$_2$; and
(c) $R^{20}$ is —$SO_2(CH_2)_{11}CH_3$; or a pharmaceutically acceptable salt thereof.

Still other preferred embodiments comprise a compound selected from those of the following

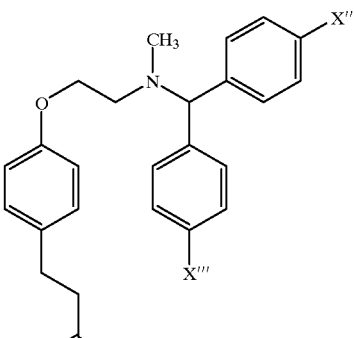

wherein (a) X" and X'" are Cl;

(b) X" and X'" are F;

(c) X" and X'" are OCH$_3$; and (c) X" is Cl and X'" is OCH$_3$; or a pharmaceutically acceptable salt thereof.

Another preferred embodiment comprises a compound of the formula

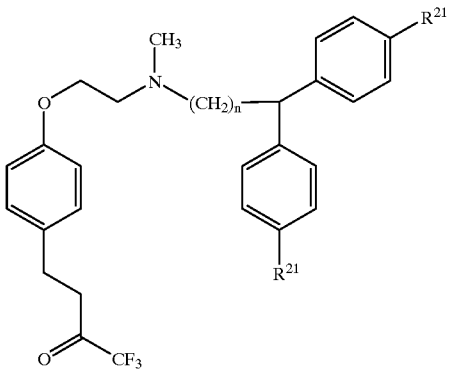

wherein (a) n is 1 and R$^{21}$ is OCH$_3$;

(b) n is 1 and R$^{21}$ is Cl;

(c) n is 2 and R$^{21}$ is OCH$_3$; and (d) n is 1–4 and R$^{21}$ is OCH$_3$ or Cl; or a pharmaceutically acceptable salt thereof.

Another preferred embodiment comprises a compound of the formula

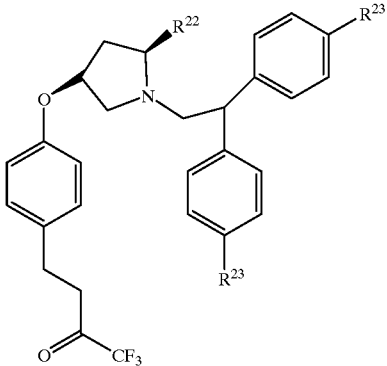

wherein (a) R$^{22}$ is hydrogen and R$^{23}$ is Cl; or (b) R$^{22}$ is —CO$_2$CH$_3$ and R$^{23}$ is —OCH$_3$; or a pharmaceutically acceptable salt thereof.

Another preferred embodiment comprises a compound of the formula

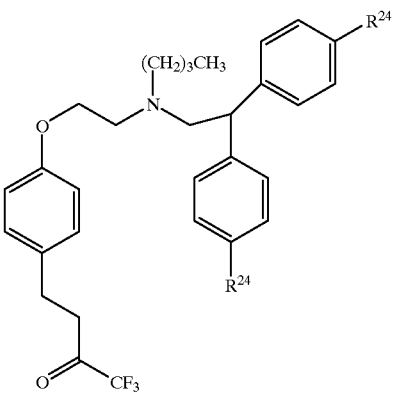

wherein R$^{24}$ is Cl or —OCH$_3$; or a pharmaceutically acceptable salt thereof.

Another preferred embodiment comprises a compound of the formula

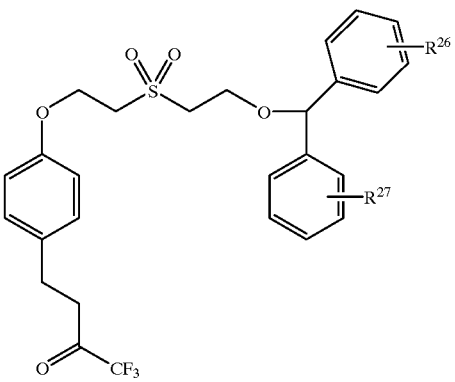

wherein (a) R$^{26}$ and R$^{27}$ are both CH$_3$ or (C$_1$–C$_6$)alkyl-CF$_3$;

(b) R$^{26}$ and R$^{27}$ are both Cl, F or Br;

(c) R$^{26}$ and R$^{27}$ are both OCH$_3$ or SCH$_3$;

(d) R$^{26}$ is Cl and R$^{27}$ is OCH$_3$; or (e) R$^{26}$ and R$^{27}$ are both —COO—(C$_1$–C$_6$)alkyl; or a pharmaceutically acceptable salt thereof.

Still other preferred embodiments comprise a compound selected from those of the following

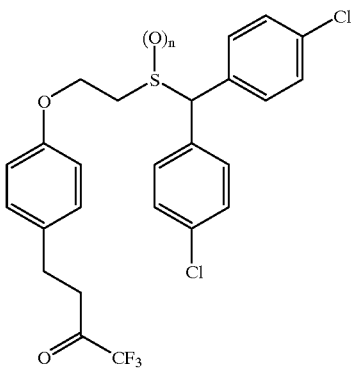
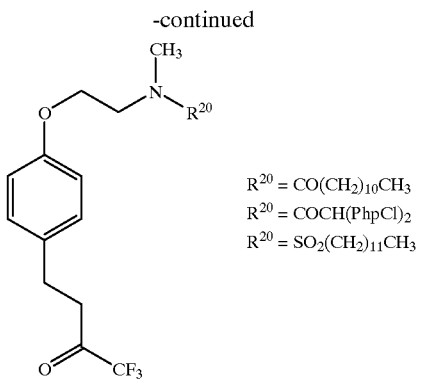
wherein
(a) n is 0;
(b) n=1; and
(c) n=2; or a pharmaceutically acceptable salt thereof.
Still other preferred embodiments comprise a compound selected from those of the formula
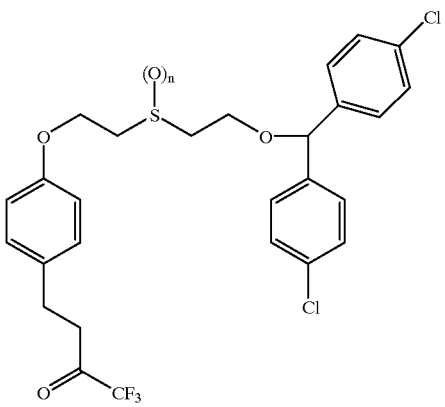
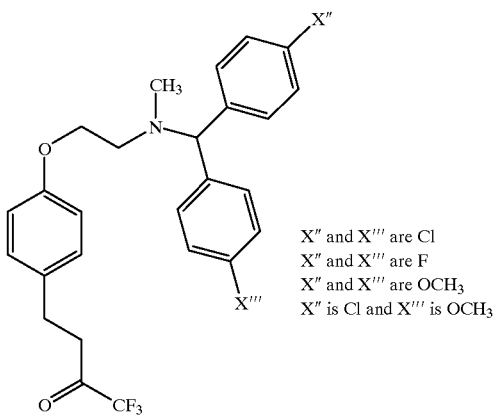
wherein
(a) n=0;
(b) n=1; and
(c) n=2; or a pharmaceutically acceptable salt thereof.
Some specific preferred embodiments of the present invention are:
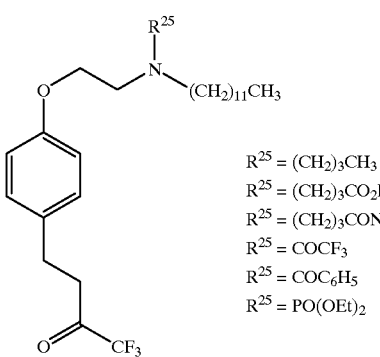
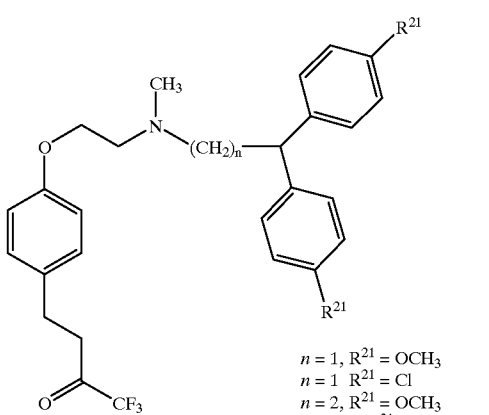

-continued
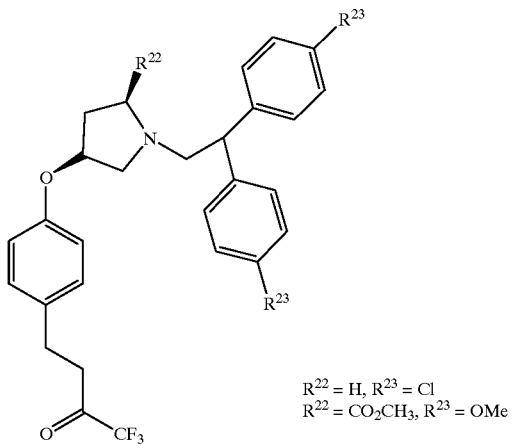
R²² = H, R²³ = Cl
R²² = CO₂CH₃, R²³ = OMe
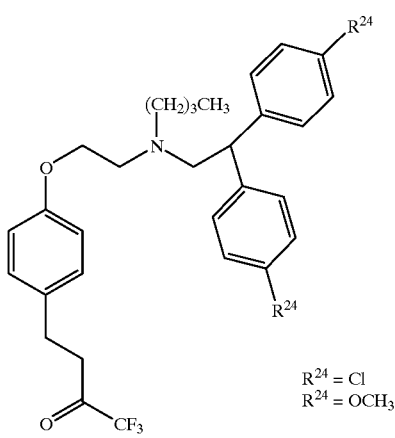
R²⁴ = Cl
R²⁴ = OCH₃
and
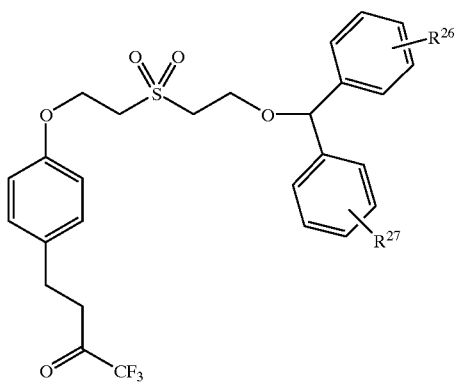
wherein
(a) $R^{26}$ and $R^{27}$ are both $CH_3$ or $-(C_1-C_6)$alkyl-$CF_3$;
(b) $R^{26}$ and $R^{27}$ are both Cl, F or Br;
(c) $R^{26}$ and $R^{27}$ are both $OCH_3$ or $SCH_3$;
(d) $R^{26}$ is Cl and $R^{27}$ is $OCH_3$; or
(e) $R^{26}$ and $R^{27}$ are both $-COO-(C_1-C_6)$alkyl.
Especially preferred embodiments of the present invention include:
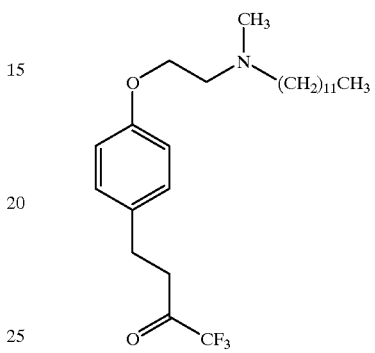
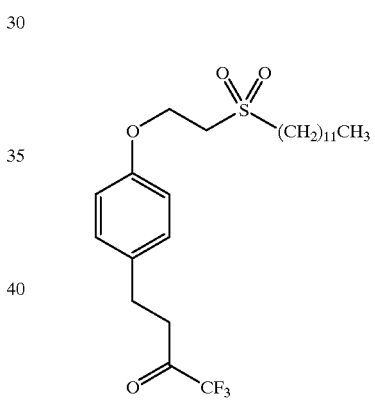
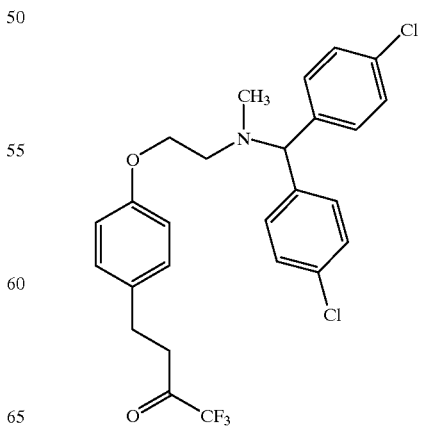

-continued

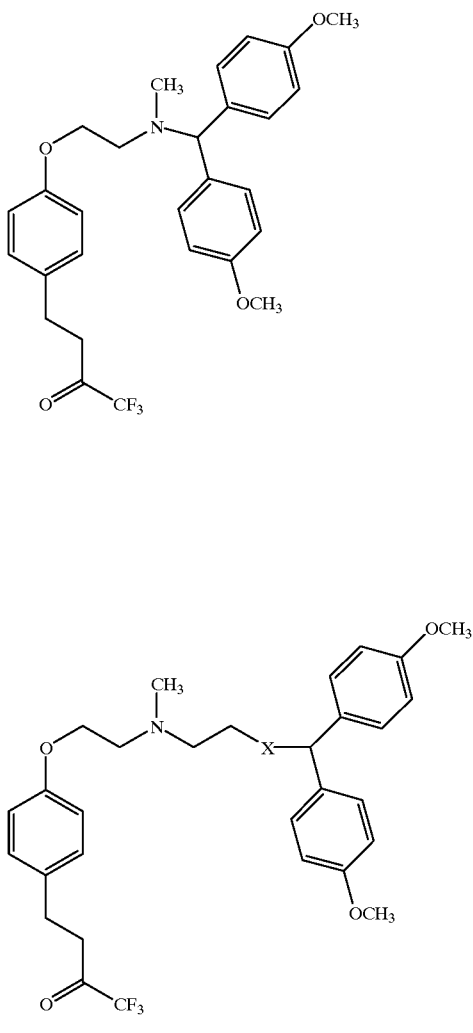

X = O
X = C

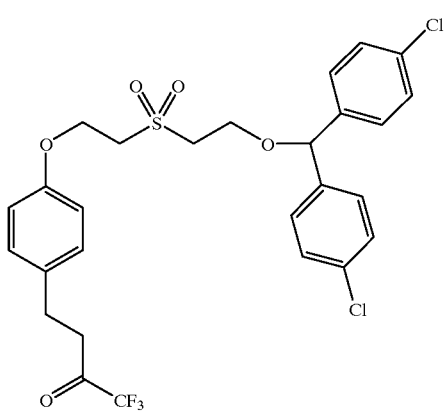

-continued

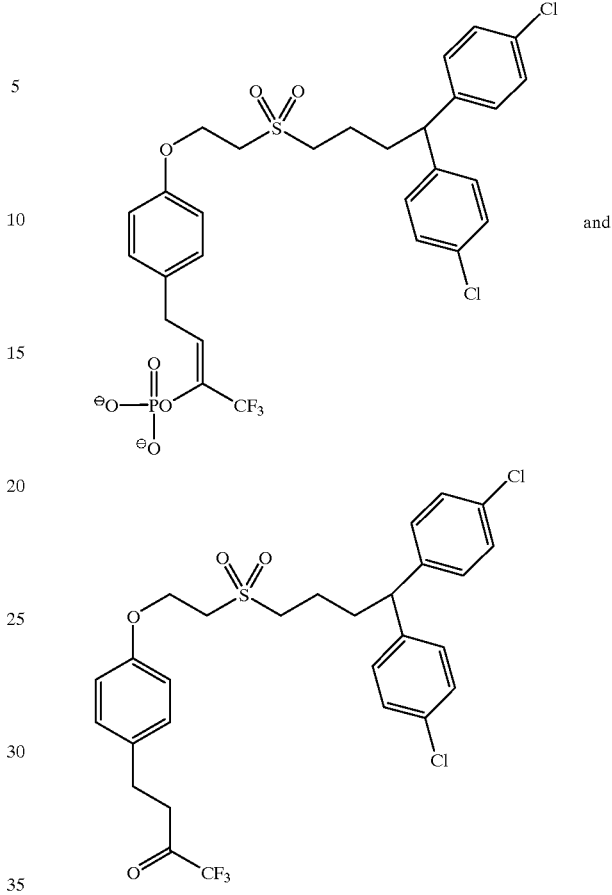

and

The present inventors have discovered that many of the compounds of general formula I, although exhibiting good in vitro potency, are metabolized in vivo resulting in a significant decrease in in vivo activity. However, if the "A" substituent of the formula I compounds is a group of the formula

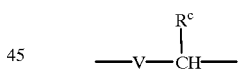

which V is O, S, SO, $SO_2$, —CONH— or —NHCO— and $R^c$ is hydrogen or $CH_3$, the metabolic stability of the compounds is surprisingly increased, resulting in good in vivo as well as in vitro potency.

In view of this discovery, the present invention in another aspect provides compounds of the general formula

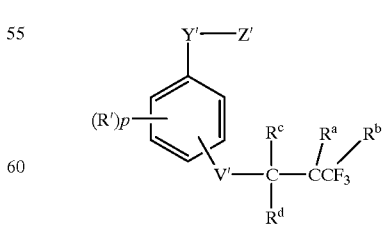

III in which R' is $(C_1-C_6)$alkyl, $(C_2-C_6)$alkenyl, $(C_2-C_6)$alkynyl, $(C_1-C_6)$alkoxy, $(C_1-C_6)$alkylthio, halo, hydroxy, cyano,

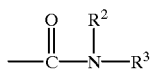

in which $R^2$ and $R^3$ are each independently hydrogen or $(C_1-C_6)$alkyl, —COO—$(C_1-C_6)$alkyl, $CF_3$, $(C_1-C_6)$alkylphenyl, phenyl or phenyl substituted by one or more of $(C_1-C_6)$alkyl, —COO—$(C_1-C_6)$alkyl,

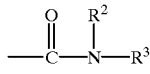

in which $R^2$ and $R^3$ are as defined above, halo, hydroxy, —O—$(C_1-C_6)$alkyl, —S—$(C_1-C_6)$alkyl or $(C_2-C_6)$alkenyl;

p is 0, 1 or 2;

V' is —O—, —S—, —SO—, —SO$_2$—, —NHCO— or —CONH—;

$R^c$ and $R^d$ are each independently hydrogen or methyl;

$R^a$ and $R^b$ when taken together form an oxo (=O) group, or $R^a$ and $R^b$ are each independently hydrogen or OH;

Y' is —O—, —S—, —SO—, —SO$_2$—,

or $CH_2$ in which $R^d$ is hydrogen, —COCF$_3$, —CO—C$_6$H$_5$, —COO—$(C_1-C_6)$alkyl,

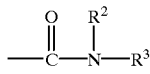

in which $R^2$ and $R^3$ are each independently hydrogen or $(C_1-C_6)$alkyl, $(C_1-C_{18})$alkyl or $(C_1-C_{18})$alkyl substituted by one or more of phenyl or phenyl substituted by 1–5 fluoro, 1–3 halo (other than fluoro), 1–3 $(C_1-C_6)$alkoxy, 1–3 $(C_1-C_6)$alkyl, 1–3 nitro, 1–3 cyano, 1–3 hydroxy, 1–3 trifluoromethyl, 1–3 $(C_1-C_6)$alkylthio, 1–3 amino, 1–3 $(C_1-C_6)$alkylamino, 1–3 di $(C_1-C_6)$alkylamino, 1–3 carboxyl, 1–3 —COO—$(C_1-C_6)$alkyl, 1–3 —SO$_3$H, 1–3 —SO$_2$NHR$^{15}$ in which $R^{15}$ is hydrogen or $(C_1-C_6)$alkyl, or

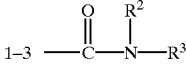

in which $R^2$ and $R^3$ are each independently hydrogen or $(C_1-C_6)$alkyl; and Z' is $(C_1-C_{18})$alkyl, $(C_2-C_{18})$alkenyl or $(C_2-C_{18})$alkynyl in which one or more carbon atoms in such alkyl, alkenyl or alkynyl group are optionally replaced by S, SO, SO$_2$,

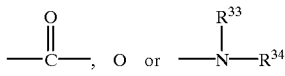

in which $R^{33}$ and $R^{34}$ are each independently hydrogen, —COCF$_3$, —CO—C$_6$H$_5$, —COO—$(C_1-C_6)$alkyl

in which $R^2$ and $R^3$ are each independently hydrogen or $(C_1-C_{18})$alkyl, $(C_1-C_{18})$alkyl, $(C_1-C_{18})$alkyl substituted by one or more of phenyl or phenyl substituted by 1–5 fluoro, 1–3 halo (other than fluoro), 1–3 $(C_1-C_6)$alkoxy, 1–3 $(C_1-C_6)$alkyl, 1–3 nitro, 1–3 cyano, 1–3 hydroxy, 1–3 trifluoromethyl, 1–3 $(C_1-C_6)$alkylthio, 1–3 amino, 1–3 $(C_1-C_6)$alkylamino, 1–3 di $(C_1-C_6)$alkylamino, 1–3 carboxyl, 1–3 —COO—$(C_1-C_6)$alkyl, 1–3 —SO$_3$H, 1–3 —SO$_2$NHR$^{15}$ in which $R^{15}$ is hydrogen or $(C_1-C_6)$ alkyl, or

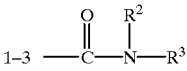

in which $R^2$ and $R^3$ are each independently hydrogen or $(C_1-C_6)$alkyl; or $(C_1-C_{18})$alkyl substituted at a terminal carbon atom by

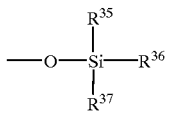

in which $R^{35}$, $R^{36}$ and $R^{37}$ are each independently $(C_1-C_6)$alkyl, aryl, aryl $(C_1-C_6)$alkyl, heterocyclic or heterocyclic $(C_1-C_6)$alkyl in which the aryl or heterocyclic rings may be optionally substituted by 1–3 halo, $(C_1-C_6)$alkoxy, $(C_1-C_6)$alkyl, nitro, cyano, hydroxy, trifluoromethyl, $(C_1-C_6)$alkylthio, amino, di $(C_1-C_6)$alkylamino, —CO$_2$H, —COO—$(C_1-C_6)$alkyl, —SO$_3$H, —SO$_2$NHR$^{15}$ in which $R^{15}$ is hydrogen or $(C_1-C_6)$alkyl or

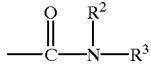

in which $R^2$ and $R^3$ are each independently hydrogen or $(C_1-C_6)$alkyl, providing that when Y' is O, Z' cannot be $(C_1-C_{18})$alkyl; or pharmaceutically acceptable salts and/or prodrugs thereof.

Within the compounds encompassed by general formula III, a preferred embodiment of the present invention comprises the compounds in which V' is in the p-position and Z' is

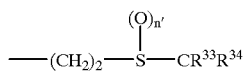

in which n' is 0, 1 or 2 and $R^{33}$ and $R^{34}$ are phenyl or phenyl substituted by 1–5 fluoro, 1–3 halo (other than fluoro), 1–3 ($C_1$–$C_6$)alkoxy, 1–3 ($C_1$–$C_6$)alkyl, 1–3 nitro, 1–3 cyano, 1–3 hydroxy, 1–3 trifluoromethyl, 1–3 ($C_1$–$C_6$)alkylthio, 1–3 amino, 1–3 ($C_1$–$C_6$)alkylamino, 1–3 di(alkylamino), 1–3 carboxy, 1–3 —COO—($C_1$–$C_6$)alkyl, 1–3 —$SO_3H$, 1–3 —$SO_2NHR^{15}$ in which $R^{15}$ is hydrogen or ($C_1$–$C_6$)alkyl, or

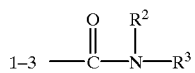

in which $R^2$ and $R^3$ are each independently hydrogen or ($C_1$–$C_6$)alkyl;

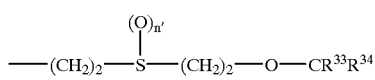

in which n' is 0, 1 or 2 and $R^{33}$ and $R^{34}$ are as defined above;

(c)

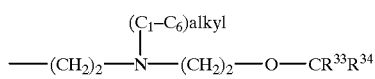

in which and $R^{33}$ and $R^{34}$ are as defined above;

(d) —$(CH_2)_2$—S—$(CH_2)_2$—$CR^{33}R^{34}$ in which and $R^{33}$ and $R^{34}$ are as defined above;

(e)

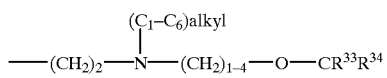

in which and $R^{33}$ and $R^{34}$ are as defined above; and (f)

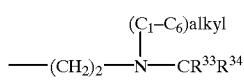

in which and $R^{33}$ and $R^{34}$ are as defined above, including pharmaceutically acceptable salts and prodrugs thereof.

Specific preferred embodiments of the present invention comprise the following compounds:

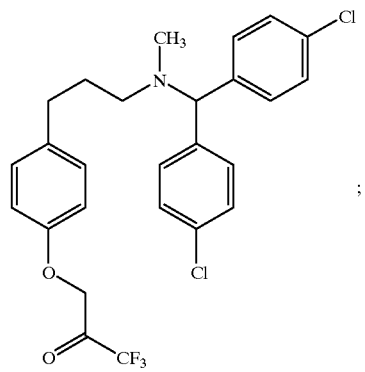

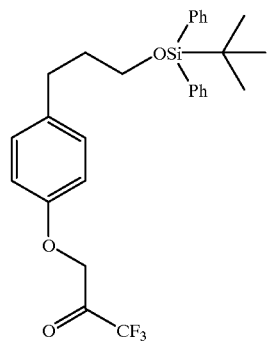

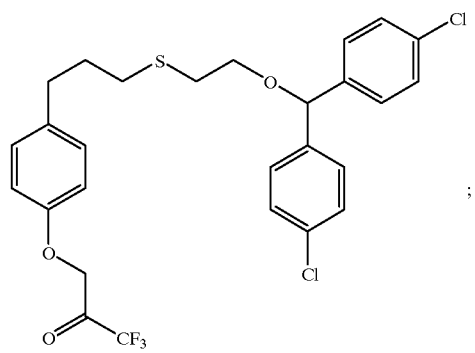

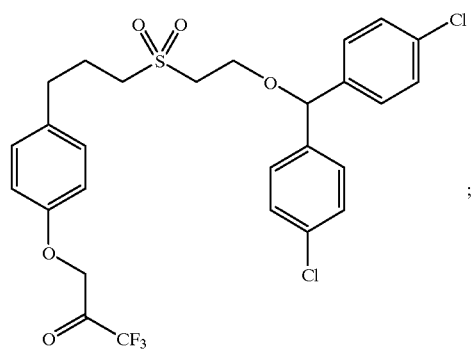

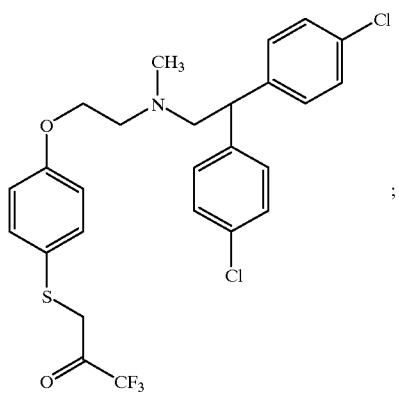
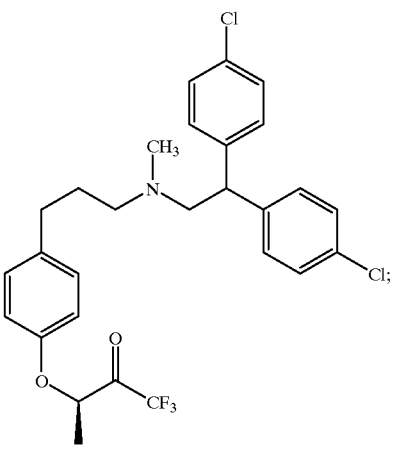
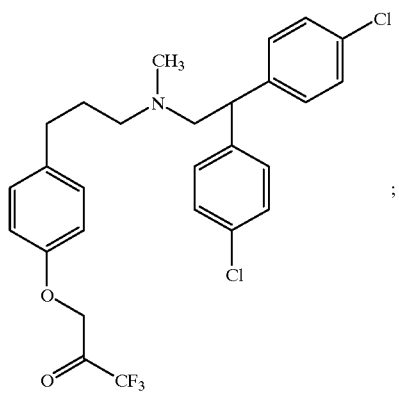
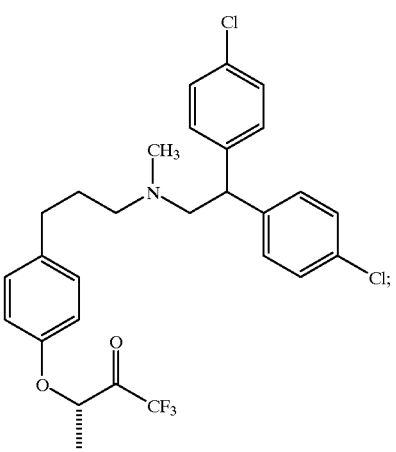
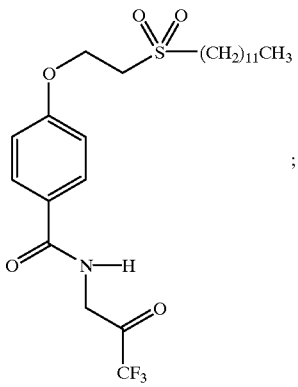
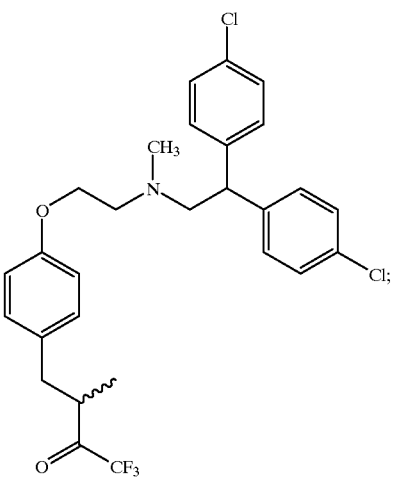
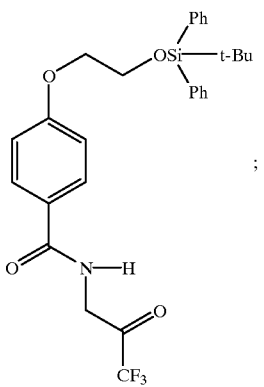

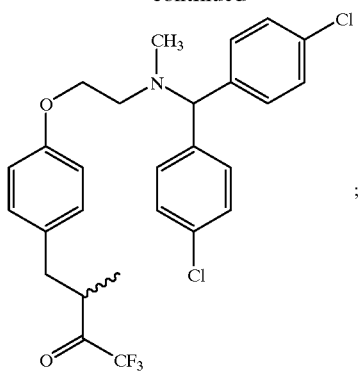
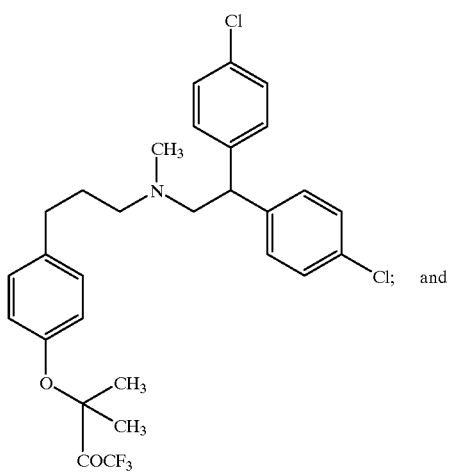
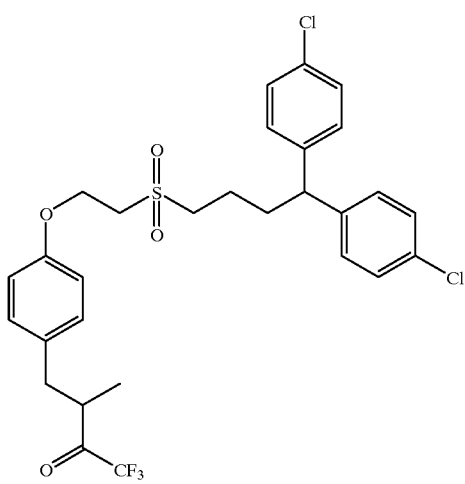
or a pharmaceutically acceptable salt or prodrug thereof.
The compounds of the present invention can be prepared by various methods which are known in the art. Illustrative methods of preparation are provided in the reaction schemes which follow and in the Examples.
Scheme 1
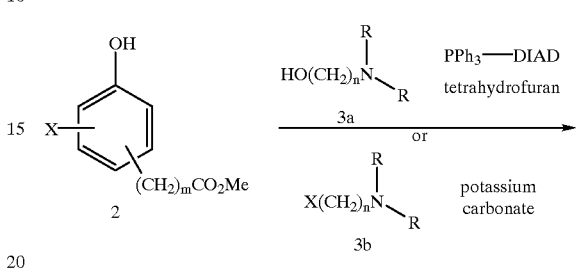
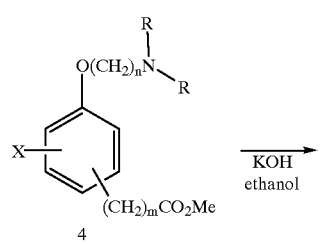
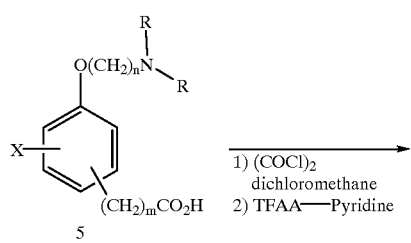
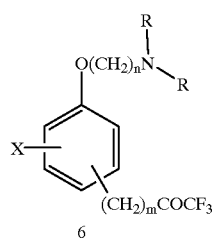

Scheme 2
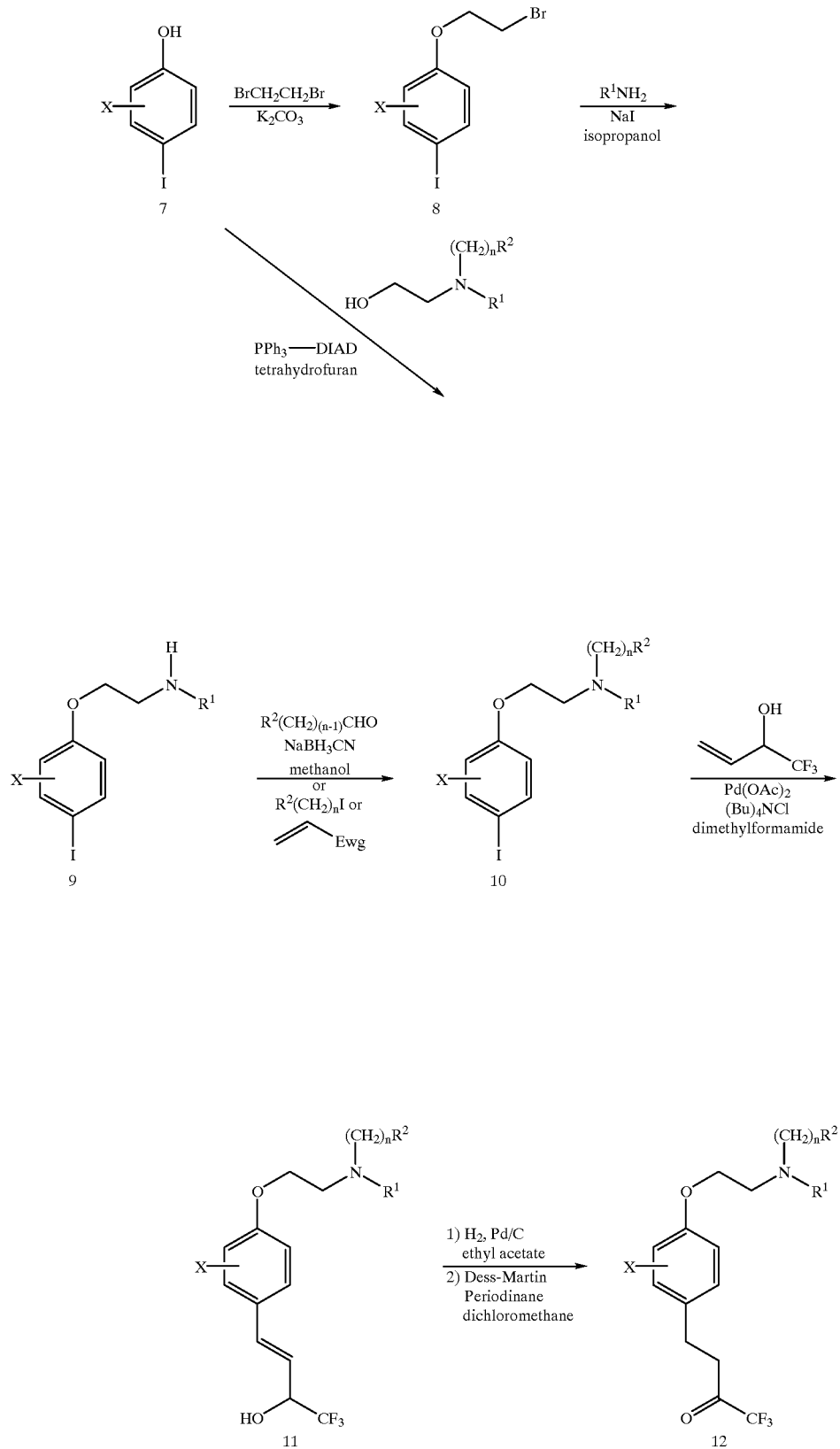

Scheme 3
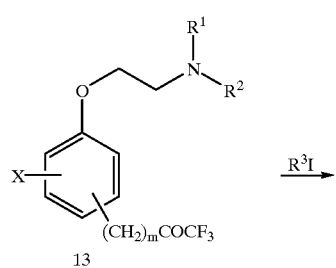
R³I →
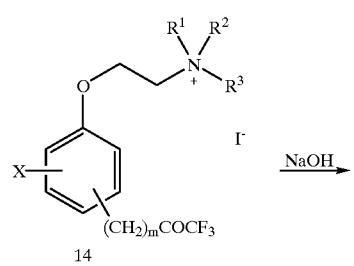
NaOH →
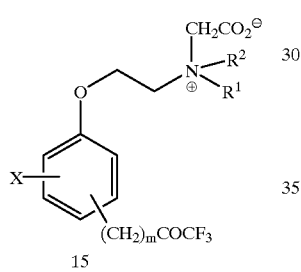
Scheme 4
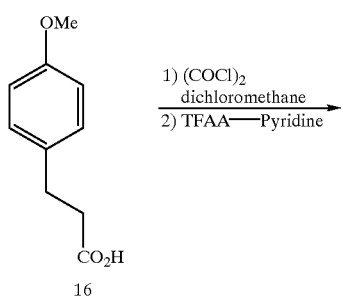
1) (COCl)₂ dichloromethane
2) TFAA—Pyridine →
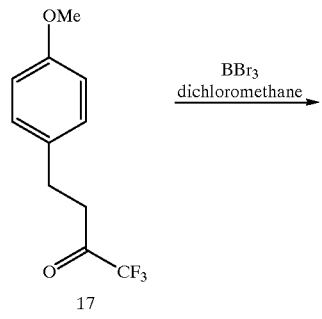
BBr₃ dichloromethane →
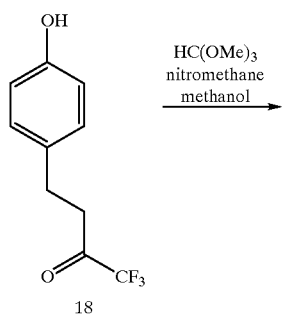
HC(OMe)₃ nitromethane methanol →
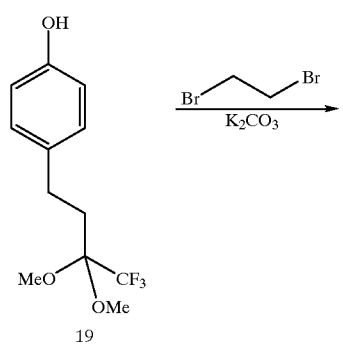
Br(CH₂)₂Br K₂CO₃ →
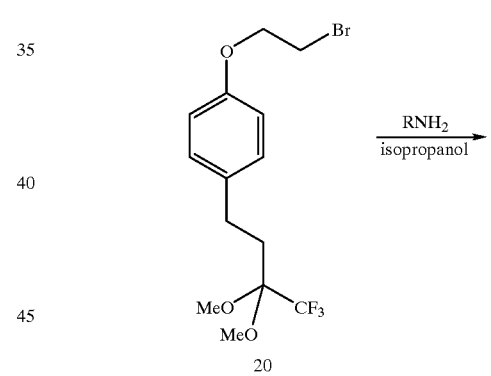
RNH₂ isopropanol →
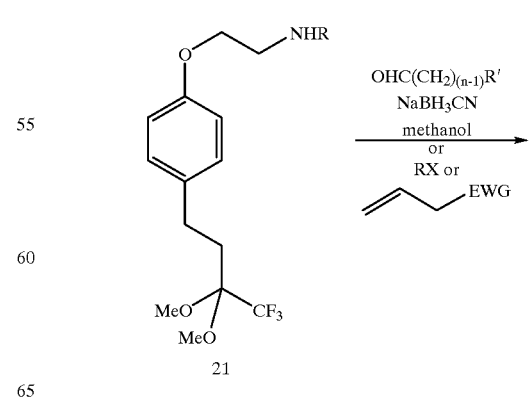
OHC(CH₂)₍ₙ₋₁₎R' NaBH₃CN methanol or RX or ⟶EWG

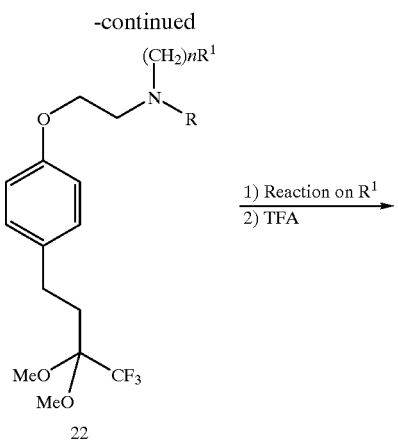
22
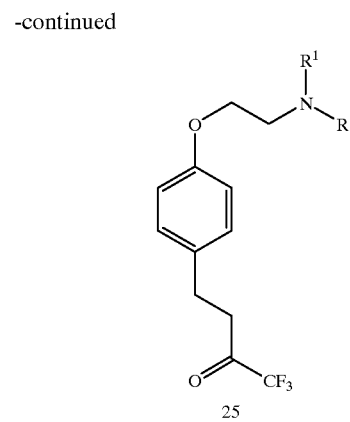
25
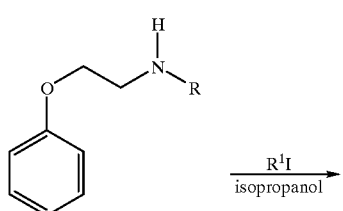
23
Scheme 5
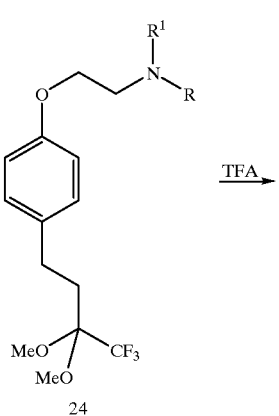
21
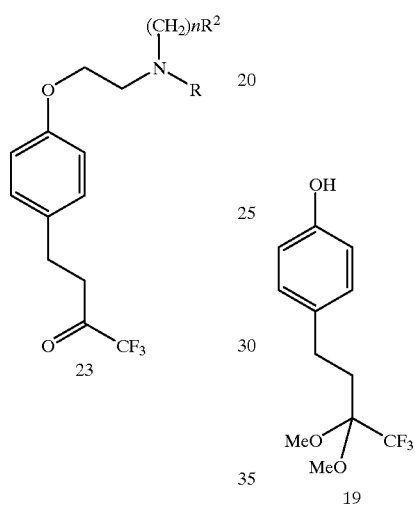
24
Scheme 6
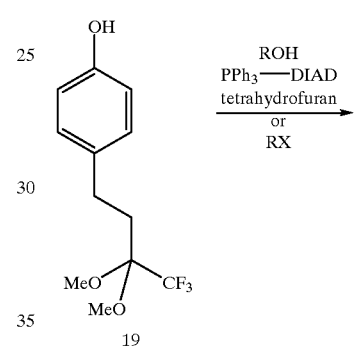
19
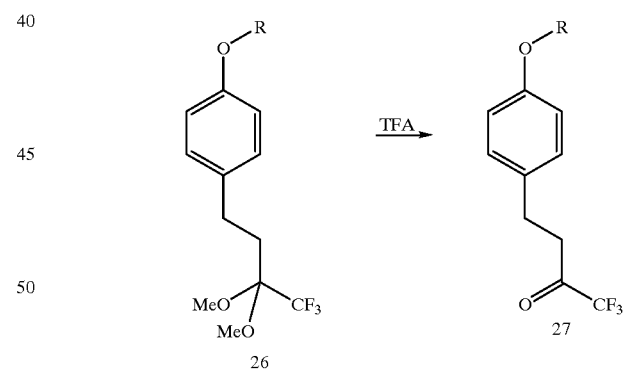
26  27
Scheme 7
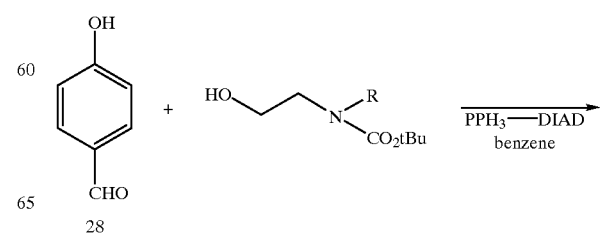
28

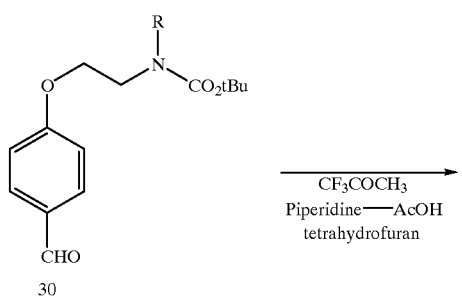
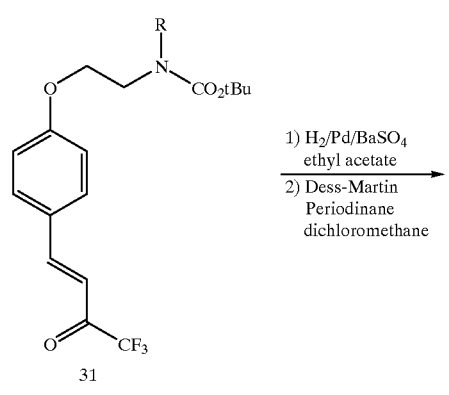
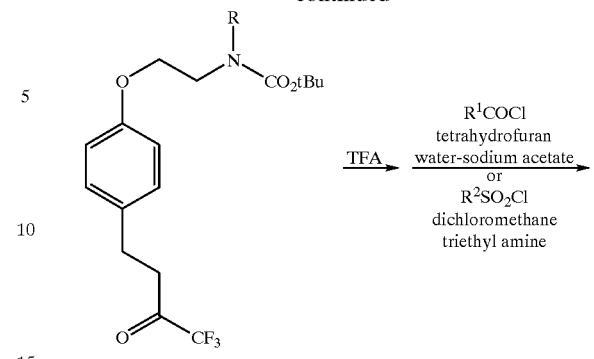
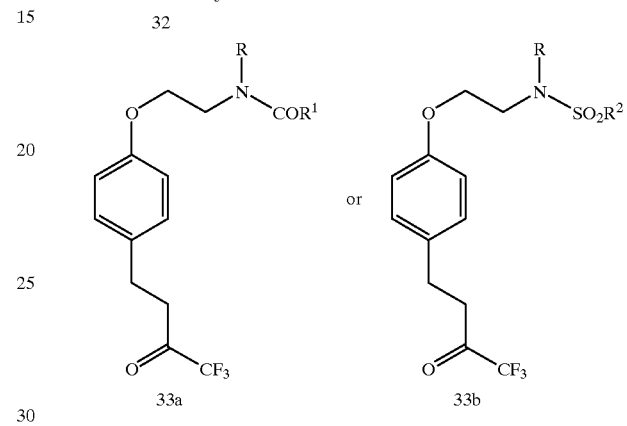
Scheme 8
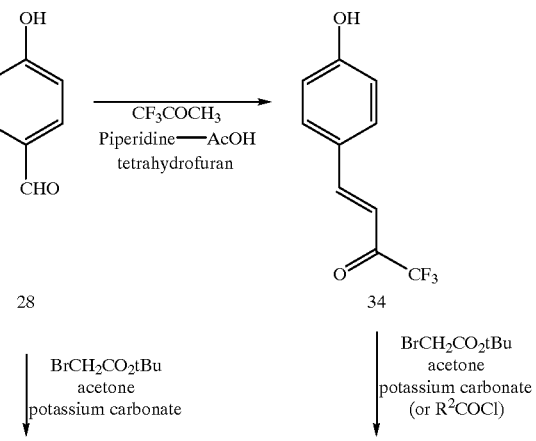

-continued
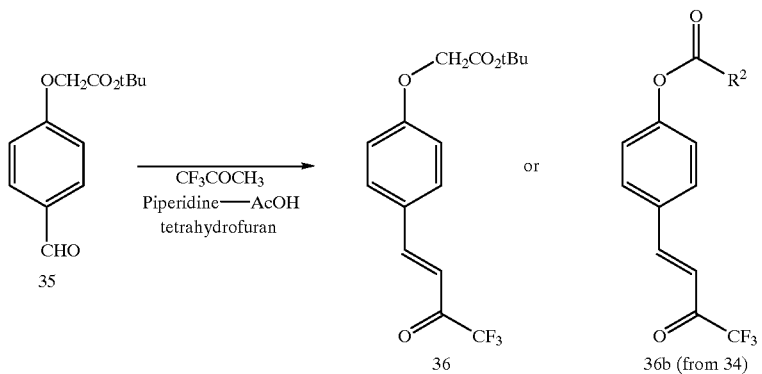
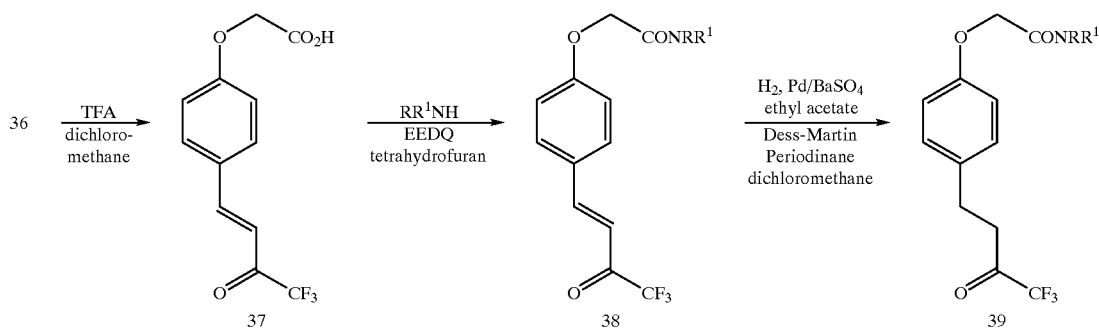
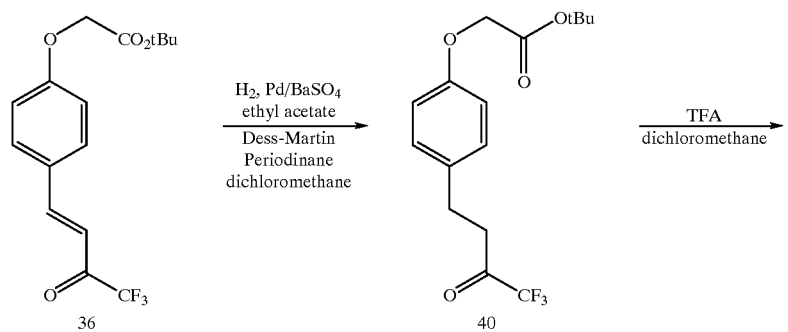
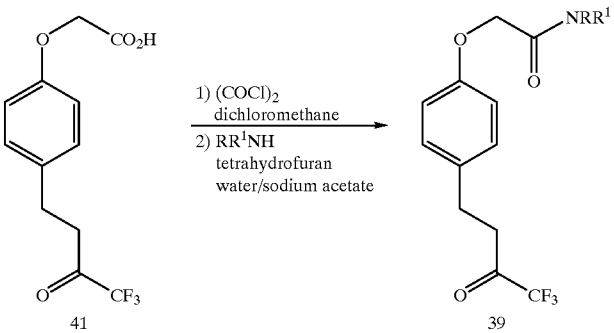
Scheme 9
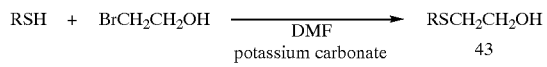

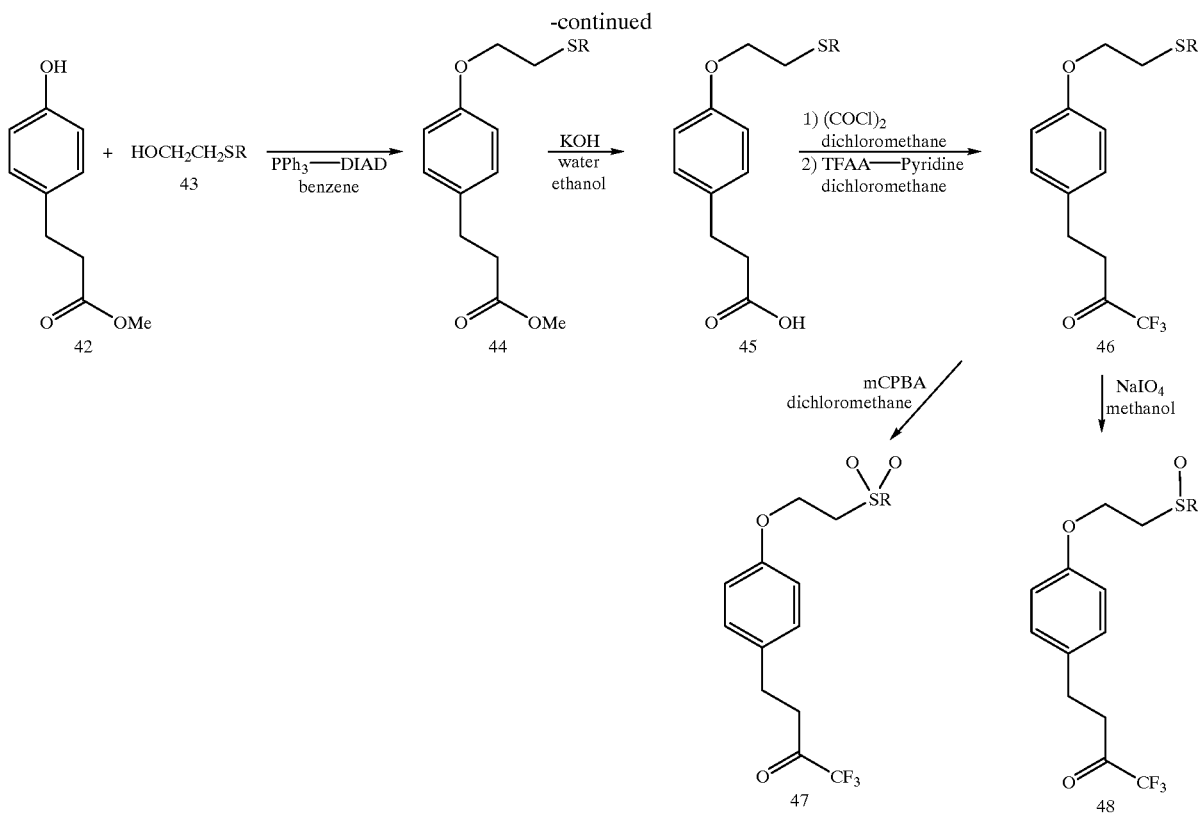

R = C$_1$–C$_{18}$ alkyl
= (C$_1$–C$_6$) alkyl X(C$_1$–C$_6$) mono or bis aryl or mono or bis heterocycles
X = N—R$^1$O, S, SO, SO$_2$

METHOD OF PREPARATION

Preparation of compounds of formula I may be accomplished via one or more of the synthetic schemes which are described below.

Scheme 1

Scheme I shows a method of preparing compounds of general structure 6. Reaction of a phenol 2 bearing a protected carboxylate group with an alcohol 3, triphenylphosphine and diethyl azodicarboxylate or diisopropyl azodicarboxylate under Mitsunobu conditions (O. Mitsunobu, Synthesis, 1, 1981) in a solvent such as tetrahydrofuran or benzene gave the ether 4. Alternatively, the phenol 2 can be alkylated with a substituted alkyl halide (RX) and a base such as potassium carbonate in a solvent such as acetonitrile or dimethylformamide to give the ether 4. The ester group of 4 is then saponified to the acid 5 by treatment with a base such as sodium hydroxide or potassium hydroxide in a solvent such as aqueous ethanol followed by neutralization with a diluted acid. The acid 5 is then treated with oxalyl chloride or thionyl chloride in a solvent such as dichloromethane to give an intermediate acid chloride. The acid chloride is then treated with trifluoroacetic anhydride and a base such as pyridine following conditions similar to those used by S. Z. Zard (Tetrahedron 51, 2573–2584, 1995) to give the trifluoromethyl ketone 6.

Scheme 2

Scheme 2 describes a method of preparing compounds of structure 12. Reaction of an iodo-substituted phenol 7 with a dibromo alkane of structure Br(CH$_2$)$_n$Br in the presence of a base such as potassium carbonate gives 8. The bromide 8 is then displaced with a mono or disubstituted amine in the presence of sodium iodide in a solvent such as isopropanol to give 9 or 10. Alternatively, compound 10 can also be obtained under Mitsunobu conditions as described in Scheme 1. Tertiary amines 10 are also obtained by reaction of 9 with various aldehydes RCHO by reaction with a reducing agent such as sodium cyanoborohydride in a solvent such as methanol. Similar tertiary amines 10 are also prepared by reaction of 9 with an iodo compound R(CH$_2$)$_n$I in the presence of a base such as potassium carbonate in a solvent such as isopropanol.

Reaction of secondary amine 9 with a Michael-type acceptor CH$_2$=CH$_2$-EWG such as ethyl acrylate or acrylonitrile in a solvent such as ethanol also yields substituted amines 10. Reaction of iodophenol 10 with 4,4,4-trifluorobut-1-en-3-ol (J. A. Pegolotti and W. G. Young, J. Am. Chem. Soc., 1961, 83, 3251), under Heck-type conditions (T. Jeffery, J. Chem. Soc. Chem. Commun., 1287, 1984) in the presence of a palladium catalyst such as palladium (II) acetate in a solvent such as N,N-dimethylformamide gives the allylic alcohol 11. Hydrogenation of this allylic alcohol in the presence of a catalyst such as palladium on activated carbon in a solvent such as ethyl acetate gave an intermediate alcohol which was oxidized to the ketone 12 with the Dess-Martin periodinane (D. B. Dess and J. C. Martin, J. Org. Chem., 1983, 48, 4155) in a solvent such as dichloromethane.

Scheme 3

Scheme 3 describes a method of preparing quaternary structures of type 14 and 15. The tertiary amine 13 is alkylated with an alkyl iodide such as methyl iodide or ethyl iodoacetate in a solvent such as isopropanol to give the quaternary amine 14. In the case where one of the R groups contains an ester group, saponification with a base such as potassium hydroxide in a solvent such as aqueous ethanol gives the zwitterionic species 15.

Scheme 4

Scheme 4 shows a method of preparing various trifluoromethyl ketones 23 from intermediates in which the trifluoromethyl ketone is protected as a ketal group. Starting from the acid 16 which is commercially available, the trifluoromethyl ketone 17 is prepared using the method described in Scheme 1. The methyl ether 17 is then cleaved with boron tribromide in a solvent such as dichloromethane to give the phenol 18. The ketone group is then protected as a ketal 19 by reaction with an orthoester such as trimethyl orthoformate catalyzed by an acid such as trifluoromethanesulfonic acid and in solvents such as nitromethane and methanol. The phenol 19 is then treated as described for Z in Scheme 2 to give 20, 21 and 22. The protected trifluoromethyl ketone in 22 allows various modifications on $R^1$ such as reduction of an ester group with lithium aluminum hydride or diisobutyl aluminum hydride. The ketal group is then cleaved with an acid such as trifluoroacetic acid to give 23.

Scheme 5

Scheme 5 describes preparation of tertiary amines by alkylation of intermediate 21 obtained in Scheme 4 by reaction with an alkyl iodide such as iodopropane in a solvent such as isopropanol and in the presence of a hindered base such as N,N-diisopropylethylamine. The ketal 24 is then cleaved as described in Scheme 4 to give the trifluoromethyl ketone 25.

Scheme 6

Scheme 6 describes preparation of a variety of trifluoromethyl ketones 27 starting from the phenol 19 obtained in Scheme 4. Reaction of 19 with various alcohols of structure ROH under the Mitsunobu conditions described in Scheme 1 gave 26. Deprotection of the ketal group as described in Scheme 4 gives 27 possessing a variety of ether substituents.

Scheme 7

Scheme 7 shows a synthetic route to acylated or sulfonylated amines 33. Reaction of 4-hydroxybenzaldehyde with a t-butoxycarbonyl-protected amino-alcohol such as 29 under Mitsunobu conditions similar to those described in Scheme 1 gives the aldehyde 30. Aldol condensation of 30 with 1,1,1-trifluoroacetone catalyzed by piperidine and acetic acid using conditions similar to those used by R. S. H. Liu (Tetrahedron Lett., 26, 2873, 1985) gave the enone 31. The enone 31 was then hydrogenated in the presence of a catalyst such as palladium on barium sulfate and treated with Dess-Martin periodinane as described in Scheme 2 to re-oxidize the partially reduced carbonyl group to give 32. The t-butoxycarbonyl-protected amino derivative 32 is then treated with an acid such as trifluoroacetic acid in a solvent such as dichloromethane to give an intermediate amine as a trifluoroacetate salt. This amine is then acylated with various acyl chlorides such as palmitoyl chloride under Schotten-Baumann conditions in a mixture of solvents such as tetrahydrofuran and saturated aqueous sodium acetate to give amide 33. Alternatively, the amine trifluoroacetate salt can be treated with an alkylsulfonyl chloride such as 1-heptanesulfonyl chloride or an alkyl isothiocyanate such as N-decyl isothiocyanate in presence of a base such as triethylamine and in a solvent such as dichloromethane to give a sulfonamide or a thiourea respectively.

Scheme 8

Scheme 8 describes a method of preparing amides of structure 39 which are regioisomers of structures described in Scheme 7. 4-Hydroxybenzaldehyde was treated with 1,1,1-trifluoroacetone as described in Scheme 7 and alkylated with a bromoester such as t-butyl bromoacetate in the presence of a base such as potassium carbonate and in a solvent such as acetone to give 36. Alternatively 36 can be obtained via the same sequence of steps but in inverse order. The phenol 34 can also be acylated with various acid chlorides such as a palmitoyl chloride to give ester derivatives such as 36b. The t-butyl protecting group of 36 is then cleaved with an acid such as trifluoroacetic acid in dichloromethane to give the acid 37. This acid is then reacted with primary and secondary amines such as dodecylamine in the presence of a condensing agent such as N-ethoxycarbonyl-2-ethoxy-1,2-dihydroxyquinoline (EEDQ) to give the amide 38. Reduction and oxidation of the enone as described in Scheme 7 gave the amide 39. Alternatively, the enone 36 can be reduced first to 40 and then cleaved as above to the acid 41. The acid 41 is then treated with oxalyl chloride in dichloromethane to give an intermediate acid chloride. Reaction of this acid chloride with primary and secondary amines such as p-chlorobenzhydrylamine hydrochloride in a mixture of tetrahydrofuran and saturated aqueous sodium acetate also gives amides of structure 39.

Scheme 9

Scheme 9 describes a method for making compounds of structure 46, 47 and 48 which contain a sulfur atom. Reaction of an alcohol 43 which contains a sulfur atom, usually obtained by reaction of a thiol with a halogen-substituted alcohol, with phenol 42 under Mitsunobu conditions as described in Scheme 1 gives the ether 44. Preparation of the trifluoromethylketone 46 is then achieved via the two-step sequence also described in Scheme 1. Oxidation of 46 with a peracid such as m-chloroperbenzoic acid gives the sulfone 47. Oxidation of 46 with sodium periodate in a mixture of methanol and water affords the sulfoxide 48.

Preparation of compounds of formula III may be accomplished via one or more of the synthetic schemes which are described below.

Scheme A

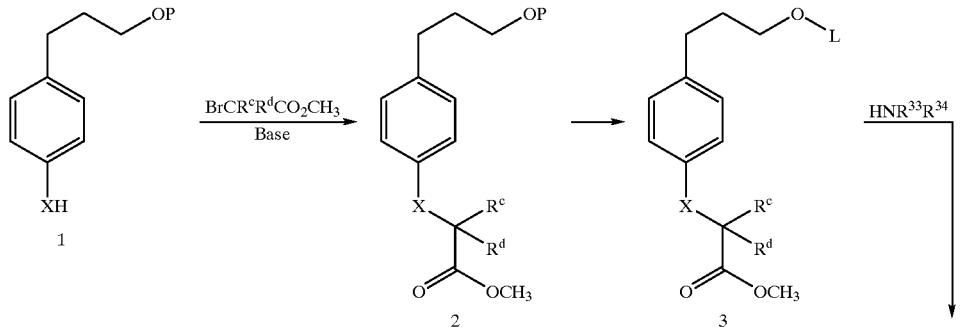

-continued

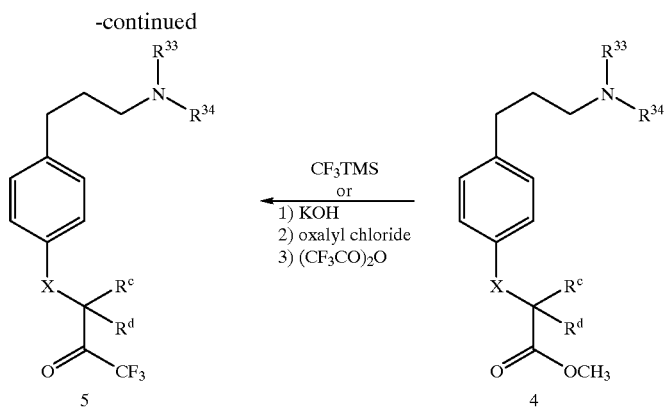

Alternative approach (for chiral compounds):

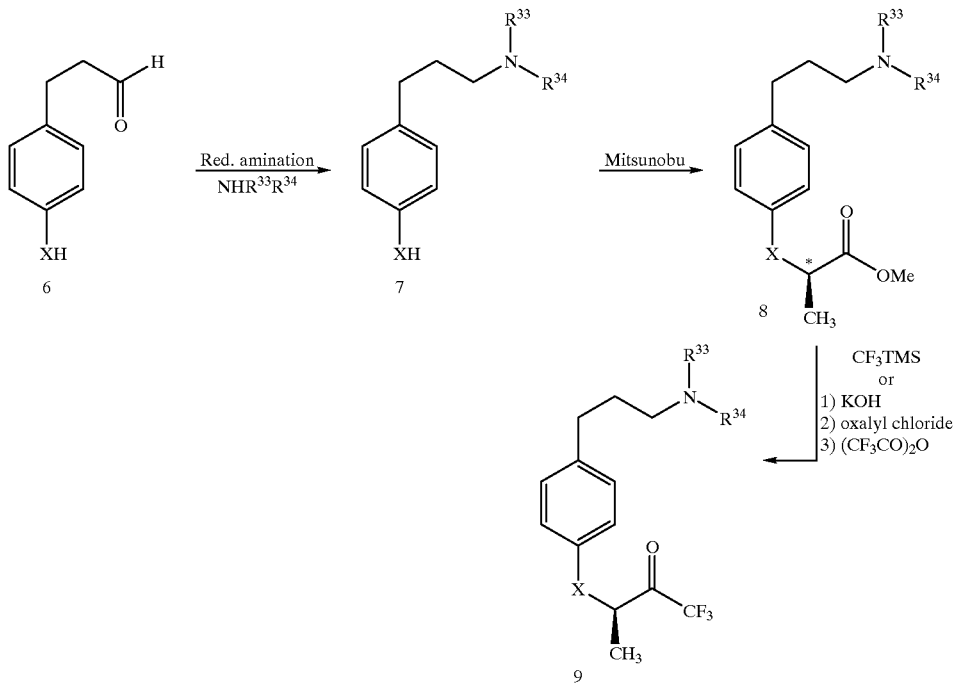

Scheme A

Scheme A describes a method of preparing compounds of generic structure III. Reaction of phenol 1 (X=O) or thiophenol 1 (X=S) in which P is a protecting group such as tert-butyl diphenylsilyl with a bromo ester such as methyl bromoacetate, methyl bromomethylacetate or methyl bromodimethylacetate in a solvent like acetonitrile or N,N-dimethylformamide in presence of a base such as potassium carbonate affords 2. Deprotection of 2 with a reagent such as tetrabutyl ammonium fluoride gave the alcohol 2 (P=H) that was activated via a group like a mesyloxy to give 3 (L=Ms). Reaction of 3 with a secondary amine $R^{33}R^{34}NH$ in a solvent such as acetonitrile gave the amine 4. Reaction of 4 with a trimethylsilylfluoroalkyl reagent such as trifluoro methyltrimethylsilane in a solvent such as toluene using a catalyst like tetrabutylammonium fluoride gave, after aqueous hydrolysis, ketone 5. Alternatively, the ester 4 can be saponified to the acid by a base such as potassium hydroxide and in a solvent such as aqueous ethanol. The acid can be reacted with a reagent such as oxalyl chloride to give an intermediate acid chloride which is then treated with an anhydride such as trifluoroacetic anhydride and a base such as pyridine in a solvent like toluene to give the ketone 5.

When $R^c$ is a methyl group and it is desired to have a chiral compound, an alternative approach may be used. Hence, the aldehyde of type 6 may be converted to the amine 7 via reductive amination conditions by the reaction of various amines in presence of a reducing agent such as triacetoxyborohydride or sodium cyanoborohydride in an inert solvent such as dichloromethane or 1,2-dichloromethane. The resulting thiol or phenol 7 was then submitted to a Mitsunobu reaction with a chiral methyl lactate in presence of triphenylphosphine and diisopropyl azodicarboxylate to give compound 8. Subsequent conversion into the trifluoromethylketone 9 by treatment with trifluoromethyltrimethylsilane in a solvent such as toluene and using a catalyst like tetrabutylammonium fluoride may then be performed. Alternatively, the methyl ester in 8 may be saponified to the corresponding acid by conditions known in the art and subsequently transformed to the acid chloride in presence of oxalyl chloride. Treatment with trifluoroacetic anhydride and a base such as pyridine in a solvent like toluene afford the ketone 9.

Scheme B

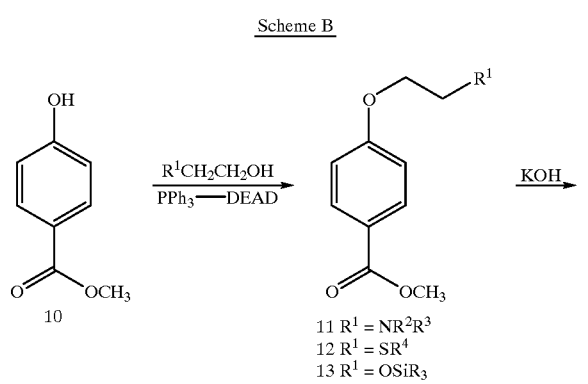

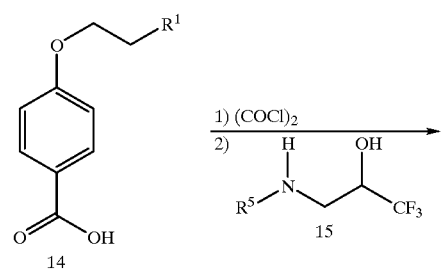

-continued

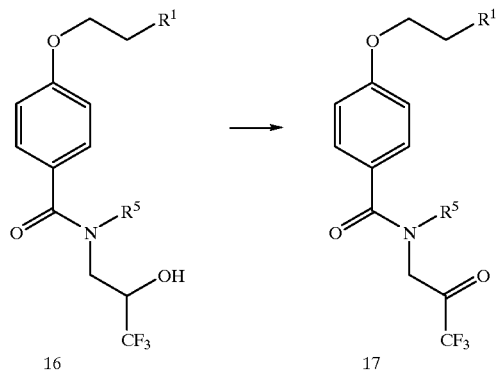

Scheme B describes a method of preparing compounds of general structure 17. Reaction of 10 with a beta-substituted amino or thio or silyloxy ethanol of general formula $R^1CH_2CH_2OH$ under Mitsunobu conditions in a solvent like toluene yielded respectively the amine 11, the sulfide 12 or the silyl derivative 13. Saponification of 11, 12 or 13 with a base such as potassium hydroxide in a solvent such as aqueous ethanol gave the acid 14. The acid 14 can be reacted with reagent such as oxalyl chloride in a solvent such as dichloromethane to give an intermediate acid chloride. Reaction of this acid chloride with an aminotrifluoroalcohol of general formula 15 ($R^5$=H, $CH_3$) in a solvent like tetrahydrofuran and aqueous sodium bicarbonate yielded the amide 16. Reaction of 16 with an oxidant such as 1,1,1-triacetoxy-1,1-dihydro-1,2-benziodoxol-3(1H)-one (Dess-Martin periodinane) or under Swern conditions (dimethylsulfoxide-oxalyl chloride) gave the ketone 17.

SPECIFIC EXAMPLES

The following examples further illustrate the preparation of the compounds of formula II or III. The examples are illustrative only and are not intended to limit the scope of the invention in any way. The following abbreviations have the indicated meanings:

| | |
|---|---|
| AcOH | acetic acid |
| EWG | electron-withdrawing groups |
| DIAD | diisopropyl azodicarboxylate |
| TFAA | trifluoroacetic anhydride |
| r.t. | room temperature |
| THF | tetrahydrofuran |
| TFA | trifluoroacetic acid |
| EEDQ | N-ethoxycarbonyl-2-ethoxy-1,2-dihydroxyquinoline |
| DMF | N,N-dimethylformamide |
| DEAD | diethyl azodicarboxylate |
| CPBA | m-chloroperbenzoic acid |
| Me | $CH_3$ |
| Ph | phenyl |
| tBu | tert-butyl |

Scheme 1

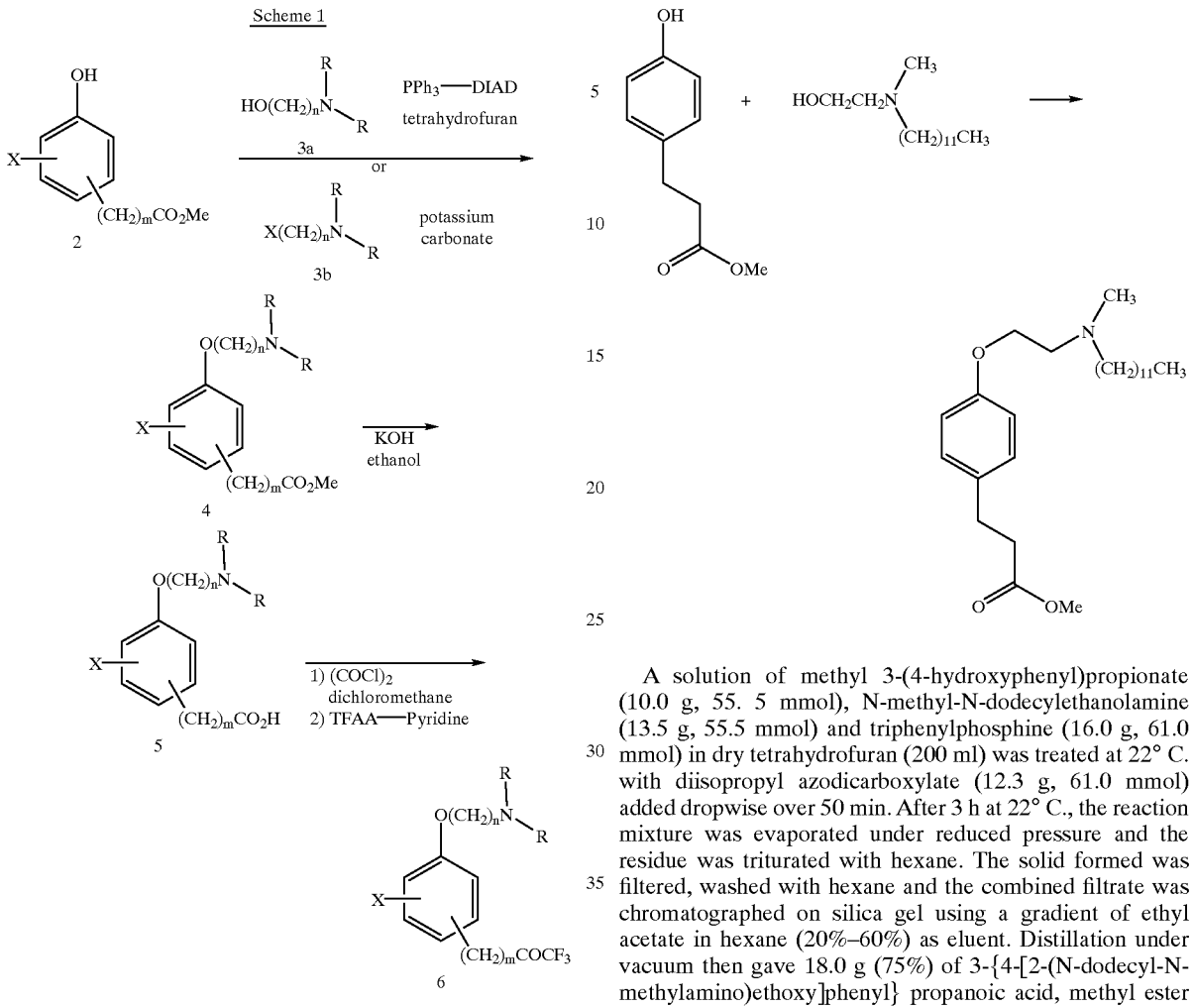

Example 1

4-[4-[2-(N-Dodecyl-N-methylamino)ethoxy)phenyl]]1,1,1-trifluoro-2-butanone
N-Methyl-N-Dodecylethanolamine

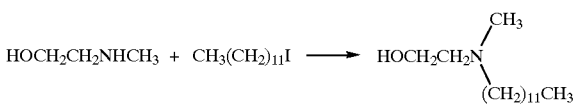

A solution of iodododecane (18.1 g, 61.09 mmol) and 2-(methylamino)ethanol (23.0 g, 0.3 mol) in isopropanol (75 ml) was heated under reflux for 3 h. The cooled mixture was diluted with ether (500 ml), washed with water, brine and dried (magnesium sulfate). Evaporation of the solvent under reduced pressure and distillation of the residue under vacuum gave 14.5 g (97%) of N-methyl-N-dodecylethanolamine as a clear oil: b.p. 100–111° C./0.3 torr (bulb to bulb distillation, air bath temperature).

IR (NaCl, film) $u_{max}$ (cm$^{-1}$) 3400 (OH).

$^1$H NMR 400 MHz (CDCl$_3$) d (ppm): 0.89 (3H, t, J=5.36 Hz, CH$_3$), 1.1–1.5 (20H, br m, (CH$_2$)$_{10}$), 2.24 (3H, s, NCH$_3$), 2.39 (2H, t, J=7.4 Hz, NCH$_2$), 2.52 (2H, t, J=5.35 Hz, OCH$\underline{C}$H$_2$N), 3.58 (2H, t, J=5.35 Hz, O$\underline{CH_2}$CH$_2$N).

3-[4-[2-(N-Dodecyl-N-methylamino)ethoxy]phenyl]-propanoic Acid Methyl Ester

A solution of methyl 3-(4-hydroxyphenyl)propionate (10.0 g, 55. 5 mmol), N-methyl-N-dodecylethanolamine (13.5 g, 55.5 mmol) and triphenylphosphine (16.0 g, 61.0 mmol) in dry tetrahydrofuran (200 ml) was treated at 22° C. with diisopropyl azodicarboxylate (12.3 g, 61.0 mmol) added dropwise over 50 min. After 3 h at 22° C., the reaction mixture was evaporated under reduced pressure and the residue was triturated with hexane. The solid formed was filtered, washed with hexane and the combined filtrate was chromatographed on silica gel using a gradient of ethyl acetate in hexane (20%–60%) as eluent. Distillation under vacuum then gave 18.0 g (75%) of 3-{4-[2-(N-dodecyl-N-methylamino)ethoxy]phenyl} propanoic acid, methyl ester as a clear oil: b.p. 180–183° C./0.02 torr (bulb to bulb distillation, air bath temperature).

$^1$H NMR 400 MHz (CDCl$_3$) d (ppm): 0.89 (3H, t, J=6.8 Hz, CH$_3$), 1.2–1.6 (20H, m, CH$_2$)$_{10}$), 2.33 (3H, s, NCH$_3$), 2.43 (2H, t, J=7.6 Hz, NCH$_2$), 2.60 (2H, t, J=7.77 Hz, CH$_2$-2), 2.78 (2H, t, J=6.06 Hz, OCH$\underline{C}$H$_2$N), 2.89 (2H, t, J=7.77 Hz, CH$_2$-3), 3.67 (3H, s, OC$\underline{H_3}$), 4.04 (2H, t, J=6.06 Hz, O$\underline{CH_2}$N), 6.84 (2H, d, J=8.55 Hz, aromatic), 7.11 (2H, d, J=8.55 Hz, aromatic).

The hydrochloride salt was obtained by treating the amine with anhydrous hydrochloric acid (1M) in ether.

Anal. Calcd. for C$_{25}$H$_{43}$NO$_3$.HCl: C 67.92, H 10.03, N 3.17. Found: C 67.74, H 9.46, N 3.25.

3-[4-[2-(N-Dodecyl-N-methylamino)ethoxy]phenyl]-propanoic Acid, Hydrochloride Salt

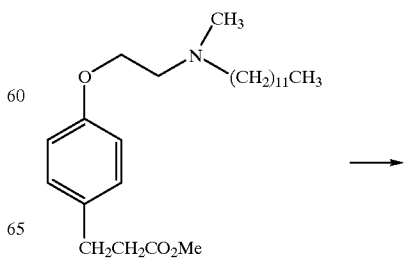

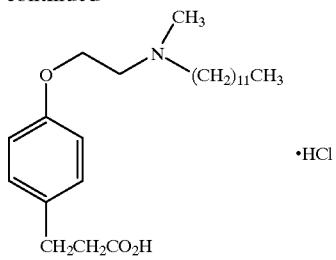

A solution of 3-[4-[2-(N-dodecyl-N-methylamino) ethoxy]phenyl]propanoic acid methyl ester (2.30 g, 5.69 mmol) in ethanol (25 ml) was treated with potassium hydroxide (0.64 g, 11.4 mmol) and water (5 ml) and stirred at 22° C. for 2 h. The reaction mixture was then acidified to pH 4 with 1M hydrochloric acid and extracted twice with ethyl acetate. The combined extracts were washed with brine, dried (MgSO$_4$) and evaporated under reduced pressure to give a white solid. Recrystallization from ethyl acetate gave 2.20 g (89%) of 3-[4-[2-(N-dodecyl-N-methylamino)ethoxy]phenyl]propanoic acid as white crystals.

IR (KBr) u$_{max}$ (cm$^{-1}$): 1725 (C=O of carboxylate).
$^1$H NMR 400 MHz (CDCl$_3$) d (ppm): 0.89 (3H, t, J=6.8 Hz, —CH$_3$), 1.2–1.4 (18H, br m, (CH$_2$)$_9$), 1.87 (2H, m, NCHCH$_2$), 2.61 (2H, t, J=7.5 Hz, CH$_2$-2), 2.87 (3H, s, NCH$_3$), 2.88 (2H, t, J=7.5 Hz, CH$_2$-3), 3.11 (2H, br t, N CH$_2$CH$_2$), 3.44 (2H, br t, OCHCH$_2$N), 4.41 (2H, br t, O CH$_2$CH$_2$N), 6.81 (2.11, d, J=8.58 Hz, aromatic), 8.56 (2H, d, J=8.58 Hz, aromatic).

Anal. Calcd. for C$_{24}$H$_{41}$NO.HCl: C 67.34, H 9.89, N 3.27. Found: C 67.08, H 9.82, N 3.18.

4-[4-[2-(N-Dodecyl-N-methylamino)ethoxyl]phenyl]-1,1,1-trifluoro-2-butanone

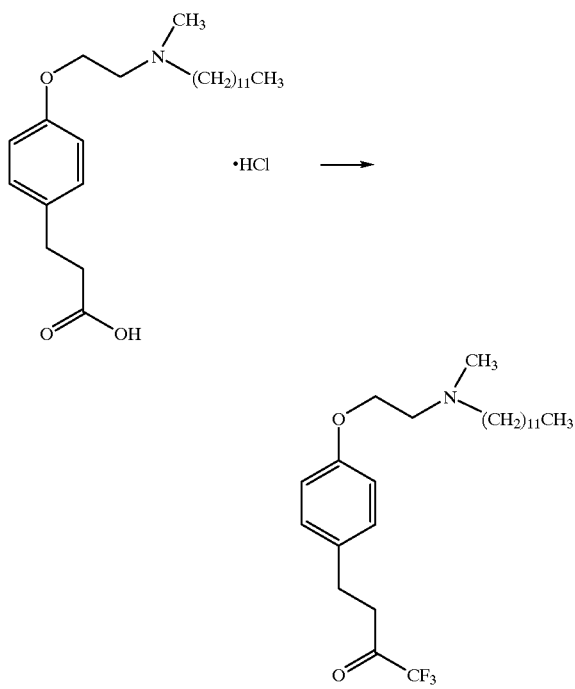

A solution of 3-[4-[2-(N-dodecyl-N-methylamino)ethyl] phenyl]propanoic acid hydrocloride salt (3.30 g, 7.71 mmol) in dry dichloromethane (35 ml) was treated with oxalyl chloride (1.61 g, 12.7 mmol) and a small drop of N,N-dimethylformamide. After 1 h at 22° C., the solvent and excess reagent were evaporated under reduced pressure and the residue was dissolved in dry dichloromethane (35 ml). This solution was then added to a solution of trifluoroacetic anhydride (5.31 g, 24.2 mmol) in dry dichloromethane (30 ml) cooled to 0° C. and treated dropwise with pyridine (1.4 ml, 17.3 mmol). After stirring for 30 min at 0° C. and another 1.5 h at 22° C., the reaction mixture was cooled again to 0° C. and treated dropwise with water (13 ml). After 30 min at 0° C. and another 30 min at 22° C., the reaction mixture was adjusted to pH 8–9 with solid sodium bicarbonate and diluted with dichloromethane (200 ml). The organic phase was then washed with brine and dried (magnesium sulfate). The solvent was evaporated under reduced pressure and the residual oil was chromatographed on silica gel. Elution with a gradient of ethyl acetate in hexane gave an oil which was distilled under vacuum to give 2.45 g (71%) of 4-[4-[2-(N-dodecyl-N-methylamino) ethoxy]phenyl]1,1,1-trifluoro-2-butanone as a clear oil: b.p. 160° C./0.02 torr (bulb to bulb distillation, air bath temperature).

IR (NaCl, film) u$_{max}$ (cm$^{-1}$): 1760 (C=O).
$^1$H NMR 400 MHz (CDCl$_3$) d (ppm): 0.89 (3H, t, J=6.8 Hz, —CH$_3$), 1.1–1.6 (20H, m, (CH$_2$)$_{10}$), 2.32 (3H, s, NCH$_3$), 2.44 (2H, t, J=7.6 Hz, NCH$_2$), 2.79 (2H, t, J=6.0 Hz, OCH CH$_2$N), 2.94 and 3.0 (2×2H, 2m, CH$_2$-3 and 4), 4.06 (2H, t, J=6.0 Hz, OCH$_2$CH$_2$N), 6.86 (2H, d, J=8.6 Hz, aromatic), 7.10 (2H, d, J=8.6 Hz, aromatic).

Anal. Calcd. for C$_{25}$H$_{40}$F$_3$NO$_2$.0.6 H$_2$O: C 68.08, H 9.09, N 3.16. Found: C 68.08, H 9.19, N 3.11.

The hydrochloride salt was obtained by treating the amine with anhydrous hydrochloric acid (1M) in ether.

Anal. Calcd. for C$_{25}$H$_{40}$F$_3$NO$_2$.HCl. 1.1 H$_2$O: C 60.07, H 8.71, N 2.80. Found: C 59.99, H 8.62, N 2.98.

Example 2

4-[4-[3-(N-Dodecyl-N-methylamino)propoxy]phenyl]-1,1,1-trifluoro-2-butanone 3-(N-dodecyl-N-methylamino)propanol A solution of 3-(methylamino)propanol (5.71 g, 64.0 mmol, S. Koepke, R. Kupper, and C. J. Michejda, J. Org. Chem., 44, 2718,1979)), and iodododecane (7.58 g, 25.6 mmol) was reacted as described in example 1 to give 6.33 g (96%) of the title material as an oil, b.p. 100–105° C./0.04 torr.

3-[4-[3-(N-dodecyl-N-methylamino)propoxy]phenyl] propanoic Acid, Methyl Ester

Methyl 3-(4-hydroxyphenyl)propanoate (1.0 g, 5.5 mmol) and 3-(N-dodecyl-N-methylamino)propanol (1.43 g, 5.5 mmol) were reacted as described in example 1 to give 1.57 g (43%) of title material as an oil.

Anal. Calcd. for C$_{26}$H$_{45}$NO$_3$: C 74.42, H 10.81, N 3.34. Found: C 74.02, H 10.54, N 3.49.

3-[4-[3-(N-Dodecyl-N-methylamino)propoxy]phenyl] propanoic Acid, Hydrochloride

3-[4-[3-(N-dodecyl-N-methylamino)propoxy]phenyl] propanoic acid, methyl ester (1.53 g, mmol) was reacted as described in example 1 to give 1.20 g (74%) of the starting material as an amorphous solid.

Anal. Calcd. for C$_{26}$H$_{45}$NO$_3$: C 74.42, H 10.81, N 3.34. Found: C 74.02, H 10.54, N 3.49.

4-[4-[3-(N-Dodecyl-N-methylamino)propoxy]phenyl]-1,1,1-trifluoro-2-butanone

3-[4-[3-(N-dodecyl-N-methylamino)propoxy]phenyl] propanoic acid, hydrochloride (0.45 g, 1.11 mmol) was reacted as described in example 1 to give 0.185 g (36%) of the title material as an oil, b.p. 140–160° C./0.04 torr (bulb to bulb distillation, air bath temperature).

Anal. Calcd. for $C_{26}H_{42}F_3NO_2.0.2H_2O$: C 67.71, H 9.27, N 3.04. Found: C 67.75, H 9.35, N 2.90.

The hydrochloride was obtained as a syrup.

Example 3
4-[4-[4-(N-Dodecyl-N-methylamino)butoxy]phenyl]-1,1,1-trifluoro-2-butanone
Methyl 3-[4-(4-bromobutoxy)phenyl]propanoate A mixture of methyl 3-(4-hydroxyphenyl) propionate (1.19 g, 6.6 mmol), 1,4-dibromobutane (10 g, 46.3 mmol) and powdered anhydrous potassium carbonate (2.3 g) was maintained at 80° C. and stirred vigorously for 24 h. Alter cooling, the solid was filtered and washed with a mixture of hexane and ethyl acetate (4:1). The filtrate was concentrated under reduced pressure and the residue was chromatographed on silica gel. Elution with a gradient of ethyl acetate (0–3%) in toluene gave 1.80 g (86%) of the title material as an oil.

Anal. Calcd. for $C_{14}H_{19}BrO_3$: C 53.25, H 6.08. Found: C 53.24, H 5.74.

3-[4-[4-(N-Dodecyl-N-methylamino)butoxy]phenyl]-propanoic Acid, Methyl Ester

A mixture of methyl 3-(4-bromobutoxy)phenyl] propanoate (1.46 g, 4.63 mmol), N-methyldodecylamine (2.31 g, 11.6 mmol) and sodium iodide (50 mg) in acetonitrile (17 ml) was heated at 75° C. for 3 h. The reaction mixture was then cooled, diluted with dichloromethane, washed with saturated sodium bicarbonate, brine and dried over anhydrous magnesium sulfate. The solvent was then evaporated under reduced pressure and the residue was chromatographed on silica gel. Elution with a gradient of methanol (0–5%) in ether gave 1.69 g (85%) of the title material as an oil.

Anal. Calcd. for $C_{27}H_{47}NO_3$: C 79.48, H 10.92, N 3.23. Found: C 74.62, H 10.58, N 3.25.

3-[4-[4-(N-Dodecyl-N-methylamino)butoxy]phenyl]-propanoic Acid, Hydrochloride

3-[4-[4-N-dodecyl-N-methylamino)butoxy]phenyl] propanoic acid, methyl ester (0.800 g, 1.84 mmol) was saponified as described in example 1 to give 0.778 g (93%) of the title material as white crystals after crystallization from ethyl acetate; m.p. 109–111° C. Anal. Calcd. for $C_{26}H_{45}NO_3.HCl$: C 68.47, H 10.17, N 3.07. Found: C 68.49, H 9.92, N 3.07.

4-[4-[4-(N-Dodecyl-N-methylamino)butoxy]phenyl]-1,1,1-trifluoro-2-butanone

3-[4-[4-(N-dodecyl-N-methylamino)butoxy]phenyl]-propanoic acid, hydrochloride (0.740 g, 1.76 mmol) was reacted as described in example 1 to give 0.420 g (51%) of the title material as an oil: b.p. 150–180° C./0.025 torr (bulb to bulb distillation, air bath temperature).

Anal. Calcd. for $C_{27}H_{44}F_3NO_2$: C 68.76, H 9.40. Found: C 68.52, H 9.38.

The hydrochloride was obtained as a syrup.

Anal. Calcd. for $C_{27}H_{44}F_3NO_2.HCl.0.5\ H_2O$: C 62.71, H 8.97, N 2.71. Found: C 62.69, H 8.71, N 2.76.

Example 4
[2-[2-(N-Dodecyl-N-methylamino)ethoxy]phenyl]-2,2,2-trifluoroethanone

2-Trifluoroacetylphenol (Matsumoto, S.; Kobayashi, H. and Ueno, K. *Bull.Chem. Soc. Jpn.* 1969, 42, 960) (490 mg, 2.57 mmol) and 2-[N-dodecyl-N-methylamino] ethanol (627 mg, 2.58 mmol) were reacted by the general procedure as described in example 1 and afforded the title compound (654 mg, 61%) as a pale yellow oil.

Analysis for $C_{23}H_{36}F_3NO_2.0.3H_2O$ calcd. C 65.63%, H 8.76%, N 3.33%; Found: C 65.44%, H 8.74%, N 3.48%.

Treatment of the above free amine with anhydrous hydrogen chloride (1.0 M in ether) gave the hydrochloride salt as a white waxy solid. Analysis for $C_{23}H_{36}F_3NO_2.HCl.0.5H_2O$ calcd. C 59.92%, H 8.31%, N 3.04%; Found: C 59.67%, H 8.49%, N 3.16%.

Example 5
4-[4-[2-(N-Dodecyl-N-methylamino)ethoxy]-2-methoxyphenyl]-1,1,1-trifluoro-2-butanone
7-[2-(N-Dodecyl-N-methylamino)ethoxy]-2H-1-benzopyran-2-one 7-Hydroxycoumarin (6.0 g, 37.0 mmol) and 2-[N-dodecyl-N-methylamino] ethanol (9.0 g, 37.0 mmol) were reacted by the general procedure as described in example 1 and afforded the title compound (6.7 g, 47%) as a white solid.

Analysis for $C_{24}H_{37}NO_3$ calcd C 74.38%, H 9.62%, N 3.61%; Found: 74.35%, H 9.45%, N 3.66%.

7-[2-(N-Dodecyl-N-methylamino)ethoxy]-3,4-dihydro-2H-1-benzopyran-2-one

7-[2-(N-Dodecyl-N-methylamino)ethoxy]-2H-1-benzopyran-2-one (5.62 g, 14.5 mmol) in ethyl acetate was hydrogenated over palladium on activated carbon uder 30 psi and afforded the title compound (4.7 g, 84%) as a white solid.

Treatment of the above free amine with anhydrous hydrogen chloride (1.0 M in ether) gave the hydrochloride salt as a white solid.

Analysis for $C_{24}H_{39}N\ O_3.HCl.0.7H_2O$ calcd. C 65.72%, H 9.51%, N 3.19%; Found: C 65.76% H 9.35% N 3.26%.

3-[4-[2-(N-Dodecyl-N-methylamino)ethoxy]-2-hydroxyphenyl]propanoic Acid, Methyl Ester A solution of 7-[2-(N-Dodecyl-N-methylamino)ethoxy]-3,4-dihydro-2H-1-benzopyran-2-one (2.0 g, 5.13 mmol) in methanol (30 ml) was stirred at 22° C. for 0.5 h. The solvent was then removed in vacuo at 40° C. to afford the title compound (2.14 g, 100%) as a white solid.

3-[4-[2-(N-Dodecyl-N-methylamino)ethoxy]-2-methoxyphenyl]propanoic Acid, Methyl Ester 3-[4-[2-(N-Dodecyl-N-methylamino)ethoxy]-2-hydroxyphenyl]propanoic acid, methyl ester (500 mg, 1.18 mmol) and methanol (0.096 ml, 2.37 mmol) were reacted under Mitsunobu conditions as described in example 1 and afforded the title compound (471 mg, 81%) as a pale yellow oil.

3-[4-[2-(N-Dodecyl-N-methylamino)ethoxy]-2-methoxyphenyl]propanoic Acid, Hydrochloride 3-[4-[2-(N-Dodecyl-N-methylamino)ethoxy]-2-methoxyphenyl]propanoic Acid, Methyl Ester (468 mg, 1.07 mmol) was saponified as described in the preparation of 3-[4-[2-(N-dodecyl-N-methylamino)ethoxy]phenyl] propanoic acid, hydrochloride and afforded the title compound (280 mg, 62%) as a white solid.

Analysis for $C_{25}H_{43}NO_4$ calcd. C 64.60%, H 9.46%, N 3.01%; Found: C 64.69%, H 9.52%, N 3.22%.

4-[4-[2-(N-Dodecyl-N-methylamino)ethoxy]-2-methoxyphenyl]-1,1,1-trifluoro-2-butanone 3-[4-[2-(N-Dodecyl-N-methylamino)ethoxy]-2-methoxyphenyl]propanoic acid, hydrochloride (274 mg, 0.598 mmol) was reacted by the general procedure as described in the preparation of 4-[4-[2-(N-dodecyl-N-methylamino)- ethoxy]phenyl]-1,1,1-trifluoro-2-butanone and afforded the title compound (165 mg, 58%) as a pale yellow oil (b.p. 138–140° C./0.015 mmHg).

Treatment of the above free amine with anhydrous hydrogen chloride (1.0 M in ether) gave the hydrochloride salt as a off-white sticky solid.

Analysis for $C_{26}H_{42}F_3NO_3 \cdot HCl \cdot 0.7\ H_2O$ calcd. C 58.80%, H 8.76%, N 2.74%; Found: C 58.89%, H 8.53%, N 2.64%.

Example 6

7-[2-(N-Dodecyl-N-methylamino)ethoxyl-3,4-dihydro-2-(trifluoromethyl)-2H-1-benzopyran-2-ol A mixture of 4-[4-[2-(N-dodecyl-N-methylamino) ethoxy]-2-methoxyphenyl]-1,1,1-trifluoro-2-butanone (157 mg, 0.33 mmol) and hydrobromic acid (47%, 3 ml) was refluxed for 3.5 h. After cooling to r.t., the mixture was diluted with water, extracted with dichloromethane. The organic layer was washed with sat. sodium bicarbonate, brine, dried over magnesium sulfate and concentrated in vacuo. The residue was chromatographed on silica gel (ethyl acetate/acetone 3:1) to afford the title compound (60 mg, 40%) as a clear oil.

Treatment of the above free amine with anhydrous hydrogen chloride (1.0 M in ether) gave the hydrochloride salt as a off-white sticky solid.

Analysis for $C_{25}H_{40}F_3NO_3 \cdot HCl \cdot 0.3H_2O$ calcd. C 59.88%, H 8.36%, N 2.79%; Found: C 59.84%, H 8.29%, N 2.79%.

Example 7

4-[4-[2-(N-Dodecyl-N-methylamino)ethoxy]-2-vinylphenyl]-1,1,1-trifluoro-2-butanone 3-[4-[2-(N-Dodecyl-N-methylamino)ethoxy]-2-[trifluoromethanesulfonyloxy]phenyl]propanoic Acid, Methyl Ester To a solution of 3-[4-[2-(N-dodecyl-N-methylamino) ethoxy]-2-hydroxyphenyl]propanoic acid, methyl ester (2.53 g, 6.0 mmol) and dry pyridine (1.94 ml, 24.0 mmol) in dichloromethane (30 ml) at 0° C. was added dropwise trifluoromethanesulfonic anhydride (2.1 ml, 12.0 mmol). After stirring for 20 h at 22° C., the mixture was diluted with ethyl acetate (120 ml), washed with water (3×50 ml), brine (50 ml), dried over magnesium sulfate and concentrated in vacuo. The residue was placed at 0° C. and triturated with diethyl ether. The formed solid (trifluoromethanesulfonic acid salt of the title compound) was dissolved in dichloromethane, washed with sat. sodium bicarbonate, brine and dried over magnesium sulfate. The solvent was removed in vacuo to afford the title compound (2.15 g, 69%) as a brown oil which solidified upon standing.

3-[4-[2-(N-Dodecyl-N-methylamino)ethoxy]-2-vinylphenyl]propanoic Acid, Methyl Ester To a solution of 3-[4-[2-(N-dodecyl-N-methylamino) ethoxy]-2-[trifluoromethanesulfonyloxy]-phenyl]propanoic acid, methyl ester (250 mg, 0.48 mmol) in 1,4-dioxane (2.5 ml) were added tributylvinyltin (1.2 ml, 4.0 mmol), lithium chloride (123 mg, 1.44 mmol), tetrakis(triphenylphosphine)-palladium(0) (10 mg) and 2,6-di-tert-butyl-4-methylphenol (10 mg). The resulting mixture was then stirred at 100° C. for 5 h. After cooling to r.t., the mixture was diluted with diethyl ether, washed with water, brine, dried over magnesium sulfate and concentrated in vacuo. The residue was chromatographed on silica gel (diethyl ether/acetone 100:0 to 80:20) to afford the title compound (170 mg, 80%) as a yellow oil.

3-[4-[2-(N-Dodecyl-N-methylamino)ethoxy]-2-vinylphenyl]propanoic Acid, Hydrochloride 3-[4-[2-(N-Dodecyl-N-methylamino)ethoxy]-2-vinylphenyl]propanoic acid, methyl ester (178 mg, 0.412 mmol) was saponified as described in the preparation of 3-[4-[2-(N-dodecyl-N-methylamino)ethoxy]phenyl] propanoic acid, hydrochloride and afforded the title compound (175 mg, 93%) as a clear oil.

4-[4-[2-(N-Dodecyl-N-methylamino)ethoxy]-2-vinylphenyl]-1,1,1-trifluoro-2-butanone 3-[4-[2-(N-Dodecyl-N-methylamino)ethoxy]-2-vinylphenyl]propanoic acid, hydrochloride (830 mg, 1.83 mmol) was reacted by the general procedure as described in the preparation of 4-[4-[2-(N-dodecyl-N-methylamino)-ethoxy]phenyl]-1,1,1-trifluoro-2-butanone. The residue was chromatographed on silica gel (ethyl acetate) to afforded the title compound (0.46 g, 54%) as a pale purple oil.

Analysis for $C_{27}H_{42}F_3NO_2 \cdot 0.5H_2O$ calcd. C 67.75%, H 9.06%, N 2.93%; Found: C 67.85%, H 8.92%, N 2.90%.

Treatment of the above free amine with anhydrous hydrogen chloride (1.0 M in ether) gave the hydrochloride salt as a pale green sticky solid.

Analysis for $C_{27}H_{42}F_3NO_2 \cdot HCl \cdot 1.3H_2O$ calcd. C 61.24%, H 8.68%, N 2.65%; Found: C 61.07%, H 8.42%, N 2.63%.

Example 8

8-[2-(N-Dodecyl-N-methylamino)ethoxy]-3-hydroxy-1-(hydroxymethyl)-3-(trifluoromethyl)-1,3,4,5-tetrahydro-2-benzoxepin A solution of 4-methylmorpholine N-oxide (31 mg, 0.23 mmol) and osmium tetroxide (1 mg, 0.004 mmol) in acetone (1 ml) and water (2.5 ml) was treated with 4-[4-[2-(N-dodecyl-N-methylamino)ethoxy]-2-vinylphenyl]-1,1,1-trifluoro-2-butanone (100 mg, 0.21 mmol) dissolved in tert-butanol (1 ml). After stirring at 22° C. for 16 h, the mixture was treated with aqueous sodium bisulfite (20%, 5 ml) and extracted with diethyl ether. The combined organic layers were washed with brine, dried over magnesium sulfate and concentrated in vacuo. The residue was chromatographed on silica gel (diethyl ether/acetone 80:20 to 50:50) to afford the title compound (40 mg, 39%) as a clear oil.

Treatment of the above free amine with anhydrous hydrogen chloride (1.0 M in ether) gave the hydrochloride salt as an off-white solid.

Analysis for $C_{27}H_{44}F_3NO_4 \cdot HCl \cdot 0.7H_2O$ calcd. C 58.67%, H 8.46%, N 2.53%; Found: C 58.67%, H 8.18%, N 2.45%.

Example 9

4-[4-[2-[N-[Bis-(4-chlorophenyl)methyl]N-methylamino] ethoxy]phenyl]-1,1,1-trifluoro-2-butanone 2-[N-[Bis-(4-chlorophenyl)methyl]N-methylamino]ethanol

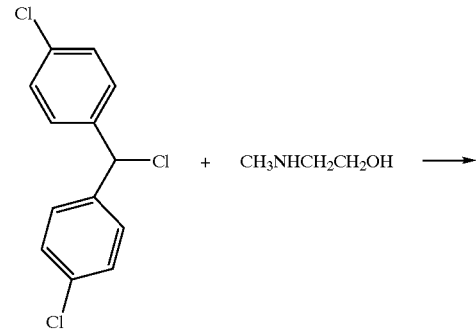

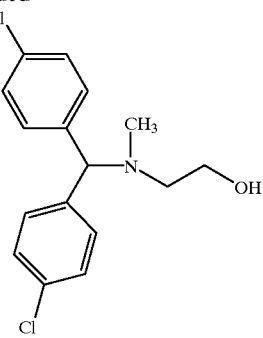

A solution of 4,4'-dichlorobenzhydryl chloride (5.20 g, 19.1 mmol) and 2-(methylamino)ethanol (9.0 g, 0.106 mol) in acetonitrile (100 ml) was treated with powdered anhydrous potassium carbonate (10 g) and the resulting mixture was heated under reflux for 4 h. The cooled mixture was filtered and the filtrate was concentrated in vacuo. The residual oil was diluted with ethyl acetate, washed with water and brine and then dried over anhydrous magnesium sulfate. Evaporation of the solvent in vacuo followed by chromatography on silica gel (elution toluene-ethyl acetate 9:1) gave 4.29 g (79%) of the title material as a white solid: mp 49–50° C.

Anal. Calcd. for $C_{16}H_{17}Cl_2NO$: C 61.95, H 5.52, N 4.52. Found: C 61.58, H 5.43, N 4.61.

3-[4-[2-[N-[Bis-(4-chlorophenyl)methyl]-N-methylamino]ethoxy]phenyl]-propanoic Acid Methyl Ester

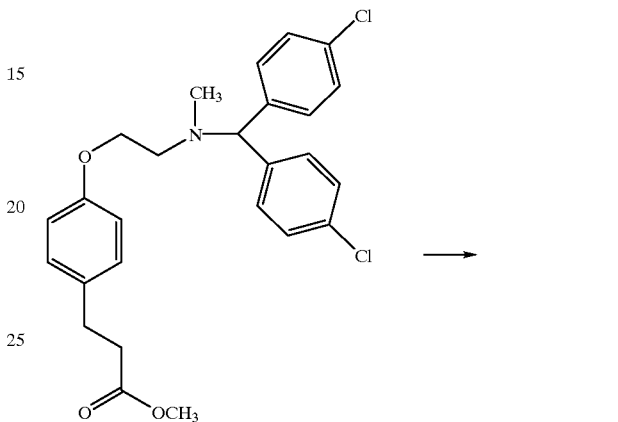

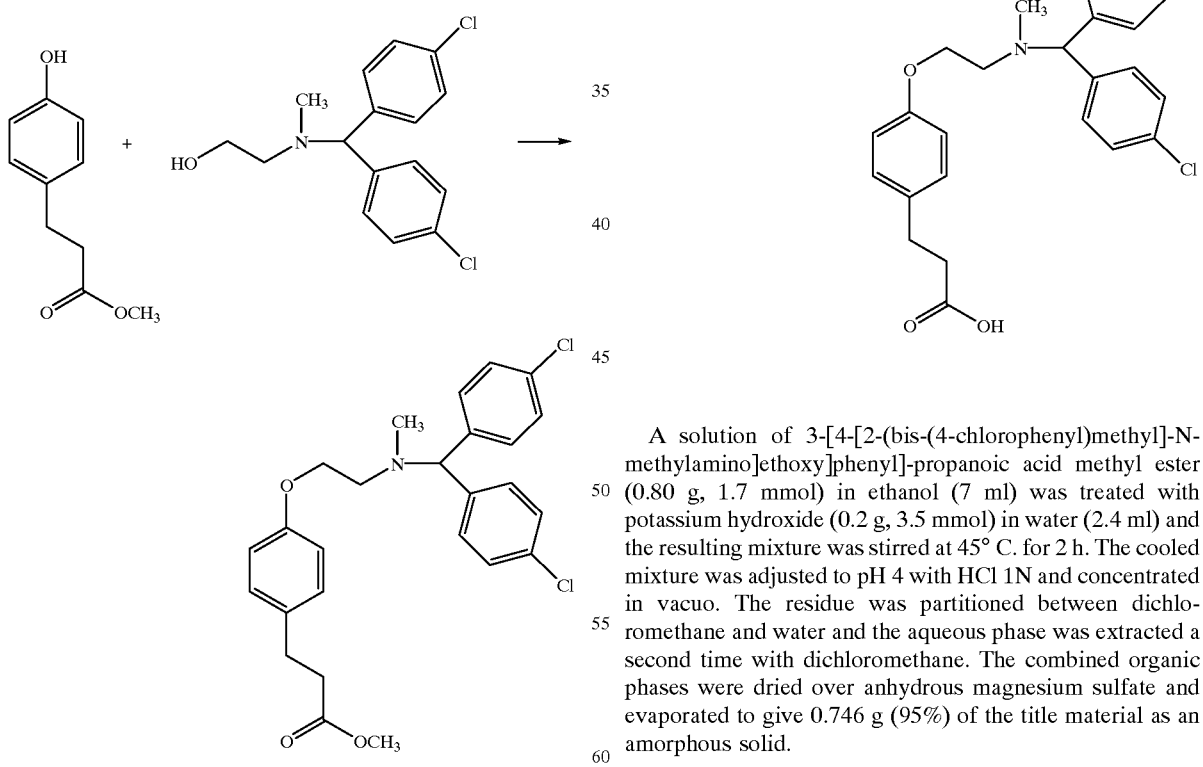

A solution of methyl 3-[4-hydroxyphenyl)propanoate (0.594 g, 3.3 mmol) and 2-[N-[bis-(4-chlorophenyl)methyl]-N-methylamino]ethanol and triphenylphosphine (0.952 g, 3.63 mmol) in tetrahydrofuran (12 ml) was treated dropwise at 22° C. with diisopropyl azodicarboxylate (0.734 g, 3.63 mmol). After 3 h, the solvent was evaporated in vacuo and the residue was chromatographed on silica gel (elution hexane-ethyl acetate 83:17) to give 1.12 g (72%) of the title material as an oil.

Anal. Calcd. for $C_{26}H_{27}Cl_2NO_3$. 0.4 $H_2O$: C 65.11, H 5.84, N 2.92. Found: C 65.34, H 5.89, N 3.08.

3-[4-[2-[N-[Bis-(4-chlorophenyl)methyl]methyl]-N-methylamino]ethoxy]phenyl]propanoic Acid A solution of 3-[4-[2-(bis-(4-chlorophenyl)methyl]-N-methylamino]ethoxy]phenyl]-propanoic acid methyl ester (0.80 g, 1.7 mmol) in ethanol (7 ml) was treated with potassium hydroxide (0.2 g, 3.5 mmol) in water (2.4 ml) and the resulting mixture was stirred at 45° C. for 2 h. The cooled mixture was adjusted to pH 4 with HCl 1N and concentrated in vacuo. The residue was partitioned between dichloromethane and water and the aqueous phase was extracted a second time with dichloromethane. The combined organic phases were dried over anhydrous magnesium sulfate and evaporated to give 0.746 g (95%) of the title material as an amorphous solid.

Anal. Calcd. for $C_{25}H_{25}Cl_2NO_3$.0.1 $C_7H_8$: C 66.01, H 5.56, N 3.00. Found: C 66.21, H 5.91, N 3.01.

4-[4-[2-[N-[Bis-(4-chlorophenyl)methyl]-N-methylamino]ethoxy]phenyl]-1,1,1-trifluoro-2-butanone

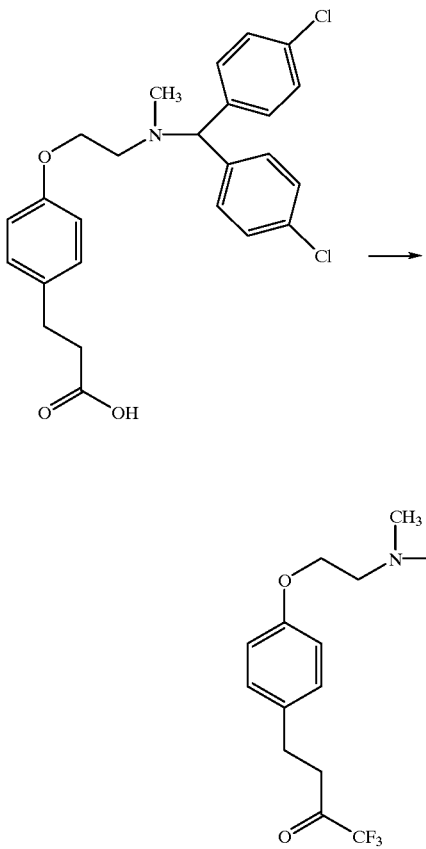

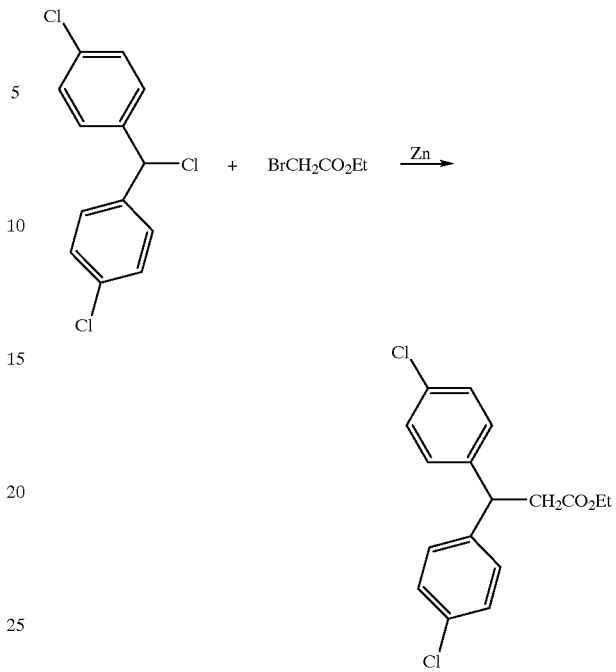

A solution of 3-[4-[2-[N-[Bis-(4-chlorophenyl)methyl]-N-methylamino]ethoxy]phenyl]-propanoic acid (0.592 g, 1.29 mmol) in dichloromethane (10 ml) was treated at 22° C. with oxalyl chloride (0.25 g, 1.97 mmol) and the resulting mixture was stirred for 1.5 h. The solvent was evaported in vacuo and the crude acid chloride was diluted with toluene (20 ml) and cooled to 0° C. Then trifluoroacetic anhydride (0.81 g, 3.87 mmol) was added followed by pyridine (0.22 g, 2.8 mmol) added dropwise over 10 min. The resulting mixture was then stirred at 22° C. for 2.5 h. The mixture was then cooled to 0° C. and treated dropwise with water (1 ml) and stirred for 15 min. The reaction mixture was then diluted with ethyl acetate, washed with saturated sodium bicarbonate, brine, and dried (magnesium sulfate). Evaporation of the solvent in vacuo and chromatography of the residue on silica gel (elution toluene ethyl acetate, 92:8) gave 0.465 g (70%) of title material as an oil.

Anal. Calcd. for $C_{26}H_{24}Cl_2F_3NO_2$: C 61.19, H 4.74, N 2.74. Found: C 61.17, H 4.60, N 2.96.

The hydrochloride salt was obtained as an amorphous solid.

Anal. Calcd. for $C_{26}H_{24}Cl_2F_3NO_2 \cdot HCl$: C 57.11, H 4.61, N 2.56. Found: C 57.09, H 4.97, N 2.38.

Example 10

4-[4-[2-[N-[3-Bis-(4-chlorophenyl)propyl]N-methylamino]ethoxy]phenyl]-1,1,1-trifluoro-2-butanone 3-Bis-(4-chlorophenyl)propanoic Acid, Ethyl Ester Ethyl bromoacetate (3.0 g, 18.0 mmol) was added dropwise to a boiling solution of zinc powder (1.7 g, 26.0 at g) and iodine (30.0 mg) in dichloromethane (5 ml) to form the Reformatsky reagent (K. Bott, Tetrahedron Lett., 1984, 35, 555–556). The mixture was then cooled to 0° C. and treated dropwise with a solution of 4,4'-dichlorobenzhydryl chloride (5.11 g, 15.8 mmol) in dichloromethane (10 ml) and the resulting mixture was stirred at 22° C. for 3 h. The reaction mixture was then diluted with ether, washed with 10% sulfuric acid, brine and dried (magnesium sulfate). Evaporation of the solvent in vacuo gave an oil which was chromatographed on silica gel to give 2.99 g (59%) of the title material as an oil: bp 110–115° C./0.1 torr.

Anal. Calcd. for $C_{17}H_{16}Cl_2O_2$: C 63.17, H 4.99. Found: C 62.94, H 4.90.

3-Bis-(4-chlorophenyl)propanoic Acid

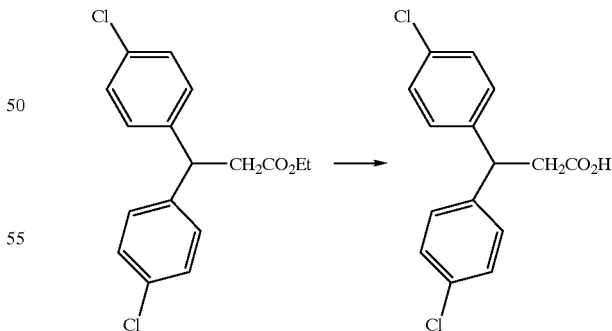

A solution of 3-Bis-(4-chlorophenyl)propanoic acid, ethyl ester (2.80 g, 8.66 mmol) in ethanol (40 ml) was treated with potassium hydroxide (1.0 g, 15.2 mmol) in water (10 ml) and the resulting mixture was heated at 60° C. for 1 h. The cooled mixture was concentrated in vacuo, water and dichloromethane were added and the aqueous phase was adjusted to $pH_3$ with 2N hydrochloric acid. The aqueous phase was extracted two times with dichloromethane and the combined organic extracts were dried (magnesium sulfate). Evaporation of the solvent gave 2.40 g (94%) of the title material as a white solid: mp 188–189° C.

N-(2-Hydroxyethyl)-N-methyl-3-bis-(4-chlorophenyl) propanamide

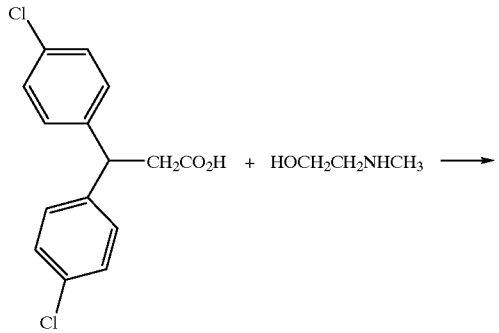

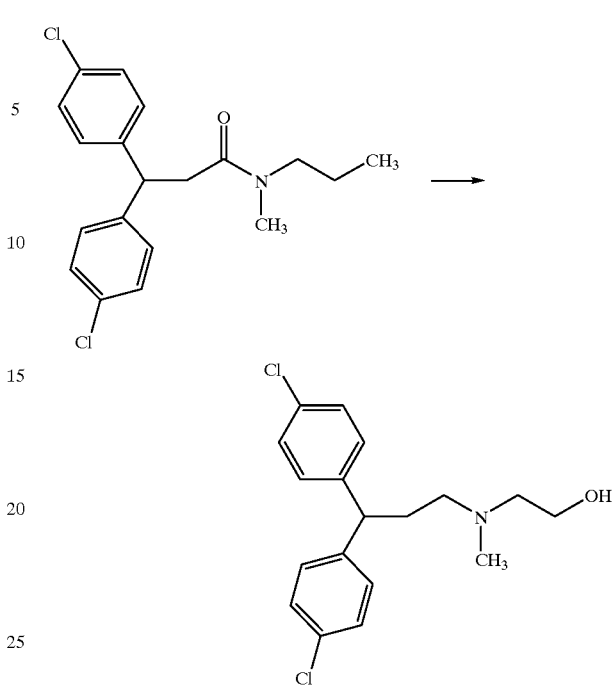

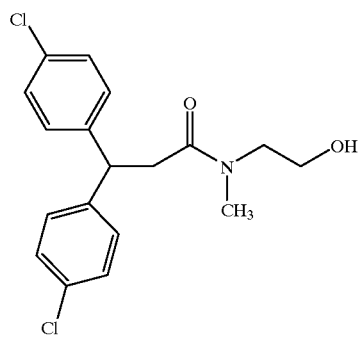

A solution of 3-Bis-(4-chlorophenyl)propanoic acid (2.33 g, 7.89 mmol) in dry dichloromethane (75 ml) was treated at 22° C. with oxalyl chloride (2.18 g, 17.2 mmol) and a small drop of N,N-dimethyl formamide. After 1 h, the solvent and excess reagent were evaporated in vacuo. The residual oil was diluted with dry tetrahydrofuran (10 ml) and added dropwise to a vigorously stirred solution of 2-(methylamino) ethanol (0.75 g, 10.0 mmol) in tetrahydrofuran (15 ml) and water (15 ml) containing sodium bicarbonate (1 g). After 2 h at 22° C., the mixture was diluted with ethyl acetate, washed with brine and dried (magnesium sulfate). Evaporation of the solvent under vacuum and chromatography of the residue on silica gel (elution dichloromethane-methanol 95:5) gave 2.63 g (93%) of the title material as an oil.

2-[N-[3-Bis-(4-chlorophenyl)propyl]-N-methylamino] ethanol

A solution of N-(2-hydroxyethyl)-N-methyl-3-bis-(4-chlorophenyl)propanamide (2.63 g, 7.47 mmol) in dry tetrahydrofuran (35 ml) was treated with solid lithium aluminum hydride (0.66 g, 17.4 mmol) added in small portion over 10 min. The resulting mixture was then heated at 60° C. for 2.5 h. The cooled solution was then quenched by successive addition of water (1 ml), 10% sodium hydroxide (1 ml) and water (2 ml). The solid formed was filtered and the filtrate was dried (magnesium sulfate) and concentrated in vacuo. The residual oil was chromatographed on silica gel (elution ethyl acetate and methanol 0–20%) to give 1.72 g (68%) of the title material as an oil.

Anal. Calcd. for $C_{18}H_{21}Cl_2NO$: C 63.91, H 6.26, N 4.14. Found: C 63.95, H 6.13, N 3.81.

3-[4-[2-[N-[3-Bis-(4-chlorophenyl)propyl]-N-methylamino]ethoxy]phenyl]-propanoic Acid, Methyl Ester

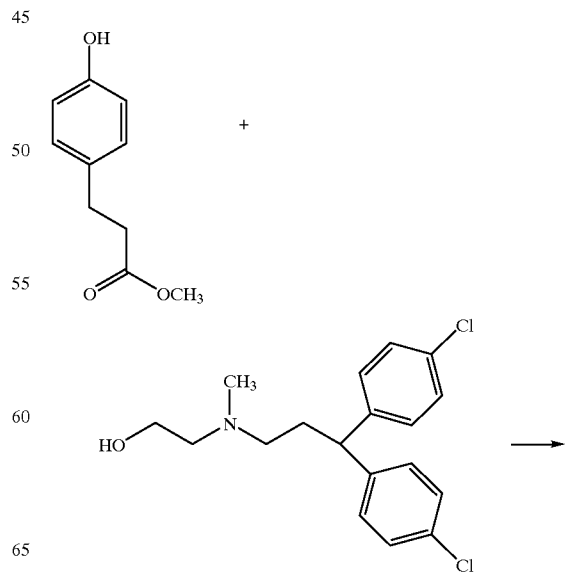

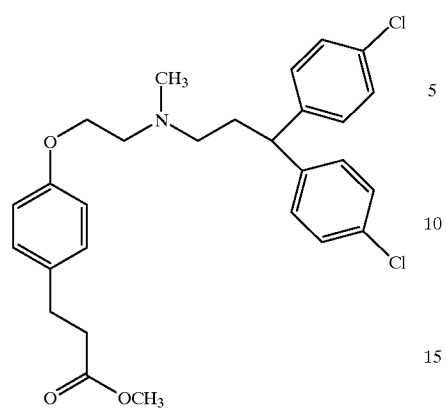

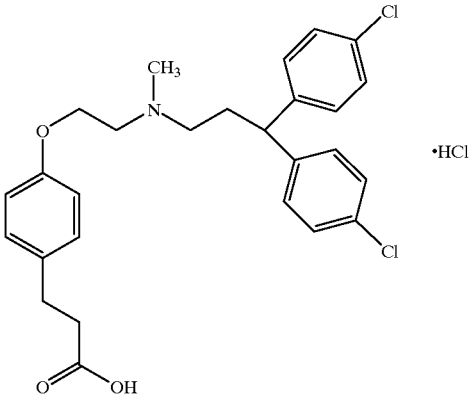

A solution of methyl 3-(4-hydroxyphenyl)propanoate (0.80 g, 4.44 mmol), 2-[N-[3-bis-(4-chlorophenyl)propyl]-N-methylamino]ethanol (1.62 g, 4.79 mmol) and triphenylphosphine (1.51 g, 5.76 mmol) in dry benzene (20 ml) was treated dropwise at 22° C. with diethyl azodicarboxylate (1.00 g, 5.77 mmol). After 3 h at 22° C., the reaction mixture was diluted in the ethyl acetate, washed with saturated sodium bicarbonate, brine and dried (magnesium sulfate). Evaporation of the solvent under vacuo and chromatography of the residue on silica gel (elution toluene-ethyl acetate 0–15%) gave 0.893 g (40%) of the title material as an oil.

Anal. Calcd. for $C_{28}H_{31}Cl_2NO_3 \cdot 0.2\ H_2O$: C 66.72, H 6.28, N 2.78. Found: C 66.60, H 6.31, N 2.92.

3-[4-[2-[N-[3-Bis-(4-chlorophenyl)propyl]-N-methylamino]ethoxy]phenyl]propanoic Acid, Hydrochloride Salt A solution of 3-[4-[2-[N-[3-Bis-(4-chlorophenyl)propyl]-N-methylamino]ethoxy]phenyl]-propanoic acid, methyl ester (0.801 g, 1.60 mmol) in ethanol (16 ml) was treated with potassium hydroxide (0.25 g, 3.8 mmol) in water (4 ml) and the resulting mixture was heated at 60° C. for 1 h. After cooling, the reaction mixture was concentrated in vacuo and the residue was diluted with water and dichloromethane. The aqueous phase was adjusted to pH 4 with 2N hydrochloric acid and extracted two times with dichloromethane. The combined organic extracts were dried (magnesium sulfate) and evaported in vacuo to give 0.700 g (90%) of the title material as a white foam.

Anal. Calcd. for $C_{27}H_{29}Cl_2NO_3 \cdot 0.7\ HCl$: C 63.34, H 5.85, N 2.74. Found: C 63.13, H 5.88, N 2.73.

4-[4-[2-[N-[3-Bis-(4-chlorophenyl)propyl]-N-methylamino]ethoxy]phenyl]-1,1,1-trifluoro-2-butanone

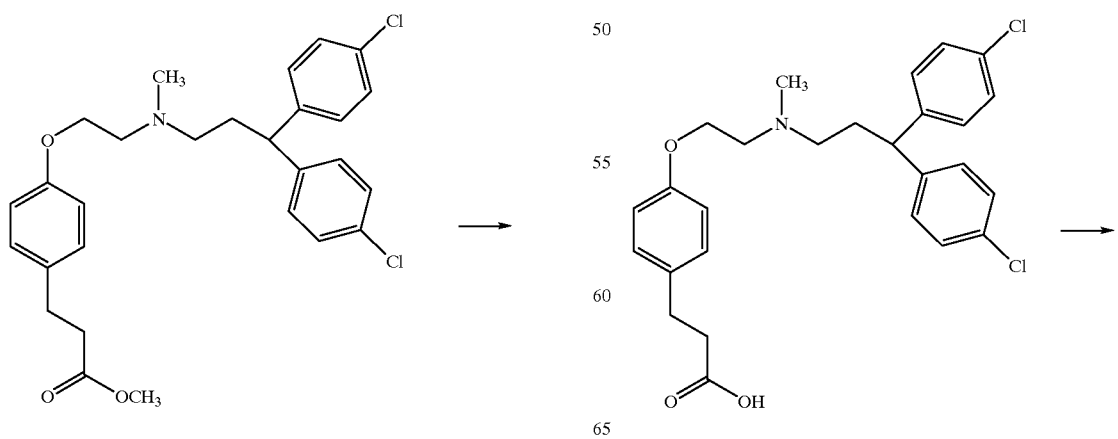

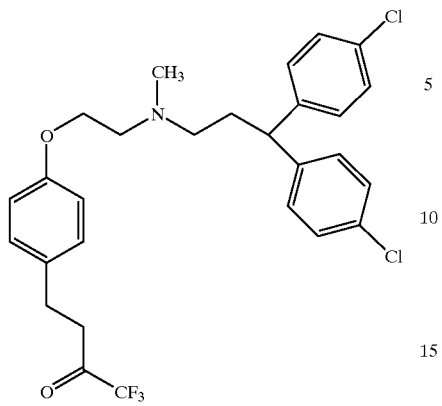

A solution of 3-[4-[2-[N-[3-Bis-(4-chlorophenyl)propyl]-N-methylamino]ethoxy]phenyl]propanoic acid, hydrochloride salt (0.660 g, 1.36 mmol) in dry dichloromethane (30 ml) was treated with oxalyl chloride (0.45 g, 3.5 mmol) and a trace of N,N-dimethylformamide. After 1 h at 25° C., the solvent and excess reagents were evaporated in vacuo. The residual oil was dissolved in dry toluene (30 ml), cooled to 0° C. and then treated with trifluoroacetic anhydride (0.6 ml, 4.25 mmol) followed by pyridine 0.3 ml, 3.71 mmol) added dropwise over 10 min. The resulting mixture was then stirred at 22° C. for 2.5 h. After cooling again to 0° C., water (5 ml) was added dropwise and the mixture was stirred at 22° C. for 30 min. The reaction mixture was then diluted with ethyl acetate, washed with saturated sodium bicarbonate, brine and dried (magnesium sulfate). Evaporation of the solvent under vacuum and chromatography of the residue on silica gel (elution gradient of toluene-ethyl acetate 1:1 to ethyl acetate) gave 0.307 g (42%) of the title material as an oil.

Anal. Calcd. for $C_{28}H_{28}Cl_2F_3NO_2 \cdot 0.5\ H_2O$: C 61.43, H 5.34, N 2.56. Found: C 61.46, H 5.13, N 2.60.

The hydrochloride salt was obtained as a white foam.

Anal. Calcd. for $C_{28}H_{28}Cl_2F_3NO_2 \cdot HCl \cdot H_2O$: C 56.72, H 5.27, N 2.36. Found: C 56.95, H 4.97, N 2.23.

The following compounds may be prepared by the general procedure of Scheme 1.

TABLE A

SCHEME 1

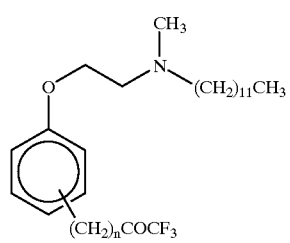

| Example No. | Position | n | Analysis |
|---|---|---|---|
| 11 | meta | 2 | $C_{25}H_{40}F_3NO_2 \cdot HCl \cdot 1.3H_2O$<br>Calcd: C 59.64, H 8.73, N 2.78<br>Found: C 59.57, H 8.99, N 2.68 |
| 12 | ortho | 2 | $C_{25}H_{40}F_3NO_2 \cdot HCl \cdot 0.4H_2O$<br>Calcd: C 61.32, H 8.65, N 2.87<br>Found: C 61.63, H 8.73, N 2.88 |
| 13 | para | 3 | $C_{26}H_{42}F_3NO_2 \cdot HCl \cdot 0.7H_2O$<br>Calcd: C 61.53, H 8.83, N 2.76<br>Found: C 61.63, H 8.72, N 2.84 |
| 14 | meta | 1 | $C_{24}H_{38}F_3NO_2 \cdot HCl \cdot 1.5H_2O$<br>Calcd: C 58.47, H 8.59, N 2.84<br>Found: C 58.43, 8.29, 3.12 |
| 15 | para | 3 | $C_{26}H_{42}F_3NO_2 \cdot 0.4H_2O$<br>Calcd: C 67.18, H 9.28, 3.01<br>Found: C 67.27, H 9.30, N 2.89 |
| 16 | para | 1 | $C_{24}H_{38}F_3NO_2 \cdot HCl \cdot 0.4H_2O$<br>Calcd: C 60.91, H 8.48, N 2.96<br>Found: C 60.94, H 8.88, N 3.21 |

TABLE B

SCHEME 1

| Example No. | R | Analysis |
|---|---|---|
| 17 | (CH$_2$)$_5$CH$_3$ | C$_{19}$H$_{28}$F$_3$NO$_2$.HCl.1.2H$_2$O<br>Calcd: C 54.66, H 7.58, N 3.35<br>Found: C 54.64, H 7.42, N 3.47 |
| 18 | (CH$_3$)$_7$CH$_3$ | C$_{21}$H$_{32}$F$_3$NO$_2$.HCl.0.7H$_2$O<br>Calcd: C 57.78, H 7.94, N 3.21<br>Found: C 57.73, H 7.84, N 3.22 |
| 19 | (CH$_2$)$_{17}$CH$_3$ | C$_{31}$H$_{52}$F$_3$NO$_2$.HCl.0.7H$_2$O<br>Calcd: C 65.57, H 9.48, N 2.47<br>Found: C 65.58, H 9.85, N 2.78 |
| 20 | (branched alkyl) | C$_{28}$H$_{42}$F$_3$NO$_2$.HCl.0.3H$_2$O<br>Calcd: C 68.48, H 9.57, N 2.85<br>Found: C 68.51, H 9.36, N 2.86 |
| 21 | (CH$_2$)$_3$C$_6$H$_5$ | C$_{22}$H$_{26}$F$_3$NO$_2$.0.3H$_2$O<br>Calcd: C 68.85, H 6.68, N 3.54<br>Found: C 66.73, H 6.51, N 3.61 |
| 22 | (CH$_2$)$_3$-C$_6$H$_4$-O(CH$_2$)$_3$CH$_3$ | C$_{26}$H$_{34}$F$_3$NO$_3$.HCl.H$_2$O<br>Calcd: C 60.05, H 7.17, N 2.69<br>Found: C 59.88, H 7.06, N 2.83 |
| 23 | CH(C$_6$H$_5$)$_2$ | C$_{26}$H$_{26}$F$_3$NO$_2$.HCl.0.5H$_2$O<br>Calcd: C 64.13, H 5.80, N 2.88<br>Found: C 64.25, H 5.75, N 2.93 |
| 24 | CH(4-F-C$_6$H$_4$)$_2$ | C$_{26}$H$_{24}$F$_5$NO$_2$.HCl.0.25H$_2$O<br>Calcd: C 60.24, H 4.96, N 2.70<br>Found: C 60.24, H 5.01, N 2.78 |

TABLE B-continued

SCHEME 1

| Example No. | R | Analysis |
|---|---|---|
| 25 | *(4-methoxyphenyl)(4-methoxyphenyl)ethyl group* | $C_{28}H_{30}F_3NO_4 \cdot HCl \cdot 0.5H_2O$<br>Calcd: C 61.48, H 5.90, N 2.56<br>Found: C 61.58, H 5.93, N 2.57 |
| 26 | *1,1-bis(3-methoxyphenyl)ethyl group* | $C_{28}H_{30}F_3NO_4 \cdot HCl \cdot H_2O$<br>Calcd: C 60.48, H 5.98, N 2.52<br>Found: C 60.91, H 5.46, N 2.68 |

$$\text{core structure: } CH_3\text{-}N(R)\text{-}CH_2CH_2\text{-}O\text{-}C_6H_4\text{-}CH_2CH_2CH_2\text{-}C(=O)CF_3$$

| Example No. | R | Analysis |
|---|---|---|
| 27 | *1-(4-chlorophenyl)-1-(3-methoxyphenyl)ethyl group* | $C_{27}H_{27}ClF_3NO_3 \cdot HCl \cdot 0.5H_2O$<br>Calcd: C 58.81, H 5.30, N 2.54<br>Found: C 58.42, H 4.94, N 2.66 |
| 28 | *1,1-bis(4-chloro-3-methoxyphenyl)ethyl group* | $C_{28}H_{28}Cl_2F_3NO_4 \cdot HCl \cdot 0.4H_2O$<br>Calcd: C 54.76, H 4.89, N 2.28<br>Found: C 54.81, H 4.87, N 2.40 |

TABLE B-continued

SCHEME 1

| Example No. | R | Analysis |
|---|---|---|
| 29 | 4-Cl, 3-OCH₃-phenyl-CH(CH₃)-3-OCH₃-phenyl | C$_{28}$H$_{29}$ClF$_3$NO$_4$·HCl<br>Calcd: C 58.75, H 5.28, N 2.45<br>Found: C 58.42, H 5.39, N 2.37 |
| 30 | 4-Cl, 3-OCH₃-phenyl-CH(CH₃)-4-Cl-phenyl | C$_{27}$H$_{26}$Cl$_2$F$_3$NO$_3$·HCl·0.4H$_2$O<br>Calcd: C 55.52, H 4.80, N 2.40<br>Found: C 55.47, H 4.92, N 2.45 |
| 31 | —CH$_2$—CH(phenyl)$_2$ | C$_{27}$H$_{28}$F$_3$NO$_2$·1.2H$_2$O<br>Calcd: C 63.13, H 6.16, N 2.73<br>Found: C 62.90, H 5.50, N 2.58 |
| 32 | —CH$_2$—CH(4-Cl-phenyl)$_2$ | C$_{27}$H$_{26}$Cl$_2$F$_3$NO$_2$·0.5H$_2$O<br>Calcd: C 56.76, H 4.94, N 2.45<br>Found: C 56.40, H 4.99, N 2.48 |

TABLE B-continued

SCHEME 1

| Example No. | R | Analysis |
|---|---|---|
| 33 | —CH₂—CH(4-OCH₃-C₆H₄)(4-OCH₃-C₆H₄) | $C_{29}H_{32}F_3NO_4 \cdot HCl \cdot H_2O$<br>Calcd: C 61.10, H 6.19, N 2.46<br>Found: C 61.17, H 5.88, N 2.27 |
| 34 | —CH₂CH₂—CH(C₆H₅)(C₆H₅) | $C_{28}H_{30}F_3NO_2 \cdot HCl \cdot H_2O$<br>Calcd: C 65.30, H 6.26, N 2.72<br>Found: C 65.30, H 6.36, N 3.10 |
| 35 | —CH₂CH₂—CH(4-OCH₃-C₆H₄)(4-OCH₃-C₆H₄) | $C_{30}H_{34}F_3NO_4 \cdot HCl \cdot 0.7H_2O$<br>Calcd: C 62.27, H 6.34, N 2.42<br>Found: C 62.28, H 6.23, N 2.41 |
| 36 | —CH₂CH₂CH₂—CH(C₆H₅)(C₆H₅) | $C_{29}H_{32}F_3NO_2 \cdot HCl \cdot H_2O$<br>Calcd: C 64.74, H 6.56, N 2.60<br>Found: C 64.80, H 6.54, N 2.63 |
| 37 | —CH₂CH₂CH₂—CH(4-Cl-C₆H₄)(4-Cl-C₆H₄) | $C_{29}H_{30}Cl_2F_3NO_2 \cdot HCl \cdot H_2O$<br>Calcd: C 57.39, H 5.48, N 2.31<br>Found: C 57.07, H 5.45, N 2.30 |

TABLE B-continued

SCHEME 1

| Example No. | R | Analysis |
|---|---|---|
| 38 | —CH$_2$CH$_2$CH$_2$—CH(4-OCH$_3$-C$_6$H$_4$)$_2$ | C$_{31}$H$_{36}$F$_3$NO$_4$·HCl·H$_2$O<br>Calcd: C 62.25, H 6.57<br>Found: C 61.89, H 6.37 |
| 39 | —CH$_2$CH$_2$CH$_2$CH$_2$—CH(C$_6$H$_5$)$_2$ | C$_{30}$H$_{34}$F$_3$NO$_2$·HCl·1.25·H$_2$O<br>Calcd: C 64.74, H 6.79, N 2.52<br>Found: C 64.78, H 6.83, N 2.56 |
| 40 | —CH$_2$CH$_2$CH$_2$CH$_2$—CH(4-Cl-C$_6$H$_4$)$_2$ | C$_{30}$H$_{32}$Cl$_2$F$_3$NO$_2$·HCl0.6·H$_2$O<br>Calcd: C 58.71, H 5.62, N 2.28<br>Found: C 58.62, H 5.39, N 2.29 |
| 41 | —CH$_2$CH$_2$O—CH(4-Cl-C$_6$H$_4$)$_2$ | C$_{28}$H$_{28}$Cl$_2$F$_3$NO$_3$·HCl0.8·H$_2$O<br>Calcd: C 55.56, H 5.10, N 2.31<br>Found: C 55.62, H 5.21, N 1.95 |

TABLE B-continued

SCHEME 1

| Example No. | R | Analysis |
|---|---|---|
| 42 | 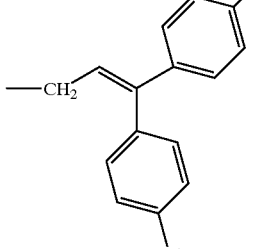 | $C_{28}H_{26}Cl_2F_3NO_2 \cdot HCl \cdot H_2O$<br>Calcd: C 56.92, H 4.95, N 2.37<br>Found: C 56.51, H 4.63, N 2.35 |
| 43 | 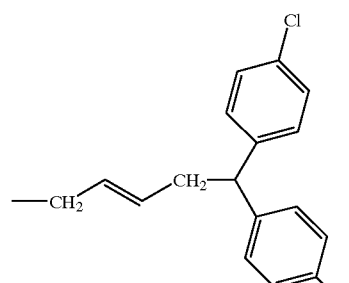 | $C_{30}H_{30}Cl_2F_3NO_2 \cdot HCl \cdot 1.5H_2O$<br>Calcd: C 57.38, H 5.46, N 2.23<br>Found: C 57.57, H 5.36, N 2.23 |
| 44 | 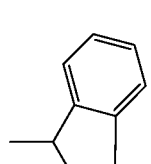 | $C_{26}H_{24}F_3NO_2 \cdot HCl \cdot 1.5H_2O$<br>Calcd: C 62.09, H 5.61, N 2.78<br>Found: C 62.08, H 5.69, N 2.82 |

TABLE C

SCHEME 1

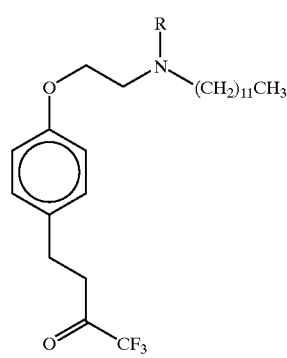

| Example No. | R | Analysis |
|---|---|---|
| 45 | CH$_2$Ph | $C_{31}H_{44}F_3NO_2 \cdot HCl \cdot 1.2H_2O$<br>Calcd: C 64.44, H 8.27, N 2.42<br>Found: C 64.53, H 8.27, N 2.37 |

TABLE C-continued

SCHEME 1

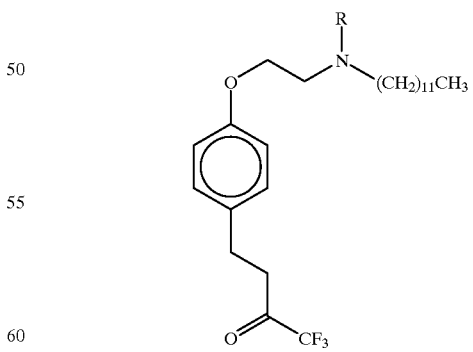

| Example No. | R | Analysis |
|---|---|---|
| 46 | (CH$_2$)$_3$CH$_3$ | $C_{28}H_{46}F_3NO_2 \cdot HCl \cdot 1.5H_2O$<br>Calcd: C 61.24, H 9.18, N 2.55<br>Found: C 61.34, H 9.14, N 2.60 |

TABLE C-continued
SCHEME 1
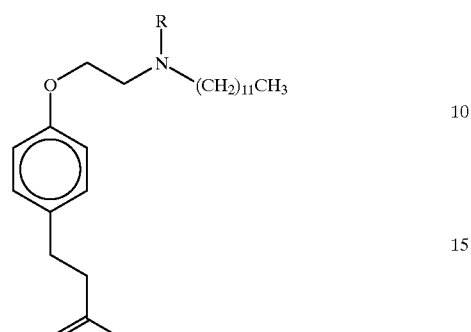
| Example No. | R | Analysis |
|---|---|---|
| 47 | 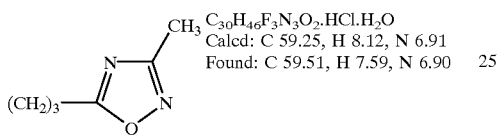 | $C_{30}H_{46}F_3N_3O_2 \cdot HCl \cdot H_2O$<br>Calcd: C 59.25, H 8.12, N 6.91<br>Found: C 59.51, H 7.59, N 6.90 |
Scheme 2
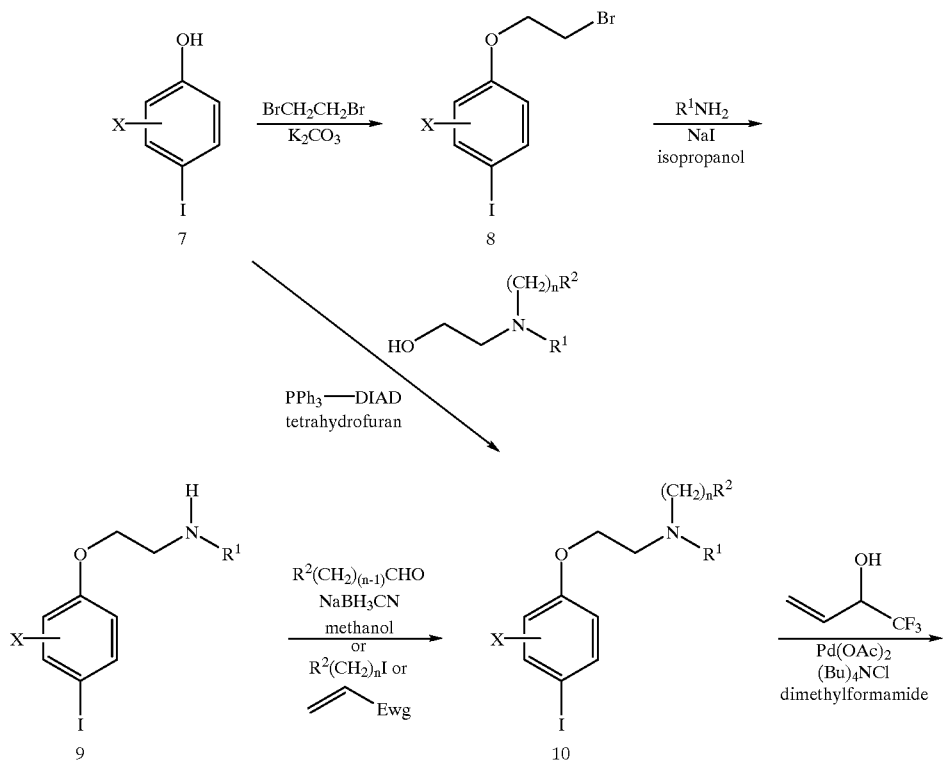

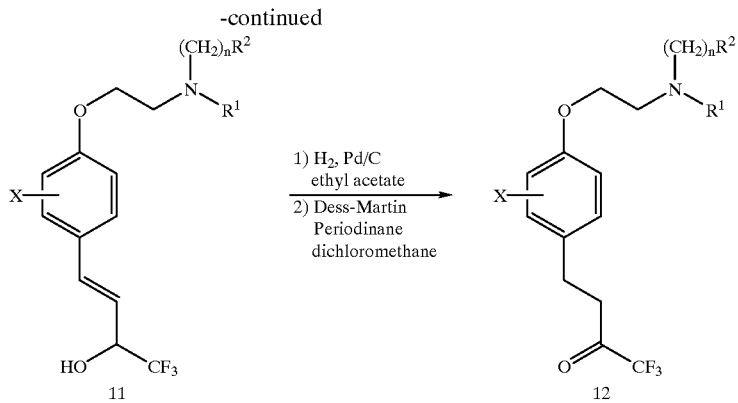

Example 48
4-[N-Dodecyl-N-[2-[4-(3-oxo-4,4,4-trifluorobut-1-yl)phenoxy]ethyl]amino]butanoic Acid, Ethyl Ester
Method I
1-[2-Bromoethoxy]-4-iodobenzene A mixture of 4-iodophenol (15.0 g, 68.2 mmol) and 1,2-dibromoethane (50 ml, 580 mmol) and potassium carbonate (14.0 g, 0.1 mol) was stirred and refluxed for 22 h. After cooling to r.t., the mixture was filtered, washed with ethyl acetate and concentrated in vacuo. The residue was chromatographed on silica gel (Hexane/ethyl acetate 40:1 to 20:1) to afford the title compound (18.7 g, 84%) as a white solid.

N-2-[4-Iodophenoxy]ethyldodecylamine

A mixture of dodecylamine (30 g, 162 mmol), diisopropylethylamine (22 ml, 128 mmol), sodium iodide (1.3 g, 8.5 mmol), 1-[2-bromoethoxy]-4-iodobenzene (13.9 g, 42.5 mmol) and isopropanol (250 ml) was stirred and refluxed for 24 h. After cooling to r.t., the mixture was filtered, washed with dichloromethane and concentrated in vacuo . The residue was chromatographed on silica gel (dichloromethane/methanol 50:1 to 20:1) to afford the title compound (15 g, 82%) as a white solid.

Analysis for its hydriodide salt $C_{20}H_{34}NIO.HI$ calcd. C 42.95%, H 6.31%, N 2.50%; Found: C 42.73%, H 6.16%, N 2.50%.

4-[N-dodecyl-N-2-[4-iodophenoxy]ethylamino]butanoic Acid, Ethyl Ester

To a mixture of N-2-[4-iodophenoxy]ethyldodecylamine (4.0 g, 9.3 mmol) and sodium cyanoborohydride (1.45 g, 23 mmol) in methanol (80 ml) was added dropwise a solution of ethyl 4-oxobutyrate (Fournet, G.; Balme, G.; Barieux, J. J. and Gore, *J.Tetrahedron*, 1988, 44, 5821) (2.4 g, 18 mmol) in methanol (20 ml) over a period of 10 min. The resulting mixture was stirred at 22° C. for 24 h, and then diluted with ethyl acetate (600 ml), washed with brine (3×250 ml). The aqueous phase was extracted with ethyl acetate (150 ml), and the combined organic layers were dried over sodium sulfate and concentrated in vacuo. The residue was chromatographed on silica gel (Hexane/ethyl acetate 8:1 to 6:1) to afford the title compound (4.5 g, 89%) as a colorless oil.

Analysis for $C_{26}H_{44}N$ $IO_3.0.3H_2O$, calcd. C 56.68%, H 8.16%, N 2.54%; Found: C 56.4% H 7.77%, N 2.63%.

4-[N-dodecyl-N-2-[4-(E)-[3-hydroxy-4,4,4-trifluorobut-1-en-1-yl]phenoxy]ethylamino]butanoic Acid, Ethyl Ester To a solution of 4-[N-dodecyl-N-2-[4-iodophenoxy]ethylamino]butanoic acid, ethyl ester (4.5 g, 8.3 mmol) and 4,4,4-trifluorobut-1-en-3-ol (Pegolotti, J. A. and Young, W. G. *J. Amer. Chem. Soc.*, 1961, 83, 3251) (complex with 1 tetrahydrofuran, 3.3 g, 16.6 mmol) in N, N-dimethylformamide (17 ml) were added sodium bicarbonate (1.75 g, 20.8 mmol), tetrabutyl ammonium chloride hydrate (2.5 g, 8.32 mmol) and palladium (II) acetate (56 mg, 0.25 mmol). The resulting mixture was stirred at 50° C. for 24 h, and then diluted with ethyl acetate (300 ml), washed with brine (100 ml), sat. aq. sodium thiosulfate (2×100 ml), brine (2×100 ml), dried over sodium sulfate and concentrated in vacuo. The residue was chromatographed on silica gel (Hexane/ethyl acetate 4:1 to 2:1) to afford the title compound (3.5 g, 78%) as a colorless oil and 0.3 g (6.6%) of 4-[N-Dodecyl-N-[2-[4-(4,4,4-trifluoro-3-oxo-but-1-yl)phenoxy]ethyl]amino]butanoic acid, ethyl ester.

Analysis for $C_{30}H_{48}F_3N$ $O_4$ calcd. C 66.27%, H 8.90%, N 2.58%; Found: C 65.92%, H 8.73%, N 2.59%

4-[N-Dodecyl-N-2-[4-[3-hydroxy-4,4,4-trifluorobutyl]phenoxy]ethylamino]butanoic Acid, Ethyl Ester A mixture of 4-[N-dodecyl-N-2-[4-(E)-[3-hydroxy-4,4,4-trifluorobut-1-en-1-yl]phenoxy]ethylamino] butanoic acid, ethyl ester (3.5 g, 6.46 mmol), palladium on activated carbon (10%, 0.6 g) and ethyl acetate (250 ml) was hydrogenated under 30 psi for 6 h. After filtration, the solvent was removed in vacuo to give the title compound (3.3 g, 94%) as a colorless oil.

4-[N-Dodecyl-N-[2-[4-(3-oxo-4,4,4-trifluorobut-1-yl)phenoxy]ethyl]amino]butanoic Acid, Ethyl Ester A suspension of 1,1, 1-triacetoxy-1,1-dihydro-1,2-benziodoxol-3(1H)-one (Dess-Martin periodinane, 1.7 g, 4.0 mmol) in dichloromethane (20 ml) was treated with 4-[N-dodecyl-N-2-[4-[4,4,4-trifluoro-3-hydroxybutyl]phenoxy]ethylamino]butanoic acid, ethyl ester (430 mg, 0.79 mmol) dissolved in dichloromethane (5 ml). The mixture was stirred at 22° C. for 4 h, poured into a saturated aqueous sodium bicarbonate and sodium thiosulfate (100 ml) and extracted with ethyl acetate (2×100 ml). The combined oganic layers were washed with sat. sodium bicarbonate (2×60 ml), brine (60 ml), dried over sodium sulfate and concentrated in vacuo . The residue was chromatographed on silica gel (hexane/ethyl acetate 2:1 to 1.5:1) to afford the title compound (333 mg, 77%) as a colorless oil.

Analysis for $C_{30}H_{48}F_3N$ $O_4.1.1H_2O$ calcd. C 63.94%, H 8.98%, N 2.49%; Found: C 63.55% H 8.55% N 2.61%.

Treatment of the above free amine with anhydrous hydrogen chloride (1.0 M in ether) gave the hydrochloride salt as a pale yellow syrup.

Example 49
3-[N-Dodecyl-N-[2-[4-(3-oxo-4,4,4-trifluorobut-1-yl)phenoxy]ethyl]amino]propanoic Acid, Ethyl Ester
3-[N-Dodecyl-N-[2-[4-iodophenoxy]ethyl]amino]propanoic Acid, Ethyl Ester A mixture of N-2-[4-iodophenoxy]ethyldodecylamine (1.0 g, 2.3 mmol), ethyl acrylate (1.2 g, 12 mmol) and ethanol (3 ml) was stirred and refluxed for 6 h, and then concentrated in vacuo. The residue was chromatographed on silica gel (hexane/ethyl acetate 8:1) to afford the title compound (1.05 g, 86%) as a colorless oil.

Analysis for $C_{25}H_{42}IN\ O_3$ calcd. C 56.49%, H 7.97%, N 2.64%; Found: C 56.79% H 8.10% N 2.59%.

3-[N-Dodecyl-N-2-[4-(E)-[3-hydroxy-4,4,4-trifluorobut-1-en-1-yl]phenoxy]ethylamino]propanoic Acid, Ethyl Ester

[N-Dodecyl-N-[2-[4-iodophenoxy]ethyl]amino] propanoic acid, ethyl ester (0.95 g, 1.79 mmol) and 4,4,4-trifluorobut-1-en-3-ol (complex with 0.7 THF, 0.95 g, 5.4 mmol) were reacted by the general procedure as described in the preparation of 4-[N-dodecyl-N-2-[4-(E)-[3-hydroxy-4,4,4-trifluorobut-1-en-1-yl]phenoxy]ethylamino]butanoic acid, ethyl ester (Example 48) and afforded the title compound (0.633 g, 76%) as a colorless oil.

3-[N-Dodecyl-N-2-[4-[3-hydroxy-4,4,4-trifluorobutyl]phenoxy]ethylamino]propanoic Acid, Ethyl Ester

[N-dodecyl-N-2-[4-(E)-[3-hydroxy-4,4,4-trifluorobut-1-en-1-yl]phenoxy]ethylamino]propanoic acid, ethyl ester (620 mg, 1.17 mmol) was hydrogenated as described in the preparation of 4-[N-dodecyl-N-2-[4-[3-hydroxy-4,4,4-trifluorobutyl]phenoxy]ethylamino]butanoic acid, ethyl ester (Example 48) and afforded the title compound (573 mg, 92%) as a clear oil.

Analysis for $C_{29}H_{48}F_3N\ O_4$ calcd. C 65.51%, H 9.10%, N 2.63%; Found: C 65.83% H 9.41% N 2.50%.

3-[N-Dodecyl-N-[2-[4-(3-oxo-4,4,4-trifluorobut-1-yl)phenoxy]ethyl]amino]propanoic Acid, Methyl Ester 3-[N-Dodecyl-N-2-[4-[3-hydroxy-4,4,4-trifluorobutyl]phenoxy]ethylamino]propanoic acid, ethyl ester (320 mg, 0.60 mmol) was oxidized as described in the preparation of 4-[N-dodecyl-N-[2-[4-(3-oxo-4,4,4-trifluorobut-1-yl)phenoxy]ethyl]amino]butanoic acid, ethyl ester (Example 48) and afforded the title compound (216 mg, 68%) as a pale yellow oil.

Analysis for $C_{29}H_{46}F_3N\ O_4 \cdot 0.8H_2O$ calcd. C 64.02%, H 8.82%, N 2.57%; Found: C 63.94% H 8.85% N 2.59%.

Treatment of the above free amine with anhydrous hydrogen chloride (1.0 M in ether) gave the hydrochloride salt as a pale yellow syrup.

Analysis for $C_{29}H_{46}F_3N\ O_4 \cdot HCl \cdot 1.5H_2O$ calcd. C 58.72%, H 8.50%, N 2.36%; Found: C 58.45% H 8.22% N 2.55%.

Example 50

(2S, 4S)-1-N-Dodecyl-4-[4-(3-hydroxy-4,4,4-trifluorobut-1-yl)phenoxy]pyrrolidine-2-carboxylic Acid, Methyl Ester trans-4-Hydroxy-L-proline, Methyl Ester, Hydrochloride To a freshly prepared sat. solution of hydrogen chloride in methanol (100 ml) was added trans-4-hydroxy-L-proline (10.0 g, 76.26 mmol). The resulting mixture was stirred at 22° C. for 24 h, concentrated in vacuo and triturated with acetone at 0° C. Filtration afforded the title compound (12.8 g, 92%) as a white solid.

(2S, 4R)-1-N-Dodecyl-4-hydroxypyrrolidine-2-carboxylic Acid, Methyl Ester

A solution of trans-4-hydroxy-L-proline, methyl ester, hydrochloride (4.0 g, 22.02 mmol) and 1-iodododecane (3.04 g, 44.04 mmol) in methanol (30 ml) was treated with potassium carbonate. The mixture was stirred and refluxed for 7 h, cooled to r.t., diluted with ethyl acetate (700 ml), washed with water (400 ml), brine (200 ml), dried over magnesium sulfate and concentrated in vacuo. The residue was chromatographed on silica gel (petroleum ether/ethyl acetate 60:40 to 40:60) to afford the title compound (3.72 g, 54%) as a white solid.

(2S, 4S)-1-N-Dodecyl-4-(4-iodophenoxy)pyrrolidine-2-carboxylic Acid, Methyl Ester (2S, 4R)-1-N-Dodecyl-4-hydroxypyrrolidine-2-carboxylic acid, methyl ester (1.75 g, 7.94 mmol) and 4-iodophenol (2.26 g, 7.22 mmol) were reacted under Mitsunobu conditions as described in the preparation of 3-[4-[2-(N-Dodecyl-N-methylamino)ethoxy]phenyl]propanoic acid, methyl ester. The residue was chromatographed on silica gel (hexane/ethyl acetate 15:1 to 10:1) to afford the title compound (3.23 g, 79%) as a white solid. $[a]D=-30.80$ (c 1.0, $CHCl_3$)

Analysis for $C_{24}H_{38}INO_3$ calcd. C 55.92%, H 7.43%, N 2.72%; Found: C 55.87%, H 7.48%, N 2.68%.

(2S, 4S)-1-N-Dodecyl-4-[4-(E)-[3-hydroxy-4,4,4-trifluorobut-1-en-1-yl]phenoxy]pyrrolidine-2-carboxylic Acid, Methyl Ester (2S, 4S)-1-N-Dodecyl-4-(4-iodophenoxy)pyrrolidine-2-carboxylic acid, methyl ester (800 mg, 1.55 mmol) and 4,4,4-trifluorobut-1-en-3-ol (complex with 1 tetrahydrofuran, 620 mg, 3.1 mmol) were reacted by the general procedure as described in the preparation of 4-[N-dodecyl-N-2-[4-(E)-[3-hydroxy-4,4,4-trifluorobut-1-en-1-yl]phenoxy]ethylamino]butanoic acid, ethyl ester and afforded the title compound (575 mg, 72%) as a colorless oil $[[a]_D=-28.7°$ (c 0.8, $CHCl_3$)] and (2S, 4S)-1-N-dodecyl-4-[4-(3-oxo-4,4,4-trifluorobut-1-yl)phenoxy]pyrrolidine-2-carboxylic acid, methyl ester (68 mg, 9%) as a pale yellow oil.

Analysis for $C_{28}H_{42}F_3N\ O_4 \cdot 0.3H_2O$ calcd. C 64.79%, H 8.27%, N 2.70%; Found: C 64.74% H 8.23% N 2.87%.

(2S, 4S)-1-N-Dodecyl-4-[4-[3-hydroxy-4,4,4-trifluoro-1-butyl]phenoxy]pyrrolidine-2-carboxylic Acid, Methyl Ester (2S, 4S)-1-N-Dodecyl-4-[4-(E)-[3-hydroxy-4,4,4-trifluorobut-1-en-1yl]phenoxy]pyrrolidine-2-carboxylic Acid, Methyl Ester (552 mg., 1.07 mmol) was hydrogenated as described in the preparation of 4-[N-dodecyl-N-2-[4-[3-hydroxy-4,4,4-trifluorobutyl]phenoxy] ethylamino]-butanoic acid, ethyl ester and afforded the title compound (546 mg, 99%) as a clear oil. $[a]_D=-89.0°$ (c 0.4, $CHCl_3$)

Analysis for $C_{28}H_{44}F_3N\ O_4$ calcd. C 65.22%, H 8.60%, N 2.72%; Found.: C 65.13% H 8.59% N 2.68%.

Example 51

(2S, 4S)-1-N-Dodecyl-4-[4-(3-oxo-4,4,4-trifluorobut-1-yl)phenoxy]pyrrolidine-2-carboxylic Acid, Methyl Ester (2S, 4S)-1-N-Dodecyl-4-[4-[3-hydroxy-4,4,4-trifluorobutyl]phenoxy]pyrrolidine-2-carboxylic Acid, Methyl Ester (425 mg, 0.825 mmol) was oxidized as described in the preparation of 4-[N-dodecyl-N-[2-[4-(3-oxo-4,4,4-trifluorobut-1-yl)phenoxy]ethyl]amino]butanoic acid, ethyl ester and afforded the title compound (272 mg, 64%) as a pale yellow oil.

Analysis for $C_{28}H_{42}F_3N\ O_4 \cdot 0.4H_2O$ calcd. C 64.57%, H 8.28%, N 2.69%; Found: C 64.61% H 8.08% N 2.76%.

Treatment of the above free amine with anhydrous hydrogen chloride (1.0 M in ether) gave the hydrochloride salt as a pale yellow foam. $[a]_D=-9.2°$ (c 0.74, $CHCl_3$)

$C_{28}H_{43}F_3N\ O_4 \cdot HCl \cdot 1.2H_2O$ calcd. C 58.82%, H 8.00%, N 2.45%; Found: C 58.79% H 7.85% N 2.41%.

Example 52

(2S, 4S)-1-Dodecyl-4-[4-(3-oxo-4,4,4-trifluorobut-1-yl)phenoxy]pyrrolidine-2-propanoic Acid, Methyl Ester (2S, 4S)-1-N-Dodecyl-4-(4-iodophenoxy)pyrrolidine-2-methanol To a solution of (2S, 4S)-1-N-dodecyl-4-(4-iodophenoxy) pyrrolidine-2-carboxylic acid, methyl ester (2.09 g, 4.06 mmol) in tetrahydrofuran (20 ml) at −78° C. was added dropwise diisobutylaluminum hydride (1.0M in hexane, 15.0 ml, 15.0 mmol). After stirring at this temperature for 5 min. and at 0° C. for 2.5 h, the reaction was quenched with water at 0° C. After stirring at r.t. for 10 min., the mixture was diluted with ethyl acetate (250 ml), washed with 2N sodium hydroxide (3×100 ml), 35% sodium and potassium tartrate (2×100 ml), brine (100 ml), dried over sodium sulfate and concentrated in vacuo. The residue was chromatographed on silica gel (hexane/ethyl acetate 3:1 to 2:1) to afford the title compound (1.65 g, 79%) as a colorless oil. $[a]_D=-18.5°$ (c 0.92, $CHCl_3$).

Analysis for $C_{23}H_{38}F_3INO_2$ calcd. C 56.67%, H 7.86%, N 2.87%; Found: C 56.65% H 7.39% N 2.95%.

(2S, 4S)-1-N-Dodecyl-4-(4-iodolphenoxy)pyrrolidine-2-propenoic Acid Methyl Ester To a solution of oxalyl chloride (1.1 ml, 12.1 mmol) in dichloromethane (17 ml) at −60° C. was added dropwise dimethylsufoxide (1.7 ml, 24.2 mmol). After stirring for 5 min., a solution of (2S, 4S)-1-N-dodecyl-4-(4-iodophenoxy)-pyrrolidine-2-methanol (1.18 g, 2.42 mmol) in dichloromethane (6 ml) was then added dropwise. The resulting mixture was stirred, and the temperature allowed to rise gradually to −20° C. over a period of 2 h. The reaction was quenched with sat. ammonium chloride, diluted with dichloromethane, washed three times with sat. ammonium chloride, brine and dried over sodium sulfate. The solvent was removed in vacuo to afford the corresponding aldehyde which was directly used in the next step.

The above material was dissolved in dichloromethane (20 ml) and treated with methyl (triphenyl-phosphoranylidene) acetate (1.44 g, 4.3 mmol). The mixture was stirred at 22° C. for 22 h and concentrated in vacuo. The residue was chromatographed on silica gel (hexane/ethyl acetate 15:1 to 10:1) to afford E-(2 S, 4S)-1-N-Dodecyl-4-(4-iodophenoxy) pyrrolidine-2-propenoic acid, methyl ester (934 mg, 61%) as a white solid [m.p. 60–61° C., $[a]_D=-42.2°$ (c 0.96, $CDCl_3$)] and Z-(2 S, 4S)-1-N-dodecyl-4-(4-iodophenoxy) pyrrolidine-2-propenoic acid, methyl ester (149 mg, 9%) as a clear oil. $[a]_D=-79.3°$ (c 1.24, $CHCl_3$).

Analysis for E-isomer $C_{26}H_{40}INO_3$ calcd. C 57.67%, H 7.45%, N 2.59%; Found: C 57.41% H 7.50% N 2.64%.

(2S, 4S)-1-N-Dodecyl-4-[4-(E)-[3-hydroxy-4,4,4-trifluorobut-1-en-1-yl-]phenoxy]pyrrolidine-2-propenoic Acid, Methyl Ester (2S, 4S)-1-N-Dodecyl-4-(4-iodophenoxy)pyrrolidine-2-propenoic acid, methyl ester (677 mg, 1.24 mmol) and 4,4,4-trifluorobut-1-en-3-ol (complex with 1 tetrahydrofuran, 1.23 g, 6.2 mmol) were reacted by the general procedure as described in the preparation of 4-[N-dodecyl-N-2-[4-(E)-[3-hydroxy-4,4,4-trifluorobut-1-en-1-yl]phenoxy]ethylamino]butanoic acid, ethyl ester and afforded the title compound (250 mg, 37%) as a colorless oil.

Analysis for $C_{30}H_{44}F_3N$ $O_4 \cdot 0.2H_2O$ calcd. C 66.32%, H 8.24%, N 2.58%; Found: C 66.14% H 8.03% N 2.55%.

(2S, 4S)-1-N-Dodecyl-4-[4-[3-hydroxy-4,4,4-trifluoro-1-butyl]phenoxy]pyrrolidine-2-propanoic Acid, Methyl Ester (2S, 4S)-1-N-Dodecyl-4-[4-(E)-[3-hydroxy-4,4,4-trifluorobut-1-en-1-yl]phenoxy]pyrrolidine-2-propenoic acid, methyl ester (260 mg., 0.482 mmol) was hydrogenated as described in the preparation of 4-[N-dodecyl-N-2-[4-[3-hydroxy-4,4,4-trifluorobutyl]phenoxy]ethylamino]butanoic acid, ethyl ester and afforded the title compound (185 mg, 71%) as a colorless oil. $[a]_D=-35.3°$ (c 0.85, $CHCl_3$)

Analysis for $C_{30}H_{48}F_3N$ $O_4 \cdot 0.1H_2O$ calcd. C 66.05%, H 8.91%, N 2.57%; Found: C 65.89% H 8.68% N 2.51%.

(2S, 4S)-1-N-Dodecyl-4-[4-(3-oxo-4,4,4-trifluorobut-1-yl) phenoxy]pyrrolidine-2-propanoic Acid, Methyl Ester (2S, 4S)-1-N-Dodecyl-4-[4-[3-hydroxy-4,4,4-trifluorobutyl]phenoxy]pyrrolidine-2-propanoic acid, methyl ester (150 mg, 0.276 mmol) was oxidized as described in the preparation of 4-[N-dodecyl-N-[2-[4-(3-oxo-4,4,4-trifluorobut-1-yl)phenoxy]ethyl]amino]butanoic acid, ethyl ester and afforded the title compound (70 mg, 47%) as a pale yellow oil. $[a]_D=-35.7°$ (c 0.84, $CDCl_3$)

Treatment of the above free amine with anhydrous hydrogen chloride (1.0 M in ether) gave the hydrochloride salt as a pale yellow foam.

$C_{30}H_{46}F_3N$ $O_4 \cdot HCl \cdot 1.1H_2O$ calcd. C 60.26%, H 8.29%, N 2.34%; Found: C 60.29% H 8.10% N 2.34%.

The following compounds may be prepared by the general procedure of Scheme 2.

TABLE A

SCHEME 2

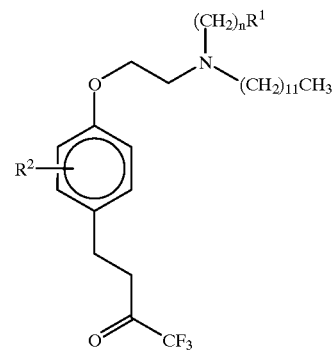

| Exp. # | n | $R^1$ | $R^2$ | Analysis |
|---|---|---|---|---|
| 53 | 1 | $CO_2Et$ | H | $C_{28}H_{44}F_3NO_4 \cdot HCl \cdot 1.5H_2O$ |
| | | | | Calcd: C 58.07, H 8.35, N 2.42 |
| | | | | Found: C 57.95, H 8.29, N 2.45 |
| 54 | 4 | $CO_2Et$ | H | $C_{31}H_{50}F_3NO_4 \cdot HCl \cdot 1.5H_2O$ |
| | | | | Calcd: C 59.94, H 8.76, N 2.25 |

TABLE A-continued

SCHEME 2

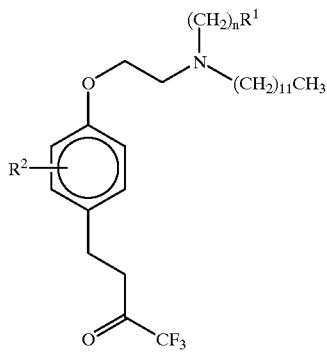

| Exp. # | n | R¹ | R² | Analysis |
|---|---|---|---|---|
| 55 | 3 | CO₂H | H | $C_{28}H_{44}F_3NO_4 \cdot 0.7HCl$<br>Calcd: C 62.14, H 8.33, N 2.59<br>Found: C 59.80, H 8.46, N 2.17<br>Found: C 62.25, H 8.36, N 2.58 |
| 56 | 4 | CO₂H | H | $C_{29}H_{46}F_3NO_4 \cdot HCl$<br>Calcd: C 61.52, H 8.37, N 2.47<br>Found: C 61.91, H 8.28, N 2.51 |
| 57 | 4 | O–C(=O)–C(CH₃)₃ | H | $C_{33}H_{54}F_3NO_4 \cdot HCl \cdot 0.7H_2O$<br>Calcd: C 62.43, H 8.95, N 2.21<br>Found: C 62.48, H 9.10, N 2.14 |
| 58 | 1 | H | 2-F | $C_{25}H_{39}F_4NO_2 \cdot HCl \cdot 1.6H_2O$<br>Calcd: C 56.99, H 8.26, N 2.66<br>Found: C 57.00, H 8.14, N 2.65 |
| 59 | 1 | H | 3-CH₂Ph | $C_{32}H_{46}F_3NO_2 \cdot HCl \cdot 0.7H_2O$<br>Calcd: C 65.95, H 8.37, N 2.40<br>Found: C 65.93, H 8.41, N 2.20 |

Scheme 3

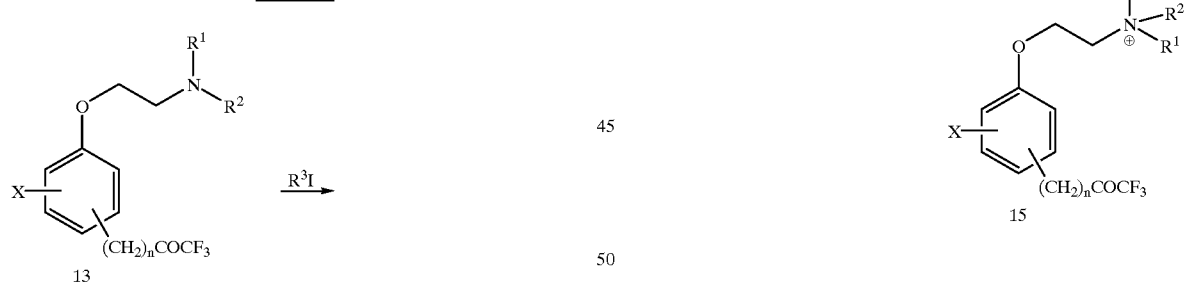

Example 60

N,N-Dimethyl-N-[2-[4-(3-oxo-4,4,4-trifluorobut-1-yl)-phenoxy]ethyl]dodecyl-ammonium, Iodide

A solution of 4-[4-[2-(N-Dodecyl-N-methylamino)ethoxy]phenyl]-1,1,1-trifluoro-2-butanone (250 mg, 0.56 mmol) in isopropanol (6 ml) and methyl iodide (2 ml) was heated to reflux for 0.5 h. After cooling to r.t., the mixture was evaporated in vacuo and the last traces of isopropanol co-evaporated with dichloromethane to afford the title compound (327 mg, 100%) as a yellow waxy solid.

Analysis for $C_{26}H_{43}F_3INO_2 \cdot 0.7H_2O$ calcd. C 52.21%, H 7.48%, N 2.34%; Found: C 52.21%, H 7.43%, N 2.40%.

Example 61

N,N-Dimethyl-N-[2-[3-(3-oxo-4,4,4-trifluorobut-1-yl)-phenoxy]ethyl]dodecyl-ammonium, Iodide 4-[3-[2-(N-Dodecyl-N-methylamino)ethoxy]phenyl]-1,1,1-trifluoro-2-butanone (300 mg, 0.68 mmol) was reacted by the general procedure as described in the preparation of N,N-dimethyl-N-[2-[4-(3-oxo-4,4,4-trifluorobut-1-yl)-phenoxy]ethyl]dodecyl-ammonium, iodide and afforded the title compound (397 mg, 100%) as a yellow syrup.

Analysis for $C_{26}H_{43}F_3INO_2 \cdot 1H_2O$ calcd. C 51.74%, H 7.52%, N 2.32%; Found: C 51.90%, H 7.58%, N 2.32%.

Example 62

N,N-Dimethyl-N-[2-[2-(3-oxo-4,4,4-trifluorobut-1-yl)-phenoxy]ethyl]dodecyl-ammonium, Iodide 4-[2-[2-(N-Dodecyl-N-methylamino)ethoxy]phenyl]-1,1,1-trifluoro-2-butanone (417 mg, 0.94 mmol) was reacted by the general procedure as described in the preparation of N,N-dimethyl-N-[2-[4-(3-oxo-4,4,4-trifluorobut-1-yl)-phenoxy]ethyl]dodecyl-ammonium, iodide and afforded the title compound (550 mg, 100%) as a yellow syrup.

Analysis for $C_{26}H_{43}F_3; INO_2 \cdot 0.5H_2O$ calcd. C 52.53%, H 7.46%, N 2.36%; Found: C 52.46%, H 7.42%, N 2.42%.

Example 63

N,N-Dimethyl-N-[2-[2-(trifluoroacetyl)phenoxy]ethyl] dodecylammonium, Iodide

[2-[2-(N,N-Dimethylamino)ethoxy]phenyl]-2,2,2-trifluoroethanone

A mixture of 2-trifluoroacetylphenol (380 mg, 2.0 mmol), 2-[N,N-dimethylamino]ethyl chloride, hydrochloride (432 mg, 6.0 mmol) potassium carbonate (1.38 g, 10 mmol) and toluene (5 ml) was refluxed for 3.5 h. After cooling to r.t., the mixture was treated with water and ether. The organic layer was washed twice with brine, dried over sodium sulfate and concentrated in vacuo. The residue was chromatographed on silica gel (acetone/ether 1:1 to 1:0) to give the title compound (375 mg, 72%) as a white solid.

N,N-Dimethyl-N-[2-[2-(trifluoroacetyl)phenoxy]ethyl] dodecylammonium, Iodide

A mixture of [2-[2-(N,N-Dimethylamino)ethoxy]phenyl]-2,2,2-trifluoroethanone (416 mg, 1.59 mmol), 1-iodododecane (1.42 g, 4.8 mmol) and isopropanol (20 ml) was refluxed for 24 h. After cooling to r.t., the solvent was removed in vacuo. The residue was chromatographed on silica gel [dicloromethane/methanol/ammonium hydroxide (28%) 90:10:1 to 85:15:1] to give a pale yellow solid. Recrystallization from acetone/ether (1:3) afforded the title compound (512 mg, 58%) as fine needles.

Analysis for $C_{24}H_{39}F_3INO_2$ calcd. C 51.71%, H 7.05%, N 2.51%; Found: C 51.83%, H 7.07%, N 2.51%.

Example 64

N,N-Dimethyl-N-[2-[2-(trifluoroacetyl)phenoxy]ethyl] octadecylammonium, Iodide

[2-[2-(N,N-Dimethylamino)ethoxy]phenyl]-2,2,2-trifluoroethanone (400 mg, 1.5 mmol) and 1-iodooctadecane (1.8 g, 4.8 mmol) were reacted by the general procedure as described in the preparation of N,N-dimethyl-N-[2-[2-(trifluoroacetyl)phenoxy]ethyl]dodecylammonium, iodide. Recrystallization from Acetone/ether (1:2) afforded the title compound (500 mg, 52%) as fine needles.

Analysis for $C_{30}H_{51}F_3INO_2$ calcd. C 56.16%, H 8.01%, N 2.18%; Found: C 56.06%, H 7.90%, N 2.13%.

Example 65

N,N-Dimethyl-N-[2-[4-(trifluoroacetyl)phenoxy]ethyl] octadecylammonium, Iodide

N,N-Dimethyl-2-(4-bromophenoxy)ethylamine

A mixture of 4-bromophenol (5.0 g, 28.9 mmol), 2-(N,N-dimethylamino)ethyl chloride, hydrochloride (6.24 g, 43.4 mmol), sodium iodide (600 mg, 4 mmol), cesium carbonate (28 g, 86.7 mmol) and methyl ethyl ketone (120 ml) was heated to reflux for 4 h. After cooling to r.t., the mixture was filtered and washed with acetone. The combined filtrates were concentrated in vacuo, and the residue was chromatographed on silica gel (dichloromethane/methanol 95:5 to 90:10) to give a pale yellow liquid. Bulb-to-bulb distillation (80–84° C./0.05 mmHg) afforded the title compound (5.19 g, 74%) as a colorless liquid.

[4-[2-(N,N-Dimethylamino)ethoxy]phenyl]-2,2,2-trifluoroethanone

To a solution of N,N-dimethyl-2-(4-bromophenoxy) ethylamine (1.0 g, 4.1 mmol) in tetrahydrofuran (10 ml) at −78° C. was added dropwise n-butyllithium (1.5M in hexane, 2.7 ml, 4.1 mmol). The mixture was stirred at this temperature for 15 min. and then transferred via a cannula into a pre-cooled solution of ethyl trifluoroacetate (0.64 g, 4.5 mmol) in ether (8 ml) at −78° C. The resulting mixture was stirred and the temperature allowed to rise gradually to r.t. over a period of 1.5 h. The reaction mixture was then quenched with water (5 ml) and diluted with ethyl acetate. The organic layer was washed with brine, dried over magnesium sulfate and concentrated in vacuo. Bulb-to-bulb distillation (82–84° C./0.01 mmHg) afforded the title compound (423 mg, 39%) as a pale yellow oil. Analysis for $C_{12}H_{14}F_3NO_2 \cdot 0.3H_2O$ calcd. C 54.05%, H 5.52%, N 5.25%; Found: C 54.12%, H 5.39%, N 5.28%.

N,N-Dimethyl-N-[2-[4-(trifluoroacetyl)phenoxy]ethyl] octadecylammonium, Iodide

[4-[2-(N,N-Dimethylamino)ethoxy]phenyl]-2,2,2-trifluoroethanone (343 mg, 1.31 mmol) and 1-iodooctadecane (1.16 g, 53.93 mmol) were reacted by the general procedures as described in the preparation of N,N-dimethyl-N-[2-[2-(trifluoroacetyl)phenoxy]ethyl] dodecylammonium, iodide. The residue was chromatographed on silica gel [dichloromethane/methanol/ ammonium hydroxide (28%) 98:2:0.5 to 90:10:1] to give the title compound (722 mg, 86%) as a white solid.

Analysis for $C_{30}H_{51}F_3INO_2$ calcd. C 56.16%, H 8.01%, N 2.18%; Found: C 56.33%, H 7.79%, N 2.09%.

Example 66

N,N-Dimethyl-N-[2-[3-(trifluoroacetyl)phenoxy]ethyl] octadecylammonium, Iodide

N,N-Dimethyl-2-(3-bromophenoxy)ethylamine

3-Bromophenol (5.0 g, 28.9 mmol) and 2-(N,N-dimethylamino)ethyl chloride, hydrochloride (6.24 g, 43.3 mmol) were reacted by the general procedures as described in the preparation of N,N-dimethyl-2-(4-bromophenoxy) ethylamine. The residue was chromatographed on silica gel (dichloromethane/methanol 100:0 to 90:10) to give the title compound (5.2 g, 74%) as a pale yellow liquid.

[3-[2-(N,N-Dimethylamino)ethoxy]phenyl]-2,2,2-trifluoroethanone

N,N-Dimethyl-2-(3-bromophenoxy)ethylamine (2.87 g, 11.7 mmol) and ethyl trifluoroacetate (2.5 g, 17.6 mmol) were reacted by the general procedure as described in the preparation of [4-[2-(N,N-dimethylamino)ethoxy]phenyl]-2,2,2-trifluoroethanone. The residue was distilled under reduced pressure to afford the title compound (1.34 g, 44%) as a pale yellow liquid. Analytically pure sample was obtained by a second distillation under reduced pressure. Analysis for $C_{12}H_{14}F_3NO_2 \cdot 0.8H_2O$ calcd. C 52.29%, H 5.70%, N 5.08%; Found: C 52.61%, H 5.53%, N 4.96%.

N,N-Dimethyl-N-[2-[3-(Trifluoroacetyl)phenoxy]ethyl] octadecylammonium, Iodide

[3-[2-(N,N-Dimethylamino)ethoxy]phenyl]-2,2,2-trifluoroethanone (438 mg, 1.67 mmol) and 1-iodooctadecane (1.9 g, 5.0 mmol) were reacted by the general procedure as described in the preparation of N,N-dimethyl-N-[2-[2-(trifluoroacetyl)phenoxy]ethyl] dodecylammonium, iodide. Recrystallization from acetone/ether (1:2) afforded the title compound (530 mg, 50%) as fine needles.

Analysis for $C_{30}H_{51}F_3INO_2 \cdot 0.2H_2O$ calcd. C 55.84%, H 8.03%, N 2.17%; Found: C 55.79%, H 7.98%, N 2.10%.

Example 67
N-[(Ethoxycarbonyl)methyl]-N-[2-[4-(3-oxo-4,4,4-trifluorobut-1-yl)phenoxy]ethyl]-N-(methyl)-dodecylammonium, Iodide A solution of 4-[4-[2-(N-Dodecyl-N-methylamino) ethoxy]phenyl]-1,1,1-trifluoro-2-butanone (620 mg, 1.4 mmol) and ethyl iodoacetate (0.5 ml, 4.2 mmol) in ethanol (20 ml) was heated to reflux for 3 h. After cooling to r.t., the mixture was concentrated in vacuo. The residue was chromatographed on silica gel [dichloromethane/methanol/ammonium hydroxide (28%) 95:5:0.5 to 90:10:1] to give a colorless syrup. This material was dissolved in aqueous tetrahydrofuran (90%), evaporated in vacuo and co-evaporated with acetonitrile to afford the title compound (855 mg, 93%) as a colorless syrup.

Example 68
N-(Carboxymethyl)-N-[2-[4-(3-oxo-4,4,4-trifluorobut-1-yl)phenoxy]ethyl]-N-(methyl)dodecyl Ammonium, Hydroxide, Inner Salt A solution of N-[(ethoxycarbonyl)methyl]-N-[2-[4-(3-oxo-4,4,4-trifluorobut-1-yl)phenoxy]ethyl]-N-(methyl)-dodecylammonium, iodide (617 mg, 0.938 mmol) in ethanol (95%, 20 ml) was treated with potassium hydroxide (63 mg, 1.12 mmol). The mixture was stirred at 22° C. for 3 h, and then concentrated in vacuo. The residue was chromatographed on silica gel [dichloromethane/methanol/ammonium hydroxide (28%) 90:10:1 to 85:15:1] to give a white solid. Recrystallization from ethanol-water (1:1) afforded the title compound (300 mg, 64%) as fine needles.

Analysis for $C_{27}H_{42}F_3NO_4 \cdot H_2O$ calcd. C 62.41%, H 8.54%, N 2.70%; Found: C 62.30%, H 8.70%, N 2.56%.

Example 69
N,N-Dimethyl-N-[2-[2-benzyl-4-(3-oxo-4,4,4-trifluorobut-1-yl)phenoxy]ethyl]dodecyl-ammonium, Iodide 4-[3-Benzyl-4-[2-(N-dodecyl-N-methylamino)ethoxy] phenyl]-1,1,1-trifluoro-2-butanone (180 mg, 0.338 mmol) was reacted by the general procedure as described in the preparation of N,N-dimethyl-N-[2-[4-(3-oxo-4,4,4-trifluorobut-1-yl)-phenoxy]ethyl]dodecyl-ammonium, iodide and afforded the title compound (228 mg, 100%) as a yellow syrup.

Analysis for $C_{33}H_{49}F_3INO_2 \cdot 1.1H_2O$ calcd. C 56.99%, H 7.42%, N 2.01%; Found: C 56.98%, H 7.25%, N 2.07%.

Example 70
N-[(Ethoxycarbonyl)methyl]-N-[2-[2-benzyl-4-(3-oxo-4,4,4-trifluorobut-1-yl)phenoxy]ethyl]-N-(methyl)-dodecylammonium, Iodide 4-[3-Benzyl-4-[2-(N-dodecyl-N-methylamino)ethoxy] phenyl]-1,1,1-trifluoro-2-butanone (340 mg, 0.638 mmol) was reacted by the general procedure as described in the preparation of N-[(ethoxycarbonyl)methyl]-N-[2-[4-(3-oxo-4,4,4-trifluorobut-1-yl)phenoxy]ethyl]-N-(methyl)-dodecylammonium, iodide and afforded the title compound (455 mg, 93%) as a yellow waxy solid.

Analysis for $C_{36}H_{53}F_3INO_4$ calcd. C 57.83%, H 7.14%, N 1.87%; Found: C 57.83%, H 7.56%, N 1.78%.

Example 71
N-(Carboxymethyl)-N-[2-[2-benzyl-4-(3-oxo-4,4,4-trifluorobut-1-yl)phenoxy]ethyl]-N-(methyl)dodecyl Ammonium, Hydroxide, Inner Salt N-[(Ethoxycarbonyl)methyl]-N-[2-[2-benzyl-4-(3-oxo-4,4,4-trifluorobut-1-yl)phenoxy]ethyl]-N-(methyl)-dodecylammonium, iodide (330 mg, 0.442 mmol) was saponified as described in the preparation of N-(carboxymethyl)-N-[2-[4-(3-oxo-4,4,4-trifluorobut-1-yl) phenoxy]ethyl]-N-(methyl)dodecyl ammonium, hydroxide, inner salt, and afforded the title compound (182 mg, 70%) as a white foam.

Analysis for $C_{34}H_{48}F_3NO_4 \cdot H_2O$ calcd. C 66.19%, H 8.30%, N 2.27%; Found: C 66.21%, H 8.15%, N 2.29%.

Example 72
N-[(Ethoxycarbonyl)methyl]-N-[2-[2-benzyl-4-(trifluoroacetyl)phenoxy]ethyl]-N-(methyl)-dodecylammonium, Iodide

[3-Benzyl-4-[2-(N-dodecyl-N-methylamino)ethoxy] phenyl]-2,2,2-trifluoroethanone (2.81 g, 5.56 mmol) was reacted by the general procedure as described in the preparation of N-[(ethoxycarbonyl)methyl]-N-[2-[4-(3-oxo-4,4,4-trifluorobut-1-yl)phenoxy]ethyl]-N-(methyl)-dodecylammonium, iodide and afforded the title compound (2.1 g, 52%) as a yellow solid.

Analysis for $C_{34}H_{48}F_3INO_4$ calcd. C 56.75%, H 6.86%, N 1.95%; Found: C 57.14%, H 6.94%, N 2.05%.

Example 73
N-(Carboxymethyl)-N-[2-[2-benzyl-4-(trifluoroacetyl) phenoxy]ethyl]-N-(methyl)dodecyl Ammonium, Hydroxide, Inner Salt N-[(Ethoxycarbonyl)methyl]-N-[2-[2-benzyl-4-(trifluoroacetyl)phenoxy]ethyl]-N-(methyl)-dodecylammonium, iodide (500 mg, 0.69 mmol) was saponified as described in the preparation of N-(carboxymethyl)-N-[2-[4-(3-oxo-4,4,4-trifluorobut-1-yl) phenoxy]ethyl]-N-(methyl)dodecyl ammonium, hydroxide, inner salt, and afforded the title compound (259 mg, 65%) as an off-white solid.

Analysis for $C_{32}H_{44}F_3NO_4 \cdot 0.7H_2O$ calcd. C 66.69%, H 7.94%, N 2.43%; Found: C 66.63%, H 8.00%, N 2.42%.

Scheme 4

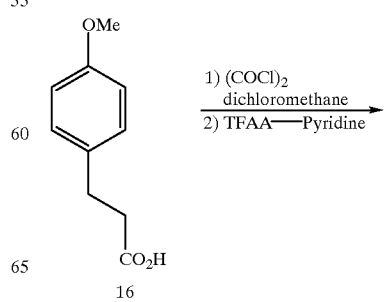

16

-continued

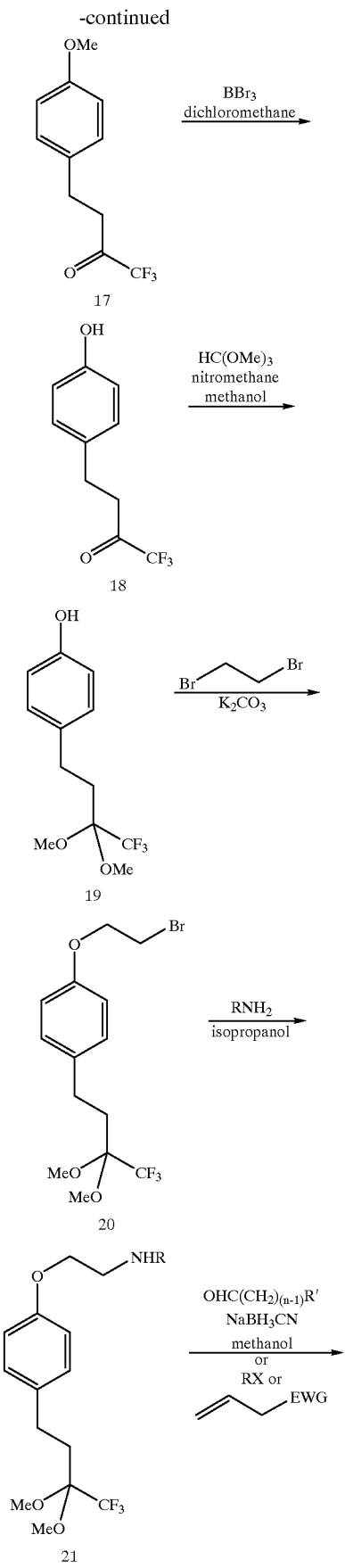

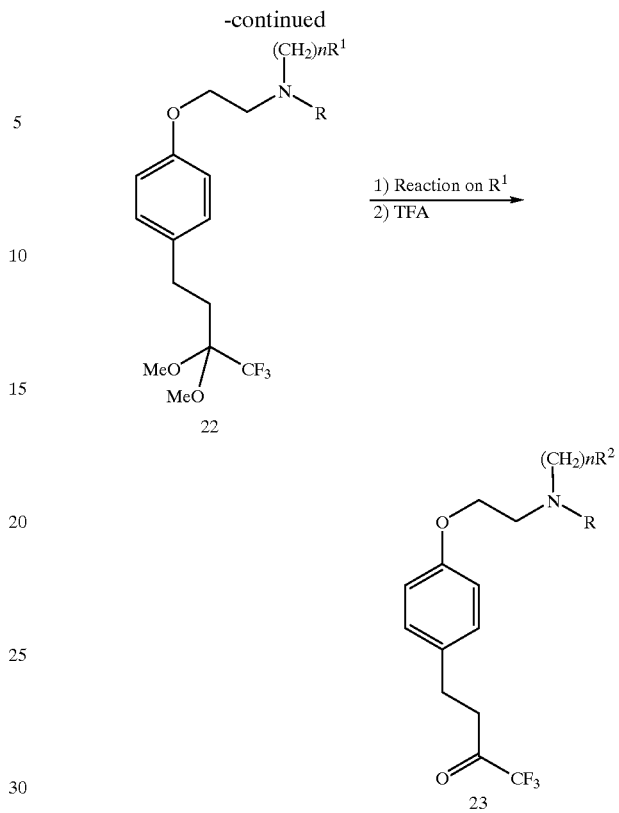

Example 74
4-[N-Dodecyl-N-[2-[4-(3-oxo-4,4,4-trifluorobut-1-yl)phenoxy]ethyl]amino]butanoic Acid, Ethyl Ester Method II 4-[4-Methoxyphenyl]-1,1,1-trifluoro-2-butanone To a solution of 3-[4-methoxyphenyl]propionic acid (40.0 g, 0.222 mol) in dichloromethane (300 ml) at 22° C. was added slowly oxalyl chloride (29 ml, 0.333 mol). After stirring for 2.5 h, the solvent and excess reagent were removed in vacuo. The residue was dissolved in dichloromethane (300 ml), and was then added to a solution of trifluoroacetic anhydride (294 ml, 0.666 mol) in dichloromethane (300 ml) at 0° C. (ice bath). Pyridine (36 ml, 0.444 mol) was then added dropwise at 0° C., and the reaction mixture was stirred for 0.5 h at which time the cooling bath was removed. After stirring at 22° C. for 3 h, the reaction was cooled again to 0° C. and quenched with distilled water (100 ml). The mixture was stirred at 22° C. for 1 h, neutralized with solid sodium bicarbonate, diluted with dichloromethane (1 L), washed with sat. aq. sodium bicarbonate (300 ml), brine (300 ml), dried over anhydrous magnesium sulfate and concentrated in vacuo. The residue was purified by bulb-to-bulb distilation (96–98° C., 0.2 mmHg) to afford the title compound (43.5 g, 84%) as a yellow liquid.

Analysis for $C_{11}H_{11}F_3O_2$ calcd. C 56.90%, H 4.78%; Found: C 56.61% H 4.98%.

4-[4-Hydroxyphenyl]-1,1,1-trifluoro-2-butanone

To a solution of 1,1,1-trifluoro-4-[4-methoxyphenyl]-2-butanone (43.5 g, 0.187 mol) in dichloromethane (500 ml) at −78° C. (dry ice-acetone) was added dropwise boron tribromide (53 ml, 0.561 mol). The mixture was then stirred at 0° C. (ice bath) for 3 h, and cautiously quenched by dropwise addition of ice-water (200 ml) over a period of 1 h. The aqueous phase was saturated with solid sodium chloride, extracted with dichloromethane (500 ml) followed by diethyl ether (500 ml). The combined organic layers were dried over anhydrous magnesium sulfate and concentrated in vacuo. The residue was purified by bulb-to-bulb distilation (96–100° C., 0.2 mmHg) to afford the title compound (34.4 g, 84%) as a yellow liquid which solidified upon standing.

Analysis for $C_{10}H_9F_3O_2.0.5H_2O$ calcd. C 52.87%, H 4.44%; Found: C 52.93% H 4.53%.

4-(3,3-Dimethoxy-4,4,4-trifluorobut-1-yl)phenol)

To a solution of 1,1,1-trifluoro-4-[4-hydroxyphenyl]-2-butanone (40.4 g, 0.185 mol) in nitromethane (300 ml) were added methanol (40 ml), trimethyl orthoformate (100 ml) and trifluoromethanesulfonic acid (1 ml). The resulting mixture was heated to 75° C. for 20 h, then cooled to r.t. and poured into sat. sodium bicarbonate (700 ml). After stirring for 10 min., the mixture was extracted with ethyl acetate (2×2 L). The combined organic layers were dried over anhydrous magnesium sulfate and concentrated in vacuo. The residue was chromatographed on silica gel (dichloromethane/methanol 98:2 to 97:3) to afford the title compound (21.5 g, 44%) as a yellow oil and 1,1,1-trifluoro-4-[4-hydroxyphenyl]-2-butanone (23 g, 57%). Analytically pure sample (20.2 g, 41%) of 4-(4,4,4-trifluoro-3,3-dimethoxybut-1-yl)phenol was obtained by bulb-to-bulb distillation (98–102° C., 0.02 mmHg).

[2-[4-(3,3-Dimethoxy-4,4,4-trifluorobut-1-yl)phenoxy]ethyl]bromide

A mixture of 4-(3,3-dimethoxy-4,4,4-trifluorobut-1-yl)phenol (1.64 g, 6.2 mmol), potassium carbonate (1.3 g, 9.3 mmol) and 1,2-dibromoethane (5 ml, 58 mmol) was stirred and heated under reflux (130° C.) for 26 h. After cooling to room temperature, the mixture was filtered and washed with ethyl actate. The filtrate was concentrated in vacuo and the residue was purified by column chromatography (silica gel, hexane/ethyl acetate 20:1 to 4:1) to give the title compound (2.0 g, 85%) as a colorless liquid.

Analysis for $C_{14}H_{18}Br F_3O_3$ calcd. C 45.30%, H 4.89%; Found: C 45.57% H 4.72%.

N-[2-[4-(3,3-Dimethoxy-4,4,4-trifluorobut-1-yl)phenoxy]ethyl]dodecanamine

A mixture of 4-[4-(2-bromoethoxy)phenyl]-1,1,1-trifluoro-2-butanone, dimethyl ketal (5.0 g, 13.5 mmol), dodecylamine (12.5 g 67.4 mmol), disopropylethylamine (7.0 ml, 40.4 mmol), NaI (2.0 g, 13.5 mmol) and isopropanol (100 ml) was stirred and heated under reflux for 16 h. After cooling to room temperature, the mixture was concentrated in vacuo, diluted with ethyl acetate (300 ml), washed with brine (100 ml), dried over anhydrous magnesium sulfate and concentrated in vacuo. The residue was chromatographed on silica gel (dichloromethane/methanol 98:2 to 96:4) to afford the title compound (5.3 g, 83%) as a colorless syrup.

Treatment of the above free amine with anhydrous hydrogen chloride (1.0 M in ether) gave the hydrochloride salt as a white solid.

Analysis for $C_{26}H_{44}F_3N$ $O_3.HCl$ calcd. C 60.98%, H 8.86%, N 2.74%; Found: C 60.73% H 8.56% N 2.73%.

4-[N-Dodecyl-N-[2-[4-(3,3-Dimethoxy-4,4,4-trifluorobut-1-yl)phenoxy]ethyl]amino]butanoic Acid, Ethyl Ester A solution of N-[2-[4-(3,3-dimethoxy-4,4,4-trifluorobut-1-yl)phenoxyethyl]dodecanamine (2.0 g, 4.2 mmol) in methanol (50 ml) was treated with sodium cyanoborohydride (0.55 g, 8.4 mmol) and ethyl 4-oxobutyrate (1.04 g, 8.4 mmol). The resulting mixture was stirred at 22° C. for 16 h, diluted with diethyl ether (350 ml), washed with water (200 ml), brine (200 ml), dried over magnesium sulfate and concentrated in vacuo. The residue was chromatographed on silica gel (hexane/AcOEt 9:1 to 6:1) to afford the title compound (1.8 g, 73%) as a liquid.

Analysis for $C_{32}H_{54}F_3N$ $O_5.0.3H_2O$ calcd. C 64.58%, H 9.25%, N 2.35%; Found: C 64.54% H 9.02% N 2.39%.

4-[N-Dodecyl-N-[2-[4-(3-oxo-4,4,4-trifluorobut-1-yl)phenoxy]ethyl]amino]butanoic Acid, Ethyl Ester A solution of 4-[N-Dodecyl-N-[2-[4-(3,3-dimethoxy-4,4, 4-trifluorobut-1-yl)phenoxy]ethyl]amino]-butanoic acid, ethyl ester (315 mg, 0.53 mmol) in trifluoroacetic acid (5 ml) was heated to 70° C. for 2 h, and then concentrated in vacuo. The residue was diluted with ethyl acetate (100 ml), washed with sat. sodium bicarbonate (30 ml), brine (30 ml), dried over magnesium sulfate and concentrated in vacuo. The residue was chromatographed on silica gel (Hexane/ethyl acetate 2:1 to 1.5:1) to afford the title compound (224 mg, 77%) as a colorless oil.

The following compounds may be prepared by the general procedure of Scheme 4.

TABLE

SCHEME 4

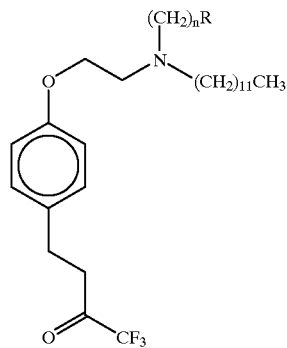

| Example No. | n | R | Analysis |
|---|---|---|---|
| 75 | 0 | H | $C_{24}H_{38}F_3NO_4.H_2O.0.3CO_2$ |
|  |  |  | Calcd: C 63.34, H 8.75, N 3.04 |
|  |  |  | Found: C 63.66, H 8.36, N 3.19 |
| 76 | 1 | $CH(CH_3)_2$ | $C_{28}H_{46}F_3NO_2.HCl.0.6H_2O$ |
|  |  |  | Calcd: C 63.10, H 9.12, N 2.63 |
|  |  |  | Found: C 62.92, H 9.18, N 2.68 |
| 77 | 1 | $C(CH_3)_3$ | $C_{29}H_{48}F_3NO_2.HCl.0.6H_2O$ |
|  |  |  | Calcd: C 63.68, H 9.25, N 2.56 |
|  |  |  | Found: C 63.51, H 8.91, N 2.61 |
| 78 | 4 | CONHEt | $C_{31}H_{51}F_3N_2O_3.HCl.1.8H_2O$ |
|  |  |  | Calcd: C 59.51, H 8.96, N 4.48 |
|  |  |  | Found: C 59.48, H 8.70, N 4.50 |
| 79 | 3 | CONHEt | $C_{30}H_{49}F_3N_2O_3.HCl.1.1H_2O$ |
|  |  |  | Calcd: C 60.15, H 8.78, N 4.68 |
|  |  |  | Found: C 60.15, H 8.54, N 4.63 |
| 80 | 5 | OH | $C_{29}H_{48}F_3NO_3.HCl.0.6H_2O$ |
|  |  |  | Calcd: C 61.87, H 8.99, N 2.49 |
|  |  |  | Found: C 61.81, H 8.58, N 2.66 |
| 81 | 4 | OH | $C_{28}H_{46}F_3NO_3.HCl0.5H_2O$ |
|  |  |  | Calcd: C 61.47, H 8.84, N 2.56 |
|  |  |  | Found: C 61.44, H 8.91, N 2.67 |
| 82 | 3 | $OCH_3$ | $C_{28}H_{46}F_3NO_3.HCl.1.2H_2O$ |
|  |  |  | Calcd: C 60.08, H 8.90, N 2.50 |
|  |  |  | Found: C 60.08, H 8.46, N 2.77 |
| 83 | 2 | CN | $C_{27}H_{41}F_3N_2O_3.HCl.0.8H_2O$ |
|  |  |  | Calcd: C 60.79, H 8.24, N 5.25 |
|  |  |  | Found: C 60.75, H 8.16, N 5.23 |

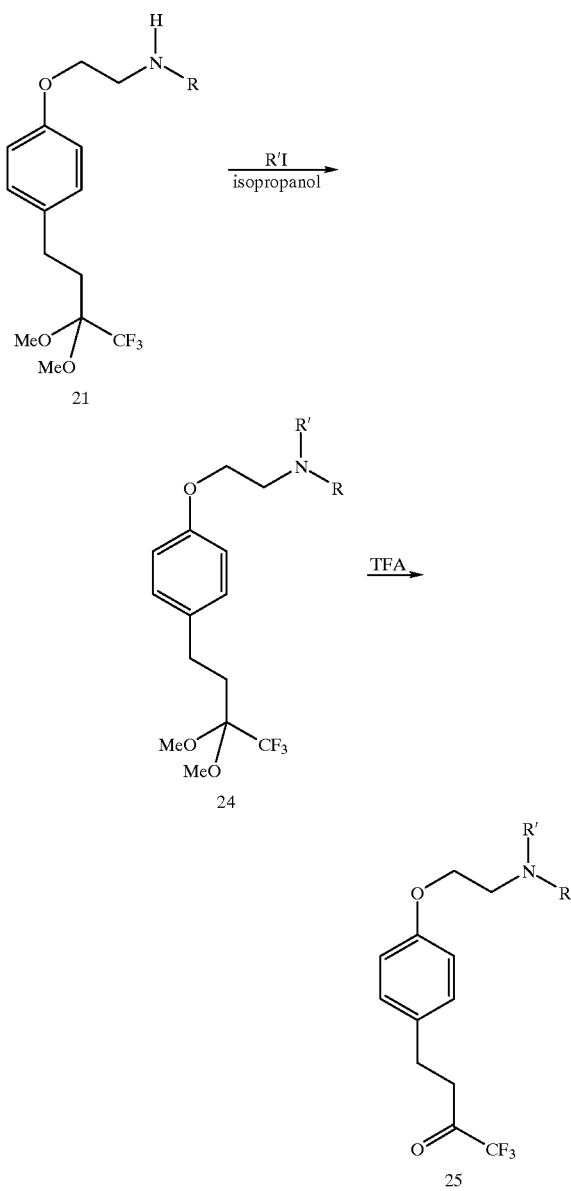

Example 84

4-[4-[2-(N-Dodecyl-N-propylamino]ethoxy]phenyl]-1,1,1-trifluoro-2-butanone

N-Propyl-N-[2-[4-(3,3-dimethoxy-4,4,4-trifluorobut-1-yl)phenoxy]ethyl]dodecylamine A solution of N-[2-[4-(3,3-dimethoxy-4,4,4-trifluorobut-1-yl)phenoxy]ethyl]dodecylamine (500 mg, 1.05 mmol), diisopropyl ethylamine (0.35 ml, 2.1 mmol) and 1-iodopropane (0.26 ml, 2.66 mmol) in isopropanol was heated to reflux for 21 h. After cooling to r.t., the mixture was diluted with ethyl acetate and filtered. The filtrate was concentrated in vacuo, and the residue was chromatographed on silica gel (dichloromethane/methanol 98:2 to 95:5) to afford the title compound (0.526 g, 73%) as a colorless oil.

4-[4-[2-(N-Dodecyl-N-propylamino]ethoxy]phenyl]-1,1,1-trifluoro-2-butanone

N-Propyl-N-[2-[4-(4,4,4-trifluoro-3,3-dimethoxybut-1-yl)phenoxy]ethyl]dodecylamine (300 mg, 0.58 mmol) was treated with trifluoroacetic acid as described in the preparation of 4-[N-dodecyl-N-[2-[4-(4,4,4-trifluoro-3-oxobut-1-yl)phenoxy]ethyl]amino]butanoic acid, ethyl ester and afforded the title compound (169 mg, 62%) as a pale yellow oil.

Analysis for $C_{27}H_{44}F_3NO_2 \cdot 0.9H_2O$ calcd. C 66.47%, H 9.46%, N 2.87%; Found: C 66.39%, H 9.10%, N 2.87%.

Treatment of the above free amine with anhydrous hydrogen chloride (1.0 M in ether) gave the hydrochloride salt as a pale yellow syrup. Analysis for $C_{27}H_{44}F_3NO_2 \cdot HCl \cdot 1.2H_2O$ calcd. C 61.22%, H 9.02%, N 2.64%; Found: C 61.38%, H 8.61%, N 2.75%.

Example 85

4-[4-[2-(N-Dodecyl-N-hexylamino]ethoxy]phenyl]-1,1,1-trifluoro-2-butanone

N-Hexyl-N-[2-[4-(3,3-dimethoxy-4,4,4-trifluorobut-1-yl)phenoxy]ethyl]dodecylamine N-[2-[4-(3,3-Dimethoxy-4,4,4-trifluorobut-1-yl)phenoxy]ethyl]dodecylamine (500 mg, 1.05 mmol) and 1-iodohexane (0.186 ml, 1.26 mmol) were reacted as described in the preparation of N-propyl-N-[2-[4-(3,3-dimethoxy-4,4,4-trifluorobut-1-yl)phenoxy]ethyl]dodecylamine and afforded the title compound (390 mg, g, 67%) as a liquid.

4-[4-[2-(N-Dodecyl-N-Hexylamino]ethoxyl]phenyl]-1,1,1-trifluoro-2-butanone

N-Hexyl-N-[2-[4-(3,3-dimethoxy-4,4,4-trifluorobut-1-yl)phenoxy]ethyl]dodecylamine (353 mg, 0.63 mmol) was treated with trifluoroacetic acid as described in the preparation of 4-[N-dodecyl-N-[2-[4-(4,4,4-trifluoro-3-oxobut-1-yl)phenoxy]ethyl]amino]butanoic acid, ethyl ester . The residue was chromatographed on silica gel (dichloromethane/methanol 98:2 to 94:6) to afford the title compound (253 mg, 78%) as a pale yellow oil.

Analysis for $C_{30}H_{50}F_3NO_2$ calcd. C 70.14%, H 9.81%, N 2.73%; Found: C 69.79%, H 9.82%, N 2.76%.

Treatment of the above free amine with anhydrous hydrogen chloride (1.0 M in ether) gave the hydrochloride salt as a pale yellow syrup.

Analysis for $C_{30}H_{50}F_3NO_2 \cdot HCl \cdot 0.7H_2O$ calcd. C 64.02%, H 9.39%, N 2.49%; Found: C 64.09%, H 9.05%, N 2.61%.

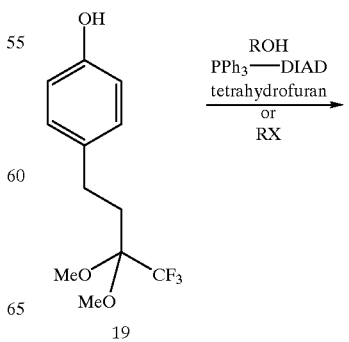

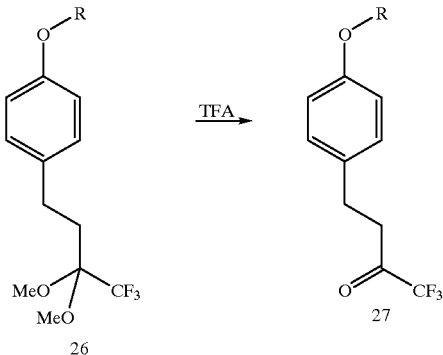

Example 86

4-[4-[2-(N-dodecyl-N-ethylamino)ethoxy]phenyl]-1,1,1-trifluoro-2-butanone

2-[N-Dodecyl-N-ethylamino]ethanol

2-[Dodecylamino]ethanol (2.0 g, 8.73 mmol), 1-iodoethane (1.63 g, 10.48 mmol) and N,N-diisopropylethylamine (2.51 g, 17.5 mmol) in isopropanol (25 ml) were heated under reflux for 4 h. The solvent was then evaporated in vacuo and the residue was diluted with ethyl acetate washed with aqueous sodium bicarbonate, brine and dried (magnesium sulfate). Evaporation of the solvent followed by chromatography on silica gel (ethyl acetate/methanol 90:10 to 80:20) afforded the title compound (1.65 g, 73%) as a white solid.

N-Ethyl-N-[2-[4-(3,3-dimethoxy-4,4,4-trifluoro-but-1-yl)phenoxy]ethyl]dodecylamine

2-[N-Dodecyl-N-ethylamino]ethanol (250 mg, 0.96 mmol) and 4-(3,3-dimethoxy-4,4,4-trifluorobut-1-yl)phenol (230 mg, 0.87 mmol) were reacted under Mitsunobu conditions as described in the preparation of 3-[4-[2-(N-dodecyl-N-methylamino)ethoxy]phenyl]propanoic acid, methyl ester. The usual work-up followed by chromatography on silica gel (Hexane/ethyl acetate 95:5 to 80:20) afforded the title compound (200 mg, 46%) as a colorless oil.

4-[4-[2-(N-dodecyl-N-ethylamino)ethoxy]phenyl]-1,1,1-trifluoro-2-butanone

N-Ethyl-N-[2-[4-(3,3-dimethoxy-4,4,4-trifluorobut-1-yl)phenoxy]ethyl]dodecylamine (123 mg, 0.244 mmol) was treated with trifluoroacetic acid as described in the preparation of 4-[N-dodecyl-N-[2-[4-(4,4,4-trifluoro-3-oxobut-1-yl)phenoxy]ethyl]amino]butanoic acid, ethyl ester and afforded the title compound (60 mg, 54%) as a pale yellow oil.

Treatment of the above free amine with anhydrous hydrogen chloride (1.0 M in ether) gave the hydrochloride salt as a pale yellow syrup.

Analysis for $C_{26}H_{42}F_3NO_2 \cdot HCl \cdot 0.6H_2O$ calcd. C 60.45%, H 8.64%, N 2.69%; Found: C 60.19%, H 8.27%, N 3.08%.

The following compounds may be prepared by the general procedure of Scheme 6.

TABLES

SCHEME 6

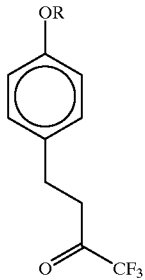

| Exp. # | R | Analysis |
|---|---|---|
| 87 | CH₂CH₂N((CH₂)₅CH₃)₂ | $C_{24}H_{38}F_3NO_2 \cdot HCl \cdot 1.4H_2O$<br>Calcd: C 58.68, H 8.58, N 2.85<br>Found: C 58.81, H 8.45, N 2.91 |
| 88 | CH₂CH₂N((CH₂)₇CH₃)₂ | $C_{28}H_{46}F_3NO_2 \cdot HCl \cdot 0.8H_2O$<br>Calcd: C 62.68, H 9.18, N 2.61<br>Found: C 62.52, H 9.25, N 2.69 |
| 89 | CH₂CH₂N(CH₂C₆H₅)₂ | $C_{26}H_{26}F_3NO_2 \cdot HCl \cdot 0.8H_2O$<br>Calcd: C 63.43, H 5.86, N 2.84<br>Found: C 63.39, H 5.95, N 2.88 |

TABLES-continued

SCHEME 6

| Exp. # | R | Analysis |
|---|---|---|
| 90 | 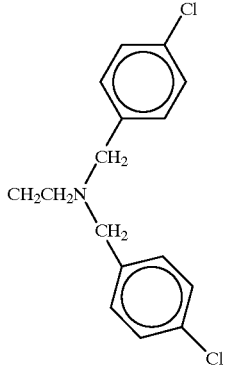 | $C_{26}H_{24}Cl_2F_3NO_2 \cdot HCl \cdot 0.7H_2O$<br>Calcd: C 55.82, H 4.76, N 2.50<br>Found: C 55.81, H 4.90, N 2.52 |
| 91 | 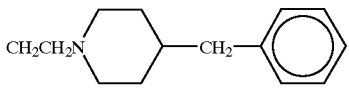 | $C_{24}H_{28}F_3NO_2 \cdot HCl \cdot 0.9H_2O$<br>Calcd: C 61.05, H 6.58, N 2.97<br>Found: C 61.17, H 6.54, N 3.05 |
| 92 | 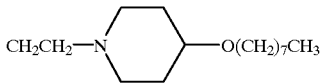 | $C_{25}H_{38}F_3NO_3 \cdot HCl \cdot 0.7H_2O$<br>Calcd: C 59.27, H 8.04, N 2.76<br>Found: C 59.26, H 8.18, N 2.98 |
| 93 | 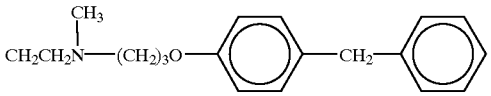 | $C_{29}H_{32}F_3NO_3 \cdot HCl \cdot 0.9H_2O$<br>Calcd: C 63.07, H 6.35, N 2.54<br>Found: C 62.95, H 6.40, N 2.67 |
| 94 | 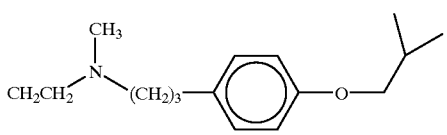 | $C_{26}H_{34}F_3NO_3 \cdot HCl \cdot H_2O$<br>Calcd: C 60.05, H 7.17, N 2.69<br>Found: C 60.03, H 7.26, N 2.79 |
| 95 | 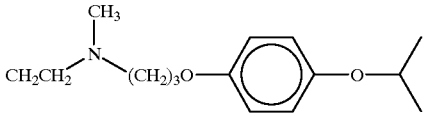 | $C_{25}H_{32}F_3NO_3 \cdot HCl \cdot 0.6H_2O$<br>Calcd: C 60.20, H 6.91, N 2.81<br>Found: C 60.11, H 7.11, N 2.89 |
| 96 | $(CH_2)_{11}CH_3$ | $C_{22}H_{33}F_3O_2$<br>Calcd: C 68.37, H 8.61<br>Found: C 68.09, H 8.42 |
| 97 | $(CH_2)_{14}CH_3$ | $C_{25}H_{29}F_3O_2 \cdot H_2O$<br>Calcd: C 69.48, H 9.19<br>Found: C 69.37, H 9.29 |
| 98 | $CH_2CH_2O(CH_2)_{11}CH_3$ | $C_{24}H_{37}F_3O_3$<br>Calcd: C 66.95, H 8.66<br>Found: C 66.76, H 8.47 |
| 99 | $CH_2\}_2$ (dimer) | $C_{22}H_{20}F_6O_4 \cdot 0.5H_2O$<br>Calcd: C 56.06, H 4.49<br>Found: C 56.11, H 4.45 |
| 100 | 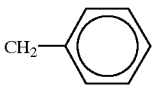 | $C_{17}H_{15}F_3O_2$.<br>Calcd: C 66.23, H 4.90<br>Found: C 66.25, H 4.99 |
| 101 | $CH_2CH_2Br$ | $C_{12}H_{12}BrF_3O_2$<br>Calcd: C 44.33, H 3.72<br>Found: C 44.71, H 3.80 |

TABLES-continued
SCHEME 6
| Exp. # | R | Analysis |
|---|---|---|
| | 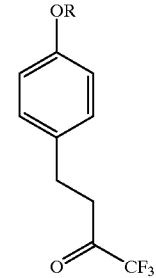 | |
| 102 | 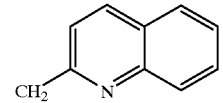 | $C_{20}H_{16}F_3NO_2 \cdot HCl \cdot 0.8H_2O$<br>Calcd: C 58.56, H 4.57, N 3.41<br>Found: C 58.31, H 4.19, N 3.45 |
| 103 | —C(O)(CH$_2$)$_{14}$CH$_3$ | $C_{26}H_{39}F_3O_3 \cdot 0.3H_2O$<br>Calcd: C 67.60, H 8.64<br>Found: C 67.55, H 8.45 |
| 104 | 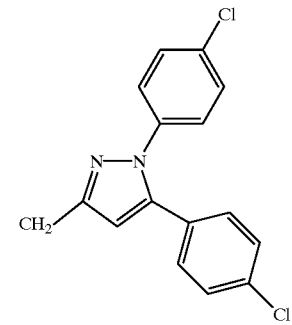 | $C_{26}H_{19}Cl_2F_3N_2O_2$<br>Calcd: C 60.13, H 3.69, N 5.39<br>Found: C 60.37, H 3.71, N 5.39 |
| 105 | 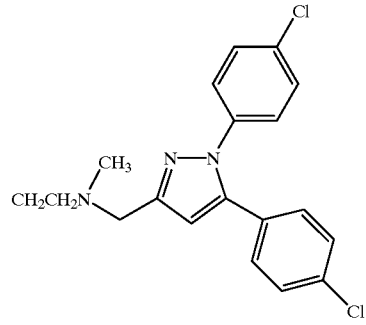 | $C_{29}H_{26}Cl_2F_3N_3O_2 \cdot HCl \cdot 1.1H_2O$<br>Calcd: C 55.05, H 4.65, N 6.64<br>Found: C 54.96, H 4.61, N 6.62 |
| 106 | 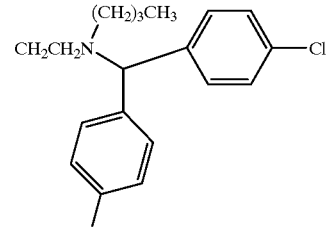 | $C_{29}H_{30}Cl_2F_3NO_2 \cdot HCl \cdot 0.7H_2O$<br>Calcd: C 57.91, H 5.43, N 2.33<br>Found: C 57.98, H 5.42, N 2.12 |

TABLES-continued

SCHEME 6

| Exp. # | R | Analysis |
|---|---|---|
| 107 | (structure: CH₂CH₂N((CH₂)₃CH₃) attached to CH bearing two 4-methoxyphenyl groups) | C₃₁H₃₆F₃NO₄·HCl·0.7H₂O<br>Calcd: C 62.82, H 6.53, N 2.36<br>Found: C 62.87, H 6.33, N 2.08 |
| 108 | (structure: CH₂CH₂N((CH₂)₃CH₃) linked via CH₂ to CH bearing two 4-chlorophenyl groups) | C₃₀H₃₂Cl₂F₃NO₂·HCl·0.6H₂O<br>Calcd: C 58.71, H 5.62, N 2.28<br>Found: C 58.64, H 5.51, N 2.33 |
| 109 | (structure: CH₂CH₂N((CH₂)₃CH₃) linked via CH₂ to CH bearing two 4-methoxyphenyl groups) | C₃₂H₃₈F₃NO₄·HCl·H₂O<br>Calcd: C 62.79, H 6.75, N 2.29<br>Found: C 62.81, H 6.82, N 2.15 |
| 110 | (structure: 3-methylpyrrolidine-N-CH₂-CH(Ph)(Ph)) | C₂₈H₂₈F₃NO₂·HCl·0.3H₂O<br>Calcd: C 66.02, H 5.86, N 2.75<br>Found: C 65.93, H 5.98, N 2.74 |
| 111 | (structure: 3-methylpyrrolidine-N-CH₂-CH(4-ClC₆H₄)(4-ClC₆H₄)) | C₂₈H₂₆Cl₂F₃NO₂·HCl·H₂O<br>Calcd: C 56.84, H 4.77, N 2.36<br>Found: C 56.76, H 4.88, N 2.42 |

TABLES-continued

SCHEME 6

| Exp. # | R | Analysis |
|---|---|---|
| 112 | [structure: 3-methylpyrrolidine N-CH2-CH(4-methoxyphenyl)(4-methoxyphenyl)] | $C_{30}H_{32}F_3NO_4 \cdot HCl \cdot 0.9H_2O$<br>Calcd: C 62.10, H 6.05, N 2.41<br>Found: C 62.11, H 6.33, N 2.48 |
| 113 | [structure: 2-CO2CH3, 4-methyl pyrrolidine N-CH2-CH(4-methoxyphenyl)2] | $C_{32}H_{34}F_3NO_6 \cdot HCl \cdot 2.5H_2O$<br>Calcd: C 57.61, H 6.04, N 2.10<br>Found: C 57.56, H 5.44, N 2.11 |
| 114 | [structure: 2-CH2OCH3, 4-methyl pyrrolidine N-CH2-CH(4-methoxyphenyl)2] | $C_{32}H_{36}F_3NO_5 \cdot HCl \cdot 1.5H_2O$<br>Calcd: C 60.52, H 6.35, N 2.21<br>Found: C 60.49, H 6.34, N 2.17 |
| 115 | [structure: 4-methylpiperidine N-CH(4-methoxyphenyl)(4-methoxyphenyl)] | $C_{30}H_{32}F_3NO_4 \cdot HCl \cdot 0.7H_2O$<br>Calcd: C 62.49, H 6.01, N 2.43<br>Found: C 62.36, H 6.00, N 2.36 |

TABLES-continued
SCHEME 6
| Exp. # | R | Analysis |
|---|---|---|
| 116 | 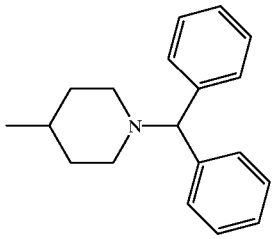 | $C_{29}H_{30}F_3NO_2 \cdot HCl \cdot 2H_2O$<br>Calcd: C 62.87, H 6.37, N 2.53<br>Found: C 62.89, H 6.02, N 2.62 |
| 117 | 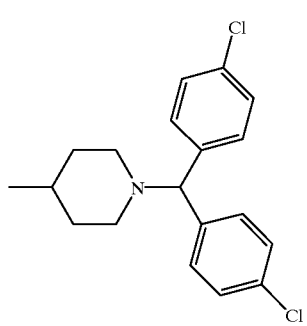 | $C_{29}H_{28}Cl_2F_3NO_2 \cdot HCl \cdot 1.6H_2O$<br>Calcd: C 56.57, H 5.27, N 2.27<br>Found: C 56.2, H 4.86, N 2.25 |
| 118 | 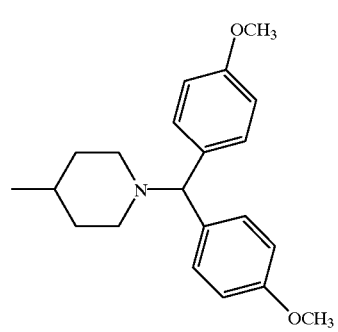 | $C_{31}H_{34}F_3NO_4 \cdot HCl0.9H_2O$<br>Calcd: C 62.65, H 6.24, N 2.36<br>Found: C 62.58, H 6.15, N 2.42 |
Scheme 7
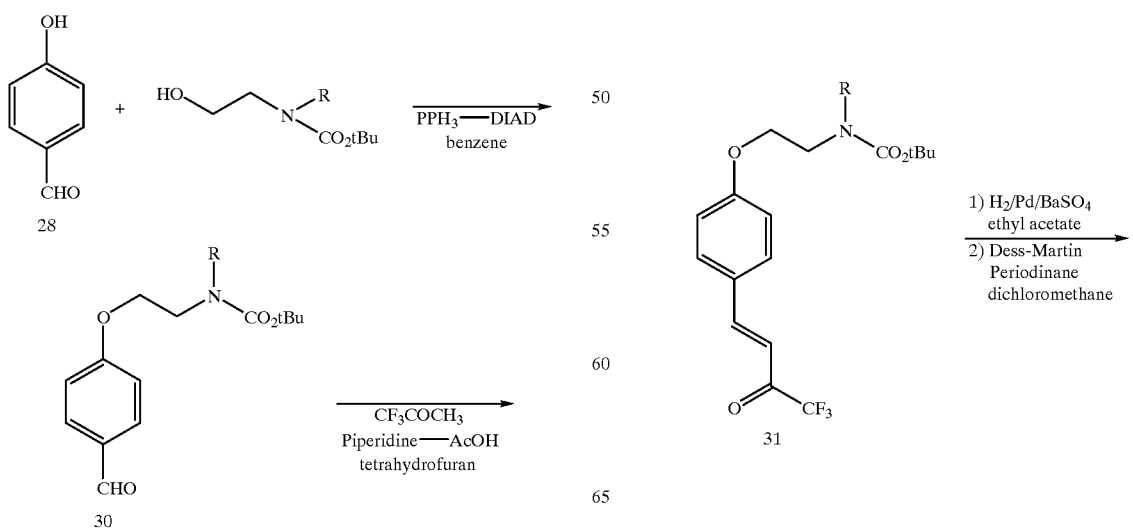

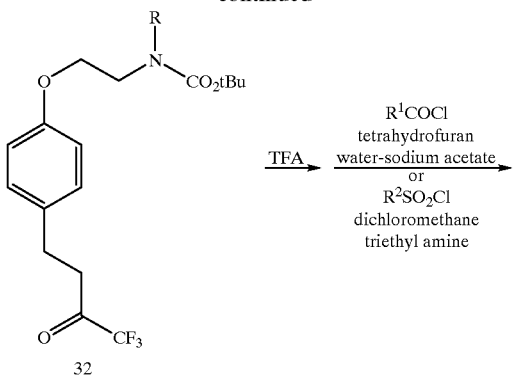

Example 119
N-[2-[4-(4,4,4-trifluoro-3-oxo-1-butyl)phenoxy]ethyl]-N-methyl Dodecanamide N-[2-(4-formylphenoxy)ethyl]-N-methylcarbamic Acid, 1,1-dimethylethyl Ester A solution of N-(2-hydroxyethyl)-N-methylcarbamic acid, 1,1-dimethylethyl ester (7.05 g, 40.2 mmol; W. S. Saari and all, J. Med. Chem. 33, 97 (1990)), 4-hydroxybenzaldehyde (3.75 g, 30.7 mmol) and triphenylphosphine (10.57 g, 40.3 mmol) in dry benzene (120 ml) was cooled to 15° C. and treated with diisopropyl azodicarboxylate (8.15 g, 40.3 mmol) in dry benzene (20 ml) added dropwise over 20 min. After 16 h at 22° C., and chromatography on silica gel (elution toluene-ethyl acetate 9:1–8:2) gave 4.40 g (52%) of the title material as white cubes: mp 62–65° C. (ether-hexane).

Anal. Calcd. for $C_{15}H_{21}NO_4$: C 64.50, H 7.58, N 5.01. Found: C 64.25, H 7.59, N 5.00.

E-N-[2-[4-(4-trifluoro-3-oxo-1-butenyl)phenoxy]ethyl]-N-methylcarbamic Acid, 1,1-dimethylethyl Ester A solution of N-[2-(4-formylphenoxy)ethyl]-N-methylcarbamic acid, 1,1-dimethylethyl ester (3.72 g, 13.3 mmol) in dry tetrahydrofuran (65 ml) was cooled to 10° C. and treated with acetic acid (1.4 ml) and piperidine (1.4 ml). Then 1,1,1-trifluoroacetone (7 ml) in dry tetrahydrofuran was added dropwise over 10 min. After 2 h and 4 h at 20° C., two other successive portions of 1,1,1-trifluoromethylacetone (2×7 ml) were also added. After another 2 h at 22° C., the reaction mixture was diluted with ethyl acetate (300 ml) washed with water, saturated ammonium chloride, saturated sodium bicarbonate and brine. The organic phase was then dried, concentrated and chromatographed on silica gel. Elution with a gradient of ethyl acetate in hexane (0–20%) gave 3.05 g (61%) of the title material as yellow crystals: mp 76–77° C. (hexane).

Anal. Calcd. for $C_{18}H_{22}NO_4F_3$: C 57.90, H 5.94, N 3.75. Found: C 57.82, H 5.92, N 3.72.

N-[2-[4-(4-trifluoro-3-oxo-1-butyl)phenoxy]ethyl]-N-methylcarbamic Acid, 1,1-dimethylethyl Ester A solution of (E)-N-[2-[4-(4-trifluoro-3-oxo-1-butenyl)phenoxy]ethyl]-N-methylcarbamic acid, 1,1-dimethylethyl ester (1.10 g, 2.95 mmol) in ethyl acetate (80 ml) was hydrogenated at atmospheric pressure over 5% palladium on barium sulfate (0.20 g) for 1 hour. The catalyst was then filtered and the filtrate was concentrated under reduced pressure. The residue was dissolved in dichloromethane (60 ml) and then treated at 22° C. with Dess-Martin periodinane reagent (2.50 g, 5.90 mmol). After 1 hour, the reaction mixture was diluted with ethyl acetate, washed with 10% aqueous sodium thiosulfate and saturated sodium bicarbonate. After drying, the organic phase was concentrated and chromatographed on silica gel. Elution with a gradient of ethyl acetate (0–10%) in toluene gave 0.880 g (79%) of the title material as an amorphous solid. By $^1H$ NMR this product is a mixture of ketone and hydrated ketone.

Anal. Calcd. for $C_{18}H_{24}NO_4F_3$. 0.7 $H_2O$: C 55.72, H 6.60, N 3.61. Found: C 55.80, H 6.52, N 3.52.

N-[2-[4-(4-trifluoro-3-oxo-1-butyl)phenoxy]ethyl]-N-methyldodecanamide

A solution of N-[2-[4-(4-trifluoro-3-oxo-1-butyl)phenoxy]ethyl]-N-methylcarbamic acid, 1,1-dimethylethyl ester (0.200 g, 0.53 mmol) in dichloromethane (10 ml) was treated with trifluoroacetic acid (1 ml) and stirred at 22° C. for 1 h. The solvent was evaporated in vacuo and the residue was co-evaporated with toluene three times. The product was then dissolved in tetrahydrofuran (10 ml) treated with 40% sodium acetate in water (10 ml) and while stirred vigorously treated with lauroyl chloride (0.116 g, 0.53 mmol) added dropwise over 2 min. After 1 hour at 22° C., the reaction mixture was diluted with ethyl acetate (150 ml), washed with water, saturated sodium bicarbonate and brine. After drying (magnesium sulfate) the solvent was evaporated in vacuo and the residue was chromatographed on silica gel. Elution with a gradient of ethyl acetate (0–30%) in toluene gave 0.181 g (74%) of the title material as a waxy solid. By $^1H$ NMR, this product is a mixture of ketone and hydrated ketone.

Anal. Calcd. for $C_{25}H_{38}F_3NO_3$. $H_2O$: C 63.14, H 8.48, N 2.95. Found: C 63.26, H 8.03, N 2.87.

The following compounds may be prepared by the general procedure of Scheme 7.

SCHEME 7

| Exp. # | R¹ | R² | Analysis |
|---|---|---|---|

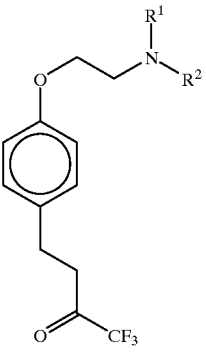

| Exp. # | R¹ | R² | Analysis |
|---|---|---|---|
| 120 | H | 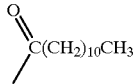 C(=O)(CH₂)₁₀CH₃ | $C_{24}H_{36}F_3NO_3 \cdot 0.2H_2O$<br>Calcd: C 64.47, H 8.21, N 3.13<br>Found: C 64.47, H 8.03, N 3.09 |
| 121 | CH₃ | 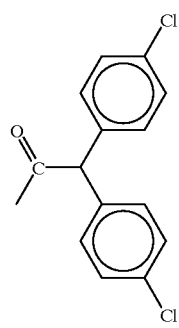 | $C_{27}H_{24}Cl_2F_3NO_3 \cdot H_2O$<br>Calcd: C 58.28, H 4.71, N 2.52<br>Found: C 58.43, H 4.38, N 2.64 |
| 122 | (CH₂)₁₁CH₃ | COCH₃ | $C_{26}H_{40}F_3NO_3 \cdot 1.7H_2O$<br>Calcd: C 62.18, H 8.71, N 2.79<br>Found: C 61.95, H 8.51, N 2.83 |
| 123 | (CH₂)₁₁CH₃ | CO₂tBu | $C_{29}H_{46}F_3NO_4$<br>Calcd: C 64.66, H 8.79, N 2.60<br>Found: C 64.81, H 8.79, N 2.70 |
| 124 | H | CO₂tBu | $C_{17}H_{22}F_3NO_4$<br>Calcd: C 56.51, H 6.14, N 3.88<br>Found: C 56.35, H 6.19, N 3.84 |
| 125 | H | SO₂(CH₂)₆CH₃ | $C_{19}H_{28}F_3NO_4S \cdot 0.2H_2O$<br>Calcd: C 53.43, H 6.70, N 3.28, S 7.51<br>Found: C 53.43, H 6.72, N 3.28, S 7.50 |
| 126 | H | SO₂(CH₂)₁₁CH₃ | $C_{24}H_{38}F_3NO_4S$<br>Calcd: C 58.40, H 7.76, N 2.84, S 6.50<br>Found: C 58.29, H 7.77, N 2.84, S 6.40 |
| 127 | CH₃ | SO₂(CH₂)₁₁CH₃ | $C_{25}H_{40}F_3NO_4S$<br>Calcd: C 59.15, H 7.94, N 2.76, S 6.32<br>Found: C 59.02, H 7.70, N 2.79, S 6.25 |
| 128 | H | CSNH(CH₂)₉CH₃ | $C_{23}H_{35}F_3N_2O_2S$<br>Calcd: C 59.98, H 7.66, N 6.08, S 6.96<br>Found: C 59.80, H 7.70, N 6.05, S 7.06 |

-continued
SCHEME 7
| Exp. # | R¹ | R² | Analysis |
|---|---|---|---|
| 129 | $(CH_2)_{11}CH_3$ | $COCF_3$ | $C_{26}H_{37}F_6NO_3 \cdot 0.4H_2O$<br>Calcd: C 58.61, H 7.15, N 2.63<br>Found: C 58.48, H 6.98, N 2.73 |
| 130 | $(CH_2)_{11}CH_3$ | $COC_6H_5$ | $C_{31}H_{42}F_3NO_3 \cdot 0.4H_2O$<br>Calcd: C 68.84, H 7.98, N 2.59<br>Found: C 68.61, H 8.05, N 2.59 |
| 131 | $(CH_2)_{11}CH_3$ | $COCH_2CH_2CO_2Et$ | $C_{30}H_{46}F_3NO_5 \cdot 0.4H_2O$<br>Calcd: C 63.79, H 8.35, N 2.48<br>Found: C 63.5, H 8.38, N 2.49 |
| 132 | $(CH_2)_{11}CH_3$ | $PO(OEt)_2$ | $C_{28}H_{47}F_3NO_5P \cdot 0.4H_2O$<br>Calcd: C 58.71, H 8.41, N 2.45<br>Found: C 58.43, H 8.59, N 2.52 |
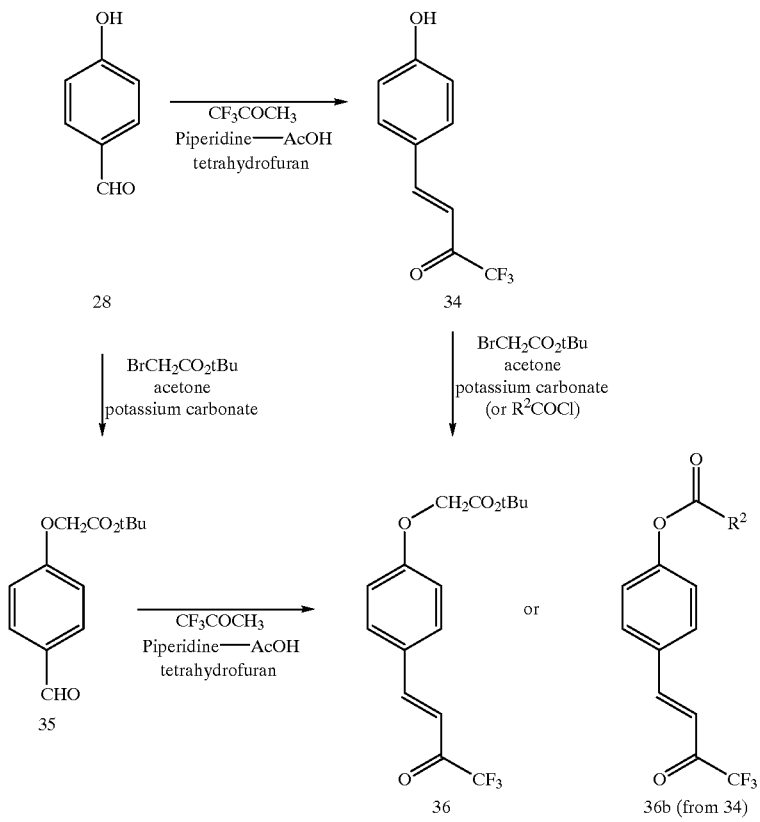
Scheme 8

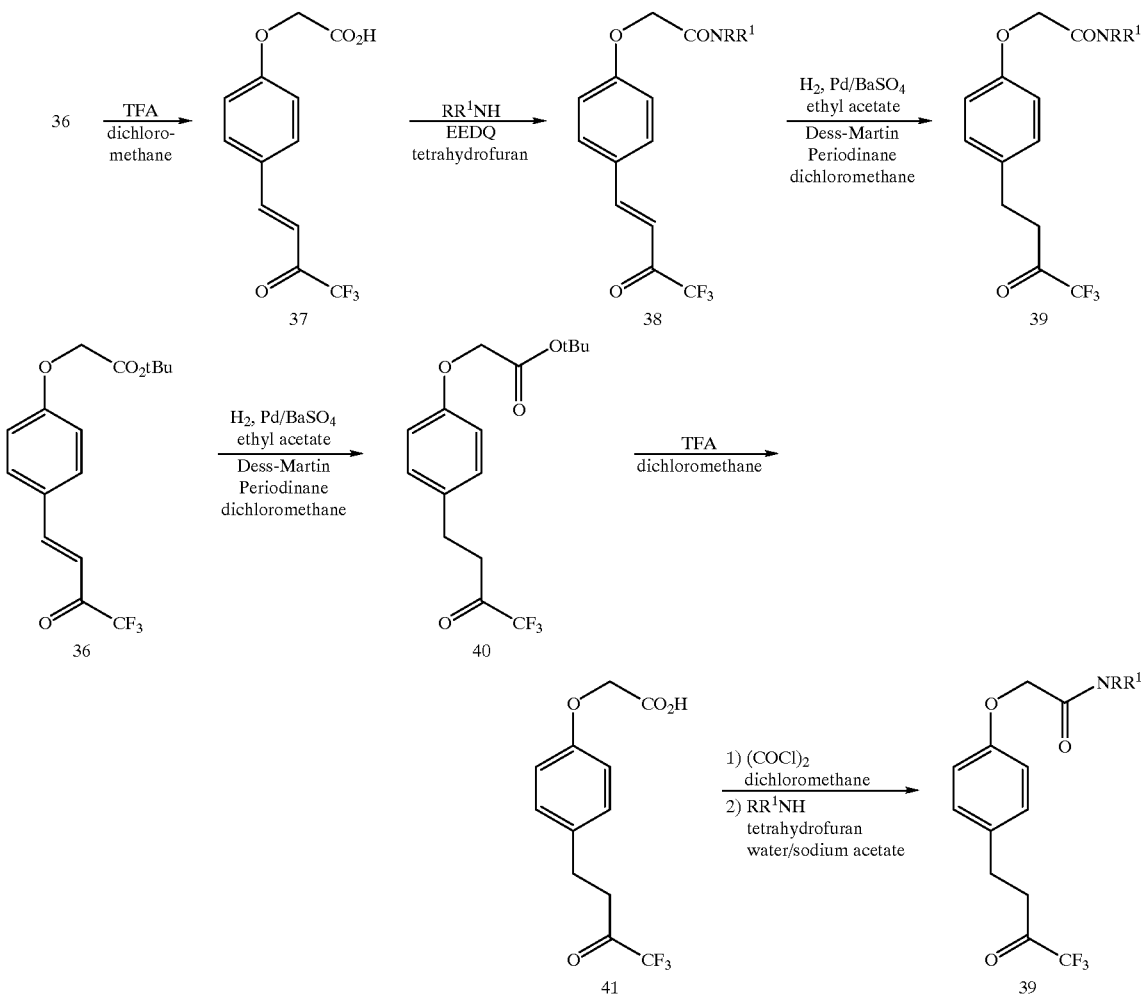

Example 133
N-Dodecyl-4-(4,4,4-trifluoro-3-oxo-1-butyl) phenoxyacetamide (E)-1,1,1-trifluoro-4-(4-hydroxyphenyl)-3-buten-2-one A solution of 4-hydroxybenzaldehyde (5.0 g, 40.9 mmol) in tetrahydrofuran (165 ml) was treated with acetic acid (3.5 ml) and piperidine (3.5 ml). Then 1,1,1-trifluoroacetone (8 ml) was added dropwise. After 2 h at 22° C., another portion of 1,1,1-trifluoroacetone (8 ml) was added and the mixture was stirred for another 3 h. The reaction mixture was then diluted with ethyl acetate, washed with water, saturated ammonium chloride, saturated sodium bicarbonate, and brine. The organic phase was dried (magnesium sulfate), concentrated under reduced pressure and chromatographed on silica gel. Elution with a gradient of ethyl acetate (0–5%) in toluene gave 4.16 g (47%) of title material as yellow needles after crystallization from ether-hexane: mp 106–107° C.

Anal. Calcd. for $C_{10}H_7F_3O_2$: C 55.57, H 3.26. Found: C 55.30, H 3.27.

(E)-4-(4,4,4-trifluoro-3-oxo-1-butenyl)phenoxyacetic Acid, 1,1-dimethylethyl Ester A solution of (E)-1,1,1-trifluoro-4-(4-hydroxyphenyl)3-buten-2-one (0.105 g, 0.49 mmol) in acetone (6 ml) was treated with powdered potassium carbonate (0.3 g) and tert-butyl bromoacetate (0.20 g, 1.02 mmol) and stirred at 22° C. for 3 h. The reaction mixture was then diluted with toluene, washed with brine, dried (magnesium sulfate) and concentrated under reduced pressure. The residue was chromatographed on silica gel (elution toluene-ethyl acetate 2%) and gave 0.150 g (94%) of the title material as yellow needles: mp 112–113° C.

Anal. Calcd. for $C_{16}H_{17}F_3O_4$: C 58.18, H 5.19. Found: C 58.12, H 5.18.

(E)-4-(4,4,4-trifluoro-3-oxo-1-butenyl)phenoxyacetic Acid

A solution of (E)-4-(4,4,4-trifluoro-3-oxo-1-butenyl) phenoxyacetic acid, 1,1-dimethylethyl ester (1.578 g, 4.77 mmol) in dichloromethane (90 ml) was treated with trifluoroacetic acid (10 ml) and stirred at 22° C. for 4 h. The solvent and excess reagent were evaporated under reduced pressure and the last traces of trifluoroacetic acid were co-evaporated with toluene. Crystallization of the residue from ethyl acetate-hexane gave 1.29 g (98%) of the title material as white cubes: mp 156–156.5° C.

Anal. Calcd. for $C_{12}H_9F_3O_4$: C 52.57, H 3.31. Found: C 52.66, H 3.29.

(E)-N-dodecyl-4-(4,4,4-trifluoro-3-oxo-1-butenyl) phenoxyacetamide

A solution of (E)-4-(4,4,4-trifluoro-3-oxo-1-butenyl) phenoxyacetic acid (0.810 g, 2.95 mmol) in tetrahydrofuran (20 ml) was treated with EEDQ (0.767 g, 3.10 mmol) and dodecylamine (0.575 g, 3.10 mmol). After 2 h at 22° C., the reaction mixture was diluted with ethyl acetate, washed with water, 0.1N hydrochloric acid, saturated sodium bicarbonate, brine and dried. Evaporation of the solvent under reduced pressure gave a solid which was chromatographed on silica gel. Elution with a mixture of toluene and ethyl acetate (8:12) gave 0.750 g (58%) of the title material as white needles after recrystallization from ethyl acetate-hexane: mp 78.5–79° C.

Anal. Calcd. for $C_{24}H_{34}F_3NO_3$: C 65.29, H 7.76, N 3.17. Found: C 65.30, H 7.73, N 3.13.

N-dodecyl-4-(4,4,4-trifluoro-3-oxo-1-butyl) phenoxyacetamide (E)-N-dodecyl-4-(4,4,4-trifluoro-3-oxo-1-butenyl) phenoxyacetamide (0.530 g, 1.20 mmol) was hydrogenated and re-oxidized as described in example 119 to give 0.490 g (92%) of the title material as an amorphous solid.

Anal. Calcd. for $C_{24}H_{36}F_3NO_3H_2O$: C 62.45, H 8.30, N 3.03. Found: C 62.54, H 8.19, N 3.18.

Example 134

N-[Bis-(4-chlorophenyl)methyl]-4-(4,4,4-trifluoro-3-oxo-1-butyl)-phenoxyacetamide 4-(4,4,4-trifluoro-3-oxo-1-butyl)-phenoxyacetacetic Acid, 1,1-dimethylethyl Ester E-(4,4,4-trifluoro-3-oxo-1-butenyl)-phenoxyacetacetic acid, 1,1-dimethylethyl ester (1.95 g, 5.90 mmol) was hydrogenated and reoxidized as described in example 133 to give 1.93 g (98%) of the title material as a wax.

Anal. Calcd. for $C_{16}H_{19}F_3O_4$: C 55.43, H 5.99. Found: C 55.32, H 5.90.

4-(4,4,4-trifluoro-3-oxo-1-butyl)phenoxyacetic Acid 4-(4,4,4-trifluoro-3-oxo-1-butyl)phenoxyacetic acid 1,1-dimethylethyl ester (0.450 g, 1.35 mmol) was treated with trifluoroacetic acid as described in example (133) to give 0.373 g (100%) of the material as a white solid.

N-[Bis-(4-chlorophenyl)methyl]-4-(4,4,4-trifluoro-3-oxo-1-butyl)phenoxyacetamide A solution of 4-(4,4,4-trifluoro-3-oxo-1-butyl) phenoxyacetic acid (0.374 g, 1.35 mmol) in dichloromethane (10 ml) was treated with oxalyl chloride (0.17 ml, 2.03 mmol) and a trace of N,N-dimethylformamide. After 30 min at 22° C., the solvent and excess reagent were evaporated under reduced pressure and the residual oil obtained was dissolved in anhydrous tetrahydrofuran (10 ml). This solution was then added dropwise to a vigorously stirred solution of p-chlorobenzhydrylamine hydrochloride (0.39 g, 1.35 mmol) in a mixture of tetrahydrofuran (10 ml) and 40% aqueous sodium acetate (10 ml). After 30 min at 22° C., the reaction mixture was diluted with ethyl acetate, washed with water, brine and dried. Evaporation of the solvent under reduced pressure gave a solid which was chromatographed on silica gel. Elution with a mixture of toluene and ethyl acetate (8:2) gave 0.603 g (87%) of the title product as white crystals: mp 145–146° C.

Anal. Calcd. for $C_{25}H_{20}ClF_3NO_3$: C 58.84, H 3.85, N 2.74, Cl 13.89, F 11.17. Found: C 58.73, H 4.07, N 2.82, Cl 13.60, F 10.46.

Scheme 9

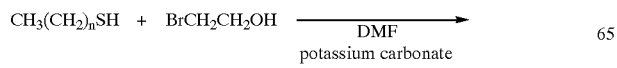

-continued

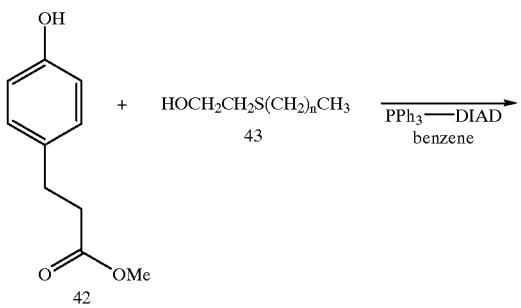

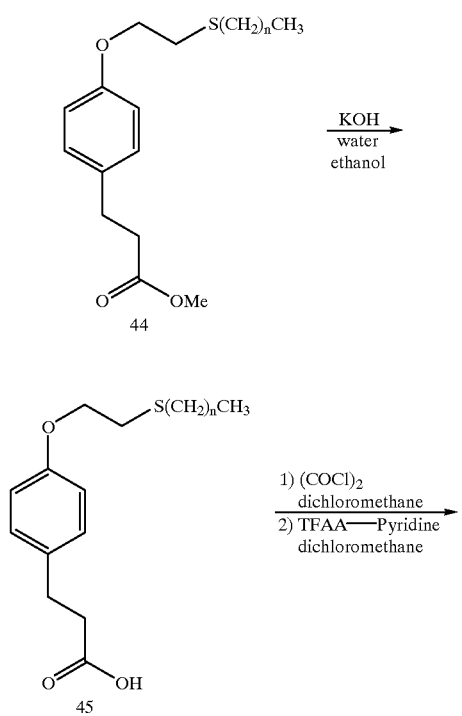

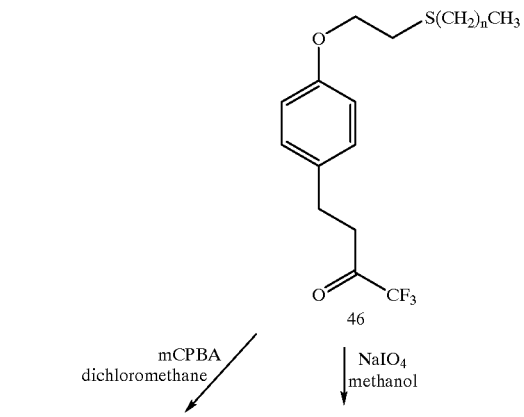

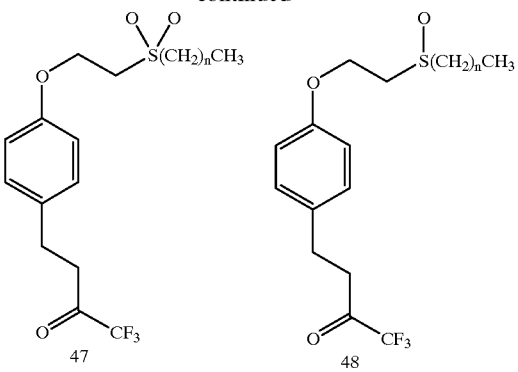

Example 135

4-[4-[2-(Dodecylthio)ethoxyphenyl]-1,1,1-trifluoro-2-butanone 2-(Dodecylthio) Ethanol

A mixture of 2-bromoethanol (6.08 g, 48.7 mmol), dodecanethiol (9.86 g, 48.7 mmol) and potassium carbonate (11 g) in dry N,N-dimethylformamide (100 ml) was stirred at 22° C. for 10 h. The reaction mixture was then diluted with toluene (400 ml) washed with water and dried (magnesium sulfate). The solvent was evaporated under reduced pressure and the residue was filtered through a silica gel pad (toluene-ethyl acetate 95:5) and distilled under vacuum to give 9.18 g (77%) of 2-(dodecylthio)ethanol as a clear oil which solidified on standing: b.p. 100–105° C./0.01 torr (bulb to bulb distillation, air bath temperature); m.p. 31–32° C.

IR (NaCl, film) $\mu_{max}$ (cm$^{-1}$): 3380 (OH).

$^1$H NMR 400 MHz (CDCl$_3$) d (ppm): 0.89 (3H, t, J=6.8 Hz, CH$_3$), 1.2–1.7 (20H, m, (CH$_2$)$_{10}$), 2.16 (1H, br t, OH), 2.52 (2H, t, J=7.4 H, SCH$_2$), 2.74 (2H, t, J=6.0 Hz, OCH$\underline{CH_2}$S), 3.7 (2H, q, J=6.0 Hz, O$\underline{CH_2}$CH$_2$S.

Anal. Calcd. for C$_{14}$H$_{30}$OS: C 68.23, H 12.27, N 13.01. Found: C 68.06, H 12.29, N 12.95.

3-[4-[2-(Dodecylthio)ethoxy]phenyl]propanoic Acid Methyl Ester

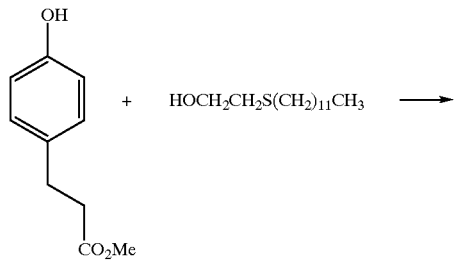

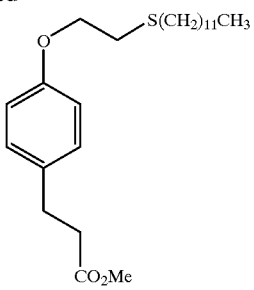

A solution of methyl 3-[4-hydroxyphenyl)propionate (2.46 g, 13.6 mmol), 2-(dodecylthio)ethanol (3.40 g, 13.7 mmol) and triphenylphosphine (3.60 g, 13.8 mmol) in dry benzene (50 ml) was treated at 22° C. with diethyl azodicarboxylate (2.43 g, 13.9 mmol) added dropwise over 10 min. After 3 h at 22° C., the reaction mixture was diluted with ethyl acetate, washed with water, brine and dried (magnesium sulfate). Evaporation under reduced pressure gave an oil which was triturated with hexane to precipitate the triphenylphosphine oxide and the hydrazine side products. The filtrate was chromatographed on silica gel using a gradient of ethyl acetate (0–5%) in hexane as eluent to give 4.70 g(84%) of 3-[4-[2-(dodecylthio)ethoxy]phenyl]propanoic acid methyl ester as a white solid. Recrystallization from methanol gives white leaflets: m.p. 48° C.

IR (KBr) $\mu_{max}$ (cm$^{-1}$): 1729 (C=O of ester).

$^1$H NMR 400 MHz (CDCl$_3$) d (ppm): 0.89 (3H, t, J=6.8 Hz, CH$_3$), 1.2–1.7 (20H, m, (CH$_2$)$_{10}$), 2.6 (4H, br t, SCH$_2$ and CH$_2$CO), 2.9 (4H, br t, OCH$\underline{CH_2}$S and Ph$\underline{CH_2}$), 3.68 (3H, s, OCH$_3$), 4.11 (2H, t, J=7.0$\overline{3}$ Hz, O$\underline{CH_2}$CH$_2$S), 6.83 (2H, d, J=8.7 Hz aromatic), 7.12 (2H, d, J=8.7 Hz, aromatic).

Anal. Calc. for C$_{24}$H$_{40}$O$_3$S: C 70.54, H 9.87, S 7.85. Found: C 70.25, H 9,38, S 7.87.

3-[4-[2-(Dodecylthio)ethoxy]phenyl]propanoic Acid

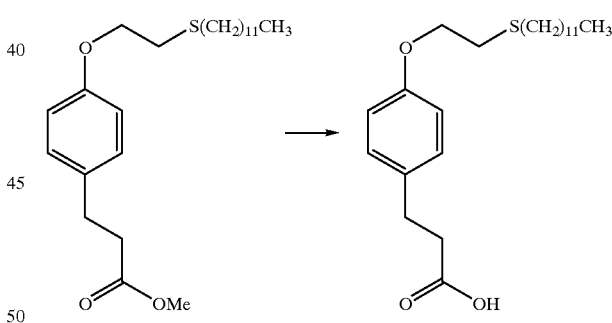

A suspension of 2-[4-[2-(dodecylthio)ethoxy]phenyl]propanoic acid methyl ester (4.70 g, 11.5 mmol) in 80% ethanol (100 ml) was treated with a solution of potassium hydroxide (1.33 g, 20.1 mmol) in water (10 ml) and the mixture was stirred at 55° C. for 1 h. The solvent was then concentrated in vacuo and the residue was diluted with water (100 ml) and dichloromethane (250 ml). The solution was then adjusted to pH 2 with diluted hydrochloric acid and the aqueous phase was extracted a second time with dichloromethane. The combined organic extracts were washed with brine and dried (magnesium sulfate). Evaporation of the solvent under reduced pressure and crystallization of the residue from ethyl acetate-hexane gave 3.56 g (78%) of 3-[4-[2-(dodecylthio)ethoxy]phenyl]propanoic acid as white prisms: m.p. 68–69° C.

IR (NaCl, film) $\mu_{max}$ (cm$^{-1}$): 1710 (C=O).

$^1$H NMR 400 MHz (CDCl$_3$) d (ppm): 0.89 (3H, t, J=6.8 Hz, —CH$_3$), 1.1–1.7 (20H, m, (CH$_2$)$_{10}$), 2.63 (4H, m, SCH$_2$ and CH$_2$CO), 2.90, (4H, m, OCH$_2$CH$_2$S and PhCH$_2$), 4.12 (2H, t, J=6.99, OCH$_2$CH$_2$S), 6.84 (2H, d, J=8.5 Hz, aromatic), 7.13 (2H, d, J=8.5 Hz, aromatic).

Anal. calcd. for C$_{23}$H$_{38}$O$_3$S. 0.1 H$_2$O: C 69.69, H 9.71, S 8.09. Found: C 69.55, H 9.86, S 8.15.

4-[4-[2-(Dodecylthio)ethoxy]phenyl]-1,1,1-trifluoro-2-butanone

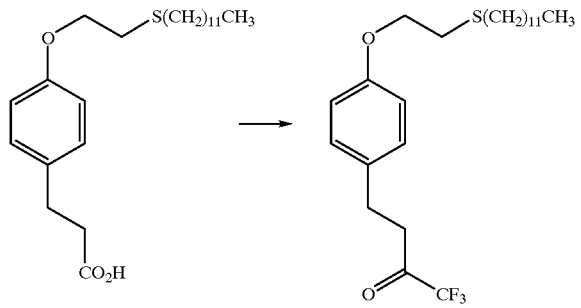

A solution of 3-[4-[2-(dodecylthio)ethoxy]phenyl] propanoic acid (14.13 g, 35.8 mmol) in dichloromethane (400 ml) was treated with oxalyl chloride (6.5 ml) and a drop of N,N-dimethylformamide and the resulting mixture was stirred at 22° C. for 1 h. The solvent and excess reagent were evaporated under reduced pressure and the residue was dissolved in dry dichloromethane (200 ml). This solution was added to a cold (0° C.) solution of trifluoroacetic anhydride (19.2 ml, 0.107 mol) in dichloromethane (200 ml). Then pyridine (6.1 ml, 75.4 mmol) was added dropwise and the resulting solution was stirred at 0° C. for 30 min and then at 22° C. for 2 h. Water (50 ml) was added and the mixture was stirred for another 30 min. The organic phase was then washed with brine, dried and concentrated under reduced pressure.

Chromatography on silica gel (elution with a gradient of ethyl acetate 0–10% in toluene) gave 10.50 g (66%) of 4-[4-[2-(dodecylthio)ethoxy]phenyl]-1,1,1-trifluoro-2-butanone as an amorphous solid.

IR (NaCl, film) $\mu_{max}$ (cm$^{-1}$): 1758 (C=O).

$^1$H NMR 400 MHz (CDCl$_3$) d (ppm): 0.89 (3H, t, J=6.8 Hz, —CH$_3$), 1.2–1.7 (20H, m, (CH$_2$)$_{10}$), 2.62 (2H, t, J=7.46 Hz, SCH$_2$), 2.89 (2H, t, J=6.95 Hz, OCH$_2$CH$_2$S), 2.9–3.1 (4H, m, CH$_2$CH$_2$CO), 4.12 (2H, t, J=6.95 Hz, OCH$_2$CH$_2$S), 6.85 (2H, d, J=8.7 Hz, aromatic), 7.11 (2H, d, J=8.7 Hz, aromatic).

Anal. Calcd. for C$_{24}$H$_{37}$F$_3$O$_2$S: C 64.54, H 8.35. Found: C 64.47, H 8.32.

Example 136

4-[4-[2-(Dodecylsulfinyl)ethoxy]phenyl]-1,1,1-trifluoro-2-butanone

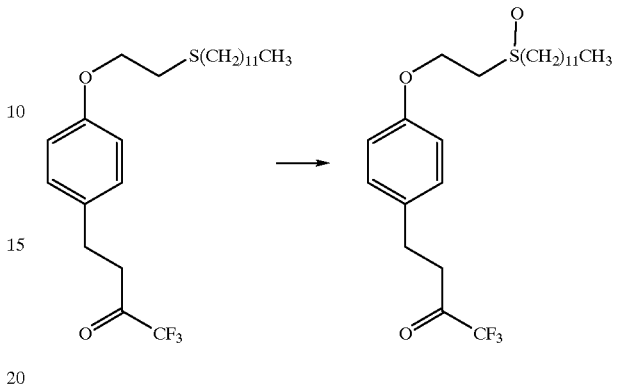

A solution of 4-[4-[2-(dodecylthio)ethoxy]phenyl]-1,1,1-trifluoro-2-butanone (0.340 g, 0.76 mmol) in methanol (15 ml) was treated with a solution of sodium periodate (0.165 g, 0.77 mmol) in water (3 ml) and the resulting mixture was stirred at 22° C. for 18 h. The solid formed was filtered and washed with methanol. This filtrate was then concentrated under reduced pressure and then partitioned between water and ethyl acetate. The organic phase was then dried (magnesium sulfate) and concentrated. The residue was chromatographed on silica gel (elution toluene-ethyl acetate 1:1) to give 0.335 g (90%) of 4-[4-[2-(dodecylsulfinyl)ethoxy]phenyl]-1,1,1-trifluoro-2-butanone as a white solid. By $^1$HNMR this product was a 6:4 mixture of trifluoromethyl ketone and hydrated trifluoromethyl ketone. The pure hydrate precipitates from ethyl acetate-hexane: m.p. 98–100° C.

IR (NaCl, film) $\mu_{max}$ (cm$^{-1}$): 3400 (OH), 1650.

$^1$H NMR 400 MHz (CDCl$_3$) d (ppm): 0.89 (3H, t, J=6.8 Hz, —CH$_3$), 1.3, 1.45 and 1.8 (16H, 2H and 2N, 3m, (CH$_2$)$_{10}$), 2.09 (2H, br t, J=8 Hz, CH$_2$CH$_2$CO), 3.7 (2H, br, OH), 4.4 (2H, m, OCH$_2$), 6.84 (2H, d, J=8.5 Hz, aromatic), 7.15 (2H, d, J=8.5 Hz, aromatic).

Anal. Calcd. for C$_{24}$H$_{37}$F$_3$S.H$_2$O: C 59.98, H 8.18, S 6.67. Found: C 60.06, H 8.17, S 6.67.

Example 137

4-[4-[2-(Dodecylsulfonyl)ethoxy]phenyl]-1,1,1-trifluoro-2-butanone

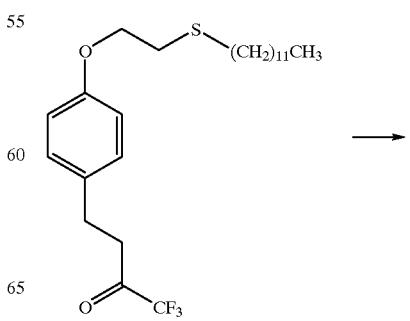

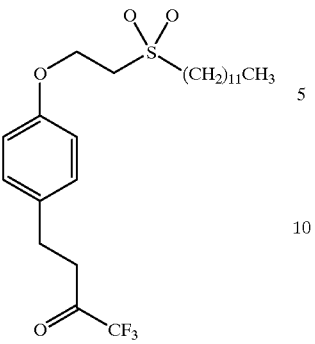

A solution of 4-[4-[2-(dodecylthio)ethoxy]phenyl]-1,1,1-trifluoro-2-butanone (0.394 g, 0.88 mmol) in dichloromethane (25 ml) was treated at 22° C. with 85% m-chloroperbenzoic acid (0.40 g, 1.8 mmol) and the resulting mixture was stirred for 2.5 h. The reaction mixture was then washed with aqueous sodium bicarbonate, brine and dried (magnesium sulfate). Evaporation and chromatography on silica gel (elution with a gradient of ethyl acetate 0–20% in toluene) gave 0.344 g (82%) of 4-[4-[2-(dodecylsulfonyl)ethoxy]phenyl]-1,1,1-trifluorobutanone as an amorphous solid. By $^1$HNMR, this product is a ~1:1 mixture of trifluoromethylketone and hydrated trifluoromethyl ketone: m.p. 55–56° C.

IR (NaCl, film) $u_{max}$ (cm$^{-1}$): 3400 (OH) and 1760 (C=O).

$^1$H NMR 400 MHz (CDCl$_3$).

Ketone Form d (ppm): 0.89 (3H, t, J=6.8 Hz, —CH$_3$), 1.28, 1.45 and 1.9 (16H, 2H and 2H, 3 m, (CH$_2$)$_{10}$), 3.0 (4H, m, CH$_2$CH$_2$CO), 3.12 (2H, m, SOCH$_2$), 3.4 (2H, t, J=5.35 Hz, OCHCH$_2$S), 4.41 (2H, t, J=5.35 Hz, OC$_2$CH$_2$S), 6.84 (2H, d, J=8.6 Hz, aromatic), 7.15 (2H, d, J=8.6 Hz, aromatic).

Hydrate Form d (ppm): 2.14 (2H, br t, J=8.1 Hz, CHCH$_2$CO), 2.87 (2H, br t, J=8.1 HJz, CH$_2$CH$_2$CO), 6.86 (2H, d, J=8.6 Hz, aromatic), 7.2 (2H, d, J=8.6 Hz, aromatic).

Anal. Calcd. for C$_{24}$H$_{37}$F$_3$O$_4$S. 0.6 H$_2$O: C 58.90, H 7.87, S 6.55. Found: C 58.86, H 7.79, S 6.63.

Example 138

4-[4-[2-[2-[Bis(4-chlorophenyl)methoxy]ethylsulfonyl]ethoxy]phenyl]-1,1,1-trifluoro-2-butanone 2-[Bis(4-chlorophenyl)methoxy]ethyl Bromide

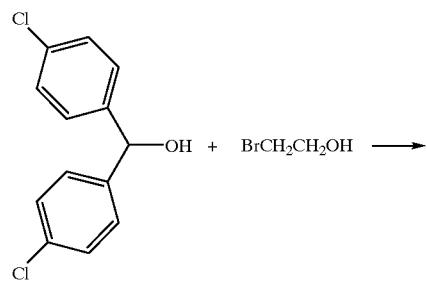

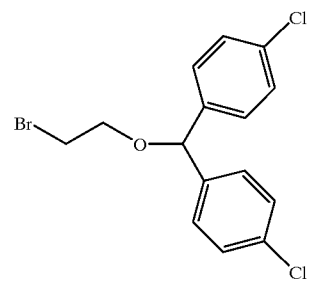

A mixture of 4,4'-dichlorobenzhydrol (4.40 g, 0.17 mmol) and 2-bromoethanol (3.0 g, 24.0 mmol) in benzene (50 ml) was treated with sulfuric acid (0.25 ml) and the resulting mixture was heated under reflux for 1 h. The cooled mixture was diluted with ethyl acetate (200 ml), washed with saturated sodium bicarbonate, brine and dried over magnesium sulfate. Evaporation of the solvent gave an oil which was chromatographed on silica gel using a mixture of toluene and hexane (1:1) as eluent to give the title compound as a clear oil (5.13 g, 82%).

2-[2-[Bis(4-chlorophenyl)methoxy]ethylthio]ethanol

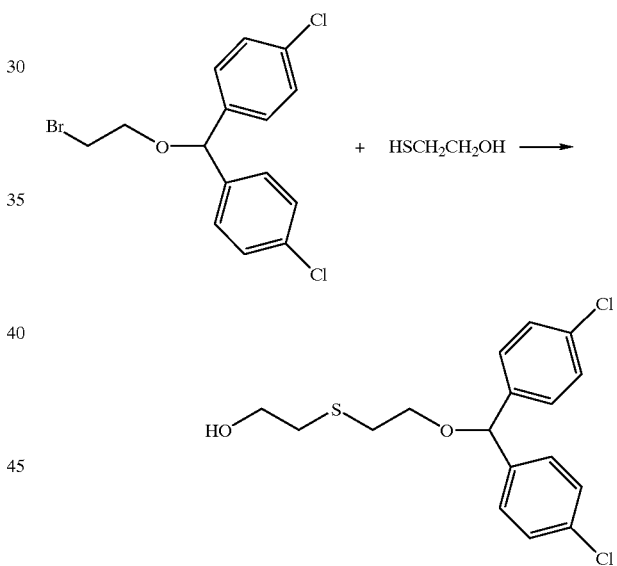

A solution of 2-[bis(4-chlorophenyl)methoxy]ethyl bromide (5.13 g, 14.2 mmol) in N,N-dimethylformamide (50 ml) was treated at 22° C. with powdered anhydrous potassium carbonate (3.0 g, 21.7 mmol) followed by 2-mercaptoethanol (1.25 g, 16.0 mmol). The resulting mixture was stirred at 22° for 18 h. The reaction mixture was then diluted with toluene (400 ml) washed with water, brine and dried over magnesium sulfate. Evaporation of the solvent gave an oil which was chromatographed on silica gel (elution ethyl acetate 0–10% in toluene) to give 4.93 g (96%) of the title material as a clear oil.

Anal. Calcd. for C$_{17}$H$_{18}$Cl$_2$O$_2$S: C 57.15, H 5.08, S 8.97. Found: C56.99, H 4.82, S 9.05.

3-[4-[2-[2-[Bis(4-chlorophenyl)methoxy]ethylthio]ethoxy]phenyl]propionic Acid Methyl Ester

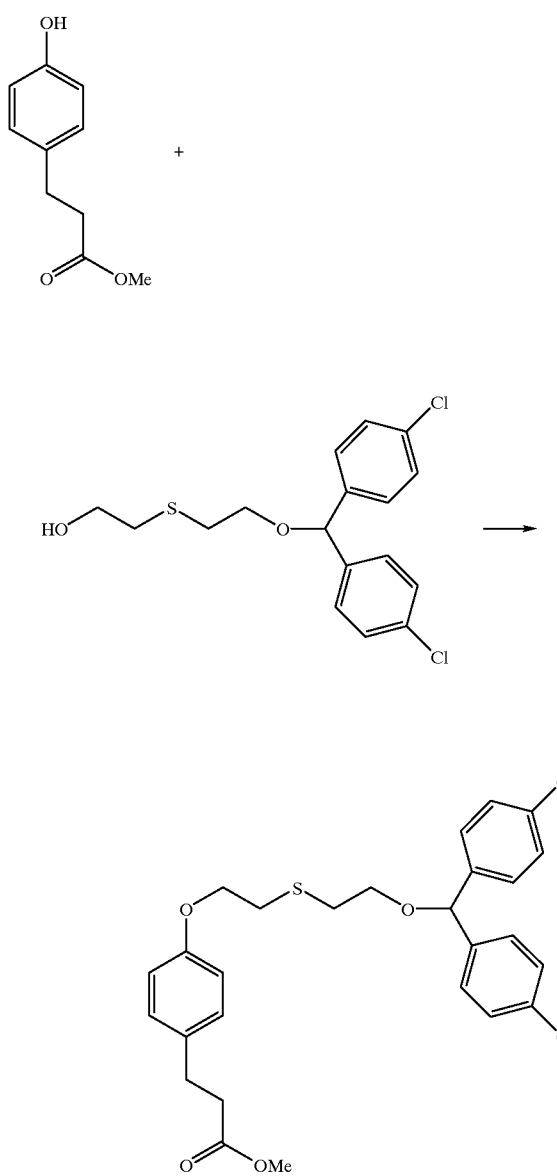

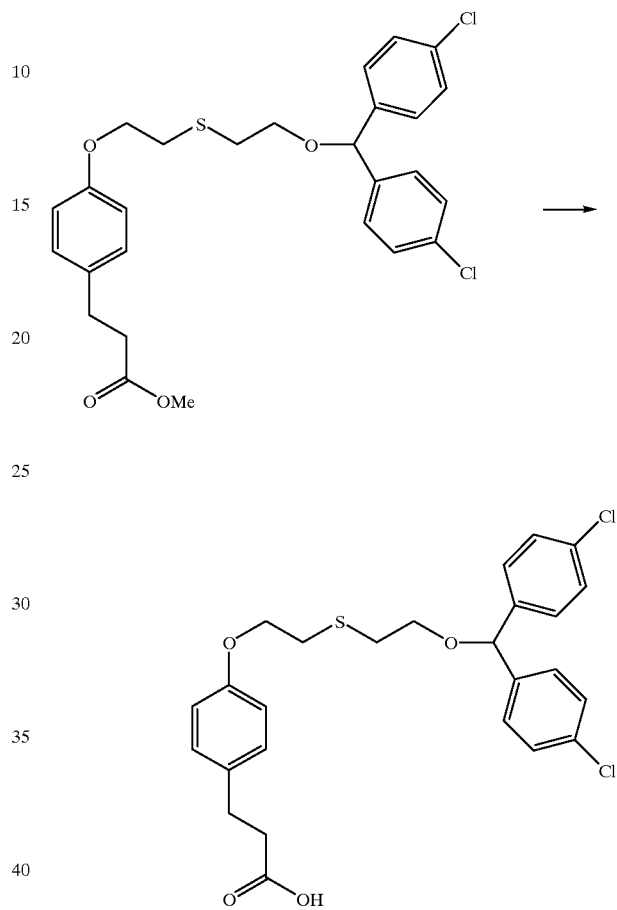

A solution of methyl 3-(4-hydroxyphenyl)propionate (1.40 g, 7.77 mmol), 2-[2-[bis(4-chlorophenyl)methoxy]ethylthio]ethanol (2.80 g, 7.80 mmol) and triphenylphosphine (2.0 g, 7.8 mmol) in dry benzene (30 ml) was treated at 22° C. with diethyl azodicarboxylate (1.34 g, 7.8) added dropwise over 5 min. After 18 h at 22° C., the reaction mixture was diluted with ethyl acetate (200 ml) washed with saturated sodium bicarbonate and dried over magnesium sulfate. Evaporation of the solvent gave an oil which was triturated in a mixture of hexane and toluene (6:4) to crystallize the triphenylphosphine oxide and the hydrazine side products. The filtrate was chromatographed on silica gel (elution ethyl acetate 0–5% in toluene) to give 2.90 g (71%) of the title material as an oil.

Anal. Calcd. for $C_{27}H_{28}Cl_2O_4S$: C 62.43, H 5.43, S 6.17. Found: C 61.89, H 5.21, S 6.11.

3-[4-[2-[2-[Bis(4-chlorophenyl)methoxy]ethylthio]ethoxy]phenyl]propionic Acid

A mixture of 3-[4-[2-[2-[Bis(4-chlorophenyl]methoxy]ethylthio]ethoxy]phenyl]propionic acid methyl ester (2.76 g, 5.31 mmol) and 80% aqueous ethanol (50 ml) was treated with a solution of potassium hydroxide (0.7 g, 10.6 mmol) in water (3 ml) and the resulting mixture was heated at 60° C. for 1 h. The solvent was then concentrated in vacuo and the residue was diluted with water (30 ml) and dichloromethane (50 ml) and acidified to pH4 with 2N hydrochloric acid. The aqueous phase was extracted a second time with dichloromethane and the combined organic extracts were washed with brine and dried (magnesium sulfate). Evaporation of the solvent under reduced pressure gave 2.63 g (98%) of the title acid as a white solid.

Anal. Calcd. for $C_{26}H_{26}Cl_2O_4S$: C 61.78, H 5.18, S 6.34. Found: C 61.42, H 5.11, S 6.34.

4-[4-[2-[2-[Bis(4-chlorophenyl)methoxy]ethylthio]ethoxy]phenyl]-1,1,1-trifluoro-2-butanone

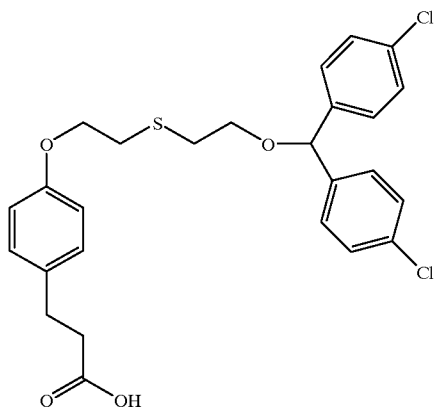

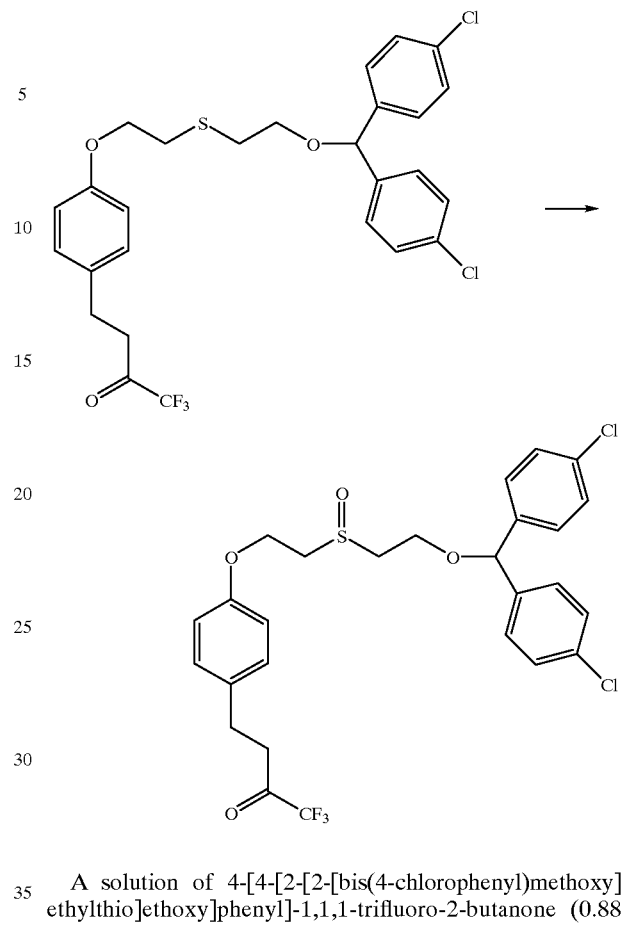

A solution of 3-[4-[2-[2-[bis(4-chlorophenyl)methoxy]ethylthio]ethoxy]phenyl]propionic acid (2.49 g, 4.93 mmol) in dry dichloromethane (25 ml) was treated at 22° C. with oxalyl chloride (1.5 g, 11.8 mmol) and a small drop of N,N-dimethylformamide. After 1 h, the solvent and excess reagent were evaporated in vacuo and the residue was diluted with dry toluene (75 ml). The solution was then cooled to 0–5° C., treated with trifluoroacetic anhydride (3.12 g, 14.9 mmol) followed by pyridine (0.98 g, 12.4 mmol) added dropwise over 10 min. The reaction mixture was then allowed to warm up to 20° C. and stirred for another 2 h. Then water (5 ml) was added dropwise and the mixture was stirred for another 15 min. The reaction mixture was then diluted with ethyl acetate (300 ml) washed with water, saturated sodium bicarbonate, brine and dried (magnesium sulfate). Evaporation gave an oil which was chromatographed on silica gel. Elution with a gradient of ethyl acetate (0–4%) in toluene gave 2.35 g (85%) of the title material as an oil.

Anal. Calcd. for $C_{27}H_{25}Cl_2F_3O_3S \cdot 0.4 H_2O$: C 57.43, H 4.63, S 5.68. Found: C 57.42, H 4.41, S 5.49.

4-[4-[2-[2-[Bis(4-chlorophenyl)methoxy]ethylsulfunyl]ethoxy]phenyl]-1,1,1-trifluoro-2-butanone A solution of 4-[4-[2-[2-[bis(4-chlorophenyl)methoxy]ethylthio]ethoxy]phenyl]-1,1,1-trifluoro-2-butanone (0.88 g, 1.58 mmol) in methanol (40 ml) was treated at 22° C. with a solution of sodium periodate (0.34 g, 1.58 mmol) in water (2 ml). After 6.5 h the solid formed was filtered and the filtrate was evaporated in vacuo. The residue was diluted with ethyl acetate, washed successively with sodium bicarbonate, water and brine, dried (magnesium sulfate) and concentrated. The residue was chromatographed on silica gel (elution ethyl acetate) to give 0.691 g (76%) of the title material as an oil.

Anal. Calcd. for $C_{27}H_{25}Cl_2F_3O_4S \cdot 0.6 H_2O$: C 55.51, H 4.52, S 5.49. Found: C 55.37, H 4.31, S 5.39.

4-[4-[2-[2-[Bis(4-chlorophenyl)methoxy]ethylsulfonyl]ethoxy]phenyl]-1,1,1-trifluoro-2-butanone

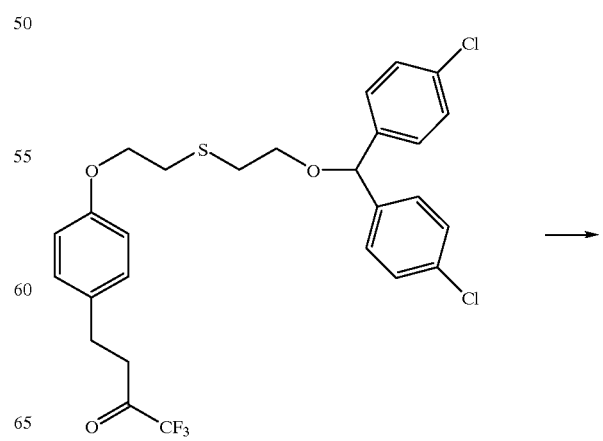

-continued

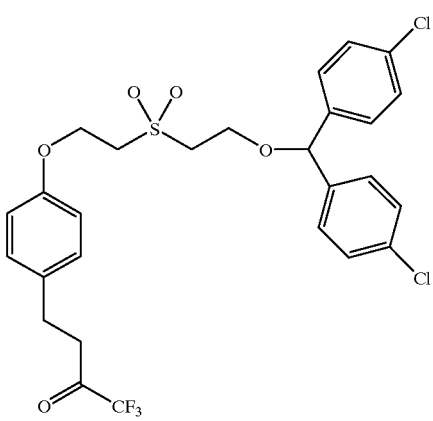

A solution of 4-[4-[2-[2-[bis(4-chlorophenyl)methoxy] ethylthio]ethoxy]phenyl]-1,1,1-trifluoro-2-butanone (1.51 g, 2.71 mmol) in dichloromethane (50 ml) was treated at 22° C. with m-chloroperbenzoic acid (0.94 g, 5.4 mmol) and the resulting mixture was stirred for 2 h. The reaction mixture was then diluted with ethyl acetate, washed with sodium bicarbonate, brine and dried (magnesium sulfate). Evaporation and chromatography on silica gel (elution toluene-ethyl acetate 8:2) gave 1.46 g (92%) of the title material as an oil which crystallized upon standing: mp 98–100° C.

IR (NaCl, film) $u_{max}$ (cm$^{-1}$) 755.

$^1$H NMR 400 MHz (CDCl$_3$) d (ppm): 2.97 (2H, m), 3.02 (2H, m), 3.45 (2H, t, J=5.6 Hz), 3.53 (2H, t, J=5.6 Hz), 3.92 (2H, t J=5.6 Hz), 4.41 (2H, m), 5.39 (1H, s), 6.92 and 7.1–7.3 (12H, aromatic). Hydrated form: 2.15 and 2.87 (2m).

Anal. Calcd. for $C_{27}H_{25}Cl_2F_3O_5S$: C 55.02, H 4.27, S 5.44. Found: C 54.83, H 4.36, S 5.54.

The following compounds may be prepared by the general procedure of Scheme 9.

SCHEME 9

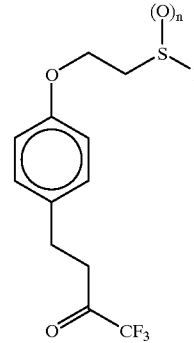

| Exp. # | n | R | Analysis |
|---|---|---|---|
| 139 | 0 | (CH$_2$)$_6$CH$_3$ | $C_{19}H_{27}F_3O_2S$<br>Calcd: C 60.62, H 7.23, S 8.52<br>Found: C 60.65, H 7.06, N 8.25 |
| 140 | 1 | (CH$_2$)$_6$CH$_3$ | $C_{19}H_{27}F_3O_3S$<br>Calcd: C 55.59, H 7.12, S 7.81<br>Found: C 55.55, H 6.94, S 7.72 |
| 141 | 2 | (CH$_2$)$_6$CH$_3$ | $C_{19}H_{27}F_3O_4S$<br>Calcd: C 55.87, H 6.66, S 7.85<br>Found: C 55.61, H 6.30, S 7.80 |

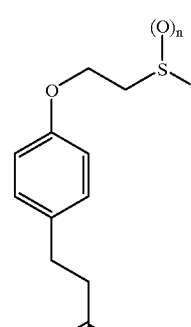

| Exp. # | n | R | Analysis |
|---|---|---|---|
| 142 | 0 | (CH$_2$CH$_2$O)$_3$CH$_3$ | $C_{19}H_{27}F_3O_5S \cdot 0.7H_2O$<br>Calcd: C 52.21, H 6.55, S 7.34<br>Found: C 52.20, H 6.76, S 7.37 |
| 143 | 1 | (CH$_2$CH$_2$O)$_3$CH$_3$ | $C_{19}H_{27}F_3O_6 \cdot 0.8H_2O$<br>Calcd: C 50.17, H 6.34, S 7.05 |

-continued
SCHEME 9
| Exp. # | n | R | Analysis |
|---|---|---|---|
| 144 | 2 | (CH$_2$CH$_2$O)$_3$CH$_3$ | Found: C 50.11, H 6.25, S 7.08<br>C$_{19}$H$_{27}$F$_3$O$_7$S·0.7H$_2$O<br>Calcd: C 48.65, H 6.10, S 6.84<br>Found: C 48.72, H 6.16, S 7.00 |
| 145 | 0 | 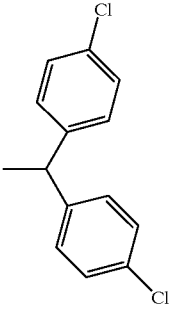 | C$_{25}$H$_{21}$Cl$_2$F$_3$O$_2$S<br>Calcd: C 58.49, H 4.12, S 6.25<br>Found: C 58.43, H 4.06, S 6.39 |
| 146 | 1 | 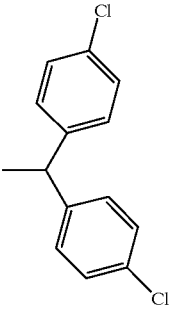 | C$_{25}$H$_{21}$Cl$_2$F$_3$O$_3$S·1.5H$_2$O<br>Calcd: C 53.96, H 4.35, S 5.76<br>Found: C 53.92, H 4.08, S 5.90 |
| 147 | 2 | 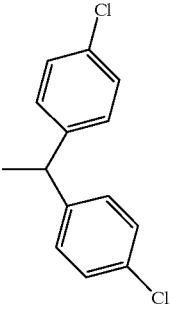 | C$_{25}$H$_{21}$Cl$_2$F$_3$O$_4$S·0.3H$_2$O<br>Calcd: C 54.52, H 3.95, S 5.82<br>Found: C 54.52, H 3.79, S 5.91 |
| 148 | 0 | 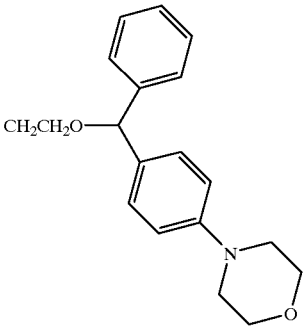 | C$_{31}$H$_{34}$F$_3$NO$_4$S·HCl·0.5H$_2$O<br>Calcd: C 60.14, H 5.86, N 2.26<br>Found: C 59.94, H 5.96, H 2.31 |

-continued

SCHEME 9

| Exp. # | n | R | Analysis |
|---|---|---|---|
| 149 | 0 | 9-fluorenyl-OCH₂CH₂– | C$_{27}$H$_{25}$F$_3$O$_3$S<br>Calcd: C 66.65, H 5.18<br>Found: C 66.83, H 5.16 |
| 150 | 2 | 9-fluorenyl-OCH₂CH₂– | C$_{27}$H$_{25}$F$_3$O$_5$S.1.1H$_2$O<br>Calcd: C 60.24, H 5.09<br>Found: C 59.96, H 4.73 |
| 151 | 0 | CH₂CH₂O–C₆H₄–O–C₆H₅ | C$_{26}$H$_{24}$ClF$_3$O$_4$S<br>Calcd: C 59.48, H 4.61, S 6.11<br>Found: C 59.21, S 4.45, S 6.16 |
| 152 | 1 | CH₂CH₂O–C₆H₄–O–C₆H₅ | C$_{26}$H$_{24}$ClF$_3$O$_5$S.0.8H$_2$O<br>Calcd: C 56.23, H 4.65, S 5.77<br>Found: C 56.13, S 4.62, S 5.96 |
| 153 | 2 | CH₂CH₂O–C₆H₄–O–C₆H₅ | C$_{26}$H$_{24}$ClF$_3$O$_6$S.0.4H$_2$O<br>Calcd: C 55.35, H 4.43, S 5.68<br>Found: C 55.30, S 4.27, S 5.88 |
| 154 | 0 | CH$_2$CH$_2$OSi(CH$_3$)$_2$tBu | C$_{20}$H$_{31}$F$_3$O$_6$SSi.0.2H$_2$O<br>Calcd: C 54.57, H 7.19<br>Found: C 54.26, H 7.01 |
| 155 | 0 | CH$_2$CH$_2$OSi(Ph)$_2$tBu | C$_{30}$H$_{35}$F$_3$O$_3$SSi<br>Calcd: C 64.26, H 6.29, S 5.72<br>Found: C 64.01, H 6.16, S 5.58 |
| 156 | 1 | CH$_2$CH$_2$OSi(Ph)$_2$tBu | C$_{30}$H$_{35}$F$_3$O$_4$SSi.0.9H$_2$O<br>Calcd: C 60.77, H 6.26, S 5.41<br>Found: C 60.45, H 6.45, S 5.41 |
| 157 | 2 | CH$_2$CH$_2$OSi(Ph)$_2$tBu | C$_{30}$H$_{35}$F$_3$O$_5$SSi.0.2H$_2$O<br>Calcd: C 60.42, H 5.98<br>Found: C 60.34, H 5.75 |
| 158 | 2 | 1-(4-chlorophenyl)-5-(4-chlorophenyl)-pyrazol-3-yl-CH₂– | C$_{28}$H$_{23}$Cl$_2$F$_3$N$_2$O$_4$S.0.4H$_2$O<br>Calcd: C 54.36, H 3.88, S 4.53<br>Found: C 54.03, H 3.76, S 4.69 |

Scheme 9B

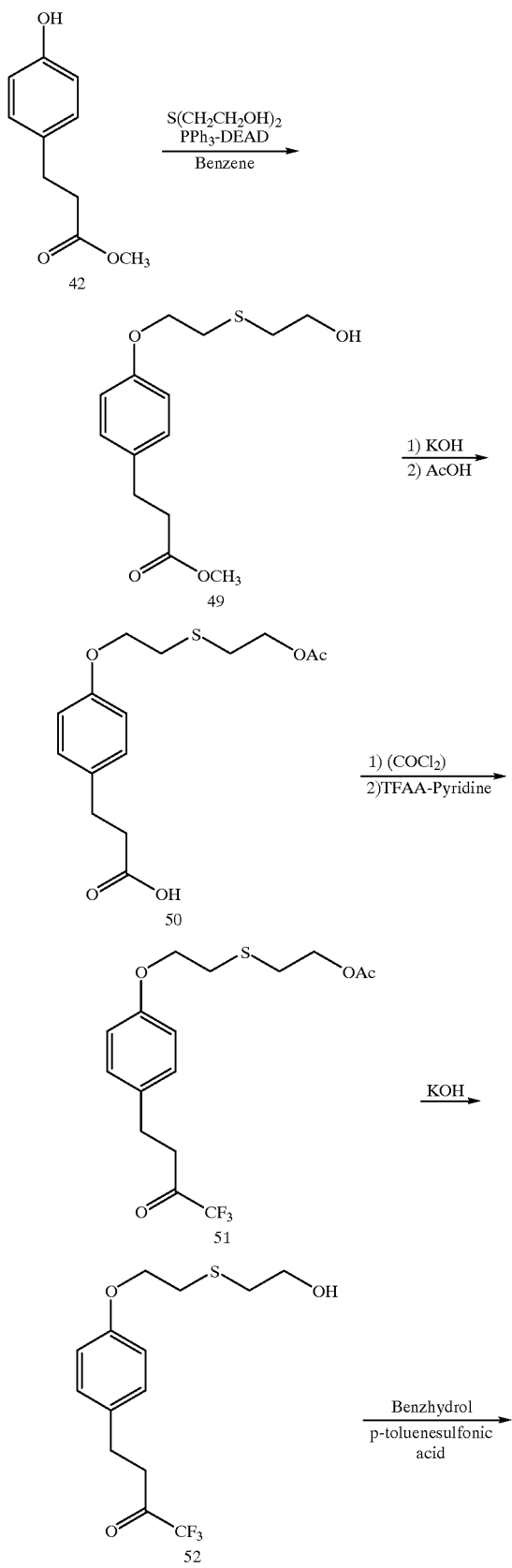

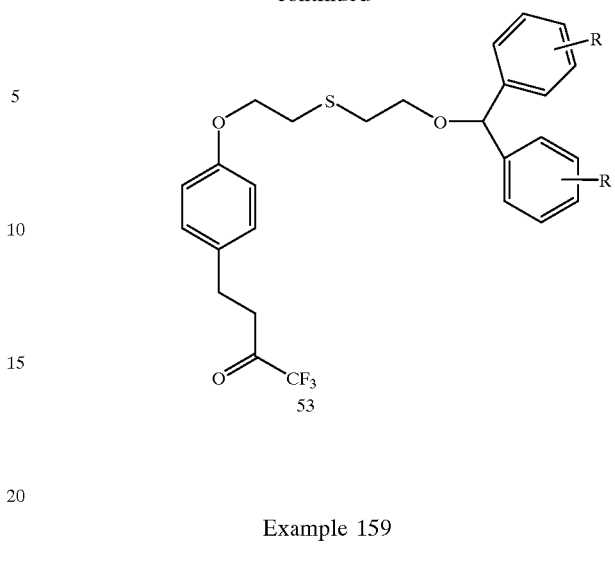

Example 159

4-[4-[2-[2-Hydroxyethylthio]ethoxy]phenyl]-1,1,1-trifluoro Butanone

3-[4-[2-(2-hydroxyethylthio)ethoxy]phenyl]propanoic Acid, Methyl Ester

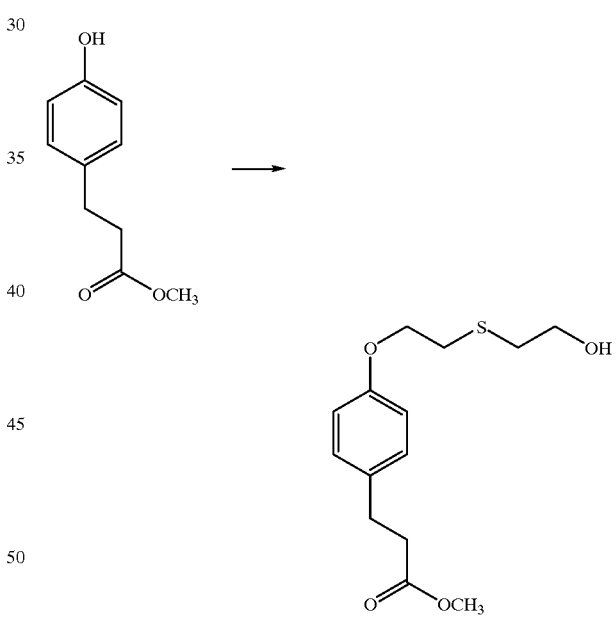

A solution of methyl 3-[4-hydroxyphenyl)propionate (30.0 g, 0.166 mol), 2,2'-thiodiethanol (61.0 g, 0.50 mol) and triphenylphosphine (48.0 g, 0.183 mol) in dry benzene (450 ml) was treated at 22° C. with diethyl azodicarboxylate (33.2 g, 0.19 mol) added dropwise over 10 min and the resulting mixutre was stirred at 22° C. for 5 h. The reaction mixture was then diluted with ether (300 ml) washed with water, saturated sodium bicarbonate and brine. After drying (magnesium sulfate) the solvent was evaporated in vacuo and the residue was chromatographed on silica gel (elution toluene-ethyl acetate 85:15) to give 37.64 g (79%) of the starting material as a white solid: mp 47–48° C.

Anal. Calcd. for $C_{14}H_{20}O_4S$: C 59.13, H 7.09. Found: C 58.94, H 7.04.

3-[4-[2-(2-hydroxyethylthio]ethoxy]phenyl]propanoic Acid

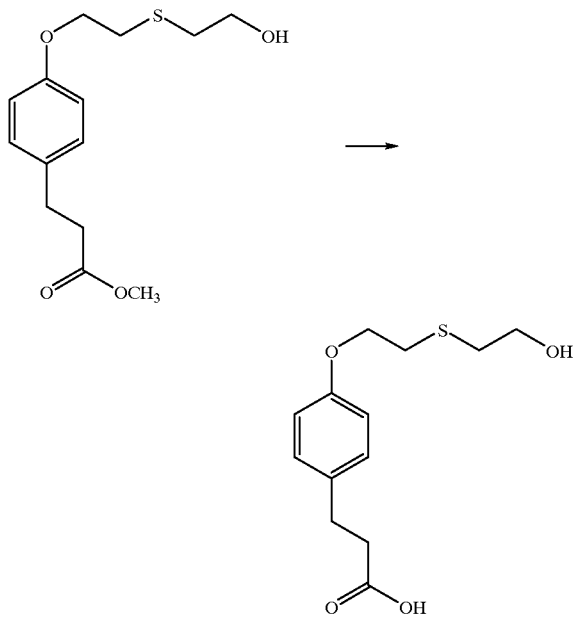

A solution of 3-[4-[2-(2-hydroxyethylthio)ethoxy]phenyl] propanoic acid, methyl ester (37.64 g, 0.132 mol) in 80% aqueous ethanol (300 ml) was treated with a solution of potassium hydroxide (17.0 g, 0.257 mol) in water (25 ml) and the resulting mixture was stirred at 22° C. for 1 h. The solvent was then concentrated in vacuo and the residue was diluted with water (200 ml) and dichloromethane (200 ml). The aqueous phase was then adjusted to pH 2 with 6N hydrochloric acid and extracted several times with dichloromethane. The combined organic extracts were washed with brine, dried (magnesium sulfate) and evaporated to give 35.67 g (100%) of the title material as a white solid: mp 64–65° C.

Anal. Calcd. for $C_{13}H_{18}O_4S$: C 57.76, H 6.71. Found: C 57.74, H 6.80.

3-[4-[2-(2-acetoxyethylthio]ethoxy]phenyl]propanoic Acid

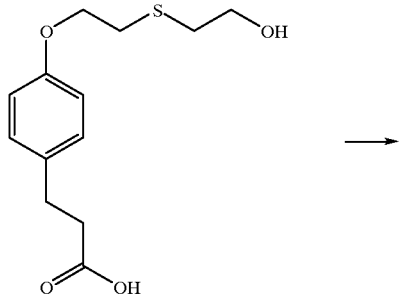

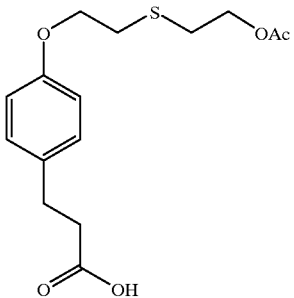

A solution of 3-[4-[2-(2-hydroxyethylthio)ethoxy]phenyl] propanoic acid, (35.67 g, 0.13 mol) in a mixture of toluene (500 ml) and acetic acid (500 ml) was treated with p-toluenesulfonic acid (1.2 g) and then heated under reflux using a Dean-Stark apparatus for 2 h. The cooled mixture was concentrated in vacuo and the residue was diluted with ethyl acetate, washed with water and dried (magnesium sulfate). Evaporation of the solvent under vacuum gave a solid which was crystallized from hexane to give 36.13 g (88%) of title material as a white solid: mp 48–49° C.

4-[4-[2-(2-acetoxyethylthio]ethoxy]phenyl]-1,1,1-trifluoro-2-butanone

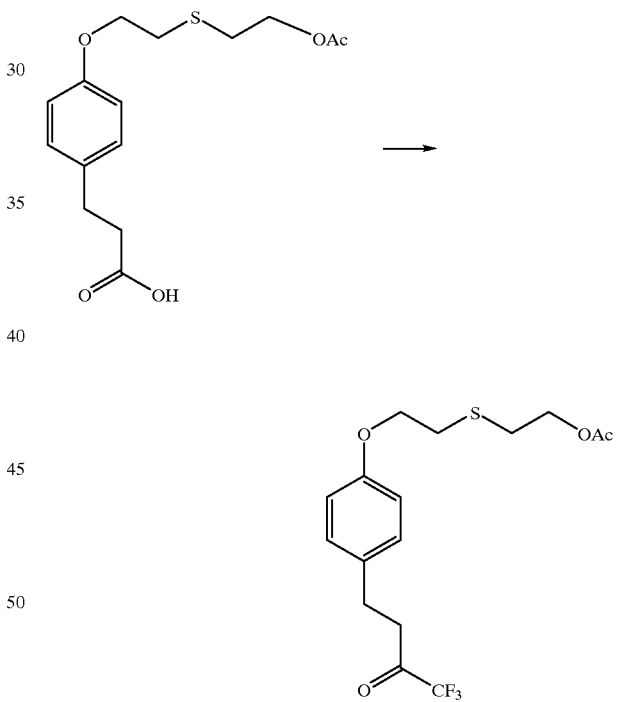

A solution of 3-[4-[2-(2-acetoxyethylthio)ethoxy]phenyl] propanoic acid, (36.13 g, 0.115 mol) in dichloromethane (250 ml) was treated with oxalyl chloride (24 ml) and a drop of N,N-dimethylformamide. After 1 h at 25° C., the solvent and excess reagent were evaporated in vacuo. The residual oil was dissolved in toluene (250 ml) cooled to 0° C. and treated with trifluoroacetic anhydride (49.0 ml, 0.347 mol). Then pyridine (19.0 ml, 0.232 mol) was added dropwise over 30 min and the resulting mixture was stirred at 22° C. for 3 h. The solution was then cooled again to 0° C., treated dropwise with water (70 ml) and then stirred at 22° C. for 30 min. The solution was then diluted with ethyl acetate, washed with water, saturated sodium bicarbonate, brine and dried (magnesium sulfate). Evaporation of the solvent in vacuo gave an oil which was chromatographed on silica gel. Elution with a mixture of dichlorimethane and ethyl acetate (0–2%) gave 26.10 g (62%) of the title material as an oil.

4-[4-[2-(2-hydroxyethylthio]ethoxy]phenyl]-1,1,1-trifluoro-2-butanone

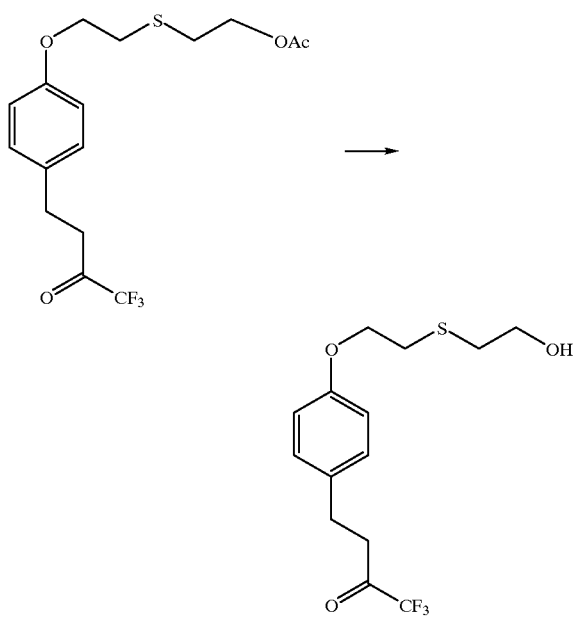

A solution of 4-[4-[2-(2-acetoxyethylthio)ethoxy] phenyl]-1,1,1-trifluoro-2-butanone (26.10 g, 71.6 mmol) in ethanol (275 ml) was treated at 22° C. with a solution of potassium hydroxide (6.0 g, 91.0 mmol) in water (70 ml) and the resulting mixture was stirred for 30 min. The solvent was then evaporated in vacuo and the residual oil was dissolved in ethyl acetate, washed with water, brine and dried (magnesium sulfate). Evaporation of the solvent gave 23.0 g (100%) of the title material as an oil.

Anal. Calcd. for $C_{14}H_{17}F_3O_3S$. 0.3 $H_2O$: C 51.31, H 5.41. Found: C 51.11, H 5.42.

Example 160

4-[4-[2-[2-[Bis(4-methylphenyl)methoxy]ethylthio]ethoxy] phenyl]-1,1,1-trifluoro-2-butanone

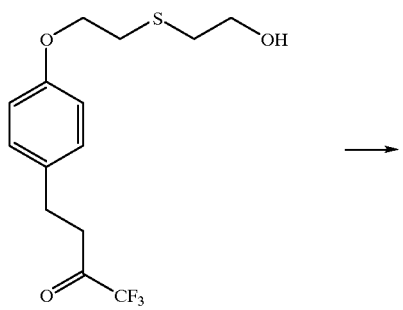

-continued

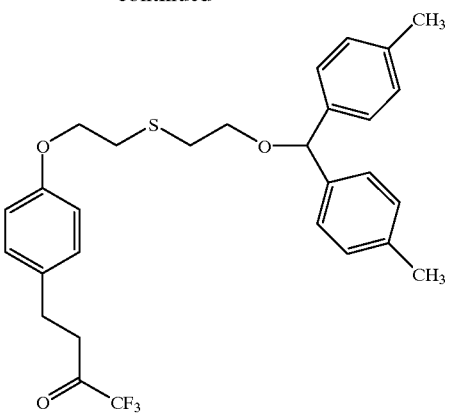

A solution of 4-[4-[2-(2-hydroxyethylthio)ethoxy] phenyl]-1,1,1-trifluoro-2-butanone (1.20 g, 3.72 mmol), 4,4'-dimethylbenzhydrol (0.95 g, 4.47 mmol) and p-toluenesulfonic acid (0.035 g) in toluene (20 ml) was heated under reflux for 15 min. The cooled reaction mixture was diluted with ethyl acetate, washed with saturated sodium bicarbonate, brine and dried (magnesium sulfate). Evaporation of the solvent in vacuo and chromatography of the residue on silica gel (elution with a gradient of ethyl acetate 20–40% in hexane) gave 1.81 g (94%) of the title material as an oil.

Anal. Calcd. for $C_{29}H_{31}F_3O_3S$: C 67.42, H 6.05. Found: C 67.43, H 6.08.

The following compounds may be prepared by the general procedure of Scheme 9B.

TABLE 9B

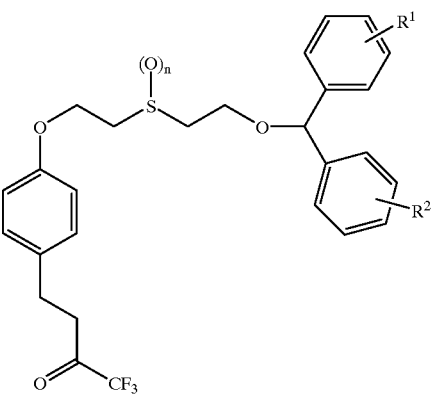

| Exp. # | n | $R^1$ | $R^2$ | Analysis |
|---|---|---|---|---|
| 161 | 0 | H | H | $C_{27}H_{27}F_3O_3S.H_2O$ <br> Calcd: C 64.02, H 5.77 <br> Found: C 63.90, H 5.50 |
| 162 | 1 | H | H | $C_{27}H_{27}F_3O_4S.0.6H_2O$ <br> Calcd: C 62.90, H 5.52 <br> Found: C 62.89, H 5.57 |
| 163 | 2 | H | H | $C_{27}H_{27}F_3O_5S.0.6H_2O$ <br> Calcd: C 61.03, H 5.35 <br> Found: C 60.99, H 5.12 |
| 164 | 1 | p-$CH_3$ | p-$CH_3$ | $C_{29}H_{31}F_3O_4S.0.6H_2O$ <br> Calcd: C 64.10, H 5.97 <br> Found: C 64.20, H 5.88 |

TABLE 9B-continued

[Structure: 4-substituted phenyl group with propyl-trifluoromethyl ketone side chain, connected via O-CH2-CH2-S(O)n-CH2-CH2-O-CH to diphenylmethyl with R¹ and R² substituents]

| Exp. # | n | R¹ | R² | Analysis |
|---|---|---|---|---|
| 165 | 2 | p-CH₃ | p-CH₃ | C₂₉H₃₁F₃O₅S·0.5H₂O<br>Calcd: C 62.46, H 5.78<br>Found: C 62.40, H 5.70 |
| 166 | 0 | p-CH₂CH₃ | H | C₂₉H₃₁F₃O₃S·0.3H₂O<br>Calcd: C 66.72, H 6.10<br>Found: C 66.84, H 5.96 |
| 167 | 1 | p-CH₂CH₃ | H | C₂₉H₃₁F₃O₄S·0.5H₂O<br>Calcd: C 64.31, H 5.96<br>Found: C 64.38, H 6.08 |
| 168 | 2 | p-CH₂CH₃ | H | C₂₉H₃₁F₃O₅S·0.3H₂O<br>Calcd: C 62.87, H 5.75<br>Found: C 62.88, H 5.73 |
| 169 | 0 | p-tBu | H | C₃₁H₃₅F₃O₃S·0.4H₂O<br>Calcd: C 67.47, H 6.54<br>Found: C 67.51, H 6.41 |
| 170 | 1 | p-tBu | H | C₃₁H₃₅F₃O₄S·0.5H₂O<br>Calcd: C 65.36, H 6.37<br>Found: C 65.37, H 6.29 |
| 171 | 2 | p-tBu | H | C₃₁H₃₅F₃O₅S·0.4H₂O<br>Calcd: C 63.77, H 6.18<br>Found: C 63.84, H 5.81 |
| 172 | 0 | p-Cl | H | C₂₇H₂₆ClF₃O₃S<br>Calcd: C 62.01, H 5.01<br>Found: C 62.40, H 4.80 |
| 173 | 2 | p-Cl | H | C₂₇H₂₆ClF₃O₅S<br>Calcd: C 58.43, H 4.72<br>Found: C 58.14, H 4.71 |
| 174 | 0 | m-Cl | H | C₂₇H₂₆ClF₃O₃S<br>Calcd: C 62.01, H 5.01<br>Found: C 61.97, H 5.04 |
| 175 | 1 | m-Cl | H | C₂₇H₂₆ClF₃O₄S·0.5H₂O<br>Calcd: C 59.18, H 4.97<br>Found: C 59.15, H 4.80 |
| 176 | 2 | m-Cl | H | C₂₇H₂₆ClF₃O₅S·0.5H₂O<br>Calcd: C 57.50, H 4.63<br>Found: C 57.51, H 4.65 |
| 177 | 0 | m-Cl<br>p-Cl | H | C₂₇H₂₅Cl₂F₃O₃S·0.2H₂O<br>Calcd: C 57.80, H 4.56<br>Found: C 57.93, H 4.59 |
| 178 | 2 | m-Cl<br>p-Cl | H | C₂₇H₂₅Cl₂F₃O₄S·0.5H₂O<br>Calcd: C 54.19, H 4.38<br>Found: C 54.20, H 4.35 |
| 179 | 2 | m-Cl | m-Cl | C₂₇H₂₅Cl₂F₃O₄S·H₂O<br>Calcd: C 53.38, H 4.48<br>Found: C 53.15, H 4.14 |
| 180 | 0 | p-F | p-F | C₂₇H₂₅F₅O₃S<br>Calcd: C 61.82, H 4.80, S 6.11<br>Found: C 61.90, H 4.66, S 6.07 |
| 181 | 1 | p-F | p-F | C₂₇H₂₅F₅O₄S<br>Calcd: C 57.59, H 4.92, S 5.69<br>Found: C 57.55, H 4.66, S 5.83 |
| 182 | 2 | p-F | p-F | C₂₇H₂₅F₅O₅S·0.25H₂O<br>Calcd: C 57.80, H 4.58, S 5.71<br>Found: C 57.66, H 4.34, S 5.83 |
| 183 | 0 | p-Br | p-Br | C₂₇H₂₅Br₂F₃O₃S<br>Calcd: C 50.17, H 3.90, S 4.96<br>Found: C 49.97, H 3.88, S 5.06 |
| 184 | 1 | p-Br | p-Br | C₂₇H₂₅Br₂F₃O₄S·1.2H₂O<br>Calcd: C 47.41, H 4.04, S 4.69<br>Found: C 47.22, H 3.77, S 4.74 |
| 185 | 2 | p-Br | p-Br | C₂₇H₂₅Br₂F₃O₅S·H₂O<br>Calcd: C 46.57, H 3.91, S 4.60<br>Found: C 46.71, H 3.87, S 4.71 |
| 186 | 2 | penta-F | penta-F | C₂₇H₁₇F₁₃O₅S·0.7H₂O<br>Calcd: C 45.48, H 2.60<br>Found: C 45.53, H 2.49 |
| 187 | 0 | p-Cl | p-Ph | C₃₃H₃₀ClF₃O₃S<br>Calcd: C 66.16, H 5.05<br>Found: C 66.08, H 4.81 |
| 188 | 1 | p-Cl | p-Ph | C₃₃H₃₀ClF₃O₄S·0.6H₂O<br>Calcd: C 63.32, H 5.02<br>Found: C 63.08, H 4.75 |
| 189 | 2 | p-Cl | p-Ph | C₃₃H₃₀ClF₃O₅S·0.8H₂O<br>Calcd: C 61.40, H 4.93<br>Found: C 61.27, H 4.46 |
| 190 | 0 | m-NO₂ | m-NO₂ | C₂₇H₂₅F₃N₂O₇S·0.8H₂O<br>Calcd: C 54.69, H 4.52, N 4.72, S 5.41<br>Found: C 54.57, H 4.36, N 4.76, S 5.36 |
| 191 | 1 | m-NO₂ | m-NO₂ | C₂₇H₂₅F₃N₂O₈S·H₂O<br>Calcd: C 52.94, H 4.44, N 4.57, S 5.23<br>Found: C 52.97, H 4.22, N 4.59, S 5.38 |
| 192 | 2 | m-NO₂ | m-NO₂ | C₂₇H₂₅F₃N₂O₉S·0.5H₂O<br>Calcd: C 52.34, H 4.23, N 4.52, S 5.18<br>Found: C 52.29, H 4.02, N 4.47, S 5.39 |
| 193 | 0 | p-Cl | H | C₂₇H₂₅ClF₃NO₅S<br>Calcd: C 57.09, H 4.44, N 2.47<br>Found: C 57.12, H 4.47, N 2.73 |
|  |  | m-NO₂ |  |  |
| 194 | 2 | p-Cl | H | C₂₇H₂₅ClF₃NO₇S·0.3H₂O<br>Calcd: C 53.37, H 4.26, N 2.31<br>Found: C 53.56, H 4.26, N 2.47 |
|  |  | m-NO₂ |  |  |
| 195 | 0 | p-Cl | p-Cl | C₂₇H₂₃Cl₂F₃N₂O₇S·0.3H₂O<br>Calcd: C 49.67, H 3.64, N 4.29, S 4.91<br>Found: C 49.40, H 3.47, N 4.59, S 4.81 |
|  |  | m-NO₂ | m-NO₂ |  |
| 196 | 1 | p-Cl | p-Cl | C₂₇H₂₃Cl₂F₃N₂O₈S·0.3H₂O<br>Calcd: C 48.49, H 3.56, N 4.19, S 4.79<br>Found: C 48.52, H 3.73, N 4.15, S 4.85 |
|  |  | m-NO₂ | m-NO₂ |  |
| 197 | 2 | p-Cl | p-Cl | C₂₇H₂₃Cl₂F₃N₂O₉S<br>Calcd: C 47.73, H 3.41, N 4.12, S 4.72 |
|  |  | m-NO₂ | m-NO₂ |  |

TABLE 9B-continued

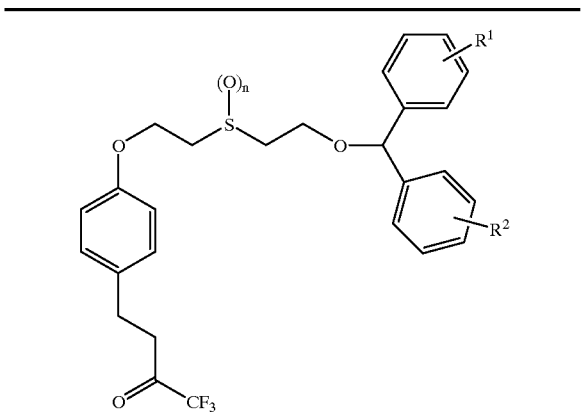

| Exp. # | n | R¹ | R² | Analysis |
|---|---|---|---|---|
| | | | | Found: C 47.57, H 3.31, N 4.14, S 4.76 |
| 198 | 0 | m-OCH₃ | m-OCH₃ | $C_{29}H_{31}F_3O_5S \cdot 0.5H_2O$ Calcd: C 62.46, H 5.78 Found: C 62.51, H 5.79 |
| 199 | 1 | m-OCH₃ | m-OCH₃ | $C_{29}H_{31}F_3O_6S \cdot 0.9H_2O$ Calcd: C 59.97, H 5.69 Found: C 59.98, H 5.53 |
| 200 | 2 | m-OCH₃ | m-OCH₃ | $C_{29}H_{31}F_3O_7S \cdot 0.2H_2O$ Calcd: C 59.62, H 5.42 Found: C 59.55, H 5.47 |
| 201 | 0 | p-OCH₃ | p-OCH₃ | $C_{29}H_{31}F_3O_5S \cdot 0.1H_2O$ Calcd: C 63.28, H 5.71 Found: C 62.90, H 5.60 |
| 202 | 1 | p-OCH₃ | p-OCH₃ | $C_{29}H_{31}F_3O_6S \cdot 0.6H_2O$ Calcd: C 60.53, H 5.64, S 5.57 Found: C 60.41, H 5.54, S 5.62 |
| 203 | 2 | p-OCH₃ | p-OCH₃ | $C_{29}H_{31}F_3O_7S \cdot 0.7H_2O$ Calcd: C 58.72, H 5.51, S 5.40 Found: C 58.5, H 5.48, S 5.47 |
| 204 | 0 | p-OAllyl | p-OAllyl | $C_{33}H_{35}F_3O_5S$ Calcd: C 65.98, H 5.87, S 5.34 Found: C 65.89, H 5.93, S 5.36 |
| 205 | 1 | p-OAllyl | p-OAllyl | $C_{33}H_{35}F_3O_6S \cdot 0.6H_2O$ Calcd: C 63.17, H 5.81, S 5.11 Found: C 63.10, H 5.69, S 5.14 |
| 206 | 2 | p-OAllyl | p-OAllyl | $C_{33}H_{35}F_3O_7S \cdot 0.4H_2O$ Calcd: C 61.94, H 5.64, S 5.01 Found: C 61.89, H 5.53, S 5.05 |
| 207 | 0 | p-OCH₃ | H | $C_{28}H_{29}F_3O_4S \cdot 0.3H_2O$ Calcd: C 64.18, H 5.69 Found: C 64.14, H 5.82 |
| 208 | 1 | p-OCH₃ | H | $C_{28}H_{29}F_3O_5 \cdot 0.6H_2O$ Calcd: C 61.66, H 5.58 Found: C 61.86, H 5.51 |
| 209 | 2 | p-OCH₃ | H | $C_{28}H_{29}F_3O_6S \cdot 0.6H_2O$ Calcd: C 59.91, H 5.42 Found: C 59.90, H 5.20 |
| 210 | 0 | m-CF₃ | H | $C_{28}H_{26}F_6O_3S$ Calcd: C 60.43, H 4.71 Found: C 60.43, H 4.54 |
| 211 | 1 | m-CF₃ | H | $C_{28}H_{26}F_6O_4S \cdot 0.7H_2O$ Calcd: C 57.47, H 4.72 Found: C 57.29, H 4.46 |
| 212 | 2 | m-CF₃ | H | $C_{28}H_{26}F_6O_5S \cdot 0.5H_2O$ Calcd: C 56.28, H 4.55 Found: C 56.28, H 4.53 |
| 213 | 0 | p-CF₃ | H | $C_{28}H_{26}F_6O_3S$ Calcd: C 60.43, H 4.71 Found: C 60.45, H 4.78 |
| 214 | 1 | p-CF₃ | H | $C_{28}H_{26}F_6O_4S \cdot 0.5H_2O$ Calcd: C 57.83, H 4.68 Found: C 57.82, H 4.57 |
| 215 | 2 | p-CF₃ | H | $C_{28}H_{26}F_6O_5S \cdot 0.2H_2O$ Calcd: C 56.79, H 4.49 Found: C 56.83, H 4.44 |

TABLE 9B-continued

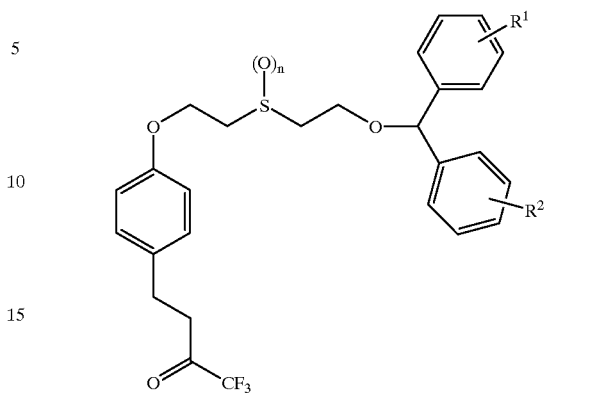

| Exp. # | n | R¹ | R² | Analysis |
|---|---|---|---|---|
| 216 | 2 | p-CF₃ | p-CF₃ | $C_{29}H_{25}F_9O_5S \cdot 0.2H_2O$ Calcd: C 52.76, H 3.86 Found: C 52.63, H 3.87 |
| 217 | 2 | m-CF₃ | m-CF₃ | $C_{29}H_{25}F_9O_5S$ Calcd: C 53.05, H 3.84 Found: C 52.96, H 3.79 |
| 218 | 2 | m-CF₃ | p-CF₃ | $C_{29}H_{25}F_9O_5S \cdot 0.4H_2O$ Calcd: C 52.48, H 3.92 Found: C 52.43, H 3.90 |
| 219 | 0 | p-OCH₃ | p-Cl | $C_{28}H_{28}ClF_3O_4S$ Calcd: C 60.81, H 5.10 Found: C 60.67, H 5.07 |
| 220 | 1 | p-OCH₃ | p-Cl | $C_{28}H_{28}ClF_3O_5S \cdot 0.7H_2O$ Calcd: C 57.82, H 5.09 Found: C 57.82, H 5.05 |
| 221 | 2 | p-OCH₃ | p-Cl | $C_{28}H_{28}ClF_3O_6S \cdot 0.4H_2O$ Calcd: C 56.79, H 4.90 Found: C 56.77, H 4.81 |
| 222 | 0 | p-OCH₃ | p-F | $C_{28}H_{28}F_4O_4S$ Calcd: C 62.68, H 5.26 Found: C 62.61, H 5.30 |
| 223 | 1 | p-OCH₃ | p-F | $C_{28}H_{28}F_4O_5S \cdot 0.4H_2O$ Calcd: C 60.08, H 5.19 Found: C 60.05, H 5.24 |
| 224 | 2 | p-OCH₃ | p-F | $C_{28}H_{28}F_4O_6S \cdot 0.3H_2O$ Calcd: C 58.59, H 5.02 Found: C 58.50, H 5.10 |
| 225 | 0 | m-Cl o-OCH₃ | H | $C_{28}H_{28}ClF_3O_4S$ Calcd: C 60.81, H 5.10 Found: C 60.70, H 5.20 |
| 226 | 1 | m-Cl o-OCH₃ | H | $C_{28}H_{28}ClF_3O_5S \cdot 0.3H_2O$ Calcd: C 58.55, H 5.02 Found: C 58.53, H 4.72 |
| 227 | 2 | m-Cl o-OCH₃ | H | $C_{28}H_{28}ClF_3O_6S \cdot 0.4H_2O$ Calcd: C 56.79, H 4.990 Found: C 56.73, H 4.95 |
| 228 | 0 | p-Cl | p-SCH₃ | $C_{28}H_{28}ClF_3O_3S_2$ Calcd: C 59.09, H 4.96 Found: C 59.06, H 5.00 |
| 229 | 1 | p-Cl | p-SCH₃ | $C_{28}H_{28}ClF_3O_4S_2 \cdot 0.8H_2O$ Calcd: C 56.10, H 4.98 Found: C 56.10, H 4.79 |
| 230 | 2 | p-Cl | p-SCH₃ | $C_{28}H_{28}ClF_3O_5S_2 \cdot 0.2H_2O$ Calcd: C 55.62, H 4.73 Found: C 55.59, H 4.66 |
| 231 | 1 | p-Cl | p-SOCH₃ | $C_{28}H_{28}ClF_3O_5S_2 \cdot H_2O$ Calcd: C 54.32, H 4.88 Found: C 54.31, H 5.06 |
| 232 | 2 | p-Cl | p-SOCH₃ | $C_{28}H_{28}ClF_3O_6S_2 \cdot H_2O$ Calcd: C 52.96, H 4.76 Found: C 53.05, H 4.68 |
| 233 | 2 | p-Cl | p-SO₂CH₃ | $C_{28}H_{28}ClF_3O_7S_2 \cdot 0.4H_2O$ Calcd: C 52.52, H 4.53 Found: C 52.53, H 4.55 |

TABLE 9B-continued

[Structure: aryl-O-CH2CH2-S(O)n-CH2CH2-O-CH(Ar-R1)(Ar-R2) with 4-substituted phenyl bearing -CH2CH2-C(=O)-CF3]

| Exp. # | n | R¹ | R² | Analysis |
|---|---|---|---|---|
| 234 | 2 | p-SCH₃ | p-SCH₃ | $C_{29}H_{31}F_3O_5S_3 \cdot 0.4H_2O$ |
| | | | | Calcd: C 56.18, H 5.17 |
| | | | | Found: C 56.11, H 5.06 |
| 235 | 0 | p-SO₂N(CH₃)₂ | H | $C_{29}H_{32}F_3NO_5S_2 \cdot 0.3H_2O$ |
| | | | | Calcd: C 57.95, H 5.47, N 2.33, S 10.69 |
| | | | | Found: C 58.10, H 5.41, N 2.49, S 10.29 |
| 236 | 2 | p-SO₂N(CH₃)₂ | H | $C_{29}H_{32}F_3NO_7S_2 \cdot H_2O$ |
| | | | | Calcd: C 53.94, H 5.31, N 2.17, S 9.93 |
| | | | | Found: C 54.04, H 5.13, N 2.25, S 9.44 |
| 237 | 0 | p-CO₂CH₃ | H | $C_{29}H_{29}F_3O_5S \cdot 0.7H_2O$ |
| | | | | Calcd: C 62.29, H 5.48 |
| | | | | Found: C 62.15, H 5.07 |
| 238 | 1 | p-CO₂CH₃ | H | $C_{29}H_{29}F_3O_6S \cdot 2H_2O$ |
| | | | | Calcd: C 58.19, H 5.56 |
| | | | | Found: C 57.77, H 5.03 |
| 239 | 2 | p-CO₂CH₃ | H | $C_{29}H_{29}F_3O_7S \cdot 0.3H_2O$ |
| | | | | Calcd: C 59.64, H 5.11 |
| | | | | Found: C 59.66, H 4.87 |
| 240 | 0 | m-CO₂CH₃ | H | $C_{29}H_{29}F_3O_5S \cdot 0.6H_2O$ |
| | | | | Calcd: C 62.49, H 5.46 |
| | | | | Found: C 62.39, H 5.25 |
| 241 | 1 | m-CO₂CH₃ | H | $C_{29}H_{29}F_3O_6S \cdot 1.3H_2O$ |
| | | | | Calcd: C 59.44, H 5.44 |
| | | | | Found: C 59.17, H 5.14 |
| 242 | 2 | m-CO₂CH₃ | H | $C_{29}H_{29}F_3O_7S \cdot H_2O$ |
| | | | | Calcd: C 58.38, H 5.24 |
| | | | | Found: C 58.03, H 4.87 |
| 243 | 2 | m-CO₂H | H | $C_{28}H_{27}F_3O_7S \cdot 1.9H_2O$ |
| | | | | Calcd: C 56.16, H 5.18 |
| | | | | Found: C 56.31, H 4.63 |

Example 244

Scheme 9C

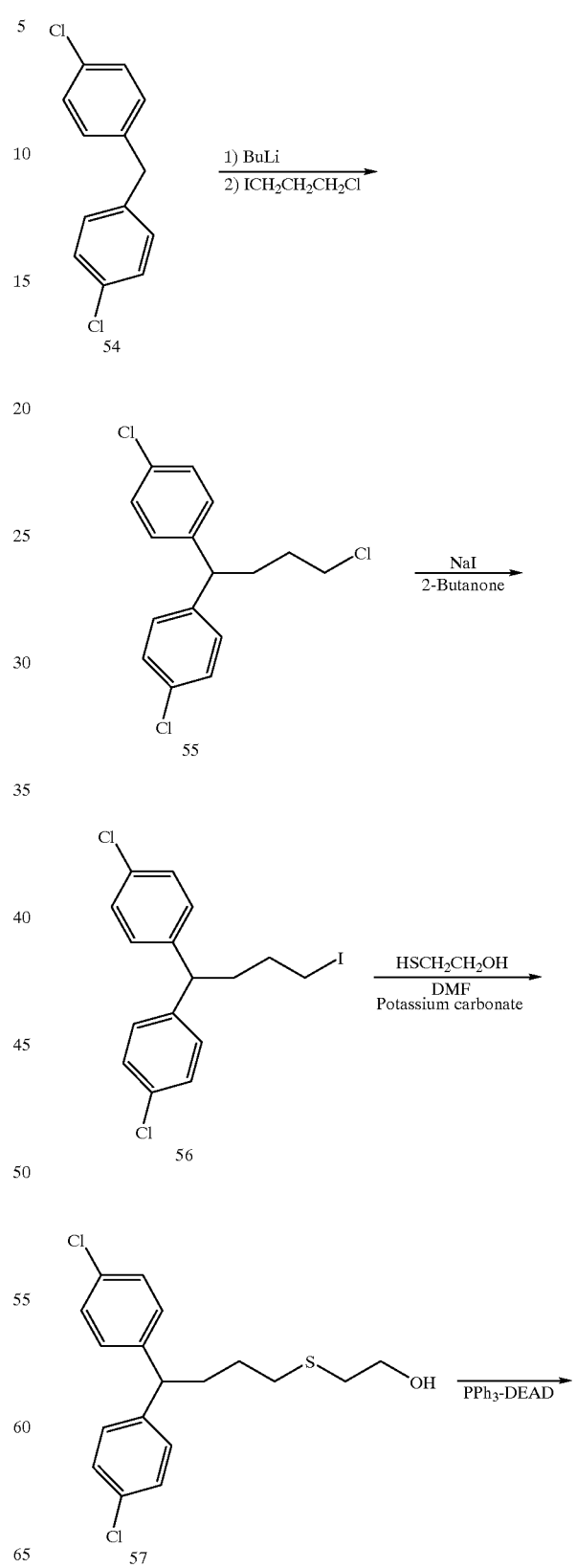

161
-continued

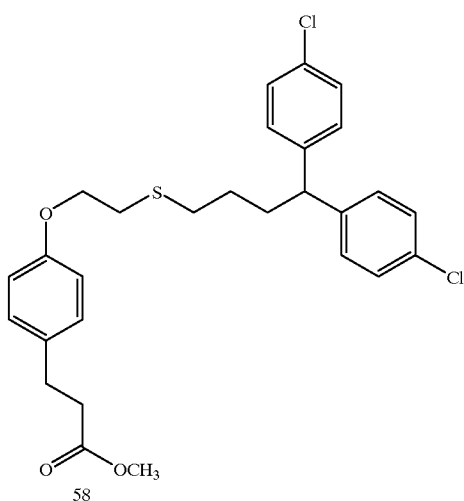
58

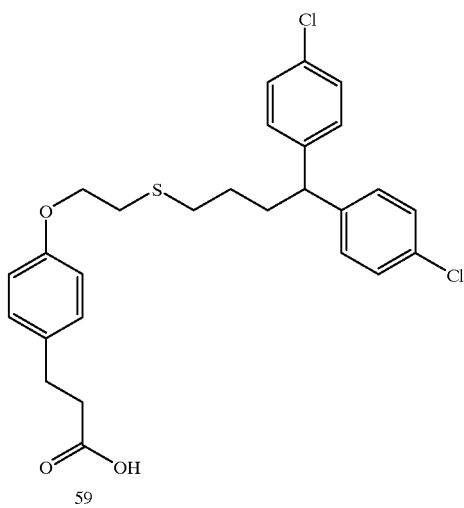
59

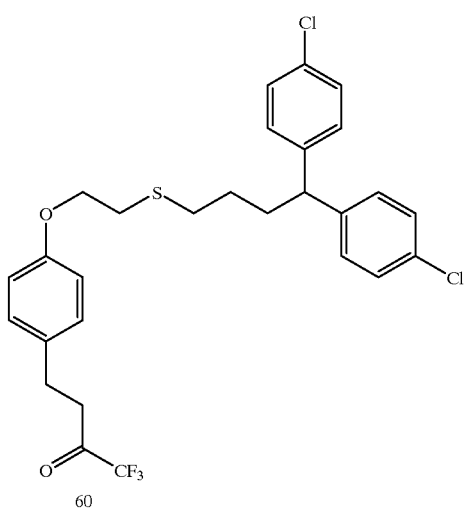
60

162
-continued

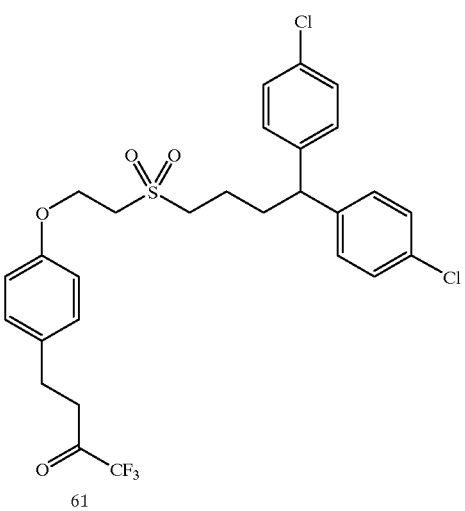
61

4-[4-[2-[4-Bis(4-methylphenyl)butylsulfonyl]ethoxy]phenyl]-1,1,1-trifluoro-2-butanone 1-Chloro-4,4-di-(4-chlorophenyl)butane

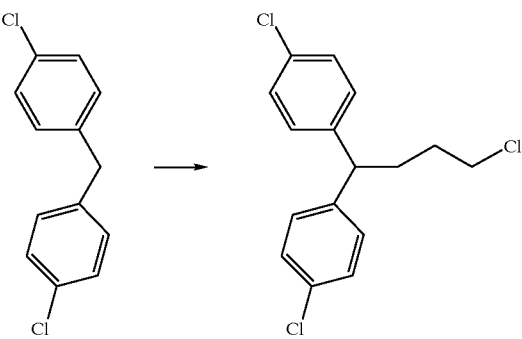

A solution of 4,4'-dichlorodiphenylmethane (4.37 g, 18.4 mmol) (Blackwell, J. et all, J. Chem. Soc., 1961, 1405) in dry tetrahydrofuran (50 ml) was treated at 0° C. with butyllithium (12.1 ml of 1.6 M, 19.36 mmol) added dropwise over 15 min. After 15 min, the red solution was then added dropwise to a cold (−78° C.) solution of 1-chloro-3-iodopropane (15.0 g, 73.4 mmol) in dry tetrahydrofuran (120 ml). After 20 min at −78° C., the reaction mixture was quenched by the addition of saturated ammonium chloride (100 ml) and diluted with toluene. The organic phase was washed with brine and dried. The oil obtained after evaporation of the solvent was purified on silica gel (elution hexane-toluene 85:15) and distilled under vacuum to give 2.54 g (44%) of the title material as a clear oil: bp 110–130° C./1.5 torr (air bath temperature).

1-Iodo-4,4-di-(4-chlorophenyl)butane

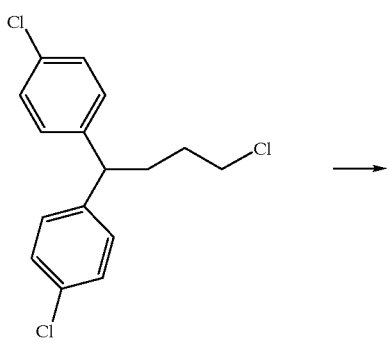

A solution of methyl 1-chloro-4,4-di-(4-chlorophenyl) butane (1.77 g, 5.64 mmol) in 2-butanone (20 ml) was treated with sodium iodide (1.5 g) and heated under reflux for 18 h. The solid formed was filtered, the filtrate was evaporated and purified on silica gel (elution hexane-toluene 96:5) to give 2.13 g (93%) of the title material as a clear oil.

2-[4-Bis-(4-chlorophenyl)butylthio]ethanol

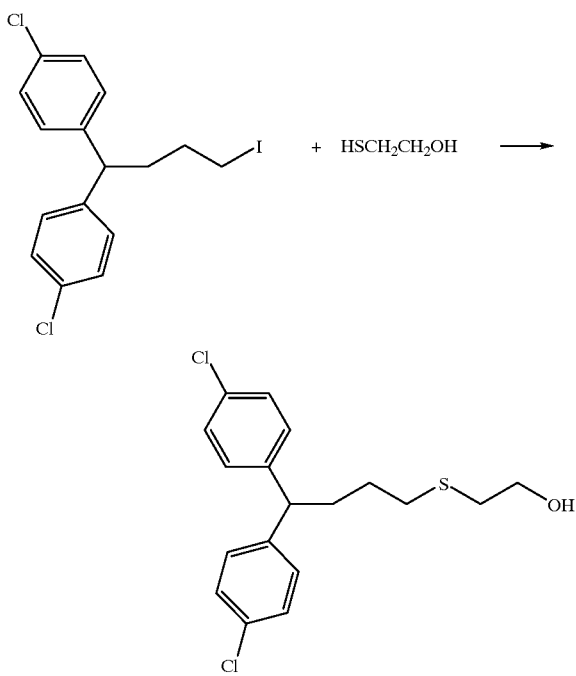

A solution of 1-iodo-4,4-di-(4-chlorophenyl)butane (3.22 g, 7.96 mmol) in N,N-dimethyl formamide (45 ml) was treated at 22° C. with powdered anhydrous potassium carbonate (2.2 g) followed by 2-mercaptoethanol (0.71 g, 9.20 mmol) and the resulting mixture was stirred at 22° C. for 18 h. The reaction mixture was then diluted with toluene (400 ml) washed with water and brine and dried over anhydrous magnesium sulfate. After evaporation of the solvent, the residue was chromatographed on silica gel (elution toluene-ethyl acetate 8:2) to give 2.58 g (92%) of the title material as a clear oil.

Anal. Calcd. for $C_{18}H_{20}Cl_2OS$: C 60.84, H 5.67, S 9.02. Found: C 61.12, H 5.75, S 9.28.

3-[4-[2-[4-Bis-(4-chlorophenyl)butylthio]ethoxy]phenyl] propionic Acid Methyl Ester

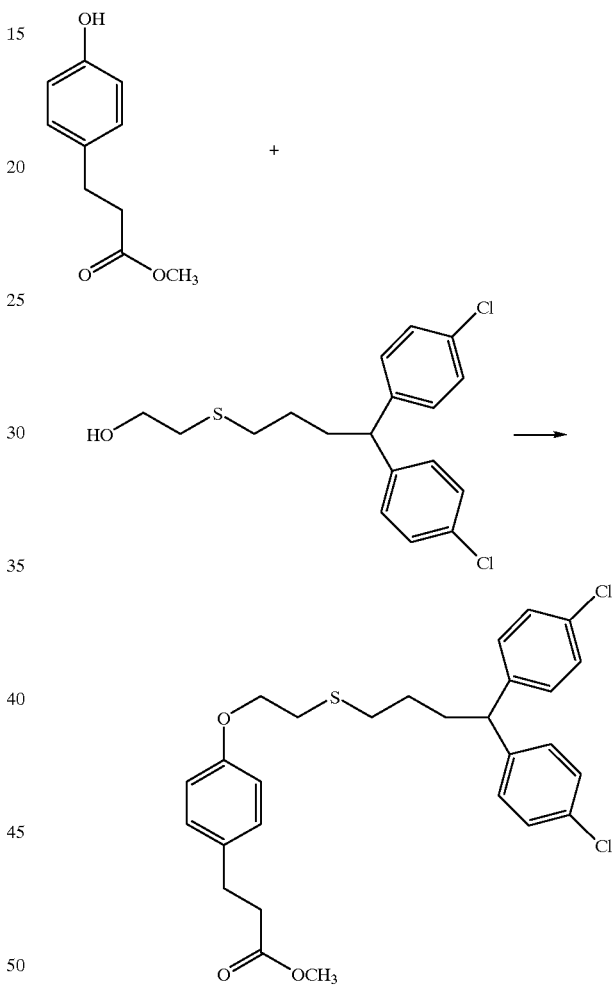

A solution of methyl 3-(4-hydroxyphenyl)propionate (1.22 g, 6.77 mmol), 2-[4-bis-(4-chlorophenyl)butylthio] ethanol (2.58 g, 7.26 mmol) and triphenylphosphine (1.95 g, 7.43 mmol) in dry benzene (30 ml) was treated at 22° C. with diethyl azodicarboxylate (1.29 g, 7.41 mmol) added drowise over 10 min. After 3 h at 22° C., the solvent was evaporated and the residue was chromatographed on silica gel (elution hexane ethyl acetate, 84:16) to give 3.17 g (91%) of the title material as a clear oil.

Anal. Calcd. for $C_{28}H_{30}Cl_2O_3S$: C 64.99, H 5.84, S 6.20. Found: C 65.01, H 5.86, S 6.38.

3-[4-[2-[4-Bis-(4-chlorophenyl)butylthio]ethoxy]phenyl] propionic Acid

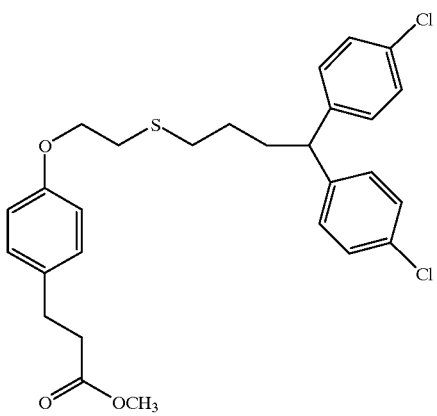

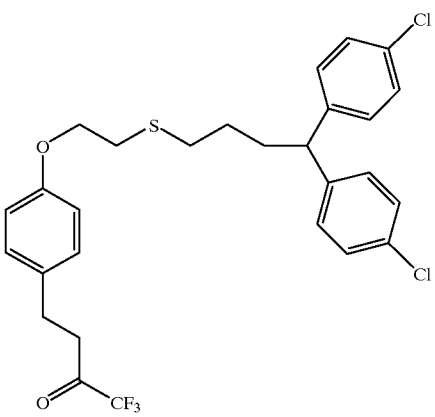

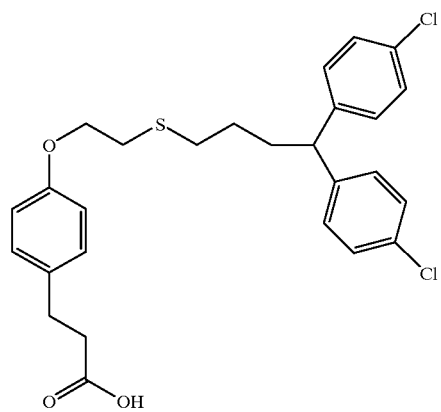

A suspension of 3-[4-[2-[4-bis-(4-chlorophenyl) butylthio]ethoxy]phenyl]propionic acid, methyl ester (3.09 g, 5.98 mmol) in ethanol (25 ml) was treated with a solution of potassium hydroxide (0.8 g, 14.3 mmol) in water (9.5 ml) and the resulting mixture was maintained at 35° C. for 2 h. The pH of the solution was then adjusted to 4.0 with 1N hydrochloric acid and the mixture was extracted with dichloromethane. The organic extract was dried (magnesium sulfate) and evaporated to give a white solid. Recrystallization from cyclohexane gave 2.93 g (97%) of the title material as a white solid: mp 89–92° C.
4-[4-[2-[4-Bis-(4-chlorophenyl)butythio]ethoxy]phenyl]-1,1,1-trifluoro-2-butanone A solution of 3-[4-[2-[4-bis-(4-chlorophenyl)butylthio] ethoxy]phenyl]propionic acid (2.85 g, 5.66 mmol) in dichloromethane (25 ml) was treated with oxalyl chloride (1.65 g, 13.0 mmol) and a small drop of N,N-dimethylformamide. After 1 h at 22° C., the solvent and excess reagent were evaporated in vacuo and the residual acid chloride was dissolved in dry toluene (85 ml). The solution was then cooled to 0° C. and treated with trifluoroacetic anhydride (3.57 g, 17.0 mmol) in dry toluene (15 ml) added dropwise over 10 min. After 3.5 h at 22° C., the mixture was cooled again to 0° C. and treated dropwise with water (5 ml) and stirred for 15 min. The reaction mixture was then diluted with toluene (200 ml), washed with saturated sodium bicarbonate, brine and dried (magnesium sulfate). Evaporation of the solvent gave an oil which was chromatographed on silica gel. Elution with a mixture of hexane and ethyl acetate (75:25) gave 2.62 g (83%) of the title material as an oil.

Anal. Calcd. for $C_{28}H_{27}Cl_2F_3O_2S$: C 60.54, H 4.90, S 5.77. Found: C 60.43, H 4.85, S 5.88.

4-[4-[2-[4-Bis-(4-chlorophenyl)butylsulfinyl]ethoxy]phenyl]-1,1,1-trifluoro-2-butanone

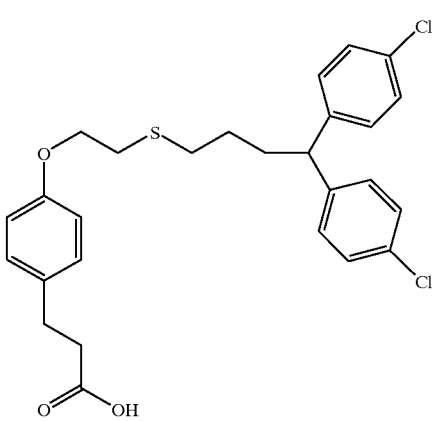

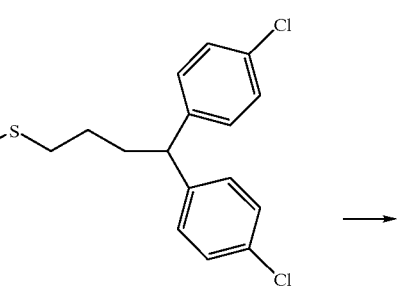

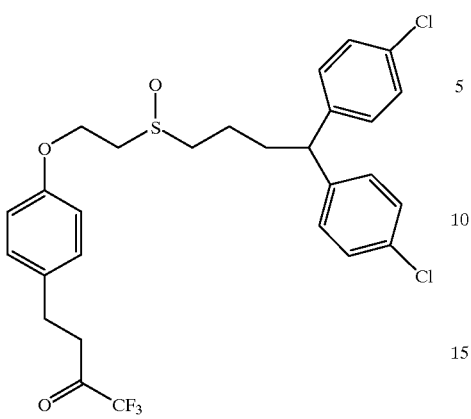

A solution of 4-[4-[2-[4-bis-(4-chlorophenyl)butylthio]ethoxy]phenyl]-1,1,1-trifluoro-2-butanone (0.741 g, 1.33 mmol) in methanol (35 ml) was treated with a solution of sodium periodate (0.32 g, 1.5 mmol) in water (1.5 ml) and the resulting mixture was stirred at 22° C. for 18 h. The solid formed was filtered and the filtrate was evaporated in vacuo. The residue was diluted with ethyl acetate, washed with saturated sodium bicarbonate, brine and dried (magnesium sulfate). Evaporation of the solvent in vacuo gave an oil which was chromatographed on silica gel. Elution with a gradient of ethyl acetate in dichloromethane (40–90%) gave 0.654 g (86%) of the title material as a white solid: mp 31–35° C.

Anal. Calcd. for $C_{28}H_{27}Cl_2F_3O_3S$. 0.4 $H_2O$: C 58.12, H 4.84, S 5.54. Found: C 58.05, H 4.97, S 5.73.

4-[4-[2-[4-Bis-(4-chlorophenyl)butylsulfonyl]ethoxy]phenyl]-1,1,1-trifluoro-2-butanone

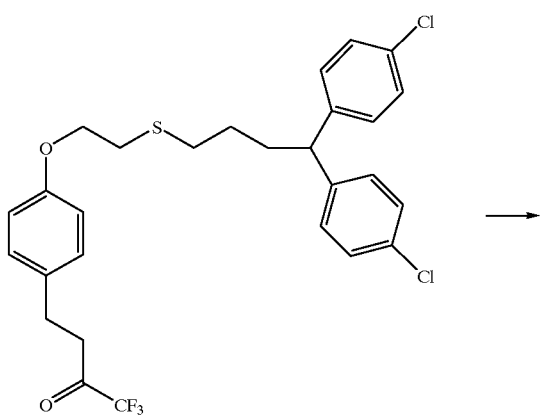

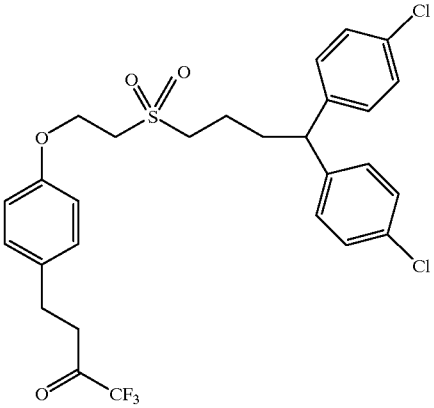

A solution of 4-[4-[2-[4-bis-(4-chlorophenyl)butylthio]ethoxy]phenyl]-1,1,1-trifluoro-2-butanone (0.583 g, 1.05 mmol) in dichloromethane (25 ml) was treated at 22° C. with m-chloroperbenzoic acid (0.592 g, 3.43 mmol) and the resulting mixture was stirred for 2 h. The reaction mixture was then diluted with ethyl acetate, washed with sodium bicarbonate, brine and dried (magnesium sulfate). Evaporation of the solvent in vacuo and chromatography of the residue on silica gel (elution ethyl acetate-hexane 1:1) gave 0.533 g (70%) of the title material as a clear oil.

Anal. Calcd. for $C_{28}H_{27}Cl_2F_3O_4S$. 0.4 $H_2O$: C 56.55, H 4.71 S 5.39. Found: C 56.43, H 4.61, S 5.46.

The following compounds may be prepared by the general procedure shown above.

TABLE 10

| Exp. # | X | Analysis |
|---|---|---|
| 245 | $CH_2CH_2O$ | $C_{25}H_{21}Cl_2F_3O_3$ |
| | | Calcd: C 60.38, H 4.26 |
| | | Found: C 60.28, H 4.18 |
| 246 | $CH_2CH_2CH_2CH_2CH_2O$ | $C_{28}H_{27}Cl_2F_3O_3$ |
| | | Calcd: C 62.35, H 5.05 |
| | | Found: C 62.19, H 5.12 |
| 247 | $CH_2CH_2CH_2SCH_2CH_2O$ | $C_{28}H_{27}Cl_2F_3O_3S$ |
| | | Calcd: C 58.85, H 4.76, S 5.61 |
| | | Found: C 58.98, H 4.76, S 5.34 |
| 248 | $CH_2CH_2CH_2S(O)CH_2CH_2O$ | $C_{28}H_{27}Cl_2F_3O_4S.1.5H_2O$ |
| | | Calcd: C 54.73, H 4.92, N 5.22 |

TABLE 10-continued

| Exp. # | X | Analysis |
|---|---|---|
| | | Found: C 54.90, H 4.68, N 5.45 |
| 249 | CH₂CH₂CH₂S(O₂)CH₂CH₂O | C₂₈H₂₇Cl₂F₃O₅S·0.4H₂O Calcd: C 55.07, H 4.59, N 5.25 Found: C 55.0, H 4.44, N 5.46 |
| 250 | CH₂CH₂SCH₂CH₂CH₂O | C₂₈H₂₇Cl₂F₃O₃S·0.3H₂O Calcd: C 58.30, H 4.82, N 5.56 Found: C 58.31, H 4.52, N 5.11 |
| 251 | CH₂CH₂S(O)CH₂CH₂CH₂O | C₂₈H₂₇Cl₂F₃O₄S·0.8H₂O Calcd: C 55.87, H 4.79, N 5.33 Found: C 55.96, H 5.08, N 4.93 |
| 252 | CH₂CH₂S(O₂)CH₂CH₂CH₂O | C₂₈H₂₇Cl₂F₃O₅S·0.4H₂O Calcd: C 55.07, H 4.59, N 5.25 Found: C 55.07, H 4.10, N 4.78 |
| 253 | CH₂CH₂SCH₂—CH=CH—CH₂ (E) | C₂₉H₂₇Cl₂F₃O₂S Calcd: C 61.38, H 4.80, N 5.65 Found: C 61.34, H 4.83, N 5.33 |
| 254 | CH₂CH₂S(O)CH₂—CH=CH—CH₂ (E) | C₂₉H₂₇Cl₂F₃O₃S·0.7H₂O Calcd: C 58.43, H 4.80, N 5.38 Found: C 58.28, H 4.91, N 5.2 |
| 255 | CH₂CH₂S(O₂)CH₂—CH=CH—CH₂ (E) | C₂₉H₂₇Cl₂F₃O₄S Calcd: C 58.10, H 4.54, N 5.35 Found: C 57.79, H 4.39, N 5.17 |

TABLE 11

| Exp. # | X | Analysis |
|---|---|---|
| 256 | CH₂ | C₂₅H₁₉Cl₂F₃O₂ Calcd: C 62.65, H 4.00 Found: C 62.58, H 3.95 |
| 257 | CH₂CH₂SCH₂CH₂ | C₂₈H₂₅Cl₂F₃O₂S·0.7H₂O Calcd: C 59.41, H 4.70, S 5.66 Found: C 59.30, H 4.40, S 5.67 |
| 258 | CH₂CH₂S(O)CH₂CH₂ | C₂₈H₂₅Cl₂F₃O₃S·0.6H₂O Calcd: C 57.96, H 4.55, S 5.53 Found: C 58.29, H 4.53, S 5.13 |
| 259 | CH₂CH₂S(O₂)CH₂CH₂ | C₂₈H₂₅Cl₂F₃O₄S·0.5H₂O Calcd: C 56.57, H 4.41, S 5.39 Found: C 56.82, H 4.38, S 4.93 |

Example 260
(Z)-4-[4-[2-(Dodecylsulfonyl)ethoxy]phenyl]-1,1,1-trifluoro-2-acetoxy-2-butene A solution of 4-[4-[2-(dodecylsulfonyl)ethoxy]phenyl]-1,1,1-trifluoro-2-butanone (1.10 g, 2.30 mmol) in dichloromethane (15 ml) was cooled to −25° C. and treated with triethylamine (0.5 ml) and 4-dimethylaminopyridine (0.560 g, 4.58 mmol). Then acetic anhydride (0.65 ml, 6.9 mmol) was added and the resulting mixture was stirred at −25° C. for 2.5 h. The solution was then diluted with ethyl acetate, washed with saturated sodium bicarbonate, dried (magnesium sulfate) and evaporated in vacuo. The residue was chromatographed on silica gel (elution toluene-ethyl acetate, 9:1) to give 0.94 g (78%) of a solid which was recrystallized from hexane to give white crystals: mp 48–49° C.

Anal. Calcd. for $C_{26}H_{39}F_3O_5S$: C 59.98, H 7.55, S 6.16. Found: C 59.95, H 7.51, S 6.38.

Example 261
4-[4-[2-[Bis(4-chlorophenyl)methoxy]ethylsulfonyl]ethoxy]phenyl]-1,1,1-trifluoro-2-butanol

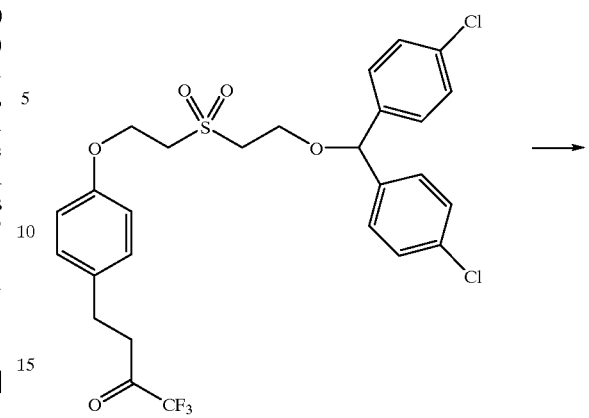

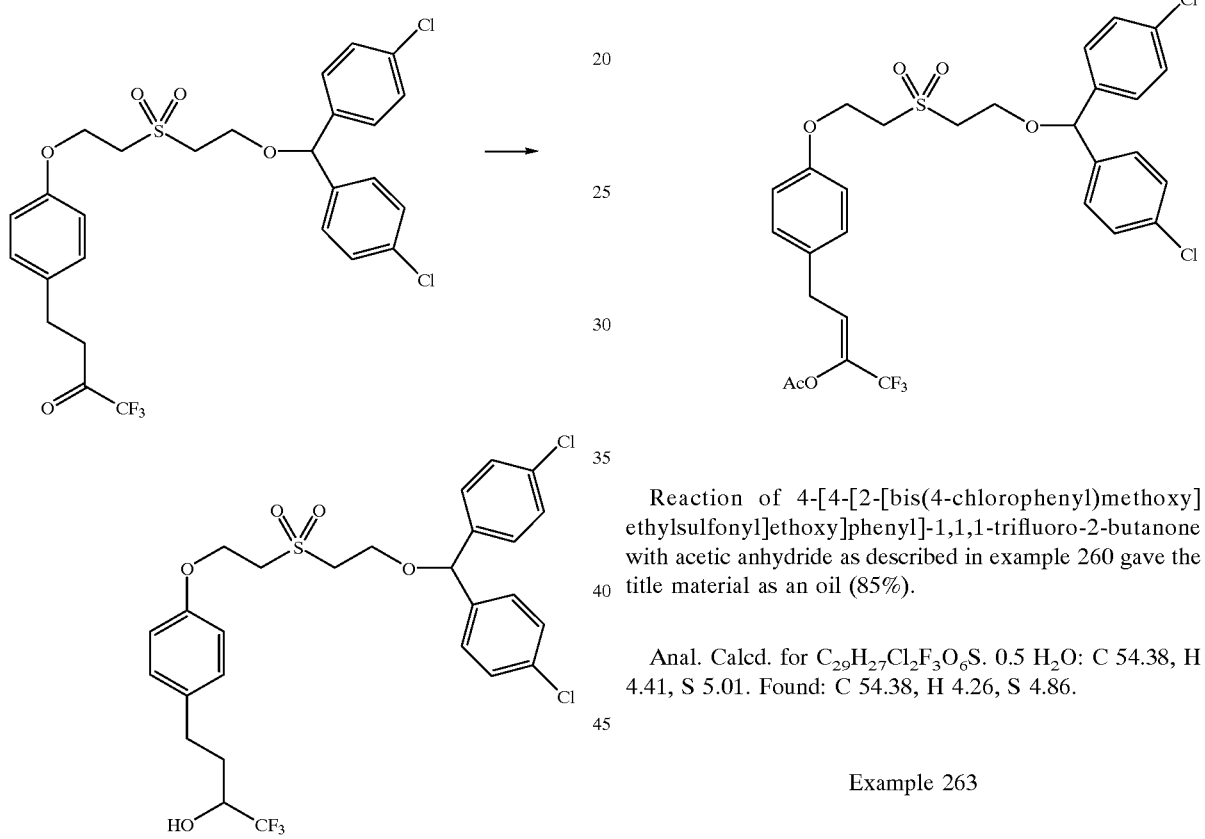

A solution of 4-[4-[2-[bis(4-chlorophenyl)methoxy]ethylsulfonyl]ethoxy]phenyl]-1,1,1-trifluoro-2-butanone (0.77 g, 1.30 mmol) in tetrahydrofuran (45 ml) and water (5 ml) was treated with sodium borohydride (0.10 g, 2.6 mmol) and the resulting mixture was stirred at 22° C. for 1 h. The reaction mixture was then diluted with ethyl acetate, washed successively with water and brine and then dried (magnesium sulfate). Evaporation of the solvent under reduced pressure gave an oil which was chromatographed on silica gel. Elution with a mixture of toluene and ethyl acetate (8:2) gave the title material as a white solid: mp 75–76° C.

Anal. Calcd. for $C_{27}H_{27}Cl_2F_3O_5S$: C 54.83, H 4.60, S 5.42. Found: C 54.84, H 4.39, S 5.07.

Example 262
(Z)-4-[4-[2-[Bis-(4-chlorophenyl)methoxy)ethylsulfonyl)ethoxy]phenyl]-1,1,1-trifluoro-2-acetoxy-2-butene Reaction of 4-[4-[2-[bis(4-chlorophenyl)methoxy]ethylsulfonyl]ethoxy]phenyl]-1,1,1-trifluoro-2-butanone with acetic anhydride as described in example 260 gave the title material as an oil (85%).

Anal. Calcd. for $C_{29}H_{27}Cl_2F_3O_6S$. 0.5 $H_2O$: C 54.38, H 4.41, S 5.01. Found: C 54.38, H 4.26, S 4.86.

Example 263
(Z)-4-[4-[2-(Dodecylsulfonyl)ethoxy]phenyl]-1,1,1-trifluoro-2-propionyloxy-2-butene

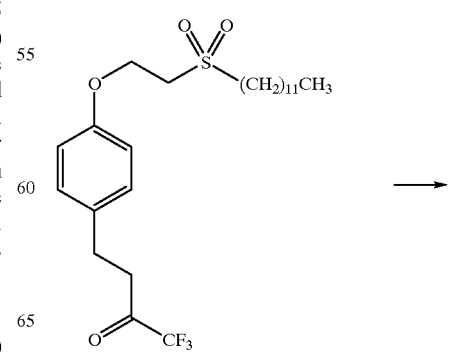

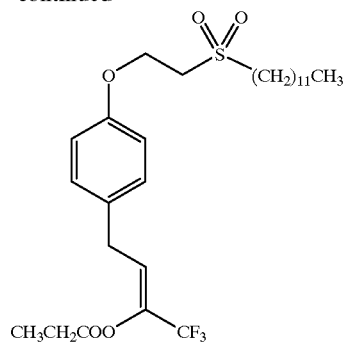

Reaction of 4-[4-[2-(dodecylsulfonyl)ethoxy]phenyl]-1,1,1-trifluoro-2-butanone (0.87 g, 1.82 mmol) with propionic anhydride using the procedure described above gave 0.866 g (89%) of the title material as a white solid: mp 60–63° C.

Anal. Calcd. for $C_{27}H_{41}F_3O_5S$: C 60.65, H 7.73, S 6.00. Found: C 60.51, H 7.83, S 6.01.

Example 264

4-[4-[2-(Dodecylsulfonyl)ethoxy]phenyl]-1,1,1-trifluoro-2-butanone, Glycolic Acid-ketal Ester

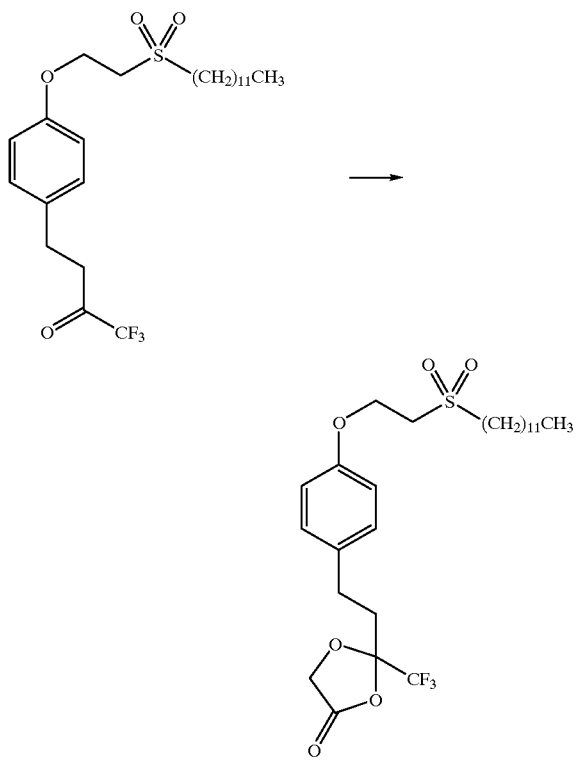

A solution of 4-[4-[2-(dodecylsulfonyl)ethoxy]phenyl]-1,1,1-trifluoro-2-butanone (0.80 g) in toluene (40 ml) was treated with glycolic acid (0.16 g) and p-toluene sulfonic acid (0.10 g) and the resulting mixture was heated under reflux for 6 h. Additional quantities of glycolic acid (5×0.16 g) and p-toluenesulfonic acid (5×0.06 g) were added periodically after every hour of heating. The cooled reaction mixture was diluted with ethyl acetate, washed with saturated sodium bicarbonate and brine and dried over magnesium sulfate. Evaporation of the solvent under reduced pressure and chromatography of the residue on silica gel (elution toluene-ethyl acetate 8:2) gave 0.187 g (21%) of the title material as a white solid: mp 69–71° C.

Anal. Calcd. for $C_{26}H_{39}F_3O_6S$: C 58.19, H 7.33, S 5.97. Found: C 58.11, H 7.35, S 6.09.

Example 265

4-[4-[2-(Dodecylsulfonyl)ethoxy]phenyl]-1,1,1-trifluorobutanone, Thiazolidine Derivative With 2-aminoethanethiol

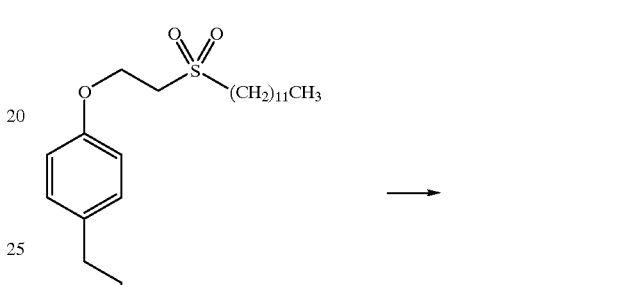

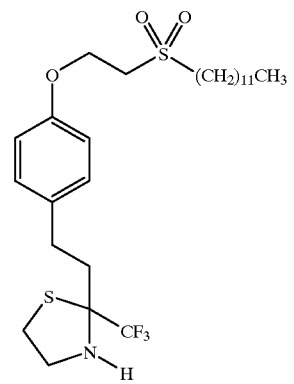

A solution of 4-[4-[2-(dodecylsulfonyl)ethoxy]phenyl]-1,1,1-trifluorobutanone (0.60 g, 1.25 mmol) in dry toluene (50 ml) was heated under reflux and then treated with 2-aminoethanethiol (3×0.20 g) added in three portions over 12 h. The reaction mixture was then washed with brine and dried over magnesium sulfate. Evaporation of the solvent in vacuo and chromatography of the residue on silica gel (elution toluene-ethyl acetate 85:15) gave 0.603 g (89%) of the title thiazolidine as a syrup.

Anal. Calcd. for $C_{26}H_{42}F_3NO_3S_2$: C 58.07, H 7.87, N 2.60, S 11.93. Found: C 57.93, H 8.09, N 2.52, S 11.46.

Example 266

(Z)-4-[4-[2-(Dodecylsulfonyl)ethoxy]phenyl]-1,1,1-trifluoro-2-diethylphosphoryloxy-2-butene

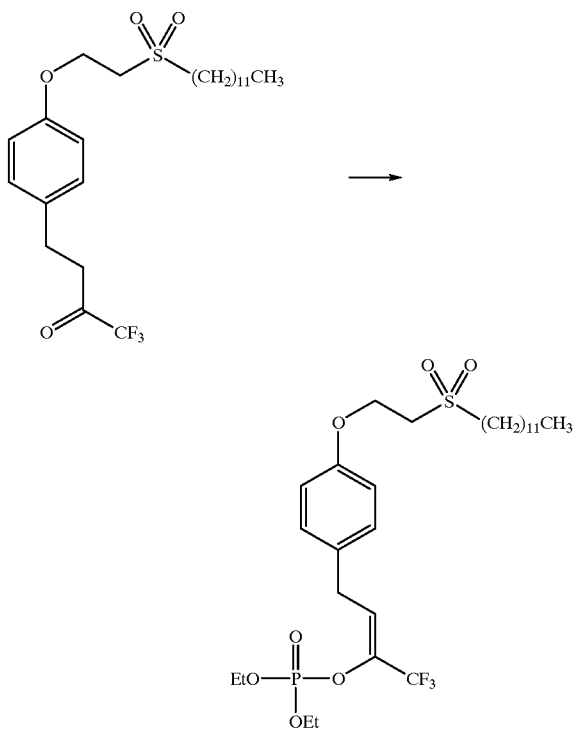

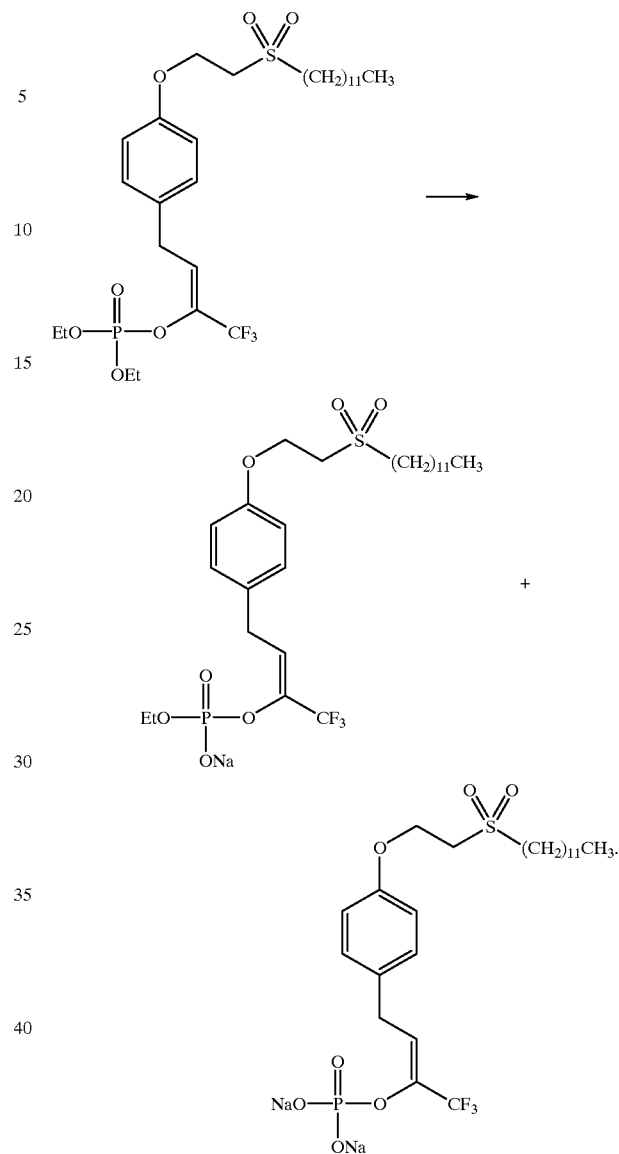

A solution of 4-[4-[2-(dodecylsulfonyl)ethoxy]phenyl]-1,1,1-trifluorobutanone (1.50 g, 3.13 mmol) in dry dichloromethane (40 ml) was cooled to 0° C. and treated with triethylamine (0.87 ml) and 4-dimethylaminopyridine (0.77 g) then diethyl phosphorochloridate (1.35 ml) was added dropwise and the resulting mixture was stirred at 0° C. for 2 h. The reaction mixture was then diluted with ethyl acetate, washed with sodium bicarbonate, brine and dried (magnesium sulfate). After evaporation of the solvent under reduced pressure, the residue was chromatographed on silica gel (elution toluene-ethyl acetate, 8:2) to give 1.539 (80%) of the title enol phosphate as white crystals (hexane): mp 33° C.

Anal. Calcd. for $C_{28}H_{46}F_3O_7PS$: C 54.71, H 7.54, S 5.22. Found: C 54.82, H 7.64, S 5.39.

Example 267

(Z)-4-[4-[2-(Dodecylsulfonyl)ethoxy]phenyl]-1,1,1-trifluoro-2-ethylphosphoryloxy-2-butene Sodium Salt and (Z)-4-[4-[2-(Dodecylsulfonyl)ethoxy]phenyl]-1,1,1-trifluoro-2-phosphoryloxy-2-butene, Disodium Salt A solution of (Z)-4-[4-[2-(dodecylsulfonyl)ethoxy]phenyl]-1,1,1-trifluoro-2-diethylphosphoryloxy-2-butene (0.778 g, 1.27 mmol) in acetonitrile (20 ml) was treated with chlorotrimethylsilane (1.0 ml) and potassium iodide (0.63 g) and the resulting mixture was heated under reflux for 5 h. The cooled mixture was then treated with sodium bicarbonate (1 g) and water (5 ml) and stirred for 30 min. The solid was then removed by filtration and the filtrate was concentrated in vacuo.

The residue was then purified on silica gel using a mixture of ethyl acetate, methanol and water (7:3:0 to 65:35:5) as eluent.

The first fractions gave the ethyl-phosphoryloxy sodium salt (0.210 g, 27%) as a white solid.

Anal. Calcd. for $C_{26}H_{41}F_3O_7PSNa$. 0.3 $H_2O$: C 50.86, H 6.83, S 5.22. Found: C 50.81, H 6.98, S 5.32.

The tail fractions gave the phosphoryloxy disodium salt (0.259 g, 34%) as a white solid.

Anal. Calcd. for $C_{24}H_{36}F_3O_7PSNa_2$. 0.3 $H_2O$: C 43.90, H 6.45, S 4.88. Found: C 43.97, H 6.08, S 5.08.

The following prodrugs may be prepared by the general procedure described above.

TABLE

Pro-drugs (1)

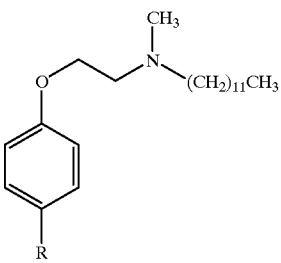

| Exp. No. | R | Analysis |
| --- | --- | --- |
| 268 | ![structure: CH2=C(OAc)(CF3)] | $C_{27}H_{42}F_3NO_3 \cdot HCl \cdot 0.5H_2O$<br>Calcd: C 61.06, H 8.35, N 2.64<br>Found: C 60.76, H 7.83, N 2.70 |
| 269 | ![structure: CH2=C(OC(O)C(CH3)3)(CF3)] | $C_{30}H_{48}F_3NO_3 \cdot HCl \cdot 0.5H_2O$<br>Calcd: C 62.87, H 8.79, N 2.44<br>Found: C 62.91, H 8.98, N 2.52 |
| 270 | ![structure: dioxolanone with CH2CH2 and CF3] | $C_{27}H_{42}F_3NO_4 \cdot HCl$<br>Calcd: C 60.27, H 8.05, N 2.60<br>Found: C 60.15, H 7.52, N 2.62 |

Pro-drugs (2)

| EXP. # | STRUCTURE | ANALYSIS |
| --- | --- | --- |
| 271 | 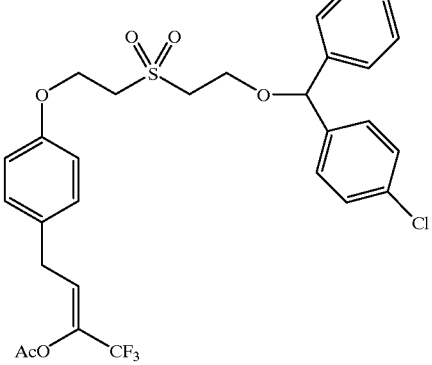 | $C_{29}H_{27}Cl_2F_3O_6S \cdot HCl \cdot 0.5H_2O$<br>Calcd: C 54.38, H 4.41, N 5.01<br>Found: C 54.38, H 4.26, N 4.86 |

TABLE-continued
| | | |
|---|---|---|
| 272 | 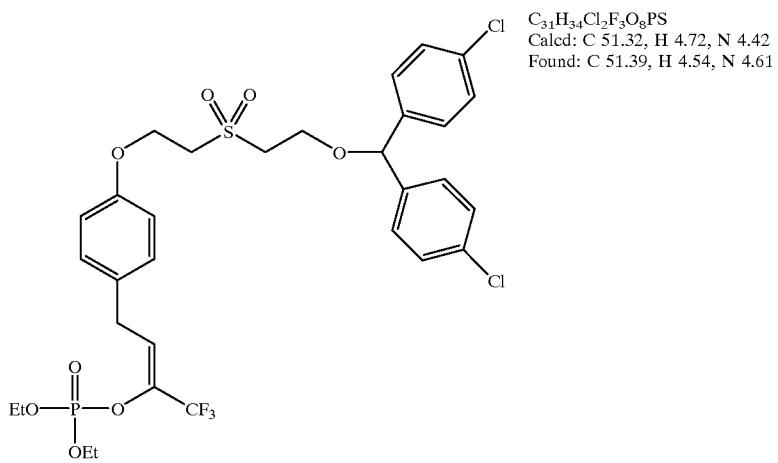 | $C_{31}H_{34}Cl_2F_3O_8PS$<br>Calcd: C 51.32, H 4.72, N 4.42<br>Found: C 51.39, H 4.54, N 4.61 |
| 273 | 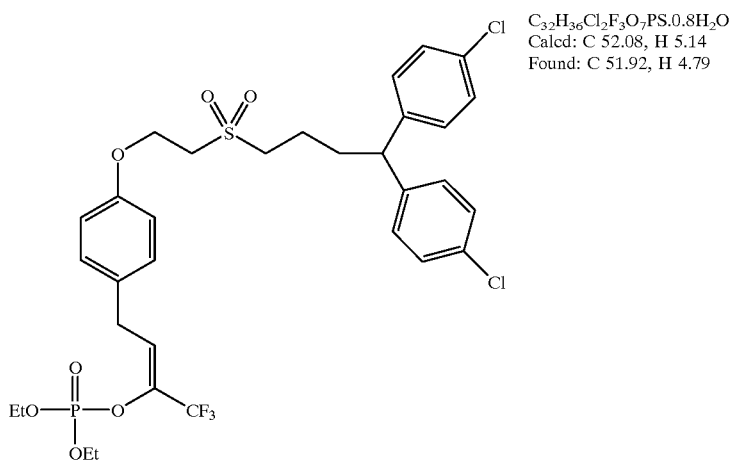 | $C_{32}H_{36}Cl_2F_3O_7PS \cdot 0.8H_2O$<br>Calcd: C 52.08, H 5.14<br>Found: C 51.92, H 4.79 |
| 274 | 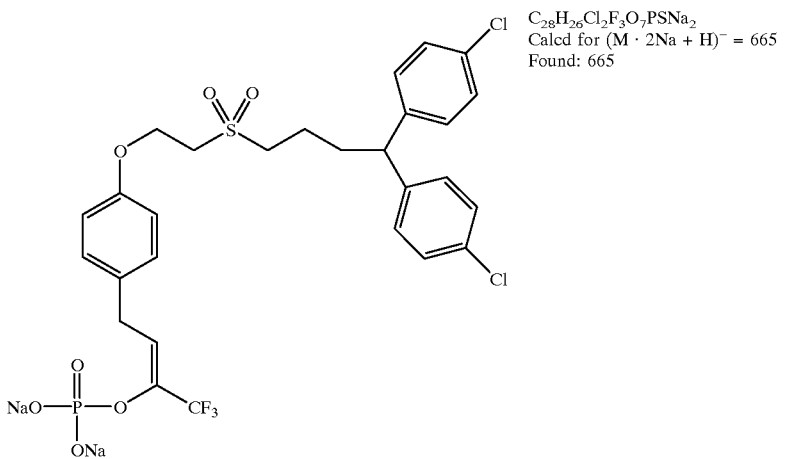 | $C_{28}H_{26}Cl_2F_3O_7PSNa_2$<br>Calcd for $(M \cdot 2Na + H)^- = 665$<br>Found: 665 |

Synthesis of Example 275
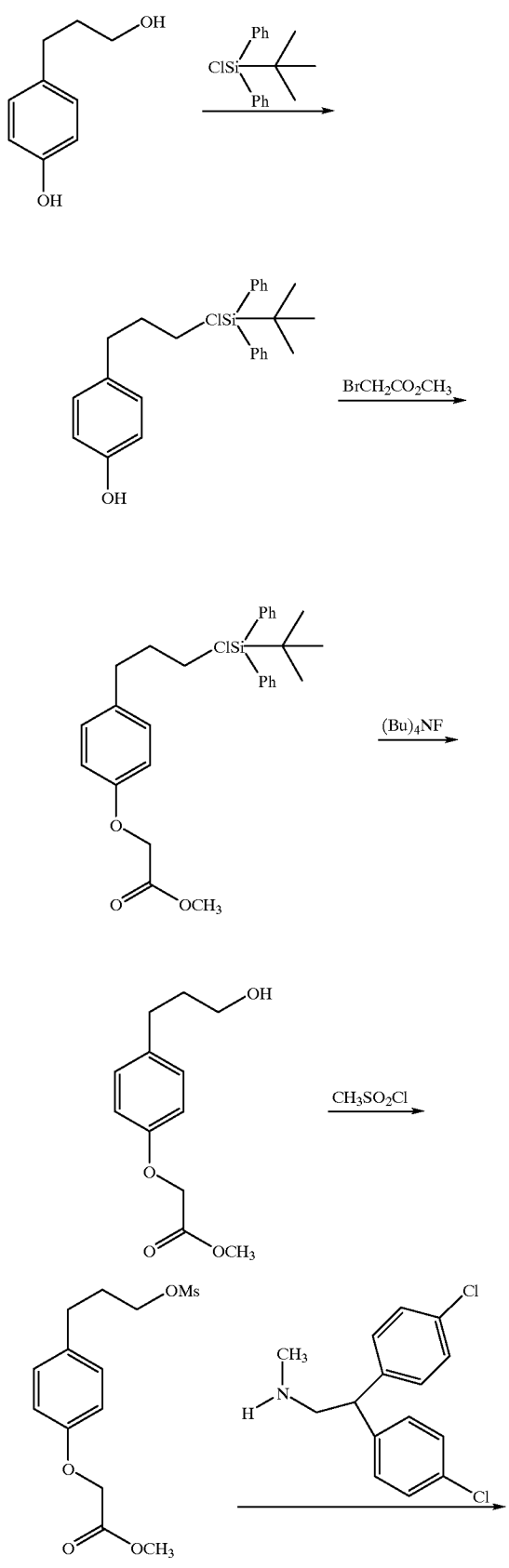
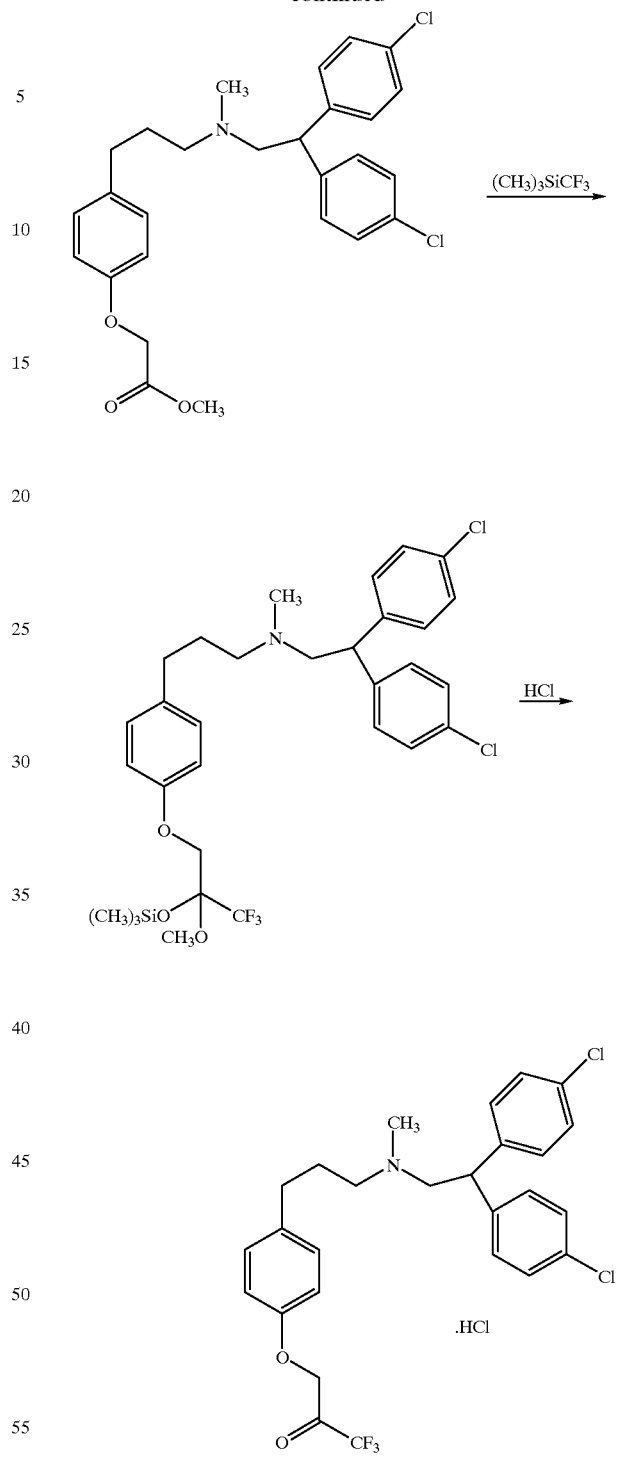
Example No. 275
3-[4-[3-[N-[2-Bis-(4-chlorophenyl)ethyl]-N-methylamino]propyl]phenoxy]-1,1,1-trifluoro-2-propanone, Hydrochloride Salt
3-(4-Hydroxyphenyl)-1-(tert-butyldiphenylsilyloxy)propane

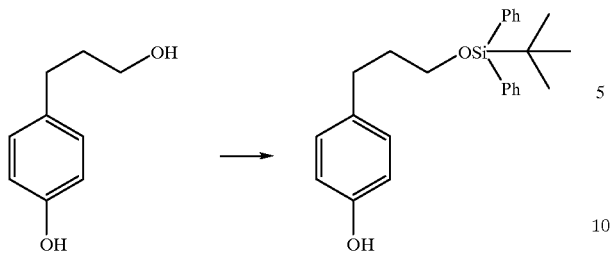

A solution of 3-(4-hydroxyphenyl)-1-propanol (10.0 g, 66.0 mmol) and imidazole (6.7 g, 98.4 mmol) in N,N-dimethylformamide (50 ml) was cooled to 0–5° C. and treated dropwise with tert-butylchlorodiphenylsilane (21.5 g, 78.2 mmol). The resulting mixture was stirred at 0–5° C. for 2 h and then quenched by addition of water (400 ml) and toluene (500 ml). The organic phase was washed with water, brine and dried over anhydrous magnesium sulfate. Evaporation of the solvent and chromatography of the residue or silica gel (elution toluene-ethyl acetate, 95:5) gave 24.8 g (96%) of the title material as a clear oil.

Anal. Calcd for $C_{25}H_{30}O_2Si$: C 76.88, H 7.74. Found: C 76.74, H 7.67.

Methyl [4-[3-(tert-butyldiphenylsilyloxy)propyl]phenoxy]acetate

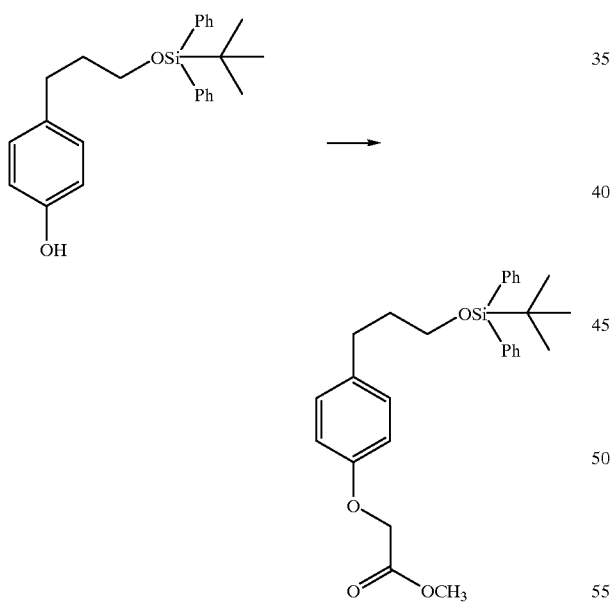

A solution of 3(4-hydroxyphenyl)-1-(tert-butyldiphenylsilyloxy)propane (3.91 g, 10.0 mmol) and methyl bromoacetate (3.0 g, 19.7 mmol) in acetonitrile (100 ml) was treated with powdered anhydrous potassium carbonate (10 g) and the resulting mixture was heated under reflux for 1 h. The cooled mixture was filtered and the filtrate was concentrated in vacuo. Chromatography of the residue as silica gel (elution toluene-ethyl acetate, 98:2) gave 4.36 g (94%) of the title material as clear oil.

Methyl [4-(3-hydroxypropyl)phenoxy]acetate

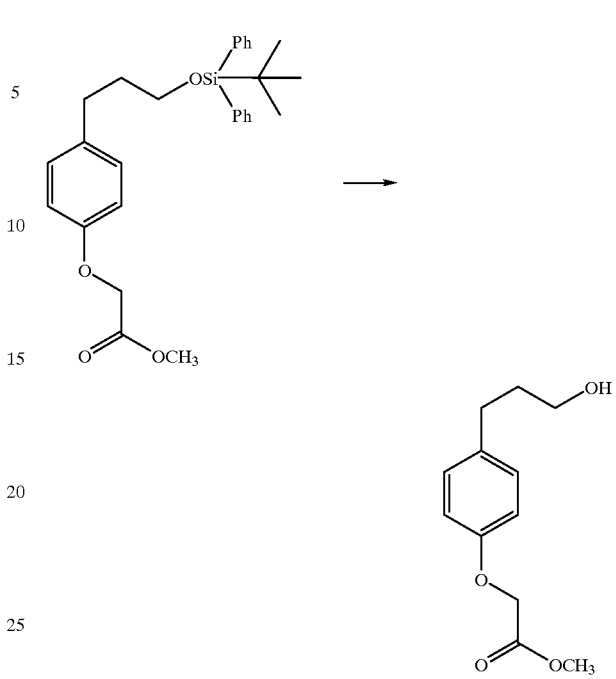

A solution of methyl [4-[3-tert-butyldiphenylsilyloxy)propyl]phenoxy]acetate (11.42 g, 24.68 mmol) in tetrahydrofuran (330 ml) was treated with acetic acid (12.4 g, 0.206 mol) followed by 76.1 ml (76.1 mmol) of 1M tetrabutylammonium fluoride in tetrahydrofuran and the resulting solution was maintained at 45° C. for 18 h. The resulting mixture was diluted with dichloromethane, washed with saturated sodium bicarbonate, brine and dried over anhydrous magnesium sulfate. Evaporation of the solvent and chromatography of the residue on silica gel (elution dichloromethane-ethyl acetate 85:15) gave 4.76 g (86%) of the title material as a white solid: mp 47–48° C.

Anal. Calcd for $C_{12}H_{16}O_4$: C 64.27, H 7.19. Found: C 63.86, H 7.04.

Methyl [4-(3-methanesulfonyloxypropyl)phenoxy]acetate

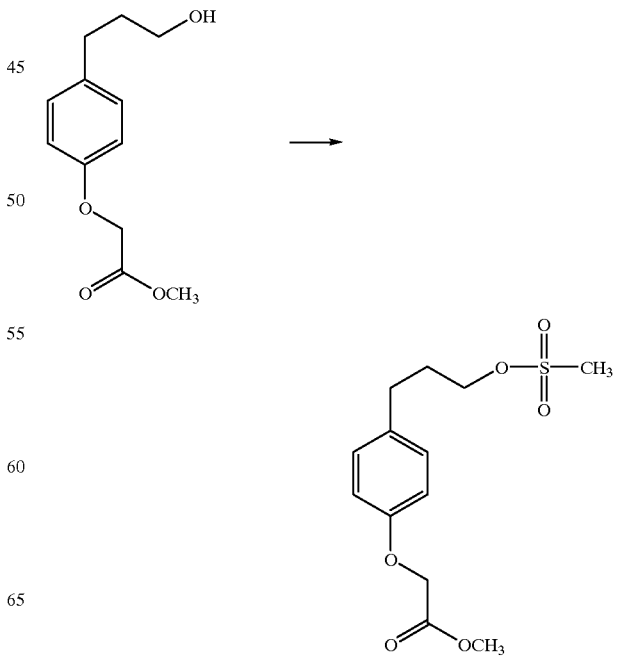

A solution of methyl [4-(3-hydroxypropyl)phenoxy] acetate (4.5 g, 20.5 mmol) in dichloromethane (50 ml) was treated at 0° C. with triethylamine (4.36 g, 43.1 mmol) followed by methanesulfonyl chloride (3.99 g, 34.8 mmol) added dropwise over 5 min. After 30 min at 0° C., the reaction mixture was diluted with dichloromethane, washed with 1N hydrochloric acid, water and dried over anhydrous sodium sulfate. Evaporation of the solvent and chromatography of the residue on silica gel (elution toluene-ethyl acetate, 8:18) gave 5.51 g (89%) of the title material as a white solid: mp 49–51° C.

Anal. Calcd for $C_{13}H_{18}O_6S$: C 51.64, H 6.0, S 10.60. Found: C 51.54, H 6.01, S 10.84.

Methyl [4-[3-[N-[2-Bis-(4-chlorophenyl)ethyl]-N-methylamino]propyl]phenoxy]acetate

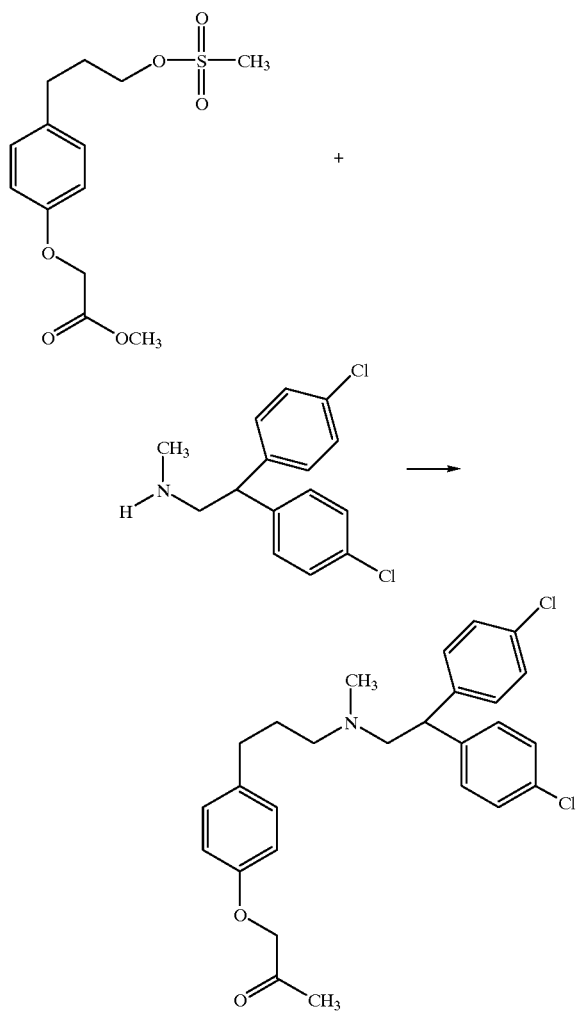

To a solution of methyl [4-(3-methanesulfonyloxypropyl)phenoxy]acetate (0.931 g, 3.08 mmol) and N-methyl-2-bis-(4-chlorophenyl)ethylamine (B. E. Maryanoff, S. O. Nortey and J. F. Gardocki, J. Med. Chem. (1984), 27, 1067–1071), (2.16 g, 7.71 mmol) in acetonitrile (10 ml) was added sodium iodide (33 mg) and the resulting mixture was heated at 80° C. for 18 h. The reaction mixture was then diluted with dichloromethane, washed with saturated sodium bicarbonate, brine and dried over anhydrous magnesium sulfate. Evaporation of the solvent and chromatography of the residue on silica gel (elution hexane-ethyl acetate, 65:35) gave 1.37 g (91%) of the title material as a clear oil.

Anal. Calcd for $C_{27}H_{29}Cl_2NO_3 \cdot 0.1\ H_2O$: C 66.42, H 6.03, N 2.87. Found: C 66.23, H 5.72, N 2.79.

3-[4-[3-[N-[2-Bis-(4-chlorophenyl)ethyl]-N-methylamino]propyl]phenoxy]-2-methoxy-2-trimethylsilyloxy-1,1,1-trifluoropropane

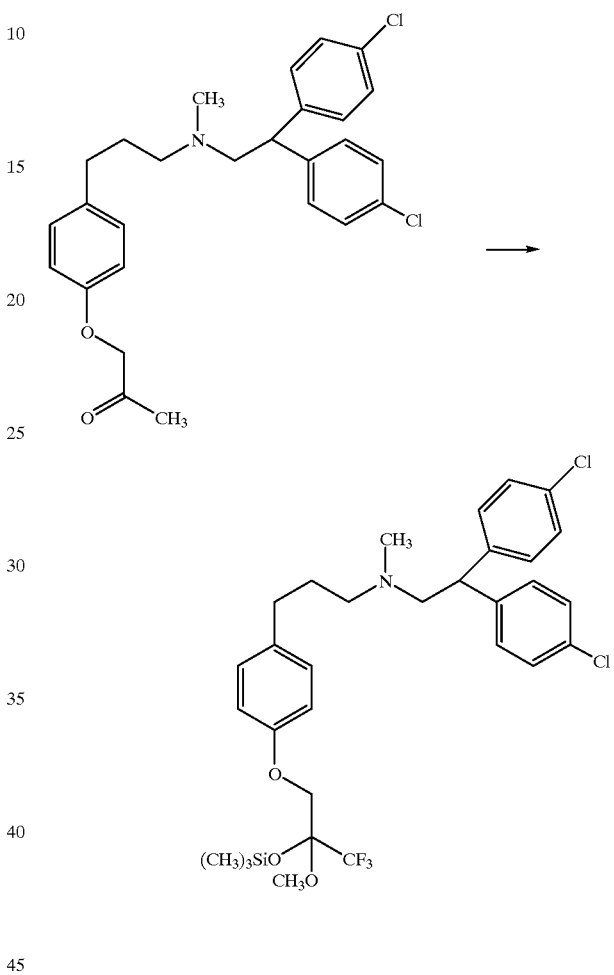

A solution of methyl [4-[3[N-[2-bis-(4-chlorophenyl)ethyl]-N-methylamino]propyl]phenoxy]acetate (1.37 g, 2.62 mmol) in dry toluene (3 ml) was treated at –55° C. and under argon with trifluoromethyltrimethylsilane (0.48 ml, 3.40 mmol) followed by anhydrous tetrabutylammonium fluoride (0.13 mmol, 0.13 ml of a 1M solution in tetrahydrofuran). The reaction mixture was then allowed to warm slowly to room temperature and stirred for 18 h. The solvent was then evaporated in vacuo and the residue was chromatographed on silca gel. Elution with a gradient of ether (8–15%) in toluene gave 1.07 g (65%) of the title material as oil.

Anal. Calcd for $C_{31}H_{38}Cl_2F_3NO_3Si$: C 59.23, H 6.09, N 2.23. Found: C 59.38, H 6.00, N 2.25.

3-[4-[3-[N-[2-Bis-(4-chlorophenyl)ethyl]-N-methylamino]propyl]phenoxy]-1,1,1-trifluoro-2-propanone, Hydrochloride Salt

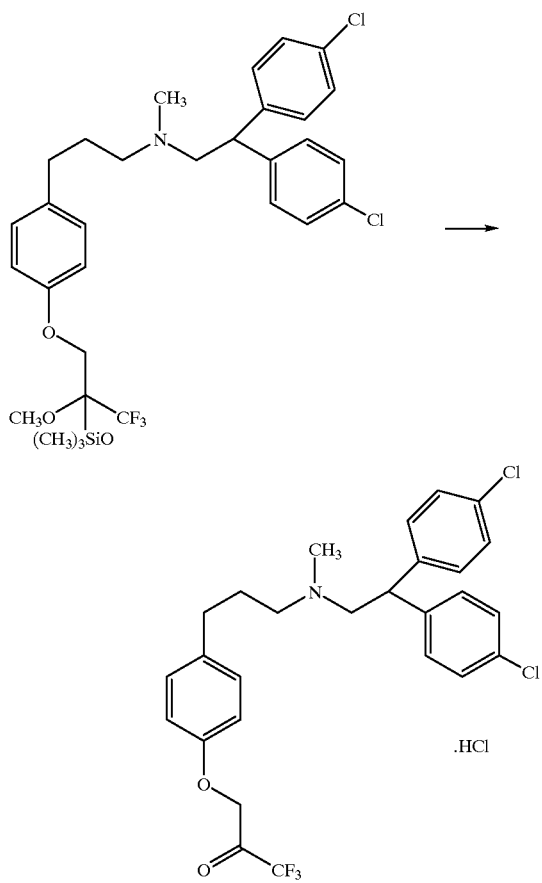

A solution of 3-[4-[3-[N-[2-bis-(4-chlorophenyl)ethyl]-N-methylamino]propyl]phenoxy]-2-methoxy-2-trimethylsilyloxy-1,1,1-trifluoropropane (1.07 g, 1.70 mmol) in tetrahydrofuran (40 ml) was treated at 22° C. with 10.6 ml (10.6 mmol) of a 1M solution of hydrogen chloride in ether. After 4 h, the solvent was evaporated in vacuo to give 0.984 g (quantitative) of the title material as a white solid.

Anal. Calcd for $C_{27}H_{28}Cl_2F_3NO_3 \cdot HCl \cdot 0.4\ H_2O$: C 55.33, H 5.13, N 2.39. Found: C 55.32, H 5.43, N 2.24.

Example No. 276
3-[4-[3-(tert-butyldiphenylsilyloxy)propyl]phenoxy]-1,1,1-trifluoro-2-propanone
[4-[3-(tert-butyldiphenylsilyloxy)propyl]phenoxy]acetic Acid

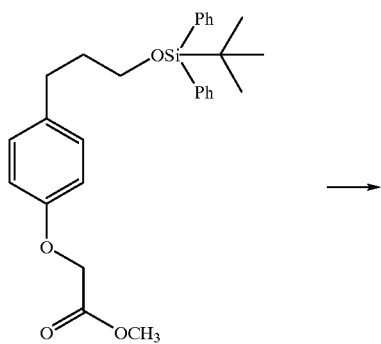

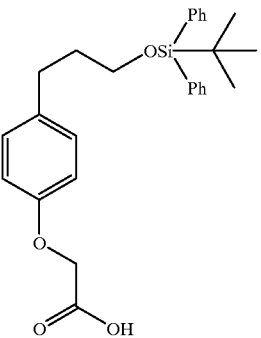

A solution of methyl [4-[3-(tert-butyldiphenylsilyloxy)propyl]phenoxy]acetate (4.36 g, 9.4 mmol) in 80% aqueous ethanol (100 ml) was treated with potassium hydroxide (2 g) and the resulting mixture was heated at 50° C. for 2 h. The solvent was then evaporated in vacuo. Ice water and ethyl acetate were added and the aqueous phase was carefully adjusted to pH4 with 1N hydrochloric acid. The organic phase was then washed with brine, dried (magnesium sulfate) and evaporated under reduced pressure to give a white solid. Recrystallization from hexane gave 3.41 g (81%) of the title acid as white crystals: mp 87–88° C.
3-[4-[3-(tert-butyldiphenylsilyloxy)propyl]phenoxy]-1,1,1-trifluoro-2-propanone

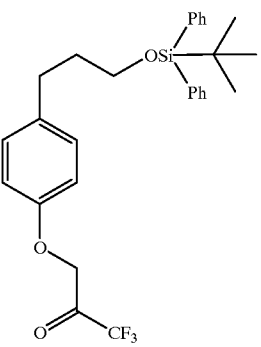

A solution of [4-[3-(tert-butyldiphenylsilyloxy)propyl]phenoxy]acetic acid (0.68 g, 1.52 mmol) in dichloromethane (12 ml) was treated with oxalyl chloride (0.44 g, 3.5 mmol) and a small drop of N,N-dimethylformamide and the resulting mixture was stirred at 22° C. for 1 h. The solvent and excess reagent were then evaporated in vacuo and the residual oil was diluted with toluene (25 ml) and cooled to 0° C. The solution was then treated with trifluoroacetic anhydride (0.96 g, 4.6 mmol) followed by pyridine (0.48 g, 6.1 mmol) added dropwise over 5 min. The mixture was then warmed to 22° C. and stirred for 45 min. The solution was then cooled again to 0° C., treated dropwise with water (2 ml) and stirred for 10 min. The mixture was diluted with ethyl acetate, washed with water, saturated sodium bicarbonate and brine. After drying (magnesium sulfate), the organic phase was evaporated and the residual oil was chromatographed on silica gel. Elution with a mixture of toluene and ether (9:1) gave 0.046 g (6%) of the title material as a clear oil: ir (NaCl, film) $v_{max}$ 1782 cm$^{-1}$. Mass spectrum m/e 499 (M−H)$^-$.

Example No. 277
3-[4-[3-[2-[Bis-(4-chlorophenyl)methoxy]ethylthio]-propyl]phenoxy]-1,1,1-trifluoro-2-propanone
Methyl[4-[3-[2-[bis-(chlorophenyl)methoxy]ethylthio]propyl]phenoxy]acetate

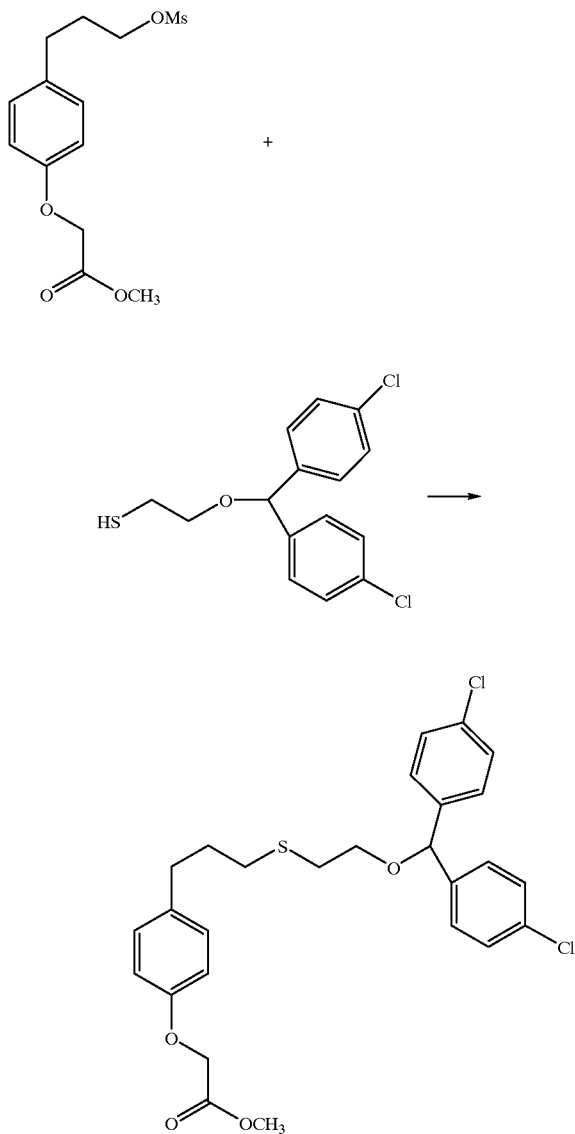

A solution of methyl [4-(3-methanesulfonyloxypropyl)phenoxy]acetate (0.154 g, 0.51 mmol) and 2-[bis-(4-chlorophenyl)methoxy]ethanethiol (0.38 g, 1.21 mmol) in N,N-dimethylformamide (5 ml) was treated with powdered potassium carbonate (0.21 g) and potassium iodide (0.012 g) and the resulting mixture was stirred at 35° C. for 6 h. The reaction mixture was then diluted with dichloromethane, washed with water and dried (magnesium sulfate). Evaporation of the solvent and chromatography of the residue on silica gel (elution toluene-ethyl acetate, 94:60) gave 0.236 g (94%) of the title material as clear oil.

3-[4-[3-[2-[Bis-(4-chlorophenyl)methoxy]ethylthio]-propyl]phenoxy]-1,1,1-trifluoro-2-propanone

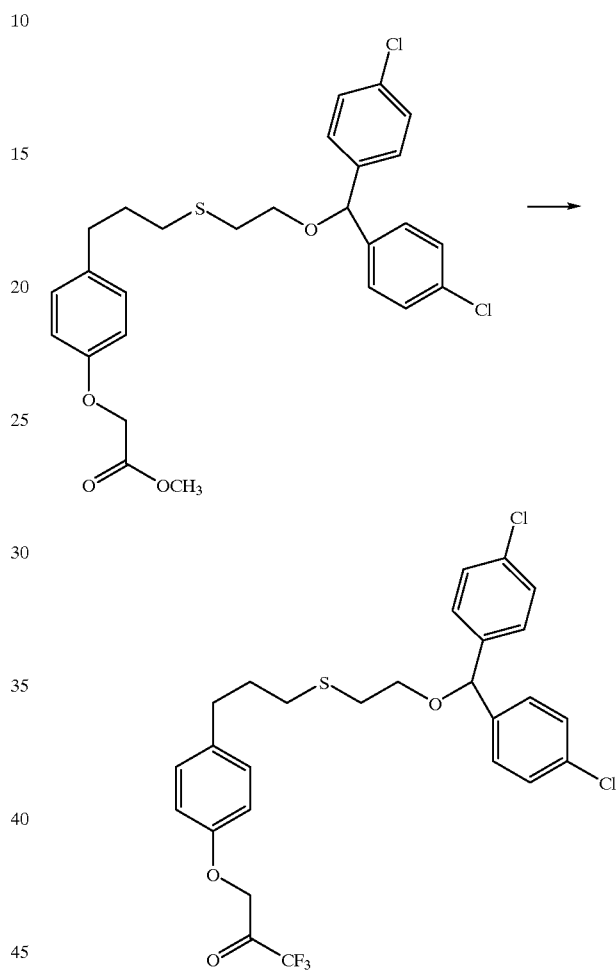

A solution of methyl [4-[3-[2-[bis-(4-chlorophenyl)methoxy]ethylthio]propyl]phenoxy]acetate (0.11 g, 0.22 mmol) in dry toluene (1 ml) was cooled to −78° C. and treated with trifluoromethyltrimethylsilane (0.039 g, 0.27 mmol) followed by 0.011 ml (0.011 mmol) of a 1M tetrabutylammonium fluoride in dry tetrahydrofuran. The mixture was then warmed to 22° C. and stirred for 48 h. The solvent was then evaporated in vacuo and the residue was chromatographed on silica gel (elution toluene-hexane-triethylamine, 60:40:1) to give 0.036 g (24%) of the intermediate mixed trimethylsilylmethyl ketal as an oil. This ketal was then dissolved in tetrahydrofuran (1 ml) and treated at 0 °C. with acetic acid (0.019 ml) and 0.012 ml of a 1M solution of tetrabutylammonium fluoride in tetrahydrofuran. After 18 h at 0° C., the reaction mixture was quenched by the addition of saturated sodium bicarbonate and dichloromethane. The organic phase was washed with brine, dried (magnesium sulfate) and evaporated. Chroma tography of the residue on silica gel (elution toluene-ethyl acetate-triethylamine, 80:20:1) gave 0.021 g (68%; overall yield 17%) of the title material as an oil.

Mass spectrum: m/e 555, (M–H)⁻.

Example No. 278
3-[4-[3-[2-Bis-(4-chlorophenyl)methoxy]ethylsulfonyl] propyl]phenoxy-1,1,1-trifluoro-2-propanone
Methyl [4-[3-[2-[bis-(4-chlorophenyl)methoxy] ethylsulfonyl]propyl]phenoxy]acetate

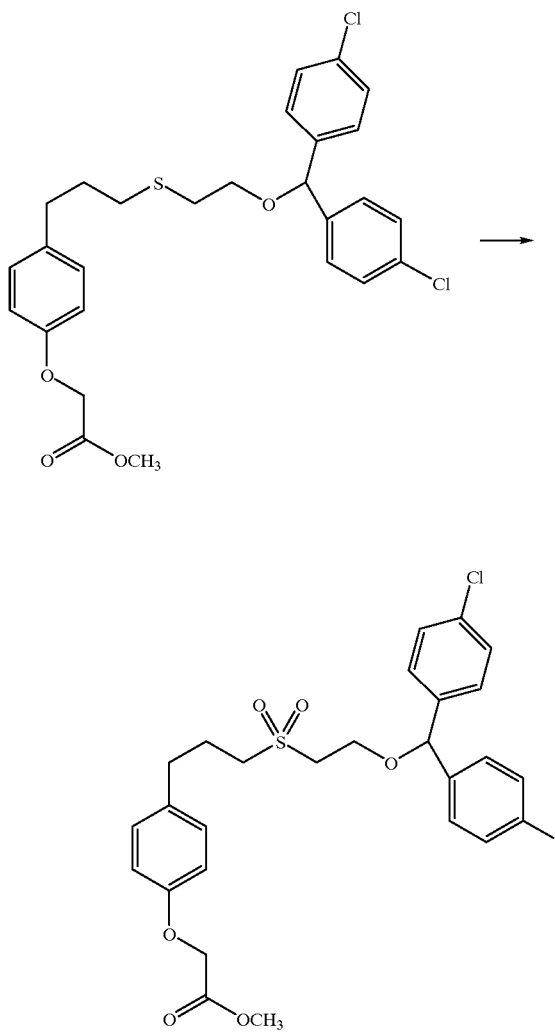

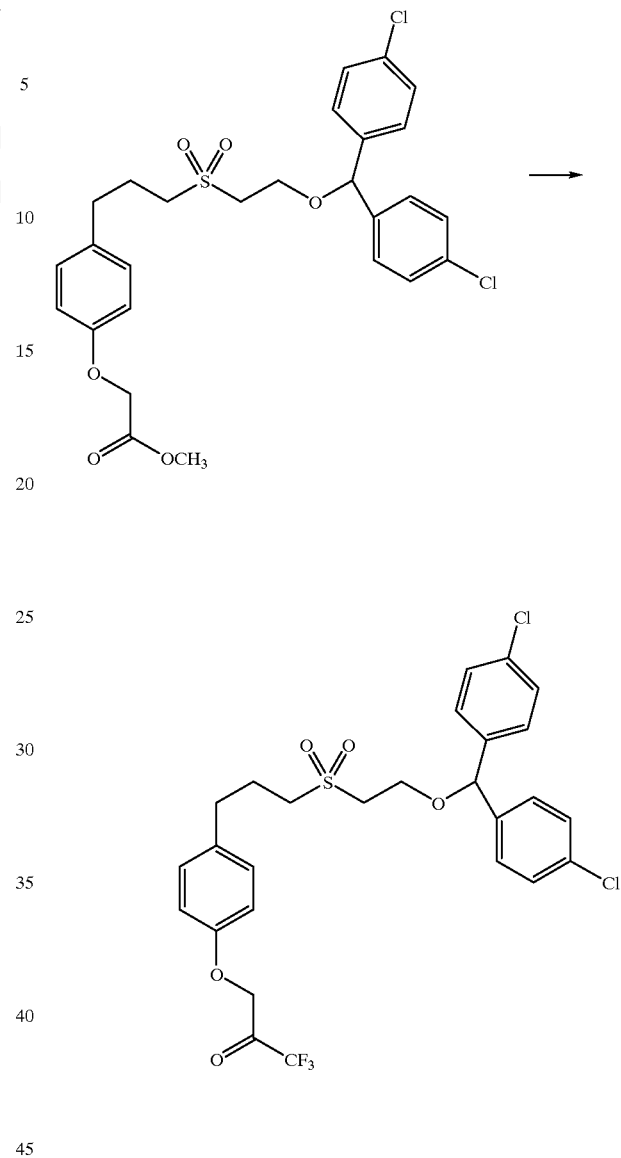

A solution of methyl [4-[3-[2-[bis-(4-chlorophenyl) methoxy]ethylthio]propyl]phenoxy]acetate (0.278 g, 0.56 mmol) in dichloromethane (8 ml) was treated with m-chloroperoxybenzoic acid (0.314 g, 1.8 mmol) and the resulting mixture was stirred at 22° C. for 2 h. The reaction mixture was then diluted with ethyl acetate, washed with saturated sodium bicarbonate, brine and dried (magnesium sulfate). Evaporation of the solvent and chromatography of the residue on silica gel (elution hexane-ethyl acetate, 6:4) gave 0.268 g (87%) of the title material as oil: ir (NaCl, film) vmax: 1759 cm⁻¹.

3-[4-[3-[2-[Bis-(4-chlorophenyl)methoxy]ethylsulfonyl] propyl]phenoxy]-1,1,1-trifluoro-2-propanone A solution of methyl [4-[3-[2-[bis-(4-chlorophenyl) methoxy]ethylsulfonyl]propyl]phenoxy]acetate (0.254 g, 0.46 mmol) in toluene (1 ml) was cooled to –55° C. and treated with trifluoromethyltrimethylsilane (0.082 g, 0.58 mmol) followed by 0.023 ml (0.023 mmol) of a 1M solution of tetrabutylammonium fluoride in tetrahydrofuran. The mixture was then warmed to 22° C. and stirred for 60 h. The solvent was then evaporated in vacuo and the residue was chromatographed on silica gel (elution hexane-ether, 8:2) to give 0.039 g (22%) of the intermediate mixed trimethylsilyl-methyl ketal as oil. The ketal was then dissolved in tetrahydrofuran (1 ml) and treated at 0° C. with acetic acid (0.019 ml) followed by 0.12 ml of a 1M solution of tetrabutylammonium fluoride in tetrahydrofuran. After 18 h at 0° C., the reaction was quenched by addition of saturated aqueous sodium bicarbonate and dichloromethane. The organic phase was dried (magnesium sulfate) and evaporated. Chromatography of the residue on silica gel (elution toluene-ethyl, 4:6) gave 0.004 g (12%) of the title material as a white amorpous solid.

Mass spectrum: m/z 507 (M–H)⁻.
Scheme

Example No. 279

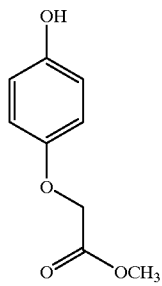

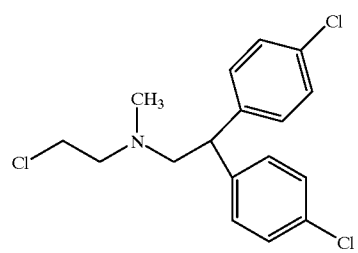

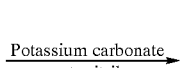
Potassium carbonate
acetonitrile

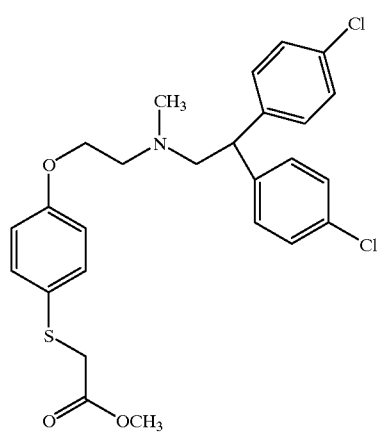

CF₃Si(CH₃)₃
Tetrabutylammonium fluoride

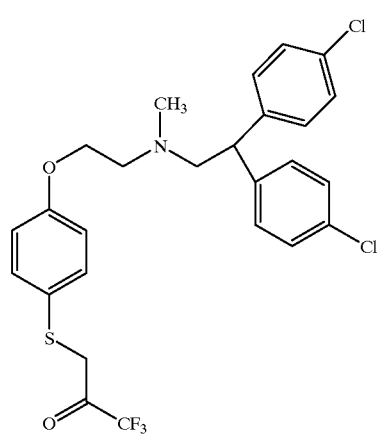

Example No. 279
3-[4-[2-[N-[2-Bis-(4-chlorophenyl)ethyl]-N-methylamino]ethoxy]phenylthio]-1,1,1-trifluoro-2-propanone

[4-[2-[N-[2-Bis-(4-chlorophenyl)ethyl]-N-methylamino]ethoxy]phenylthio]-acetic Acid, Methyl Ester

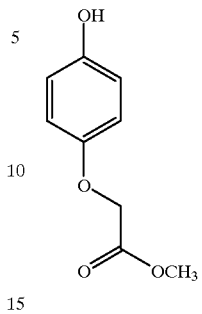

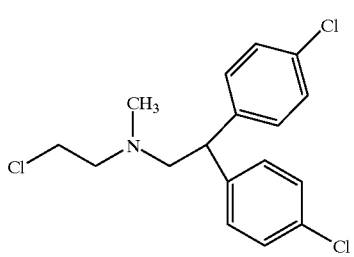

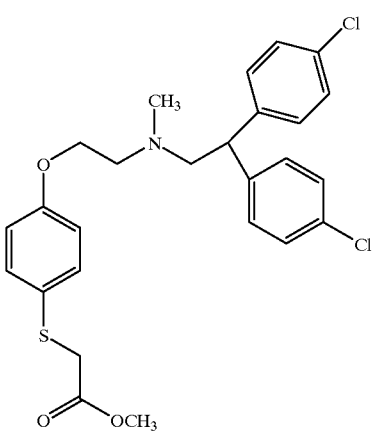

A mixture of 4-hydroxyphenylthioacetic acid methyl ester (1.97 g, 9.9 mol) (Chem. Abstr., 74, 76171) and 2-[N-[bis-(4-chlorophenyl)methyl]N-methylamino]ethyl chloride hydrochloride (3.76 g, 9.9 mmol) in dry acetonitrile (30 ml) was treated with powdered potassium carbonate (10 g) and the resulting mixture was heated under reflux for 3 h. The cooled reaction mixture was diluted with ethyl acetate, washed with water, brine and dried (anhydrous magnesiium sulfate). Evaporation of the solvent and chromatography of the residue on silica gel (elution toluene-ethyl acetate 8:2) gave 4.66 g (93%) of the title material as an oil.

Anal. Calcd. for C₂₆H₂₇Cl₂NO₃S:. C 61.90, H 5.39, N 2.78. Found: C 61.91, H 5.49, N 2.77.

3-[4-[2-[N-[2-Bis-(4-chlorophenyl)ethyl]-N-methylamino]ethoxy]phenylthio]-1,1,1-trifluoro-2-propanone

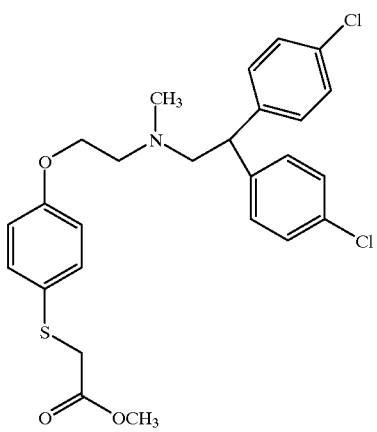

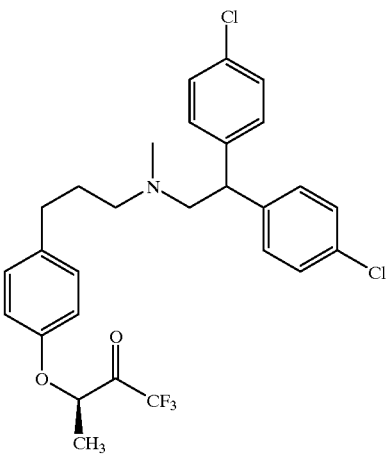

3-[4-[3-[N-[2-Bis-(4-chlorophenyl)ethyl]-N-methylamino]propyl]phenol

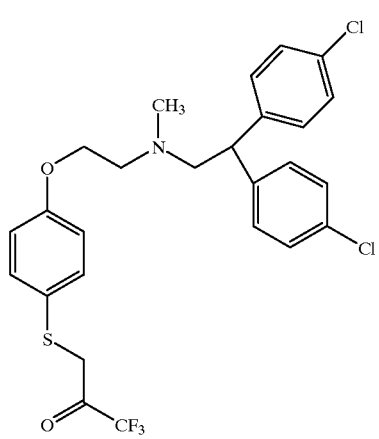

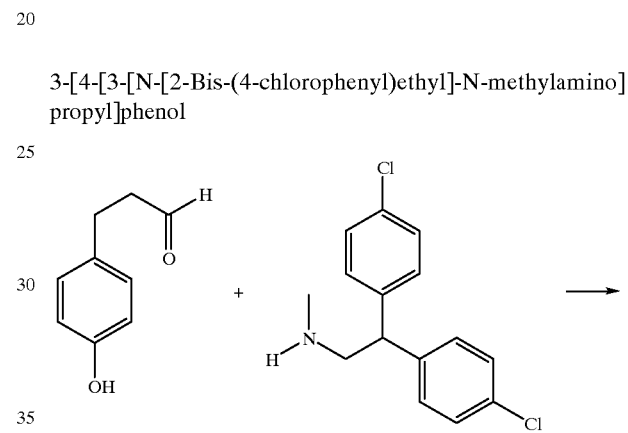

A solution of [4-[2-[N-[2-bis-(4-chlorophenyl)ethyl]-N-methylamino]ethoxy]phenyl thio]-acetic acid, methyl ester (1.0 g, 2.0 mmol) in toluene (2 ml) was cooled to −50° C. and treated with trifluoromethyltrimethylsilane (0.355 g, 2.5 mmol) followed by anhydrous tetrabutylammonium fluoride (2.0 mmol, 2 ml of a 1M solution in tetrahydrofuran). The cooling bath was removed and the solution was stirred at 22° C. for 18 h. Then 6.2 ml of 2M hydrochloric acid were added and the mixture was stirred for 30 min. The reaction mixture was then diluted with ether, washed with saturated sodium bicarbonate, brine and dried (magnesium sulfate). Evaporation of the solvent and chromatography of the residue on silica gel (elution toluene-ethyl acetate 7:3) gave 0.077 g (7%) of the title material as an oil. The hydrochloride salt was obtained as a white solid.

Anal. Calcd for $C_{26}H_{24}Cl_2F_3NO_2S \cdot HCl \cdot 0.5\ H_2O$; C 53.12, H 4.46, N 2.38. Found: C 53.04, H 4.80, N 2.32.

Example No. 280

(3R)-3-[4-[3-[N-[2-Bis-(4-chlorophenyl)ethyl]-N-methylamino]propyl]phenoxy]-1,1,1-trifluoro-2-butanone

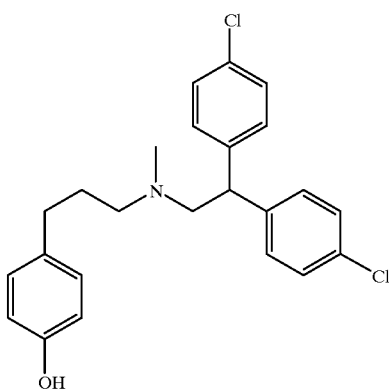

A solution of 3-(4-hydroxyphenyl)propanal (784 mg, 2.8 mmol) and N-methyl-2-bis-(4-chlorophenyl)ethylamine (860 mg, 40%, 2.3 mmol) in 1,2-dichloromethane was treated with sodium triacetoxyborohydride (1.1 g, 5.2 mmol). The mixture was stirred at room temperature for 2 h, quenched with sat. aqueous sodium bicarbonate and diluted with ethyl acetate. The organic phase was washed with brine, dried over sodium sulfate and concentrated in vacuo.

197

The residue was chromatographed on silica gel (first column: hexane:ethyl acetate=2:1; second column: dichloromethane:ethyl acetate=4:1) to afford the title material (720 mg, 75%) as a colorless syrup.

Methyl, (2R)-2-[4-[3-[N-[2-Bis-(4-chlorophenyl)ethyl]-N-methylamino]propylphenoxy]propionate

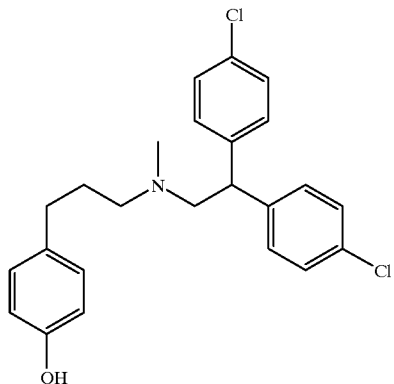

To a solution of 3-[4-[3-[N-[2-bis-(4-chlorophenyl)ethyl]-N-methylamino]propyl]phenol (100 mg, 0.241 mmol), methyl (S)-lactate (28 μl, 0.29 mmol) and triphenylphosphine (76 mg, 0.29 mmol) in THF was added dropwise diisopropyl azodicarboxylate (57 μl, 0.29 mmol). The mixture was stirred at room temperature for 2 h and concentrated in vacuo. The residue was chromatographed on silica gel (hexane:ethyl acetate:triethylamine=20:1:1 to 15:1:1) to give the title compound (63 mg, 52%) as a colorless oil.

198

(3R)-3-[4-[3-[N-[2-Bis-(4-chlorophenyl)ethyl]-N-methylamino]propyl]phenoxy]-2-methoxy-2-trimethylsilyloxy-1,1,1-trifluoro-2-butane

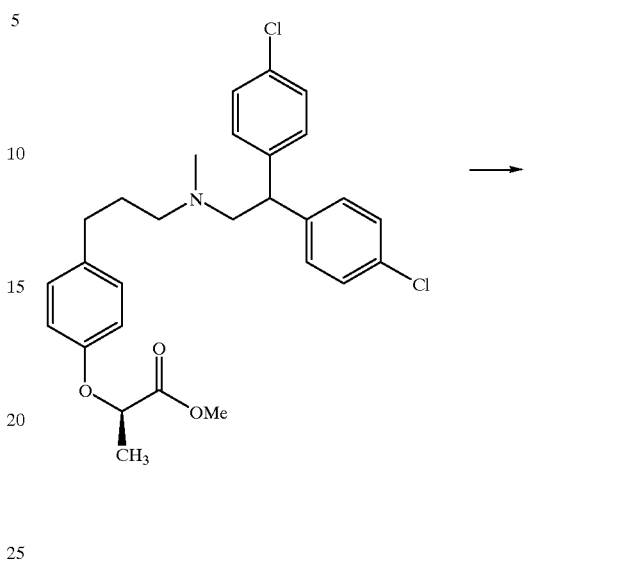

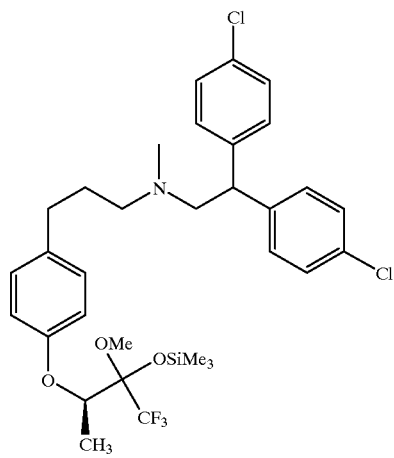

A solution of methyl (2R)-2-[4-[3-[N-[2-bis-(4-chlorophenyl)ethyl]-N-methylamino]propylphenoxy] propionate (54 mg, 0.108 mmol) and trifluoromethyltrimethylsilane (110 μl, 0.745 mmol) in toluene (1 ml) at −78° C. was treated with tetrabutylammonium fluoride (1.0M in THF, 5 μl, 0.005 mmol). The cooling bath was removed, and reaction mixture was stirred at room temperature for 0.5 h and concentrated in vacuo. The residue was chromatographed on silica gel (hexane:ethyl acetate=1:0 to 4:1) to give the title compound (52 mg, 77%) as a pale yellow oil.

(3R)-3-[4-[3-[N-[2-Bis-(4-chlorophenyl)ethyl]-N-methylamino]propyl]phenoxy]-1,1,1-trifluoro-2-butanone

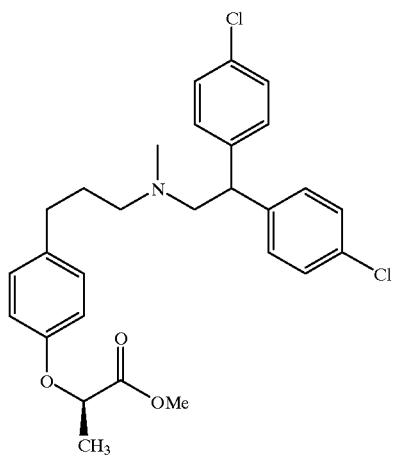

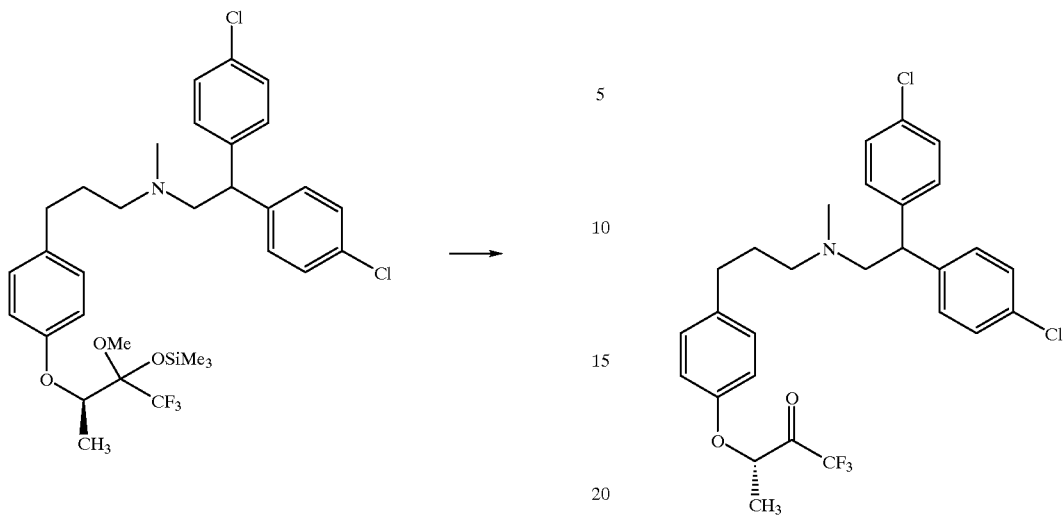

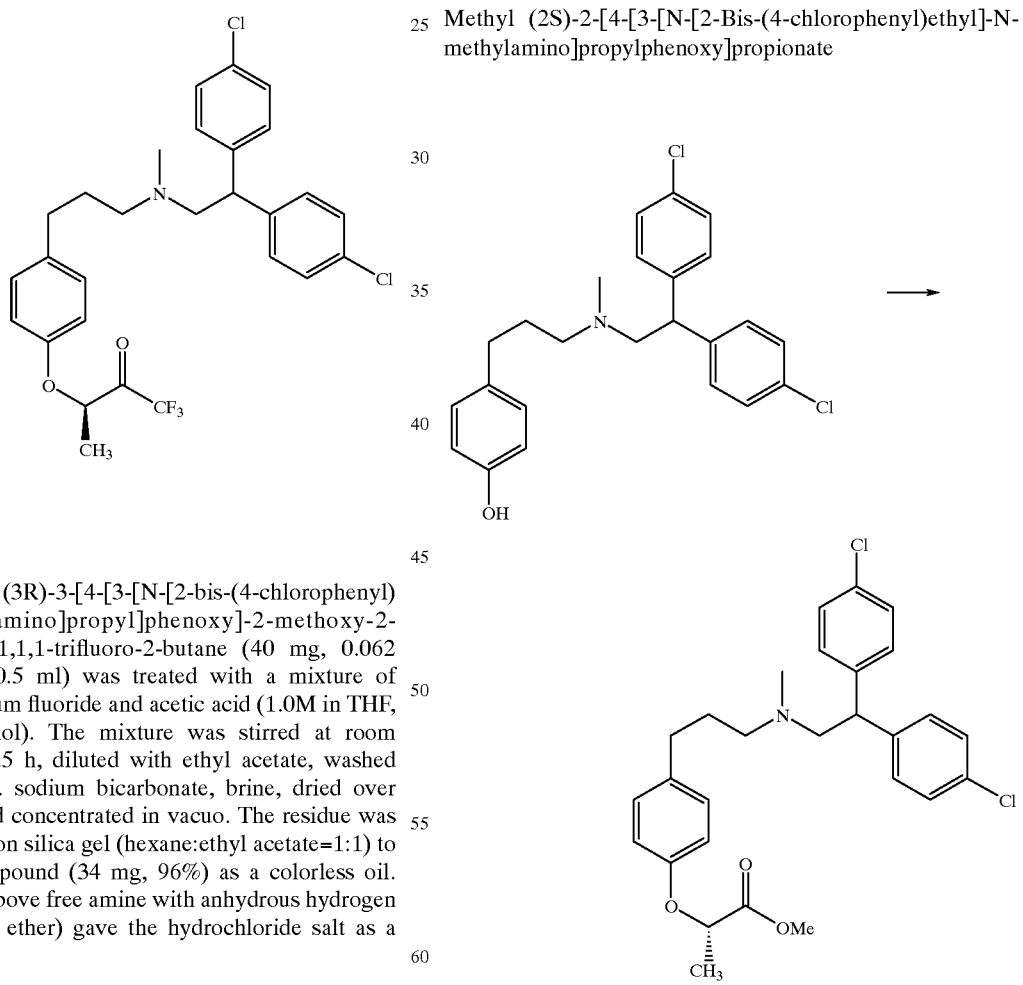

Methyl (2S)-2-[4-[3-[N-[2-Bis-(4-chlorophenyl)ethyl]-N-methylamino]propylphenoxy]propionate A solution of (3R)-3-[4-[3-[N-[2-bis-(4-chlorophenyl)ethyl]-N-methylamino]propyl]phenoxy]-2-methoxy-2-trimethylsilyloxy-1,1,1-trifluoro-2-butane (40 mg, 0.062 mmol) in THF (0.5 ml) was treated with a mixture of tetrabutylammonium fluoride and acetic acid (1.0M in THF, 77 µl, 0.077 mmol). The mixture was stirred at room temperature for 0.5 h, diluted with ethyl acetate, washed with sat. aqueous. sodium bicarbonate, brine, dried over sodium sulfate and concentrated in vacuo. The residue was chromatographed on silica gel (hexane:ethyl acetate=1:1) to give the title compound (34 mg, 96%) as a colorless oil. Treatment of the above free amine with anhydrous hydrogen chloride (1.0M in ether) gave the hydrochloride salt as a white solid.

Example No. 281

(3S)-3-[4-[3-[N-[2-Bis-(4-chlorophenyl)ethyl]-N-methylamino]propyl]phenoxy]-1,1,1-trifluoro-2-butanone 3-[4-[3-[N-[2-bis-(4-chlorophenyl)ethyl]-N-methylamino]propyl]phenol (122 mg 0.295 mmol) and methyl (R)-lactate (47 µl, 0.454 mmol) were reacted by the general procedure as described in Example no. 280 for the preparation of methyl (2R)-2-[4-[3-[N-[2-bis-(4-chlorophenyl)ethyl]-N-methylamino]propylphenoxy]propionate and afforded the title compound (74 mg, 50%) as a colorless oil.

(3S)-3-[4-[3-[N-[2-Bis-(4-chlorophenyl)ethyl]-N-methylamino]propyl]phenoxy]-2-methoxy-2-trimethylsilyloxy-1,1,1-trifluoro-2-butane

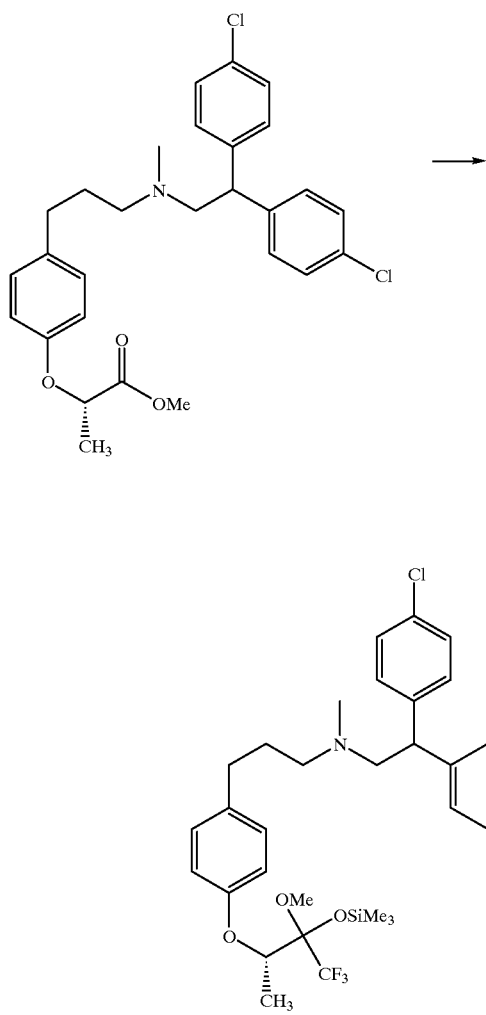

Methyl (2S)-2-[4-[3-[N-[2-bis-(4-chlorophenyl)ethyl]-N-methylamino]propylphenoxy]propionate (74 mg, 0.148 mmol and trifluoromethyl trimethylsilane (220 μl, 1.48 mmol were reacted by the general procedure as described in Example no. 280 for the preparation of (3R)-3-[4-[3-[N-[2-bis-(4-chlorophenyl)ethyl]-N-methylamino=9 propyl] phenoxy]-2-methoxy-2-trimethylsilyloxy-1,1,1-trifluoro-2-butane and afforded the title compound (76 mg, 80%) as a pale yellow oil.

(3S)-3-[4-[3-[N-[2-Bis-(4-chlorophenyl)ethyl]-N-methylamino]propyl]phenoxy]-1,1,1-trifluoro-2-butanone

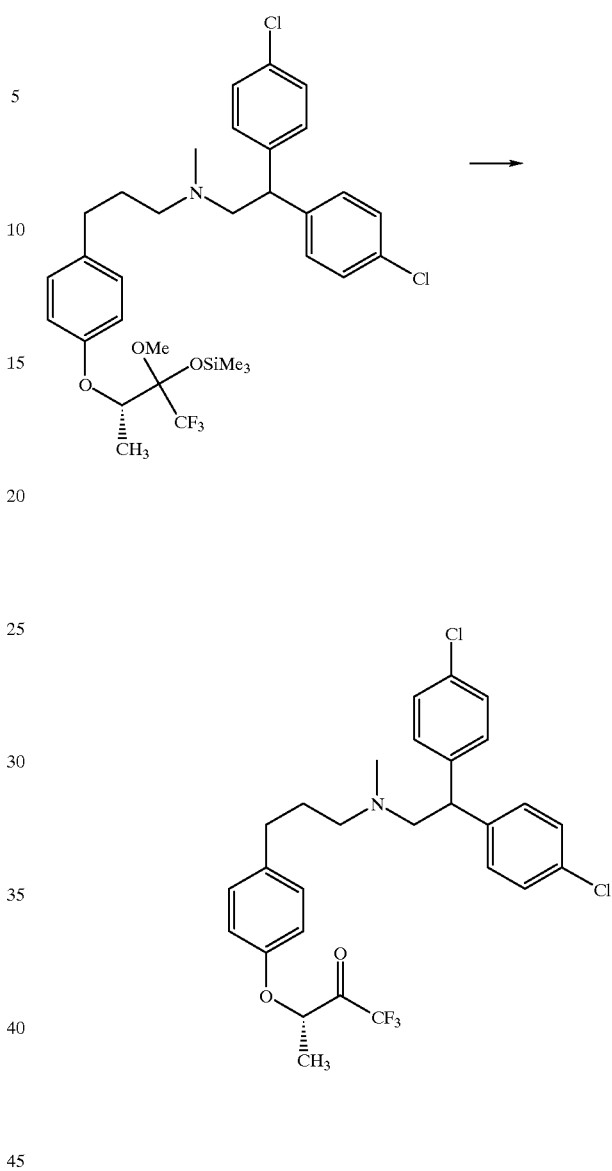

(3S)-3-[4-[3-[N-[2-Bis-(4-chlorophenyl)ethyl]-N-methylamino]propyl]phenoxy]-2-methoxy-2-trimethylsilyloxy-1,1,1-trifluoro-2-butane (74 mg, 0.115 mmol and tetrabutyl ammonium fluoride and acetic acid (1.0M in THF, 140 μl, 0.14 mmol) were reacted by the general procedure as described in the preparation of (3S)-3-[4-[3-[N-[2-bis-(4-chlorophenyl)ethyl]-N-methylamino] propyl]phenoxy]-1,1,1-trifluoro-2-butanone to give the title compound (60 mg, 94%) as a colorless oil. Treatment of the above free amine with anhydrous hydrogen chloride (1.0M in ether) gave the hydrochloride salt as a white solid.

Example No. 282

3-[4-[3-[N-[2-Bis-(4-chlorophenyl)ethyl]-N-methylamino] propyl]phenoxy]-3-methyl-1,1,1-trifluoro-2-butanone

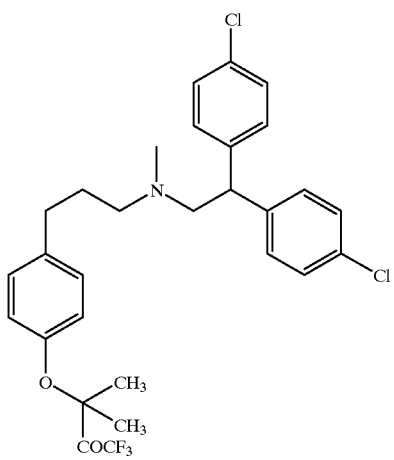

Methyl 2-[4-[3-(tert-butyldiphenylsilyloxy)propyl]phenoxy]-2-methyl-propionate

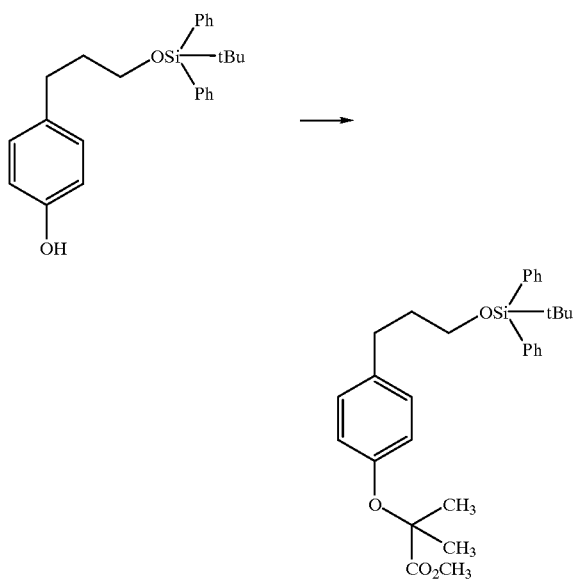

A solution of 3-(4-hydroxyphenyl)-1-(tert-butyldiphenylsilyloxy)propane (5.00 g, 12.8 mmol and methyl 2-bromo-2-methylpropionate (4.53 g, 25.0 mmol in dry acetonitrile (25 ml) was treated with cesium carbonate (8.3 g, 25.4 mmol and the resulting mixture was heated at 60° C. for 3.5 h. The cooled mixture was diluted with ethyl acetate, washed with water, brine and dried (magnesium sulfate). Evaporation of the solvent and chromatography of the residue on silica gel (elution toluene) gave 5.88 g (93%) of the title material as a clear oil.

$^1$H NMR 400 MHz (CDCl$_3$) δ (ppm): 1.08 (9H, s, t-Bu) 1.59 (6H, s, CH$_3$), 1.86 (2H, m, CH$_2$), 2.67 (2H, t, J=7.91 Hz, CH$_2$), 3.69 (2H, t, J=6.21 Hz, OCH$_2$), 3.80 (3H, s, OCH$_3$), 6.76 (2H, t, J=8.6 Hz, aromatic), 7.05 (2H, d, J=8.6 Hz, aromatic), 7.4 and 7.7 (6H and 4H, 2m, aromatic).

Anal. Calcd. for C$_{30}$H$_{38}$O$_4$Si: C 73.43, H 7.81. Found: C 73.5, H 7.96.

Methyl 2-[4-[3-hydroxypropyl]phenoxy]-2-methyl-propionate

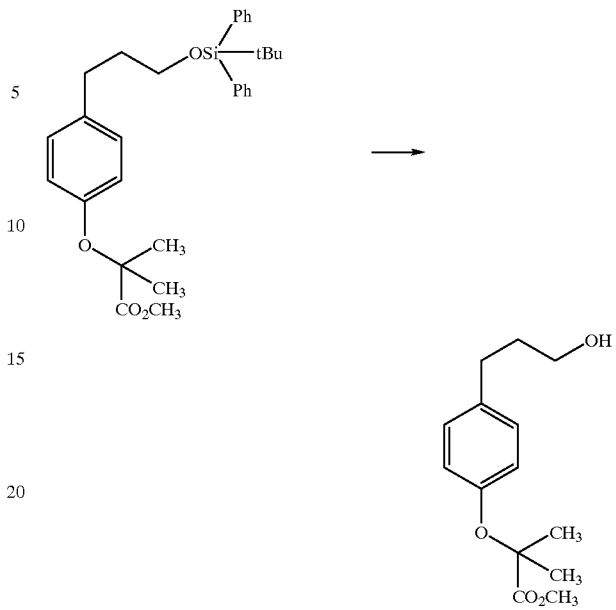

To a stirred solution of methyl 2-[4-[3-(tert-butyldiphenylsilyloxy)propyl]phenoxy]-2-methyl-propionate (1.83 g, 3.73 mmol in tetrahydrofuran (56 ml) at room temperature was treated with tetrabutylammonium fluoride (1M in THF, 5.64 ml) and stirred at room temperature for 1 hour. The mixture was diluted with water (70 ml) and dichloromethane (315 ml) and the organic phase was separated and dried over anhydrous magnesium sulfate, filtered and concentrated. The residue was purified by silica gel chromatography (EtOAc/dichloromethane 15% to 19%) to give the title material (0.840 g, 89%).

$^1$H NMR 400 MHz (CDCl$_3$) δ (ppm): 1.60 (6H, s, 2×—CH$_3$), 1.88 (2H, m, —CH$_2$—C$\underline{H}_2$—CH$_2$—), 2.66 (2H, t, J=7.6 Hz, —CH$_2$Ar), 3.68 (2H, t, J=6.4 Hz, —CH$_2$O—), 3.80 (3H, s, —CO$_2$Me), 6.78 (2H, d, J=8.6 Hz, aromatic H), 7.08 (2H, d, J=8.6 Hz, aromatic H).

Anal. Calcd. for C$_{14}$H$_{20}$O$_4$. 0.1 H$_2$O: C 66.17, H 8.01. Found: C 66.09, H 8.02.

MS (ESI): 270 (M+NH$_4$)$^+$

Methyl 2-[4-[3-methanesulfonyloxypropyl]phenoxy]-2-methyl-propionate

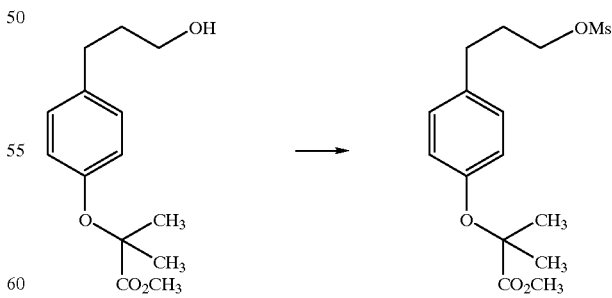

A stirred solution of methyl 2-[4-[3-hydroxypropyl]phenoxy]-2-methyl-propionate (0.790 g, 3.13 mmol) in dichloromethane at 0° C. was treated dropwise with triethylamine (0.916 ml, 6.57 mmol) and methanesulfonyl chloride (0.412 ml, 5.32 mmol). The mixture was stirred at 0° C. for 30 minutes, diluted with dichloromethane and washed with 1N HCl. The organic phase was dried over anhydrous sodium sulfate, filtered and concentrated. The residue was purified by silica gel chromatography to give the title material (1.02 g, 100%).

$^1$H NMR 400 MHz (CDCl$_3$) δ (ppm): 1.60 (6H, s, 2×—CH$_3$), 2.06 (2H, m, —CH$_2$—C$\underline{H}_2$—CH$_2$—), 2.71 (2H, t, J=7.5 Hz, —CH$_2$Ar), 3.01 (3H, s, —SO$_2$Me), 3.80 (3H, s, —CO$_2$Me), 4.24 (2H, t, J=6.3 Hz, —CH$_2$O—), 6.79 (2H, d, J=8.4 Hz, aromatic H), 7.08 (2H, d, J=8.4 Hz, aromatic H).

Anal. Calcd. for C$_{15}$H$_{22}$O$_6$S. 0.2 H$_2$O: C 53.94, H 6.76. Found: C 53.82, H 6.78.

MS (ESI): 348 (M+NH$_4$)$^+$

Methyl 2-[4-[3-[N-[2-Bis-(4-chlorophenyl)ethyl]-N-methylamino]propylphenoxy]-2-methyl-propionate

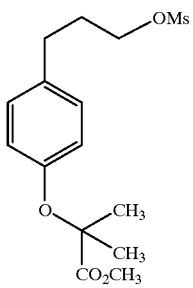

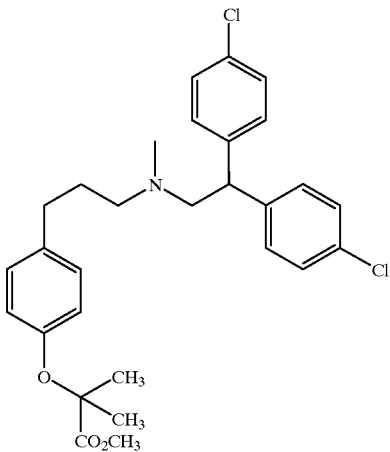

A stirred solution of methyl 2-[4-[3-methanesulfonyloxypropyl]phenoxy]-2-methyl-propionate (0.975 g, 2.95 mmol in acetonitrile (10.5 ml) was treated at room temperature with N-methyl-2-bis-(4-chlorophenyl)ethylamine (1.07 g, 3.83 mmol and N,N-diisopropylethylamine (0.617 ml, 3.54 mmol and the resulting mixture was heated at 80–85° C. overnight. The mixture was cooled down to room temperature, diluted with dichloromethane (105 ml) and washed with saturated sodium bicarbonate (50 mL) and brine (50 mL). The organic phase was dried over anhydrous magnesium sulfate, filtered and concentrated. The residue was purified by silica gel chromatography (ethyl acetate/hexane 35% to 37%) to give the title material (1.43 g, 95%).

$^1$H NMR 400 MHz (DMSO-d$_6$) δ (ppm): 1.49 (6H, s, 2×—CH$_3$), 1.58 (2H, m, —CH$_2$—), 2.17 (3H, s, —NCH$_3$), 2.30–2.33 (4H, m, —CH$_2$N— and —CH$_2$Ar), 2.86 (2H, d, J=8.1 Hz, —NCH$_2$CH—), 3.70 (3H, s, —CO$_2$Me), 4.24 (1H, t, J=8.1 Hz, —CH(Ar)$_2$), 6.67 (2H, d, J=8.6 Hz, aromatic H), 6.95 (2H, d, J=8.6 Hz, aromatic H), 7.33 (8H, s, aromatic H).

Anal. Calcd. for C$_{29}$H$_{33}$Cl$_2$NO$_3$: C 67.70, H 6.94, N 2.72. Found: C 67.91, H 6.54 N 2.94.

3-[4-[3-[N-[2-Bis-(4-chlorophenyl)ethyl]-N-methylamino]propyl]phenoxy]-3-methyl-1,1,1-trifluoro-2-butanone

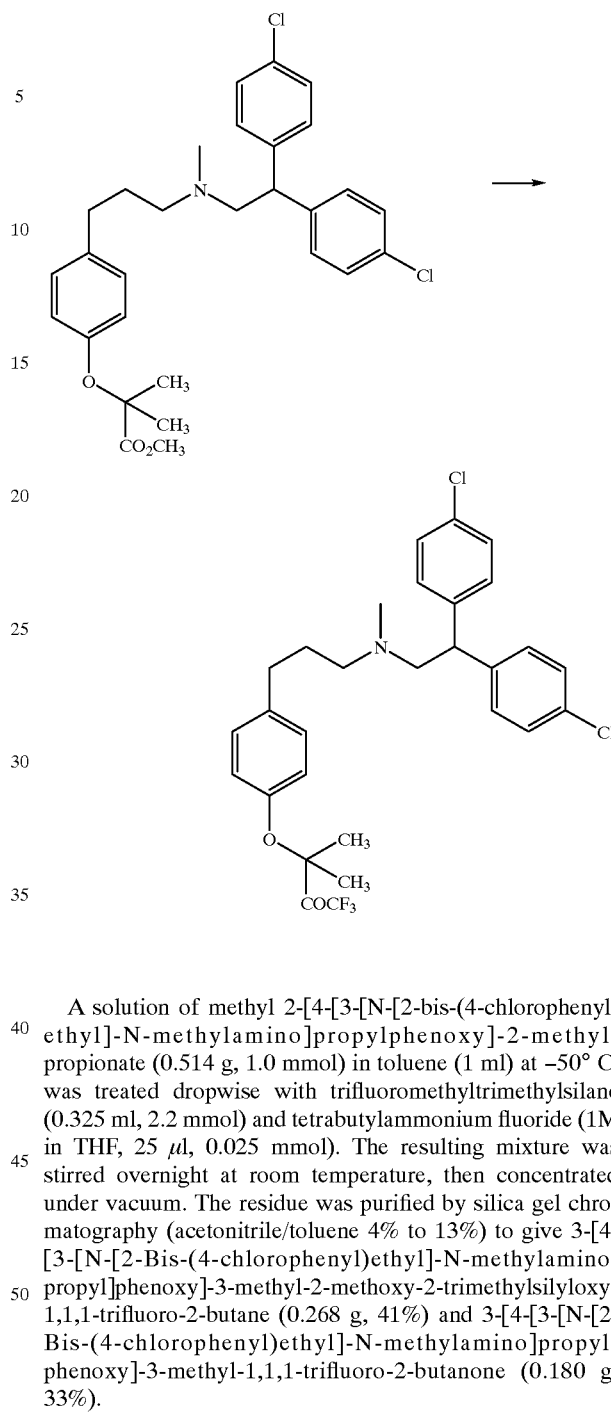

A solution of methyl 2-[4-[3-[N-[2-bis-(4-chlorophenyl)ethyl]-N-methylamino]propylphenoxy]-2-methyl-propionate (0.514 g, 1.0 mmol) in toluene (1 ml) at −50° C. was treated dropwise with trifluoromethyltrimethylsilane (0.325 ml, 2.2 mmol) and tetrabutylammonium fluoride (1M in THF, 25 μl, 0.025 mmol). The resulting mixture was stirred overnight at room temperature, then concentrated under vacuum. The residue was purified by silica gel chromatography (acetonitrile/toluene 4% to 13%) to give 3-[4-[3-[N-[2-Bis-(4-chlorophenyl)ethyl]-N-methylamino]propyl]phenoxy]-3-methyl-2-methoxy-2-trimethylsilyloxy-1,1,1-trifluoro-2-butane (0.268 g, 41%) and 3-[4-[3-[N-[2-Bis-(4-chlorophenyl)ethyl]-N-methylamino]propyl]phenoxy]-3-methyl-1,1,1-trifluoro-2-butanone (0.180 g, 33%).

$^1$H NMR 400 MHz (DMSO-d$_6$) δ (ppm): 1.25 (6H, s, 2×—CH$_3$), 1.60 (2H, m, —CH$_2$—), 2.17 (3H, s, —NCH$_3$—), 2.31–2.36 (4H, m, -CH$_2$Ar and —CH$_2$N—), 2.86 (2H, d, J=7.9 Hz, —NCH$_2$CH—), 4.23 (1H, t, J=7.9 Hz, —CH(Ar)$_2$), 6.92 (2H, d, J=8.7 Hz, aromatic H), 6.98 (2H, d, J=8.7 Hz, aromatic H), 7.33 (8H, s, aromatic H).

Anal. Calcd. for C$_{29}$H$_{32}$Cl$_2$F$_3$NO$_3$.HCl: C 57.39, H 5.48, N 2.31. Found: C 57.52, H 5.72, N 2.33.

MS (ESI): 570 (M+H$_2$O+H)$^+$

Example No. 283
3-Amino-N-[4-[2-(dodecylsulfonyl)ethoxy]benzoyl]-1,1,1-trifluoro-2-propanone 4-[2-(Dodecylthio)ethoxy]benzoic Acid, Methyl Ester

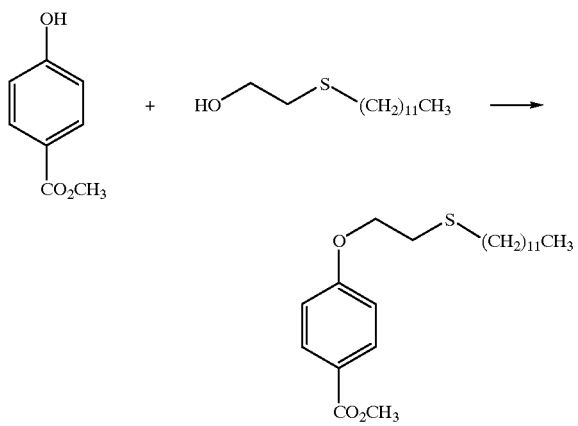

A mixture of methyl 4-hydroxybenzoate (5.67 g, 37.2 mmol), 2-(dodecylthio)ethanol (9.19 g, 37.2 mmol) and triphenylphosphine (11.7 g, 44.6 mmol) in a mixture of benzene (150 ml) and ethyl acetate (25 ml) was treated at 18° C. with a solution of diethyl azodicarboxylate (7.77 g, 44.6 mmol in benzene (20 ml) added dropwise over 15 min. After 2 h at 22° C., the reaction mixture was diluted with ethyl acetate, washed with saturated sodium bicarbonate, brine and dried (magnesium sulfate). Evaporation of the solvent and chromatography of the residue on silica gel (elution toluene-ethyl acetate 95:5) gave 12.89 g (91%) of the title material as white needles: mp 37–38° C. (hexane).

Anal. Calcd for $C_{22}H_{36}O_3S$: C 69.43, H 9.53, S 8.42. Found: C 69.33, H 9.05, S 8.49.

4-[2-(Dodecylthio)ethoxy]benzoic Acid

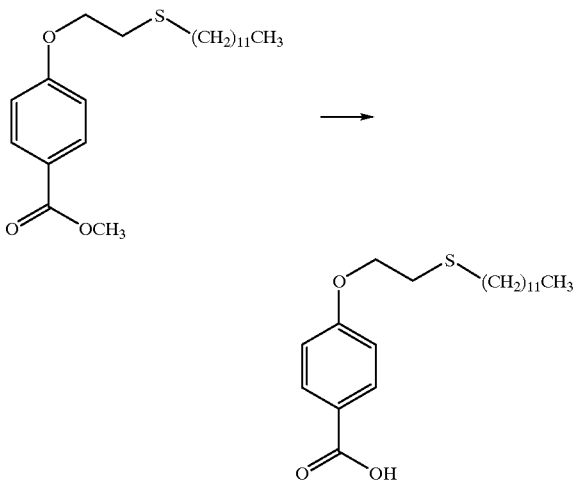

A solution of 4-[2-(dodecylthio)ethoxy]benzoic acid methyl ester (11.29 g, 29.7 mmol) in 80% aqueous ethanol (100 ml) was treated with a solution of potassium, hydroxide, (6.0 g, 0.107 mol) in water (15 ml) and the resulting mixture was heated at 80° C. for 2 h. The solvent was then concentrated in vacuo and the residue was treated with 150 ml of 1N aqueous hydrochloric acid. The aqueous phase was extracted three times with dichloromethane and the combined organic extracts were washed with brine, dried (magnesium sulfate) and evaporated. The residue was recrystallized from dichloromethane to give 10.24 g (94%) of the title material as white needles: mp 97–98° C.

Anal. Calcd for $C_{21}H_{34}O_3S$: C 68.81, H 9.35, S 8.75. Found: C 68.59, H 9.07, S 8.82.

3-Amino-N-[4-[2-(dodecylthio)ethoxy]benzoyl]-1,1,1-trifluoro-2-propanol

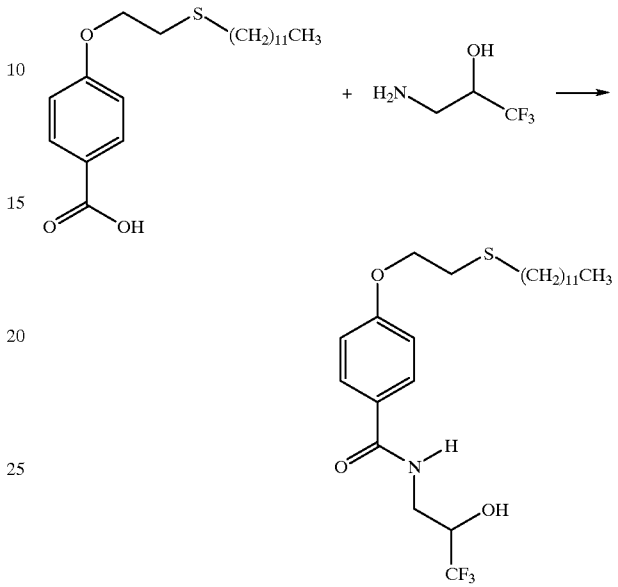

Oxalyl chloride (1.62 g, 12.8 mmol was added at 22° C. to a solution of 4-[2-(dodecylthio)ethoxy]benzoic acid (1.18 g, 3.2 mmol in dichloromethane (30 ml). A small drop of N,N-dimethylformamide was added and the resulting mixture was stirred at 22° C. for 2 h. The solvent and excess reagents were then evaporated in vacuo and the residual acid chloride was dissolved in tetrahydrofuran. The solution of acid chloride was then added dropwise to a solution of (R and S)-1-amino-3,3,3-trifluoro-2-propanol (0.45 g, 3.48 mmol (P. V. Ramachandran, B. Gong and H. C. Brown, J. Org. Chem., 1995, 60 4146) in a mixture of tetrahydrofuran (20 ml), water (20 ml) and sodium bicarbonate (2 g). After 30 min, the reaction mixture was diluted with ethyl acetate, washed with brine and dried (magnesium sulfate). Evaporation of the solvent and chromatography of the residue on silica gel (elution toluene-ethyl acetate, 8:2) gave 1.50 g (98%) of the title material as white needles: mp 108.5–109° C. (methanol).

Anal. Calcd for $C_{24}H_{38}F_3NO_3S$: C 60.35, H 8.02, N 2.93, S 6.71. Found: C 60.43, H 8.11, N 2.98, S 6.87.

3-Amino-N-[4-[2-(dodecylsulfonyl)ethoxy]benzoyl]-1,1,1-trifluoro-2-propanol

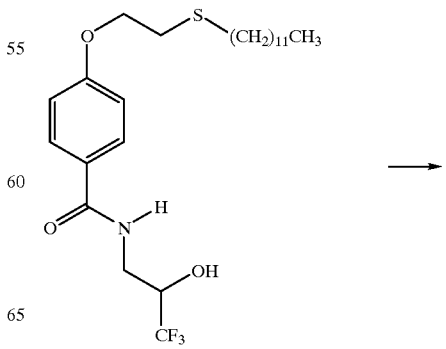

-continued

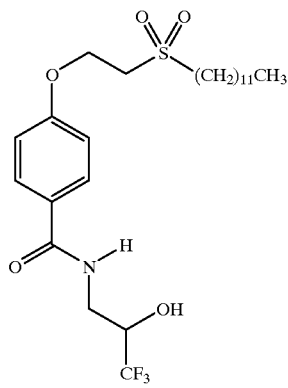

A solution of 3-amino-N-[4-[2-(dodecylthio)ethoxy]benzoyl]-1,1,1-trifluoro-2-propanol (0.440 g, 0.92 mmol in chloroform (50 ml) was treated at 22° C. with m-chloroperoxybenzoic acid (0.38 g, 2.2 mmol and the resulting mixture was stirred for 2 h. The reaction mixture was then diluted with ethyl acetate, washed with 1% ferrous sulfate, saturated sodium bicarbonate and brine. After drying (magnesium sulfate), the solvent was evaporated and the residue was recrystallized from chloroform to give 0.437 g (93%) of the title material as white needles: mp 149–150° C.

Anal. Calcd for $C_{24}H_{38}F_3NO_3S$: C 56.56, H 7.52, N 2.75. Found: C 56.62, H 7.50, N 2.82.

3-Amino-N-[4-[2-(dodecylsulfonyl)ethoxy]benzoyl]-1,1,1-trifluoro-2-propanone

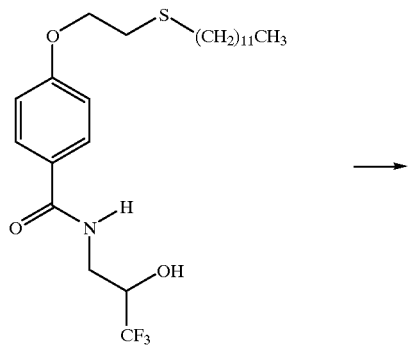

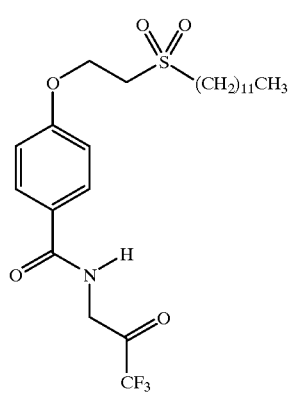

A solution of 3-amino-N-[4-[2-(dodecylthio)ethoxy]benzoyl]-1,1,1-trifluoro-2-propanol (0.387 g, 0.76 mmol in a mixture of dichloromethane (100 ml) and ethyl acetate (100 ml) was treated with 1,1,1-triacetoxy-1,1-dihydro-1,2-benziodoxol-3(1H)-one (Dess-Martin periodinane) (1.29 g, 3.03 mmol and the resulting mixture was stirred at 22° C. for 3.5 h. The reaction mixture was then diluted with ethyl acetate, washed with 5% sodium thiosulfate, sodium bicarbonate, brine and dried (magnesium sulfate). Evaporation of the solvent and chromatography of the residue on silica gel (elution toluene-ethyl acetate, 6:4) gave 0.340 g (90%) of the title material as white needles: mp 144–146° C. (chloroform-ethyl acetate).

Anal. Calcd for $C_{24}H_{36}F_3NO_5S \cdot H_2O$: C 54.84, H 7.29, N 2.66, S 6.10. Found: C 54.96, H 7.22, N 2.71, S 6.02.

Example No. 284

3-[N-Methyl-N-[4-[2-(tert-butyldiphenylsilyloxy)ethoxy]benzoyl]]amino-1,1,1-trifluoro-2-propanone 4-[2-(tert-Butyldiphenylsilyloxy)ethoxy]benzoic Acid, Methyl Ester

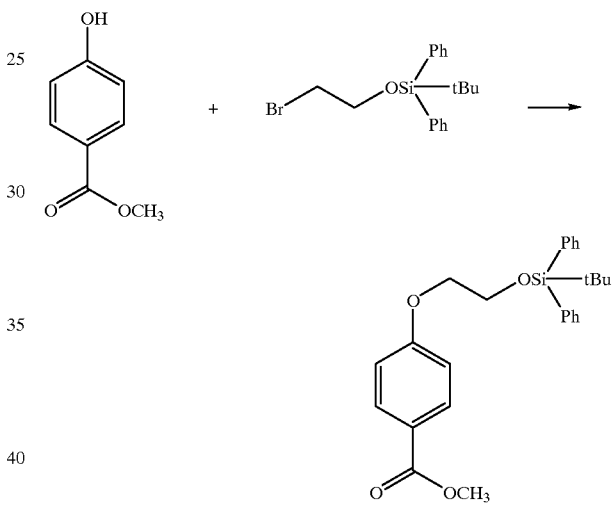

A mixture of methyl 4-hydroxybenzoate (3.25 g, 22.0 mmol, 2-(tert-butyldiphenylsilyloxy) ethyl bromide (8.0 g, 22.0 mmol, powdered anhydrous potassium carbonate (12 g) and potassium iodide (0.1 g) in acetone (250 ml) was heated under reflux for 48 h. The solid was then filtered and the filtrate was evaporated under reduced pressure.

Chromatography of the residue on silica gel (elution toluene) gave 7.22 g (75%) of the title material as an oil.

Anal. Calcd. for $C_{26}H_{34}O_4Si$: C 71.85, H 6.96. Found: C 71.81, H 7.04.

4-[2-(tert-Butyldiphenylsilyloxy)ethoxy]benzoic Acid

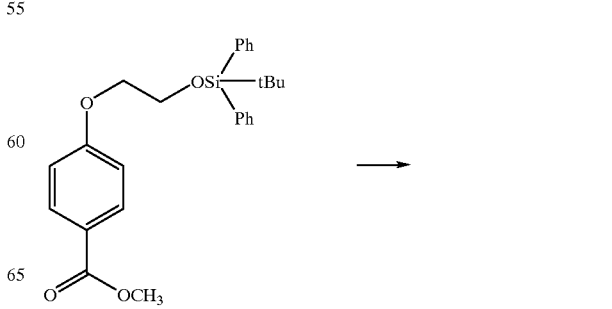

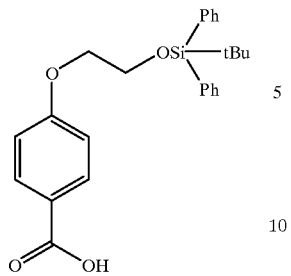

A mixture of 4-[2-(tert-butyldiphenylsilyloxy)ethoxy] benzoic acid, methyl ester (1.67 g, 3.84 mmol and lithium iodide (10 g) in pyridine (80 ml) was heated under reflux for 6 days. The solvent was evaporated in vacuo and the residue was diluted with ethyl acetate and acidified with 0.1N hydrochloric acid. The organic phase was washed with brine, dried (magnesium sulfate) and evaporated. Chromatography of the residue in silica gel (elution toluene-ethyl acetate, 6:4) gave 0.86 g (53%) of the starting material as white crystals: mp 156–157° C. (ethyl acetate-hexane).

Anal. Calcd for $C_{25}H_{28}O_4Si$: C 71.40, H 6.71. Found: C 71.37, H 6.63.

(R and S) 1-N-Methylamino-3,3,3-trifluoro-2-propanol

(R and S)-(trifluoromethyl)oxirane (2.40 g, 21.4 mmol (P. V. Ramachandran, B. Long and H. C. Brown, J. Org. Chem., 1995, 60 4146) was cooled to −20° C. and treated dropwise with cold anhydrous methylamine (15 ml). The reaction flask was sealed and the resulting mixture was allowed to warm up to 22° C. and stirred for 2 h. The reaction mixture was cooled again to −20° C., carefully opened and the excess methylamine was allowed to evaporate. The title material was obtained as white needles (2.97 g, 97%): mp 53–54° C. (ether-hexane).

Anal. Calcd. for $C_4H_8F_3NO$: C 33.57, H 5.63, N 9.79. Found: C 33.35, H 5.39, N 9.74.

3-[N-Methyl-N-[4-[2-(tert-butyldiphenylsilyloxy)ethoxy] benzoyl]]amino-1,1,1-trifluoro-2-propanol

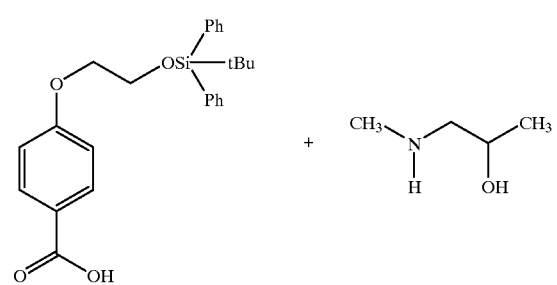

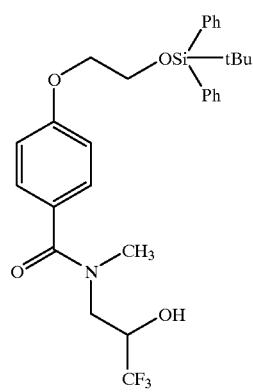

A solution of 4-[2-(tert-butyldiphenylsilyloxy)ethoxy] benzoic acid (1.19 g, 2.83 mmol in dichloromethane (20 ml) was treated with oxalyl chloride (0.4 ml, 4.6 mmol and a small drop of N,N-dimethyl formamide. After 1 h at 22° C. the solvent and excess reagent were evaporated under reduced pressure and the residual oil was dissolved in dry tetrahydrofuran (10 ml). The acid chloride solution was then added dropwise and with good stirring to a solution of (R and S) 1-N-methylamino-3,3,3-trifluoro-2-propanol (0.445 g, 3.11 mmol in a mixture of tetrahydrofuran (10 ml), water (8 ml) and sodium bicarbonate (2 g). After 1 h at 22° C., the reaction mixture was diluted with ethyl acetate, washed with water, brine and dried (magnesium sulfate). Evaporation of the solvent and chromatography of the residue on silica gel (elution toluene-ethyl acetate, 85:15) gave 1.30 g (84%) of the title material as a white solid: mp 74–75° C. (hexane).

Anal. Calcd for $C_{29}H_{34}F_3NO_4Si$: C

3-[N-Methyl-N-[4-[2-(tert-butyldiphenylsilyloxy)ethoxy] benzoyl]]amino1,1,1-trifluoro-2-propanone

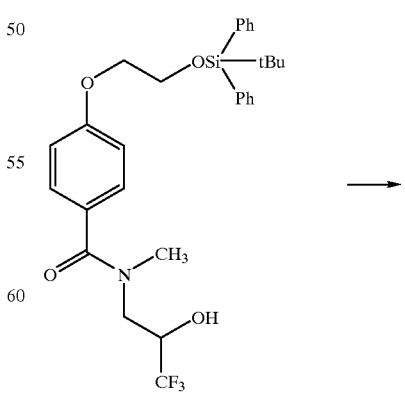

-continued

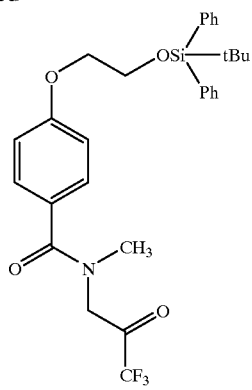

A solution of 3-[N-methyl-N-[4-[2-(tert-butyldiphenylsilyloxy)ethoxy]benzoyl]]amino-1,1,1-trifluoro-2-propanol (1.14 g, 2.09 mmol in dichloromethane (30 ml) was treated with 1,1,1-triacetoxy-1,1-dihydro-1,2-benziodoxol-3(1H)-one (Dess-Martin periodinane) (2.67 g, 6.29 mmol and the resulting mixture was stirred at 22° C. for 2 h. The reaction mixture was then diluted with ethyl acetate, washed with 10% aqueous sodium thiosulfate, saturated sodium bicarbonate, brine and dried (magnesium sulfate). Evaporation of the solvent and chromatography of the residue on silica gel (elution toluene-ethyl acetate, 9:1) gave 0.424 g (37%) of the title material as white needles mp 95–96° C. (ethyl acetate-hexane). Anal. Calcd for $C_{29}H_{32}F_2NO_4Si$: C

BIOLOGICAL ACTIVITY

Assay for determining activity as $cPLA_2$ inhibitors:

$^3$H-arachidonate-labeled U937 membranes were prepared from U937 cells grown in RPMI 1640 medium containing L-glutamine supplemented with 10% fetal calf serum and 50 µg/ml gentamycin in a 5% $CO_2$ incubator at 37° C. Sixteen hours prior to harvesting the cells, $^3$H-arachidonate (100 Ci/mmol was added to the cell culture ($1\times10^6$ cells/ml, 0.5 µCi/ml). After washing the cells with HBSS (Hank's Balanced Salts) containing 1 mg/ml HSA (Human Serum Albumin), the cells were lysed by nitrogen cavitation and the homogenate was centrifuged at 2,000× g for 10 minutes. The supernatant was further centrifuged at 50,000× g for 30 minutes after which the pellet was resuspended in water and autoclaved at 120° C. for 15 minutes to inactivate any residual phospholipase $A_2$ activity. This suspension was then recentrifuged at 50,000× g for 30 minutes and the pellet resuspended in distilled water.

Assays of $cPLA_2$ activity using these $^3$H-arachidonate-labeled U937 membranes as substrate typically employ human recombinant $cPLA_2$ (see Burke et al., *Biochemistry* 34: 15165–15174, 1995) and membrane substrate (22 µm phospholipid) in 20 mm HEPES [N-(2-hydroxyethyl)piperazine-N'-(2-ethanesulfonic acid)] buffer, pH 8, containing 6 mm $CaCl_2$, 0.9 mg/ml albumin and 4 m glycerol. Enzyme assays are allowed to proceed for 3 hours at 37° C. before removing the non-hydrolyzed membranes. The hydrolyzed, radiolabeled fatty acid is then measured by liquid scintillation counting of the aqueous phase.

The effects of inhibitor are calculated as percent inhibition of $^3$H-arachidonate formation, after correcting for nonenzymatic hydrolysis, as compared to a control lacking inhibitor according to the following formula:

percent inhibition=((Control DPM−Inhibitor DPM)/Control DPM)×100%

Various concentrations of an inhibitor were tested, and the percent inhibition at each concentration was plotted as log concentration (abscissa) versus percent inhibition (ordinate) to determine the $IC_{50}$ values.

In this assay the compounds of the illustrative examples below exhibited $cPLA_2$ $IC_{50}$ values in the range of from about 1 to 50 µm.

Since the compounds of the present invention are selective inhibitors of cytosolic phospholipase $A_2$, they are of value in the treatment of a wide variety of clinical conditions.

Inflammatory disorders which may be treated by inhibition of cytosolic $cPLA_2$ include such conditions as arthritis, psoriasis, asthma, inflammatory bowel disease, gout, trauma-induced inflammation such as spinal cord injury, Alzheimer's Disease, cerebral ischemia, chronic skin inflammation, shock, damage to skin resulting from exposure to ultraviolet light or burns, allergic rhinitis, acute pancreatitis, and the like.

The compounds of formula I and formula III are usually administered in the form of pharmaceutical compositions. They can be administered by a variety of routes including oral, rectal, transdermal, subcutaneous, intravenous, intramuscular, and intranasal. The compounds are effective as both injectable and oral compositions. Such compositions are prepared in a manner well known in the pharmaceutical art and comprise at least one active compound defined by formula I or formula III and a pharmaceutically acceptable carrier.

In making the compositions employed in the present invention the active ingredient is usually mixed with an excipient, diluted by an excipient or enclosed within a carrier which can be in the form of a capsule, sachet, paper or other container. When the excipient serves as a diluent, it can be a solid, semisolid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range. For example, dosages per day normally fall within the range of about 0.5 to about 30 mg/kg of body weight. In the treatment of adult humans, the range of about 1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

We claim:

1. A compound of the formula

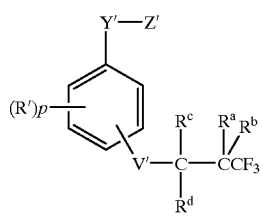

III in which $R^1$ is $(C_1-C_6)$alkyl, $(C_2-C_6)$alkenyl, $(C_2-C_6)$alkynyl, $(C_1-C_6)$alkoxy, $(C_1-C_6)$alkylthio, halo, hydroxy, cyano,

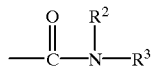

in which $R^2$ and $R^3$ are each independently hydrogen or $(C_1-C_6)$alkyl, —COO—$(C_1-C_6)$alkyl, $CF_3$, $(C_1-C_6)$alkylphenyl, phenyl or phenyl substituted by one or more, preferably 1–3, of $(C_1-C_6)$alkyl, —COO—$(C_1-C_6)$alkyl

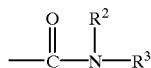

in which $R^2$ and $R^3$ are as defined above, halo, hydroxy, —O—$(C_1-C_6)$alkyl, —S—$(C_1-C_6)$alkyl, or $(C_2-C_6)$alkenyl;

p is 0, 1 or 2;

$V^1$ is —O—, —S—, —SO—, —SO$_2$—, —NHCO— or —CONH—;

$R^c$ and $R^d$ are each independently hydrogen or methyl;

$R^a$ and $R^b$ when taken together form an oxo (=O) group, or $R^a$ and $R^b$ are each independently hydrogen or OH;

$Y^1$ is O, S, SO, SO$_2$,

or —CH$_2$ in which $R^d$ is hydrogen, —COCF$_3$, —CO-phenyl, —COO—$(C_1-C_6)$alkyl,

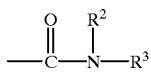

in which $R^2$ and $R^3$ are each independently hydrogen or $(C_1-C_6)$alkyl or $(C_1-C_{18})$alkyl or $(C_1-C_{18})$alkyl substituted by one or more of phenyl or phenyl substituted by 1–5 fluoro, 1–3 halo (other than fluoro), 1–3 $(C_1-C_6)$alkoxy, 1–3 $(C_1-C_6)$alkyl, 1–3 nitro, 1–3 cyano, 1–3 hydroxy, 1–3 trifluoromethyl, 1–3 $(C_1-C_6)$alkylthio, 1–3 amino, 1–3 $(C_1-C_6)$alkylamino, 1–3 di$(C_1-C_6)$ alkylamino, 1–3 carboxyl], 1–3 —COO—$(C_1-C_6)$alkyl, 1–3 —SO$_3$H, 1–3 —SO$_2$NHR$^{15}$ in which $R^{15}$ is hydrogen or $(C_1-C_6)$alkyl, or 1–3

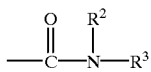

in which $R^2$ and $R^3$ are each independently hydrogen or $(C_1-C_6)$alkyl; and $Z^1$ is (a) $(C_1-C_{18})$alkyl, $(C_1-C_{18})$alkenyl or $(C_2-C_{18})$alkynyl in which one or more carbon atoms in such alkyl, alkenyl or alkynyl group is optionally replaced by S, SO, SO$_2$,

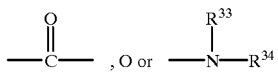

in which $R^{33}$ and $R^{34}$ are each independently hydrogen, —COCF$_3$, —CO-phenyl, —COO—$(C_1-C_6)$alkyl,

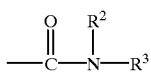

in which $R^2$ and $R^3$ are each independently hydrogen or $(C_1-C_6)$alkyl, $(C_1-C_{18})$alkyl, (b) $(C_1-C_{18})$alkyl substituted by 1–5 fluoro, 1–3 halo (other than fluoro), 1–3 $(C_1-C_6)$alkoxy, 1–3 $(C_1-C_6)$alkyl, 1–3 nitro, 1–3 cyano, 1–3 hydroxy, 1–3 trifluoromethyl, 1–3 $(C_1-C_6)$alkylthio, 1–3 amino, 1–3 $(C_1-C_6)$alkylamino, 1–3 di$(C_1-C_6)$alkylamino, 1–3 carboxyl, 1–3 —COO—$(C_1-C_6)$alkyl, 1–3 —SO$_3$H, 1–3 —SO$_2$NHR$^{15}$ in which $R^{15}$ is hydrogen or $(C_1-C_6)$alkyl, or 1–3

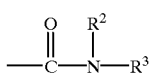

in which $R^2$ and $R^3$ are each independently hydrogen or $(C_1-C_6)$alkyl, or (c) $(C_1-C_{18})$alkyl substituted at a terminal carbon atom by $$-\text{O}-\underset{\underset{R^{37}}{|}}{\overset{\overset{R^{35}}{|}}{\text{Si}}}-R^{36}$$

in which $R^{35}$, $R^{36}$ and $R^{37}$ are each independently $(C_1-C_6)$alkyl, aryl, aryl-$(C_1-C_6)$alkyl-, heterocyclic or heterocyclic $(C_1-C_6)$alkyl- in which the aryl or heterocyclic rings may be optionally substituted by 1–3 halo, $(C_1-C_6)$alkoxy, $(C_1-C_6)$alkyl, nitro, cyano, hydroxy, trifluoromethyl, $(C_1-C_6)$alkylthio, amino, di(alkylamino), —$CO_2H$, —COO—$(C_1-C_6)$alkyl, —$SO_3H$, —$SO_2NHR^{15}$ in which $R^{15}$ is hydrogen or $(C_1-C_6)$alkyl, or $$-\overset{\overset{O}{\|}}{\text{C}}-\overset{\overset{R^2}{|}}{\text{N}}-R^3$$

in which $R^2$ and $R^3$ are each independently hydrogen or $(C_1-C_6)$alkyl, providing that when $Y^1$ is O, $Z^1$ cannot be $(C_1-C_{18})$alkyl; or a pharmaceutically acceptable salt or prodrug thereof.

2. A compound of claim 1 wherein $V^1$ is in the para-position.

3. A compound of claim 1 or 2 wherein $Z^1$ is (a)

$$-(CH_2)_2-\overset{\overset{(O)_{n'}}{|}}{\text{S}}-CR^{33}R^{34}$$

in which $n^1$ is 0, 1 or 2 and $R^{33}$ and $R^{34}$ are phenyl or phenyl substituted by 1–5 fluoro, 1–3 halo (other than fluoro), 1–3 $(C_1-C_6)$alkoxy, 1–3 $(C_1-C_6)$alkyl, 1–3 nitro, 1–3 cyano, 1–3 hydroxy, 1–3 trifluoromethyl, 1–3 $(C_1-C_6)$alkylthio, 1–3 amino, 1–3 $(C_1-C_6)$alkylamino, 1–3 di$(C_1-C_6)$alkylamino, 1–3 carboxy, 1–3 —COO—$(C_1-C_6)$alkyl, 1–3 —$SO_3H$, 1–3 —$SO_2NHR^{15}$ in which $R^{15}$ is hydrogen or $(C_1-C_6)$alkyl, or 1–3

$$-\overset{\overset{O}{\|}}{\text{C}}-\overset{\overset{R^2}{|}}{\text{N}}-R^3$$

in which $R^2$ and $R^3$ are each independently hydrogen or $(C_1-C_6)$alkyl;

(b)

$$-(CH_2)_2-\overset{\overset{(O)_{n'}}{|}}{\text{S}}-(CH_2)-O-CR^{33}R^{34}$$

in which $n^1$ is 0, 1 or 2 and $R^{33}$ and $R^{34}$ are as defined above;

(c)

$$-(CH_2)_2-\overset{\overset{(C_1-C_6)\text{alkyl}}{|}}{\text{N}}-(CH_2)_2-O-CR^{33}R^{34}$$

in which $R^{33}$ and $R^{34}$ are as defined above;

(d)

$$-(CH_2)_2-S-(CH_2)_2-O-CR^{33}R^{34}$$

in which $R^{33}$ and $R^{34}$ are as defined above;

(e)

$$-(CH_2)_2-\overset{\overset{(C_1-C_6)\text{alkyl}}{|}}{\text{N}}-(CH_2)_{1-4}-CR^{33}R^{34}$$

in which $R^{33}$ and $R^{34}$ are as defined above;

(f)

$$-(CH_2)_2-\overset{\overset{(C_1-C_6)\text{alkyl}}{|}}{\text{N}}-CR^{33}R^{34}$$

in which $R^{33}$ and $R^{34}$ are as defined above; or a pharmaceutically acceptable salt or prodrug thereof.

4. A compound of claim 1 or claim 2 in which $Y^1$ is $CH_2$ and $Z^1$ is $$(CH_2)_{1-4}-\text{O}-\underset{\underset{R^{37}}{|}}{\overset{\overset{R^{35}}{|}}{\text{Si}}}-R^{36}$$

in which $R^{35}$, $R^{36}$ and $R^{37}$ are each independently aryl or $(C_1-C_6)$alkyl, or a pharmaceutically acceptable salt or prodrug thereof.

5. A compound of claim 1 having the structure

[Structure: a compound with two 4-chlorophenyl groups attached to a CH bearing an N(CH₃) group, connected via a propyl chain to a phenyl ring with a para-O-CH₂-C(=O)-CF₃ substituent];

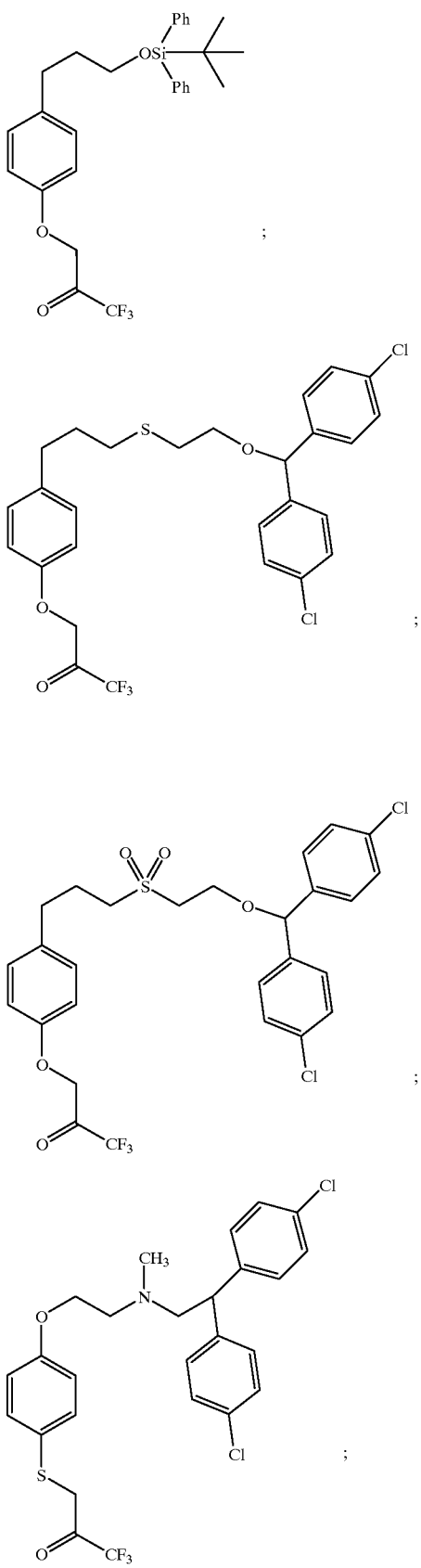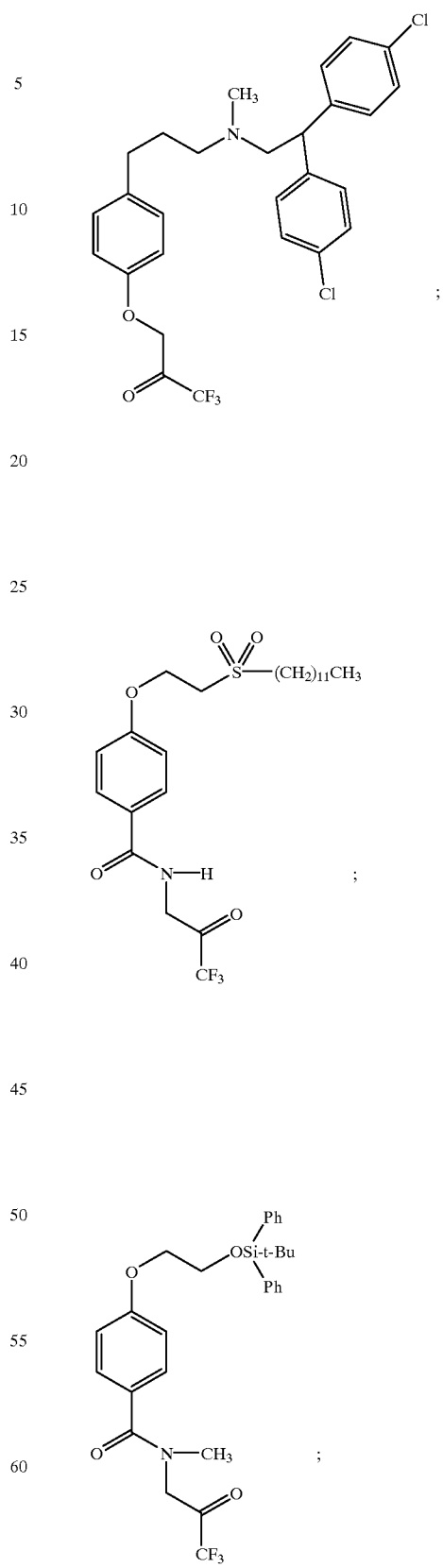

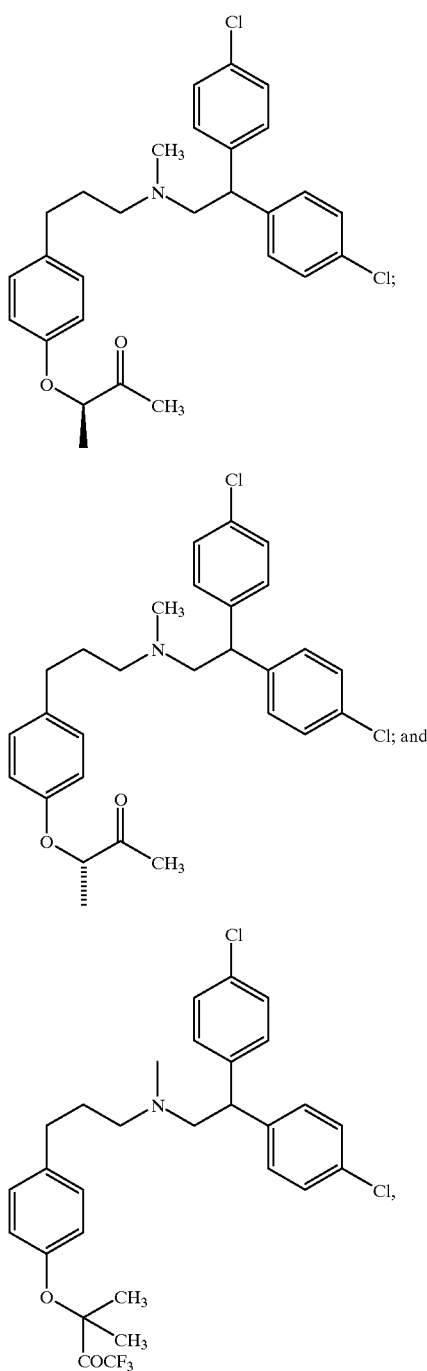

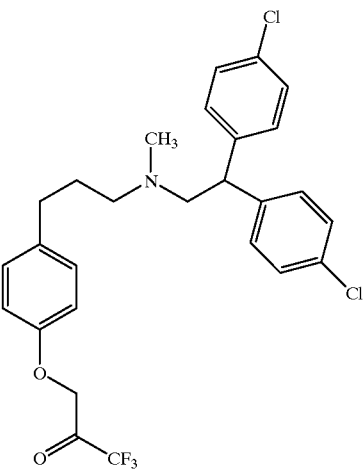

or a pharmaceutically acceptable salt or prodrug thereof.

6. A compound having the formula or a pharmaceutically acceptable salt or prodrug thereof.

7. A pharmaceutical composition for the inhibition of cytosolic phospholipase A₂ comprising a therapeutically effective amount of a compound of claim 1 and a pharmaceutically acceptable carrier.

8. A method of inhibiting cytosolic phospholipase A₂ in a mammal in need thereof, comprising administering to said mammal a therapeutically effective amount of a compound of claim 1.

* * * * *